United States Patent
Watterson et al.

(10) Patent No.: US 9,408,845 B2
(45) Date of Patent: *Aug. 9, 2016

(54) FORMULATIONS CONTAINING PYRIDAZINE COMPOUNDS

(71) Applicant: Northwestern University, Evanston, IL (US)

(72) Inventors: D. Martin Watterson, Chicago, IL (US); Linda Van Eldik, Chicago, IL (US); Wenhui Hu, Guangzhou (CN)

(73) Assignee: Northwestern University, Evanston, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/660,671

(22) Filed: Oct. 25, 2012

(65) Prior Publication Data

US 2013/0072496 A1     Mar. 21, 2013

Related U.S. Application Data

(63) Continuation of application No. 12/298,652, filed as application No. PCT/US2007/010248 on Apr. 27, 2007, now abandoned.

(60) Provisional application No. 60/796,328, filed on Apr. 28, 2006.

(51) Int. Cl.
| | |
|---|---|
| *A61K 31/506* | (2006.01) |
| *C07D 403/14* | (2006.01) |
| *A61K 31/501* | (2006.01) |
| *C07D 237/20* | (2006.01) |
| *C07D 401/12* | (2006.01) |
| *C07D 401/14* | (2006.01) |
| *C07D 403/12* | (2006.01) |

(52) U.S. Cl.
CPC ............. *A61K 31/506* (2013.01); *A61K 31/501* (2013.01); *C07D 237/20* (2013.01); *C07D 401/12* (2013.01); *C07D 401/14* (2013.01); *C07D 403/12* (2013.01); *C07D 403/14* (2013.01)

(58) Field of Classification Search
CPC ... A61K 31/50; A61K 31/501; A61K 31/502; A61K 31/505; A61K 31/506; C07D 401/14
See application file for complete search history.

(56) References Cited

U.S. PATENT DOCUMENTS

| | | |
|---|---|---|
| 2,857,384 A | 10/1958 | Druey |
| 4,169,158 A | 9/1979 | Laborit |
| 4,508,720 A | 4/1985 | Kan et al. |
| 4,654,343 A | 3/1987 | Albright |
| 4,710,499 A | 12/1987 | Wermuth |
| 4,721,711 A | 1/1988 | Chambon |
| 4,977,152 A | 12/1990 | Biziere |
| 5,045,541 A | 9/1991 | Nakao |
| 5,484,940 A | 1/1996 | Grant |
| 8,367,672 B2 * | 2/2013 | Watterson ...................... 514/247 |
| 8,933,076 B2 * | 1/2015 | Watterson ...................... 514/247 |

(Continued)

FOREIGN PATENT DOCUMENTS

| | | |
|---|---|---|
| EP | 0072726 | 2/1983 |
| EP | 0 094 038 | 11/1983 |

(Continued)

OTHER PUBLICATIONS

Shohami et al. "Inhibition of Tumor Necrosis Factor Alpha (TNFa) Activity in Rat Brain is Associated with Cerebroprotection After Closed Head Injury". Journal of Cerebral Blood Flow and Metabolism. 1996; 16:378-384.*

(Continued)

*Primary Examiner* — Leslie A. Royds Draper

(74) *Attorney, Agent, or Firm* — Millen White Zelano and Branigan, PC; John Sopp; Anthony Zelano

(57) ABSTRACT

The invention relates to chemical compounds, compositions and methods of making and using the same. In particular, the invention provides selected pyridazine compounds of the formula I wherein R1, R4, R5, R6, R7, R8, R9, R12, R13 ET R14 are independently hydrogen, hydroxyl, alkyl, alkenyl, alkynyl, alkylene, alkenylene, alkoxy, alkenyloxy, cycloalkyl, cycloalkenyl, cycloalkynyl, cycloalkoxy, aryl, aryloxy, arylalkoxy, aroyl, heteroaryl, heterocyclic, acyl, acyloxy, amino, imino, azido, thiol, thioallyl, thioalkoxy, thioaryl, nitro, cyano, halo, sulfate, sulfonyl, sulfinyl, sulfonyl, sultanate, sulfoxide, silyl, silyloxy, silylalkyl, silylthio, =O, =S, phosphonate, ureido, carboxyl, carbonyl, carbamoyl, or carboxamide; and X is optionally substituted pyrimidinyl or pyridazinyl, an isomer, a pharmaceutically acceptable salt, or derivative thereof. The invention additional relates to compositions comprising the compounds, and methods of using the compounds and compositions for modulation of cellular pathways, for treatment or prevention of inflammatory diseases, for research, drug screening, and therapeutic applications.

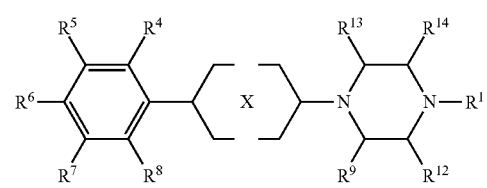

10 Claims, 41 Drawing Sheets

(56) References Cited

U.S. PATENT DOCUMENTS

| | | |
|---|---|---|
| 2003/0176437 A1 | 9/2003 | Watterson |
| 2004/0167226 A1* | 8/2004 | Serafini et al. ............... 514/619 |
| 2005/0137397 A1 | 6/2005 | Nelson |
| 2006/0073472 A1 | 4/2006 | Watterson |
| 2008/0318899 A1 | 12/2008 | Watterson et al. |
| 2009/0029985 A1 | 1/2009 | Watterson |

FOREIGN PATENT DOCUMENTS

| | | |
|---|---|---|
| EP | 0 211 457 | 2/1987 |
| EP | 0211457 | 2/1987 |
| EP | 0382634 | 8/1990 |
| EP | 0628550 | 12/1994 |
| EP | 1061077 | 12/2000 |
| FR | 2141697 | 1/1973 |
| FR | 2847253 | 5/2004 |
| WO | WO 9846574 | 10/1998 |
| WO | WO 0142241 | 6/2001 |
| WO | WO 03018563 | 3/2003 |
| WO | WO 03-047577 | 6/2003 |
| WO | WO 03047577 | 6/2003 |
| WO | WO 2004046117 | 6/2004 |
| WO | WO 2005009976 | 2/2005 |
| WO | WO 2005061509 | 7/2005 |
| WO | WO 2005063761 | 7/2005 |
| WO | WO 2006/026135 A2 | 3/2006 |
| WO | WO 2006026135 | 3/2006 |
| WO | WO 2006/050389 A2 | 5/2006 |
| WO | WO 2006050359 | 5/2006 |
| WO | WO 2007127375 | 4/2007 |
| WO | WO 2007127475 | 4/2007 |
| WO | WO 2007130383 | 4/2007 |
| WO | WO 2007 127448 | 11/2007 |
| WO | WO 2007127448 | 11/2007 |
| WO | WO 2007127474 | 11/2007 |
| WO | WO 2008109437 | 9/2008 |

OTHER PUBLICATIONS

W. Hu et al., "Validation of the Neuroinflammation Cycle as a Drug Discovery Target Using Integrative Chemical Biology and Lead Compound Development with an Alzheimer's Disease-Related Mouse Model", Current Alzheimer Research, vol. 2, No. 2, Abstract (2005).
R. Nelson, "Compound Holds Promise for Neurodegenerative Diseases", Lancet Neurology, vol. 5, No. 3 (Mar. 2006) pp. 210.
W. Hu et al., "Development of a Novel Therapeutic Suppressor of Brain Proinflammatory Cytokine Up-Regulation that Attenuates Synaptic Dysfunction and Behavioral Deficits", Bioorganic & Medicinal Chemistry Letters, vol. 17 (2007) pp. 414-418.
H. R. Ranaivo et al., "Glia as a Therapeutic Target : Selective Suppression of Human Amyloid-β-Induced Upregulation of Brain Proinflammatory Cytokine Production Attenuates Neurodegeneration", The Journal of Neuroscience, vol. 26, No. 2 (Jan. 2006) pp. 662-670.
Schafers et al. "Tumor Necrosis Factor-Alpha Induces Mechanical Allodynia after Spinal Nerve Litigation by Activation of p38 MAPK in Primary Sensory Neurons". Journal of Neuroscience, Apr. 1, 2003; 23(7):2517-2521.
Cardona et al., "Control of microglial neurotoxicity by the fractalkine receptor," Nature Neurosci., 2006, vol. 9, pp. 917-924.
Craft, J. et al., "Enhanced susceptibility of S-100B transgenic mice to neuroinflammation and neuronal dysfunction induced by intracerebroventricular infusion of human Beta-amyloid," GLIA, 2005, vol. 51, pp. 209-216.
D'Ambrosio, R. et al., "Epilepsy after head injury," Curr. Opin. Neurol., 2004, vol. 17, pp. 7431-7735.
Dogan et al., "Effects of MDL 72527, a Specific Inhibitor of Polyamine Oxidase, on Brain Edema, Ischemic Injury Volume, and Tissue Polyamine Levels in Rats After Temporary Middle Cerebral Artery Occlusion," J. Neurochem., 1999, vol. 72, pp. 765.

Dragunow M. et al., "Clusterin accumulates in dying neurons following status epilepticus," Mol. Brain. Res., 1005, vol. 32, pp. 279-290.
Dube, C. et al., "Prolonged Febrile Seizures in the immature rat model enhance hippocampal excitability long term," Ann Neurol., 2000, vol. 47, pp. 336-344.
Farlow, M. R., "Utilizing combination therapy in the treatment of Alzheimer's disease," Expert review of Neurotherapeutics, 2004, vol. 4, No. 5, pp. 799-808.
French, J. et al., "Characteristics of medial temporal lobe epilepsy. I. Results of history and physical examination," Ann Neurol., 1993, vol. 34, pp. 774-780.
Garattini et al., "Notes on Buspirone's Mchanisms of Action," J. Clin. Psych., 1982, vol. 43, pp. 19-24.
Giorgi, F et al., "Effects of status epilepticus early in life on susceptibility to ischemic injury in adulthood," Epilepsia, 2005, vol. 46, pp. 490-498.
Griffin et al., "Glial-Neuronal Interactions in Alzheimer's Disease: The Potential Role of a 'Cytokin Cycle' in Disease Progression," Brain Pathol., 1998, vol. 8, pp. 65-72.
Guo, Z. et al., "Head Injury and the risk of AD in the MIRAGE study," Neurology, 2000, vol. 54, pp. 1316-1323.
Hagberg, H. et al., "Effect of inflammation on central nervous system development and vulnerability," Curr. Opin. Neurol., 2005, vol. 18, pp. 117-123.
Han, B. et al., "Clusterin contributes to caspase-3-independent brain injury following neonatal hypoxia-ischemia," Nature Med., 2001, vol. 7, pp. 338-343.
Hansen, K. B. et al., "First Generation Process for the Prepartion of the DDP-IV Inhibitor Sitagliptin," Organic Process Research & Development, 2005, vol. 9, pp. 634-639.
Haut, S. et al., "Susceptibility of immature and adult brains to seizure effects," Lancet Neurol., 2004, vol. 3, pp. 608-617.
Heinisch, G. et al., Prog. Med. Chem. 1992, vol. 29, pp. 141-183.
Holmes, G. et al., "Seizures in the developing brain: perhaps not so benign after all," Neuron, 1998, vol. 21, pp. 1231-1234.
Holmes, G. et al., "Effects of seizures on brain development: lessons from the laboratory," Pediatr Neurol., 2005, vol. 33, pp. 1-11.
Hu et al., "S 100-Beta Stimulates Inducible Nitric Oxide Synthase Activity and Mrna Levels in Rat Cortical Astrocytes," J. Biol. Chem., 1996, vol. 271, pp. 2543-2547.
Huang, Y et al., "Glutamate transporters bring competition to the synapse," Curr. Opin. Neurobiol., 2004, vol. 14, pp. 346-352.
Jensen, F. et al., "NBQX blocks acute and late epileptogenic effects of perinatal hypoxia," Epilepsia, 1995, vol. 36, pp. 966-972.
Koh, S. et al., "Early-life seizures increase susceptibility to seizure-induced brain injury in adulthood," Neurology, 1999, vol. 53, pp. 915-921.
Letty, S. et al., "Differential impairments of spatial memory and social behavior in two models of limbic epilepsy," Epilepsia, 1995, vol. 36, pp. 973-982.
Levition, A. et al., "Brain damage markers in children. Neurobiological and clinical aspects," Acta Paediatrica, 2002, vol. 91, pp. 9-13.
Loscher, W. et al., "New Horizons in the development of antiepileptic drugs," Epilepsy Res., 2002, vol. 50, pp. 3-16.
Maragakis, N. et al., "Glutamate transporters: animal models t neurologic disease," Neurobiol Dis. 2004, vol. 15, pp. 461-473.
Minghetti, L. et al., "Role of Inflammation in neurodegenerative diseases," Curr. Opin. Neurol., 2005, vol. 18, pp. 315-321.
Mrak, R. et al., "Glia and cytoknes in progression of neurodogeneration," Neurobiol Aging, 2005, Volo. 26, pp. 349-354.
Perry, V et al., "Systemic infections and inflammation affect chronic neurodegeneration," Nat Rev Immunol., 2007, doi: 10.1038/nri 2015.
Rao, V. et al., "Antisense Knockdown of the glial glutamate transporter GLT-1 exacerbates hippocampal damage following traumatic injury to rat brain," Eur. J. Neurosci., 2001, vol. 13, pp. 119-128.
Ravizza et al., "Inflammatory response and glia activation in developing rat hippocampus after status epilepticus," Epilepsia, 2005, vol. 46, pp. S113-S117.
Rizzi et al., "Glia activation and cytokine increase in rat hippocampus by kainic acid-induced status epilepticus during postnatal development," Neurobiol. Dis., 2003, vol. 14, pp. 494-503.
Rothermundt, M. et al., "S100B in brain damage and neurodegeneration," Mircoscopy Research & Technique, 2003, vol. 60, pp. 614-632.

(56) References Cited

OTHER PUBLICATIONS

Sanchez et al., "Decreased glutamate receptor 2 expression and enchanced epileptogenesis in immature rat hippocampus after perinatal hypoxia-induced seizures," J. Neurosci., 2001, vol. 21, pp. 8154-8563.
Sayin, U., et al., "Seizures in the developing brain cause adverse long-term effects o spatial learning and anxiety," Epilepsia, 2004, vol. 45, pp. 1539-1548.
Schmid, R. et al., "Effects of neonatal seizures on subsequent seizure-induced brain injury," Neurology, 1999, vol. 53, pp. 1754-1761.
Schmued, L. et al., "Fluoro-Jade B: a high affinity fluorescent marker for the localization of neuronal degeneration," Brain Res., 2000, vol. 874, pp. 123-130.
Strohmeyer, R. et al., "Association of factor H of the alternative pathway of complement with agrin and complement receptor 3 in Alzheimer's disease brain," J. Neuroimmunol., 2002, vol. 131, pp. 135-146.
Strohmeyer, R. et al., "Molecular and cellular mediators of Alzheimer's disease inflammation," J. Alz. Dis., 2001, vol. 3, pp. 131-157.
Van Eldik et al., "The Janus face of glial-derived S100B: beneficial and detrimental functions in the brain," Restorative Neurol Neurosci., 2003, vol. 21, pp. 97-108.
Verbitsky, M. et al., "Altered hippocampal transcript profile accompanies an age-related spatial memory deficit in mice," 2004, Learning and Memory, vol. 11, pp. 253-260.
Vezzani et al., "Functional role of inflammatory cytokines and anti-inflammatory molecules in seizures and epileptogenesis," Epilepsia, 2002, vol. 43, pp. S30-S35.
Vezzani, A. et al., "Brain Inflammation in epilepsy: Experimental and clinical evidence," Epilepsia, 2005, vol. 46, pp. 1724-1743.
Vezzani, A. Epilepsy Currents, vol. 4, No. 2, Feb. 26, 2004, pp. 73-75.
Wainwright, M. et al., "Increased susceptibility of S100B transgenic mice to perinatal hypoxia-ischemia," Annals of Neurol., 2004, vol. 56, pp. 61-67.
Wainwright, M et al., "Carnitine treatment inhibits increases in cerebral carnitine esters and glutamate detected by mass spectrometry following hypoxiaischemia in newborn rats," Stroke 37,2005, pp. 524-530.
Weiss, C. et al., "Spatial learning and memory in aging C57BL/b mice," Neurosci. Res. Comm., 1998, vol. 23, No. 2, pp. 77-92.
Weiss, S. et al., "Anatomic studies of DNA fragmentation in rat brain after systemic kainic acid administration," Neuroscience, vol. 74, No. 2, pp. 541-551.
Zhang, G. et al., "Long-term alterations in glutamate receptor and transporter expression following early-life seizures are associated with increased seizure susceptibility," J. Neurochem., 2004, vol. 88, pp. 91-101.
Communication regarding the Extended European Search Report for EP 05823123 dated Mar. 2, 2009.
Supplementary European Search Report for EP05823123 dated Feb. 18, 2009.
Communication pursuant to Article 94(3) EPC for EP05823123 dated Dec. 17, 2009.
Communication pursuant to Article 94(3) EPC for EP07756162 dated Feb. 11, 2009.
Reply to Communication pursuant to Article 94(3) EPC for EP07756162 of Feb. 11, 2009 dated Nov. 19, 2009.
Communication pursuant to Article 94(3) EPC for EP07756162 dated Feb. 5, 2010.
Office Action for CN 200580037702 dated Sep. 4, 2009 with translation.
Office Action for MX/a/2007/005247 dated Aug. 25, 2009 with translation.
Reply to Office Action for MX/a/2007/005247 of Aug. 25, 2009 dated Mar. 1, 2010.
Office Action regarding POA documents for MX/a/2007/005247 dated Nov. 2, 2005.
Communication regarding the European Search Report for EP 02796459 dated Oct. 29, 2004.
Supplementary European Search Report for EP 02796459 dated Oct. 7, 2004.
Communication pursuant to Article 94(3) EPC for EP 02796459 dated Sep. 30, 2010.
Reply to Communication pursuant to Article 94(3) EPC for EP 02796459 of Sep. 30, 2010 dated Apr. 8, 2009.
Thomson Innovation, "Pyridazine derivatives, process for their preparation and pharmaceutical compositions containing them," Retrieved from Patent Record View on Sep. 1, 2010; English Abstract of EP0382634.
Thomson Innovation, "3-amino-6-aryl-1,2,4-triazolo(4,3-b) pyridazines, their preparation and use," Retrieved from Patent Record View on Sep. 1, 2010; English Abstracts of EP0094038.
Chambon, J. P. et al., "CM-40907: a structurally novel anticonvulsant in mice, rats, and baboons," The Journal of Pharmacology and Experimental Therapeutics, Jun. 1985, vol. 233, No. 3, pp. 836-844, Abstract Only.
Chitaley, K. et al., "Antagonism of Rho-Kinase stimulates rat penile erection via a nitric oxide-independent pathway," Nature Medicine, Jan. 2001, vol. 7, No. 1, pp. 119-122.
Communication pursuant to Article 94(3) EPC for related European Patent Application No. 07776351 dated Feb. 8, 2012.
Communication pursuant to Article 94(3) EPC for related European Patent Application No. 07776351 dated Oct. 9, 2009.
Correspondence from the Israeli Patent Office for related Application No. 194968 dated May 2, 2010, with English Translation.
Da Silva, J. et al., "Blockade of p38 Mitogen-activated Protein Kinase Pathway Inhibits Inducible Nitric-oxide Synthase Expression in Mouse Astrocytes," The Journal of Biological Chemistry, 1997, vol. 272, No. 45, pp. 28373-28380.
Decision on the request for further processing under rule 135(3) EPC for related European Patent Application No. 07776351 dated Aug. 3, 2010.
Donato, R., "Functional roles of S100 proteins, calcium-binding proteins of the EF-hand type," Biochimica et Biophysica Acta, 1999, vol. 1450, pp. 191-231.
Draper, T. L. et al., "Synthesis of Unsymmetrical 3,6-distributed pyridazines. A Palladium-Catalyzed Approach from 3-Iodopyridazines," J. Org. Chem., 1995, vol. 60, pp. 748-750.
English Translation of Memo concerning the official action reported in the covering letter Mexican Patent Application No. MX/a/2008/013843 dated Aug. 25, 2009.
Garcia, J. G. N. et al., "Regulation of endothelial cell gap formation and barrier dysfunction: Role of Myosin Light Chain Phophorylation," Journal of Cellular Physiology, 1995, vol. 163, pp. 510-522.
Ghajar, J., "Traumatic brain injury," The Lancet, Sep. 9, 2000, vol. 356, pp. 923-929.
Lambert, M. P. et al., "Diffusible, nonfibrillar ligands derived from $A\beta_{1-42}$ are potent central nervous systems neurotoxins," Proc. Natl. Acad., May 1998, vol. 95, pp. 6448-6453.
Maroney, A. C. et al., "CEP-1347 (KT7515), a semisynthetic inhibitor of the mixed lineage kinase family," The Journal of Biological Chemistry, 2001, vol. 276, No. 27, pp. 25302-25308.
Maroney, A. C. et al., "CEP-1347 (KT7515), an Inhibitor of JNK Activation, Rescues Sympathetic Neurons and Neuronally Differentiated PC12 Cells form Death Evoked by Three Distinct Insults," Journal of Neurochemistry, 1999, vol. 73, pp. 1901-1912.
Memo concerning the official action reported in the covering letter Mexican Patent Application No. MX/a/2008/013843 dated Aug. 25, 2009.
Office Action for related Canadian Patent Application No. 2 589 106 dated Feb. 24, 2012.
Office Action for related U.S. Appl. No. 11/666,803 dated Nov. 30, 2011.
Office Action for related U.S. Appl. No. 11/666,803 dated Jun. 3, 2011.
Parker, J. C. et al., "Inhibitors of myosin light chain kinase and phosphodiesterase reduce ventilator-induced lung injury," J. Appl. Physiol., 2000, vol. 89, pp. 2241-2248.
Petrova, T. V. et al., "Cyclopentenone prostaglandins suppress activation of microglia: Down-regulation of inducible nitric-oxide synthase by 15-deoxy-$\Delta^{12,14}$-prostaglandin $J_2$," Proc. Natl. Acad. Sci., Neurobiology, vol. 96, pp. 4668-4673.

(56) References Cited

OTHER PUBLICATIONS

Response to office action for related Australian Patent Application No. 2005 302 225 dated Apr. 11, 2012.
Response to office action for related Israeli Patent Application No. 182765 dated Apr. 24, 2012.
Response to Office Action for related U.S. Appl. No. 11/666,803 dated Feb. 29, 2012.
Response to Office Action for related U.S. Appl. No. 11/666,803 dated Sep. 20, 2011.
Response to Office Action in related European Patent Application No. 07776351 dated Jul. 20, 2010.
Rival, Y. et al., "5-HT$_3$ Antagonists derived from aminopyridazine-type muscarinic M1 Agonists," J. Med. Chem., 1998, vol. 41, pp. 311-317.
Rohet, F. et al., "Synthesis and analgesic effects of 3-substituted 4,6-Diarylpyridazine derivatives of the arylpiperazine class," Bioorganic & Medicinal Chemistry, vol. 5, No. 4, pp. 655-659.
Sauer, J. et al., "Synthesis of 3,5-distributed pyridazines by regioselective [4+2] Cycloadditions with Ethynyltributyltin and Subsequent Replacement of the Organotin Substituent," Tetrahedron, 1998, vol. 54, pp. 4297-4312.
Schumacher, A. M. et al., "Death associated protein kinase as a potential therapeutic target," Expert Opin. Ther. Targets, 2002, vol. 6, No. 4, pp. 497-506.
South, M. S. et al., "Synthesis and Reactions of Haloazodienes. A New and General Synthesis of Substituted Pyridazines," J. Org. Chem., 1996, vol. 61, pp. 8921-8934.
Supplementary European Search Report for EP 05 81 7588 dated Mar. 28, 2012.
Text of the First Office Action for related Chinese Patent Application No. 200780023749 dated Jun. 22, 2011, with English Translation.
The Details of the First Office Action for related Chinese Patent Application No. 200580037702 with English Translation, 2009.
The Details of the Second Office Action for related Chinese Patent Application No. 200580037702 with English Translation, 2010.
Translation of Notice of Reasons for Rejection for Japanese Patent Application No. 2007 539305 dated Apr. 20, 2012.
Translation of Notification of Defects in Patent Application dated Mar. 22, 2010 for related Israeli Patent Application No. 182765.
Translation of Notification of Defects in Patent Application dated Nov. 27, 2011 for related Israeli Patent Application No. 182765.
Translation of Response to Notification of Defects in Patent Application dated Jan. 11, 2011 in related Israeli Patent Application No. 182765.
Troy, C. M. et al., "β-Amyloid-induced neuronal apoptosis requires c-Jun N-terminal kinase activation," Journal of Neurochemistry, 2001, 77, pp. 157-164.
Vieth, M. et al., "Characteristic physical properties and structural fragments of marketed oral drugs," J. Med. Chem., 2004, vol. 47, pp. 224-232.
Yamamoto, M. et al., "Developmental changes in distribution of death-associated protein kinase mRNAs," Journal of Neuroscience Research, 1999, vol. 58, pp. 674-683.
First Examination Report for related Indian Patent Application No. 1977/KOLNP/2007 dated Jan. 24, 2011.
Response to First Examination Report for related Indian Patent Application No. 1977/KOLNP/2007 dated Jan. 20, 2012.
Longa, et al., "Reversible Middle Cerebral Artery Occlusion Without Craniectomy in Rats," Stroke 30:84-91 (1989).
Merck: "The Merck Manual," Merck & Co., U.S.A., p. 1398, col. 2, "prognosis and treatment of Alzheimer's disease," (1999).
Mirzoeva, et al., "Screening in a cell-based assay for inhibitors of microglial nitric oxide production reveals calmodulin-regulated protein kinases as potential drug discovery targets," Brain Res. 844:126-134 (1999).
Mirzoeva, et al., "Discovery of a 3-amino-6-phenyl-pyridazine Derivative as a New Synthetic Antineuroinflammatory Compound," J. of Medicinal Chem. 45(3):563-566 (Watterson) (2002).
Munoz, L., et al., "A novel p38 alpha MAPK inhibitor suppresses btain proinflammatory cytokine up-regulation and attenuates synaptic dysfunction and behavioral deficits in an Alzheimer's disease mouse model," J. Neuroinflammation 4:21 (Sep. 2007).
Nelson, et al., "Compound holds promise for neurodegenerative diseases," Lancet Neurology 5(3) 210 (2006).
Ohno, et al., "Differential effects of Alpha-CaMKII mutation on hippocampal learning and changes in intrinsic neuronal excitability," Eur. J. Neurosci. 23(8) 2235-2240 (2006).
Prusiner, S.B., et al. "Shattuck Lecture—Neurodegenerative Diseases and Prions," New Engl. J. Med. 344:1516-1526 (2001).
Ranaivo, H.R., et al., "Development of Orally Bioavailable Pyridazines that Suppress Neuroinflammation," 9th International Symposium on the Chemistry and Pharmacology of Pyridazines, Antwerp, Belgium, Jul. 2004, Abstract & Power.
Recanatini, et al., "QT prolongation through hERG K(+) channel blockade: current knowledge and strategies for the early prediction during drug development," Med. Res. Rev. 25(2):133-166 (Mar. 2005).
Roden, "Drug-induced prolongation of the QT interval," N. Engl. J. Med. 350(10):1013-1022 (Mar. 2004).
Saturnino, C., et al., "Heterocyclic Amidines: I. A One-Step Synthesis of New alpha-substituted Imidazolyphenylacetic acids ," Heterocycles 41(7):1491-1501 (1995).
Sheng, J., et al., "In vivo and in vitro evidence supporting a role for the inflammatory cytokine interleukin-1 as a driving force in Alzheimer pathogenesis," Neurobiol. Aging 17:761-766 (1996).
Somera-Molena K.C., et al., "Glial activation links early-life seizures and long-term neurologic dysfunction: evidence using a small molecule inhibitor of pro-inflammatory cytokine upregulation," Epilepsia 48: 1785-1800 (2007).
Sotelo, E., et al., "Efficient aromatization of 4,5-dihydro-3-(2H)-pyridazinones substituted at 5 position by using anhydrous copper (II) chloride," Synthetic Communications 30:1-7 (2000).
Sotelo, E., et al., "Pyridazines. Part 26, Efficient and regioselective Pd-catalyzed arylation of 4-bromo-6-chloro-3-phenylpyridazine," Synless (2) 223-226 (2002).
Sridhar, et al., "Protein Kinases as Therapeutics Targets," Pharm. Res. 17:1345-1353 (2000).
Stahl, P.H., et al., "Handbook of Pharmaceutical Salts, Properties, Selection, and Use," Verlag Helvetica Chimica Acta & Wiley-Vch, Weinheim, International Union of Pure and Applied Chemistry, XP-002459552 (2002).
Toma, L., et al., "6-Chloropyridazin-3-yl Derivatives Active as Nicotinic Agents: Synthesis Binding and Modeling Studies," Jrnl. of Med. Chem. 45(8):4011-4017 (2002).
Van Eldik, et al., "Glia proinflammatory cytokine upregulation as a therapeutic target for neurodegenerative diseases: function-based and target-based discovery approaches," Int. Rev. Neurobiol. 82:277-296 (2007).
Van Eldik, et al., "S100 beta expression in Alzheimer's disease: relation to neuropathology in brain regions," Biochem. Biophys. Acta 1223: 398-403 (1994).
Van Eldik, et al., "Attenuation of Human Abeta-induced Neuroinflammation, Neuronal Death, and Hippocampus-Dependent Bahavioral Deficits by a New Class of Bioavailable Small Molecules," Presentation, CNS Diseases Congress: Advances in Therapeutics, Tools and Trials, Philadelphia, Jun. 28-29, 2004.
Van Niel, M.B., et al., "A New Phridazine Series of GABAA alpha-5 Ligands," J. Med. Chem., 48(19):6004-6011 (Merck) (2005).
Velentza, et al., "A protein kinase associated with apoptosis and tumor suppression: Structure, Activity and Discovery of Peptide Substrates," Jrnl. of Biol. Chem. 276(42):38956-38965 (2001).
Velentza, et al., "Structure, Activity, REgulation and Inhibitor Discovery for a Protein Kinase Associated with Apoptosis and Neuronal Death," Pharmacology & Therapeutics 93:217-224 (Feb. Mar. 2002).
Veleltza, et al., "An aminopyridazine-based inhibitor of a pro-apoptotic protein kinase attenuates hypoxia-ischermia induced acute brain injury," Bioorganic & Medicinal Chem. Ltrs. 13:3465-3470 (Watterson) (2003).
Velentza, et al., "Discovery of Substrates and Small Molecule Inhibitors for a Death Associated Protein Kinase," Cell. Biol. Mol. Lett. 6(2B):484-485 (2001).
Wainwright, M., et al., "Protein kinase involved in lung injury susceptibility: evidence from enzyme isoform genetic knockout and in

(56) References Cited

OTHER PUBLICATIONS vivo inhibitor treatment," Proc. Nat. Acad. Sci. USA (May 13, 2003) 100(10):6233-6238, Epub. May 2, 2003.
Watterson, et al., "Ligand modulation of glial activation: cell permeable, small molecule inhibitors of serine-threonine protein kinases can block induction of interleukin 1 beta and nitric oxide synthase II," Neurochem. Intl. 39:459-468 (2001).
Watterson, et al., "Discovery of New Chemical Classes of Synthetic Ligands that Suppress Neuroinflammatory Responses," J. Mol. Neuroscience 19:89-93 (2002).
Watterson, D.M., "Development of orally bioavailable small molecule modulators of disease progression in new Alzheimer's Disease related mouse models," Institute for the Study of Aging, Investigator's Meeting, New York, Oct. 7, 2004.
Watterson, D.M., "Discovery of new small molecule modulators of disease progression in an Alzheimer's Disease related mouse model," 12th Mainzer Forum in Medicinal Chemistry, Mainz, Germany, Oct. 2004, Presentation.
Watterson, D.M., et al., "Discovery of a new class of synthetic protein kinase inhibitors that suppress selective aspects of glial activation and protect against [J]-amyloid induced injury. A foundation for future medicinal chemistry efforts focused on targeting Alzheimer's disease progression," J. Mol. Neurosci. 20:411-424 (2003).
Wermuth, C.G., et al., Selected Procedures for the Preparation of Pharmaceutically Acceptable Salts, in Stahl, P.H., Wermuth, C.G. (Ed.) Handbook of Pharmaceutical Salts, Wiley-VCH, pp. 249-264.
Wermuth, C.G., "Search for new lead compounds: The example of the chemical and pharmacological dissection of aminopyridazines," J. Heterocyclic Chem., 35:1091-1100 (1998).
Wermuth, C.G., et al., "3-aminopyridazine Derivatives with Atypical Antidepressant, Serotoneric, and Dopaminegic Activities," Jrnl. of Medical Chem. 32(3):528-537 (1989).
Wermuth, C.G., et al., "Synthesis and Structure-Activity Relationships of a Series of Aminopyridazine Derivatives of Y-Aminobutyric Acid Acting as Selective GABA-A Antagonists," J. Med. Chem. 30:239-249 (1987).
Wing, L., et al., "De novo and molecular target-independent discovery of orally bioavailable lead compounds for neurological disorders," Curr. Alzheimer Res. 3:205-214 (2006).
Zhou, et al., "HERG-like K+Channels in Microglia," J. Gen. Physiol. 111(6):781-794 (1998).
Adams, et al., "Concise Synthesis of 1H-pyrazin-2-ones and 2-Aminopyrazines," Synlett, 11:2031-2033 (2004).
Akiyama, et al., "Inflammation and Alzheimer's Disease," Neurobiol. Aging, 21:383-421 (2002).
Allen and Van Allen, "Some 3,4-Diphenylcinnolines and Related Compounds," J. Amer. Chem. Soc., 73:5854 (1951).
Apter, et al., "Buspirone: Future Directions," J. Clin. Psychopharmacol. 19:86-93 (1999).
Chayer, S., et al., "(3-Pyridazinamin-3-yl) Aplha-Aminoacids: A Facilitated Method of Preparation of Phenylalanine and Proline Representatives," Tetrahedron Letters, 39:841-844 (1998).
Chen, et al., "A Experimental Model of Closed Head Injury in Mice: Pathophysiology, Histopathology, and Cognitive Deficits," J. Neurotrauma, 13:557-568 (1996).
Cignarella, G., et al., "Synthesis and biological evaluation of substituted benzo[A]cinnolinones and 3H-benzo[6,7]cyclohepta[1,2-c]pyridazinones: higher homologues of the antihypertensive and antithrombotic 5H-indeno[1,2-c]pyridazinones," J. Med. Chem. 32:2277-2282 (1989).
Contreras, et al., "Aminopyridazines as Acetylcholinesterase Inhibitors," J. of Med. Chem., 42(4):730-741 (1999).
Contreras, et al., "Design, Synthesis, and Structure—Activity Relationships of a Series of 3-[2-(1-Benzylpiperidin-4-yl)ethylamino]pyridazine Derivatives as Acetylcholinesterase Inhibitors," Journ. of Med. Chem., 44(17):2707-2718 (2001).
Constantino, et al., "Synthesis, activity, and molecular modeling of a new series of tricyclic pyridazinones as selective aldose reductase inhibitors," Jrnl. of Med. Chem., 39:4396-4405 (1996).

Coudert, et al., "A new synthetic route to 4,6-diarylpyridazinones and some of their derivatives," Jrnl. of Hetero. Chem., 25(3):799-802 (1988).
Craft, J.M., et al., "Human amyloid beta-induced neuroinflammation is an early event in neurodegeneration," Glia 53:484-490 (2006).
Craft, J.M., et al., "Aminopyridazines attenuate hippocampus dependent behavioral deficits induced by human (J-amyloid in a murine model of neuroinflammation," J. Mol. Neurosci., 24:115-122 (2004).
Craft, J.M., et al., "Aminopyridazines inhibit B-amyloid induced glial activation and neuronal damage in vivo," Neurobiol. Aging, 25:1283-1292 (2004).
Craft, J.M., et al., "Neuroinflammation: a potential therapeutic target," Expert. Opin. Ther. Targets, 9:887-900 (2005).
Csende, F., et al., "Copper(II) Chloride as an Efficient Reagent for the Dehydrogenation of Pyridazinone Derivatives," Synthesis, 1240-1242 (1995).
Database—Caplus—XP-002515676, AN:2003:775838 (2003).
Database—Beilstein—XP-002515678, RN:4403492 (Apr. 2008).
Database—Caplus—XP-002515675, AN:1989:423528 (1989).
Database—Capkus—XP-002515677, AN:1973:537067 (1973).
Database—Medline—XP-00253989, AN: NLM3950916 (1986).
Database—Medline—XP-00253989, AN: NLM2989499 (1985).
Du, Y., et al., "Association of an interleukin 1 [alpha] polymorphism with Alzheimer's disease," Neurology 55:480-484 (2000).
Eddy, S., et al., "Efficient Aromatization of 4,5-Dihydro-3(2H)-Pyridazinones Substituted at 5 Position by Using Anhydrous Copper(II) Chloride," Synthetic Communications 30(1):1-7 (2000).
Enyedy, I.J., et al., "Pharmacophore-based discovery of substituted pyridines as novel dopamine transporter inhibitors," Bioorganic & Medicinal Chemistry Letters 13(3) 513-517 (2003).
Farlow, M.R., "Utilizing combination therapy in the treatment of Alzheimer's disease," Expert review of Neurotherapeutics 4(5) 799-808 (2004).
Finlayson et al., "Acquired QT interval prolongation and HERG: implications for drug discovery and development," Eur. J. Pharmacol. 500(1-3):129-142 (Oct. 2004).
Garattini, et al., "Notes on Buspirone's Mechanisms of Action," J. Clin. Psych, 43:19-24 (1982).
Griffin, et al., "Glial-Neuronal Interactions in Alzheimer's Disease: The Potential Role of a 'Cytokin cycle' in Disease Progression," Brain Pathol. 8:65-72 (1998).
Hansen, K.B., et al., "First Generation Process for the Preparation of the DDP-IV Inhibitor Sitagliptin," Organic process research & development, 9:634-639 (2005).
Hargreaves, et al., "A new and sensitive method for measuring thermal nociception in cutaneous hyperalgesia," Pain 32:77-78 (1988).
Heinisch, G., et al., "Pharmacologically active pyridazine derivatives, Part I," Prog. Med. Chem. 27:1-49 (1990).
Heinisch, G., et al., "Pharmacologically active pyridazine derivatives, Part II," Prog. Med. Chem. 29:141-183 (1992).
Hirohashi, et al., "Pharmacological Studies with the Alpha2-Adrenoceptor Antagonist Midaglizone." Arzneim.-Forsch./Drug Res. 41:9-18 (1991).
Hu, et al., "Apolipoprotein E Attenuates beta-amyloid-induced Astrocyte Activation," J. Nuerochem. 7:1626-1634 (1998).
Hu, W., et al., "Pyridazines as a New Chemotype for Alzheimer's Disease Drug Discovery that Targets Disease Progression," 29th National Medicinal Chemistry Symposium, University of Wisconsin—Madison, Jun. 27-Jul. 1, 2004, Abstract and Poster.
Hirohashi, et al., "Pharmacological Studies with the Alpha2-Adrenoceptor Antagonist Midaglizone." Arzneim.-Forsch./Drug Res. 41:9-18 (1991).
Igarashi, et al., "Exogenous Tumor Necrosis Factor-Alpha Mimics Nucleus Pulposus-Induced Nueropathology," Spine 25:2975-2980 (2000).

(56) References Cited

OTHER PUBLICATIONS

Jones, R.G., "Pyrazines and Related Compounds. I. A New Synthesis of Nydroxypyrazines," J. Amer. Chem. Soc. 71: 78-81 (1949).

Karpus, W.J., et al , "Inhibition of experimental autoimmune encaphalomyelitis by a novel small molecular weight proinflammatory cytokine suppressing drug," J. Neuroimmunology 203(1): 73-78 (2008).

Ladu, et al., "Apolipoprotein E receptors Mediate the Effects of beta-Amyloid on Astrocyte Vultures," J. Biol. Chem. 275:33974-33980 (2000).

Ladu, et al., "Apolipoprotein E and apolipoprotein E Receptors Modulate A beta-induced gilal neuroinflammatory responses," Nuerochem Intl. 39:427-434 (2001).

Lam, et al., "Mechanism of glial activation by S100B: involvement of the transcription factor NFxB," Nuerobiol. Aging 22:765-772 (2001).

* cited by examiner

Figure 1
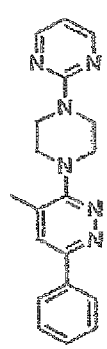
MW01-2-151SRM
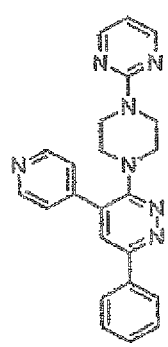
MW01-8-189WH
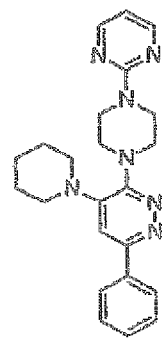
MW01-7-107WH
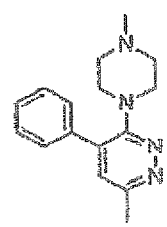
MW01-4-179LKM
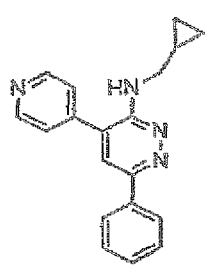
MW01-7-094WH
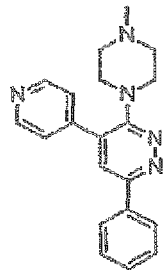
MW01-7-085WH
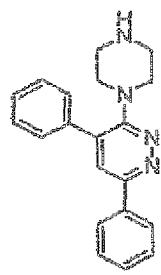
MW01-7-133WH
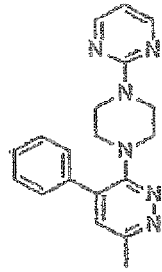
MW01-7-057

MW01-3-183WH

MW01-7-076WH          MW01-7-085WH

MW01-7-133WH

MW01-6-127WH                    MW01-7-107WH

Figure 26
*In vivo* activity of MW01-7-084WH
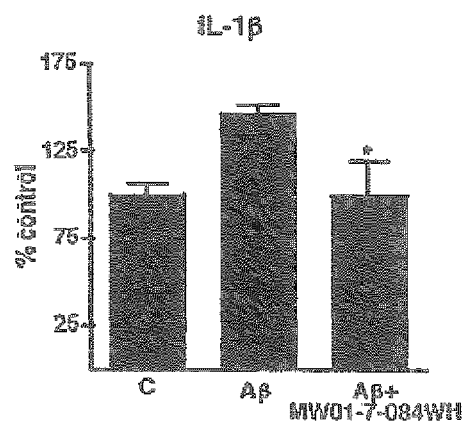
(A)
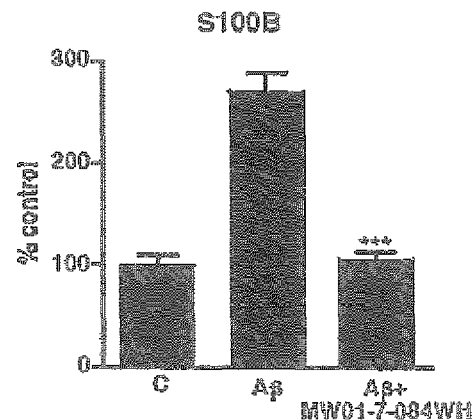
(B)
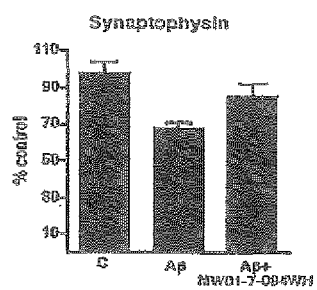
(C)
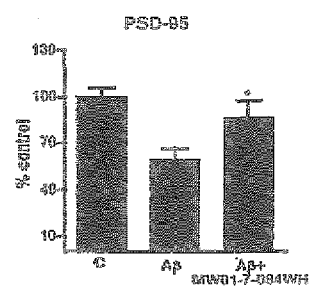
(D)
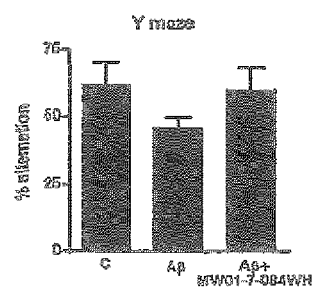
(E)

*In vivo* activity of MW01-7-085WH

FORMULATIONS CONTAINING PYRIDAZINE COMPOUNDS

This application is a divisional of U.S. Ser. No. 12/298,652, filed Oct. 27, 2008.

This invention was made with government support under grant numbers NS047586 and AG013939 awarded by the National Institutes of Health. The government has certain rights in the invention.

JOINT RESEARCH AGREEMENT

The invention described herein resulted from activities within the scope of a written joint research agreement between Northwestern University and The Universite Louis Pasteur Strasbourg.

FIELD OF INVENTION

The invention relates to chemical compounds, compositions and methods of making and using the same. In particular, the invention provides selected pyridazine compounds, compositions comprising the compounds, and methods of using the compounds and compositions for modulation of cellular pathways, for treatment or prevention of inflammatory diseases, for treatment or prevention of neurological conditions, for research, drug screening, and therapeutic applications.

BACKGROUND OF INVENTION

The treatment of neurological conditions and disorders is of great importance in medicine and there is a need for new drugs and treatments to prevent progression and reverse the impairments of these conditions and disorders. Neuroinflammation is recognized as a prominent feature in the pathology of many neurological conditions and diseases. Neuroinflammation is a process that results primarily from abnormally high or chronic activation of glia (microglia and astrocytes). This overactive state of glia results in increased levels of inflammatory and oxidative stress molecules, which can lead to neuron damage or death. Neuronal damage or death can also induce glial activation, facilitating the propagation of a localized, detrimental cycle of neuroinflammation (Griffin, W S T et al, Brain Pathol 8: 65-72, 1998). The inflammation cycle has been proposed as a potential therapeutic target in the development of new approaches to treat inflammatory disease. However, most anti-inflammatory therapeutics developed to date are palliative and provide minimal, short-lived, symptomatic relief with limited effects on inflammatory disease progression. Thus, there is a need for anti-inflammatory therapeutics that impact disease progression or prevention.

SUMMARY OF INVENTION

The present invention provides certain pyridazine compounds, compositions comprising the compounds, and methods of using the compounds and compositions for modulation of cellular pathways (e.g., signal transduction pathways), for treatment or prevention of inflammatory diseases, for treatment or prevention of neurological diseases and conditions, for research, drug screening, and therapeutic applications. In particular, the invention generally provides dosage forms, formulations and methods that provide lower risk of side effects and/or produce beneficial pharmacokinetic profiles, in particular in neuroinflammatory diseases.

The invention contemplates a composition, in particular a formulation or dosage form, effective to provide lower risk of side effects and/or a beneficial pharmacokinetic profile following treatment comprising a compound of the formula I:

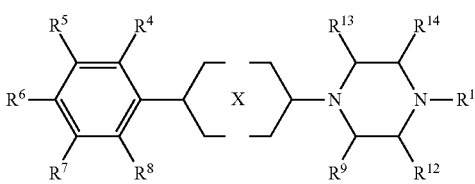

wherein $R^1$, $R^4$, $R^5$, $R^6$, $R^7$, $R^8$, $R^9$, $R^{12}$, $R^{13}$, and $R^{14}$ are independently hydrogen, hydroxyl, alkyl, alkenyl, alkynyl, alkylene, alkenylene, alkoxy, alkenyloxy, cycloalkyl, cycloalkenyl, cycloalkynyl, cycloalkoxy, aryl, aryloxy, arylalkoxy, aroyl, heteroaryl, heterocyclic, acyl, acyloxy, amino, imino, azido, thiol, thioalkyl, thioalkoxy, thioaryl, nitro, cyano, halo, sulfate, sulfenyl, sulfonyl, sulfonyl, sulfonate, sulfoxide, silyl, silyloxy, silylalkyl, silylthio, =O, =S, phosphonate, ureido, carboxyl, carbonyl, carbamoyl, or carboxamide; and X is optionally substituted pyrimidinyl or pyridazinyl; an isomer, a pharmaceutically acceptable salt, or derivative thereof.

In aspects of the invention, a compound of the formula I is provided wherein $R^1$, $R^4$, $R^5$, $R^6$, $R^7$, $R^8$, $R^9$, $R^{12}$, $R^{13}$, and $R^{14}$ are independently hydrogen, hydroxyl, alkyl, alkenyl, alkynyl, alkylene, alkenylene, alkoxy, alkenyloxy, cycloalkyl, cycloalkenyl, aryl, aryloxy, arylalkoxy, aroyl, heteroaryl, heterocyclic, acyl, acyloxy, amino, imino, azido, thiol, thioalkyl, thioalkoxy, thioaryl, nitro, cyano, halo, silyl, silyloxy, silylalkyl, silylthio, =O, =S, phosphonate, carboxyl, carbonyl, carbamoyl, ear carboxamide; and X is pyrimidinyl car pyridazinyl, an isomer, a pharmaceutically acceptable salt, or derivative thereof.

In an aspect, a composition, formulation or dosage form is provided which is effective to provide lower risk of side effects and/or a beneficial pharmacokinetic profile following treatment comprising a compound of the formula II:

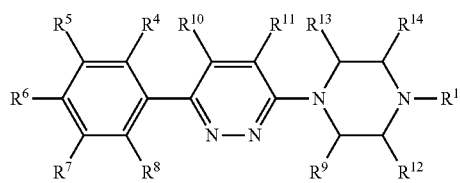

wherein $R^1$, $R^4$, $R^5$, $R^6$, $R^7$, $R^8$, $R^9$, $R^{10}$, $R^{11}$, $R^{12}$, $R^{13}$, and $R^{14}$ are independently hydrogen, hydroxyl, alkyl, alkenyl, alkynyl, alkylene, alkenylene, alkoxy, alkenyloxy, cycloalkyl, cycloalkenyl, cycloalkynyl, cycloalkoxy, aryl, aryloxy, arylalkoxy, aroyl, heteroaryl, heterocyclic, acyl, acyloxy, amino, imino, azido, thiol, thioalkyl, thioalkoxy, thioaryl, nitro, cyano, halo, sulfonyl, sulfonyl, sulfonyl, sulfonate, sulfate, sulfoxide, silyl, silyloxy, silylalkyl, silylthio, =O, =S, phosphonate, ureido, carboxyl, carbonyl, carbamoyl, or carboxamide; or an isomer, a pharmaceutically acceptable salt, or derivative thereof.

In an aspect of the invention, a compound of the formula II is provided wherein $R^1$, $R^4$, $R^5$, $R^6$, $R^7$, $R^8$, $R^9$, $R^{10}$, $R^{11}$, $R^{12}$, $R^{13}$, and $R^{14}$ are independently hydrogen, hydroxyl, alkyl, alkenyl, alkynyl, alkylene, alkenylene, alkoxy, alkenyloxy, cycloalkyl, cycloalkenyl, aryl, aryloxy, arylalkoxy, aroyl, heteroaryl, heterocyclic, acyl, acyloxy, amino, imino, azido, thiol, thioalkyl, thioalkoxy, thioaryl, nitro, cyano, halo, silyl, silyloxy, silylalkyl, silylthio, =O, =S, carboxyl, carbonyl, carbamoyl, or carboxamide; or an isomer, a pharmaceutically acceptable salt, or derivative thereof.

In aspects of the invention, $R^1$ in a compound of the formula I or II is substituted or unsubstituted alkyl, cyclohexyl, aryl, arylalkoxy, aroyl, or heteroaryl.

In a particular aspect, $R^1$ in a compound of the formula I or II is substituted or unsubstituted aryl, arylalkoxy, aroyl, or heteroaryl.

In certain aspects of the invention $R^1$ in a compound of the formula I or II is:

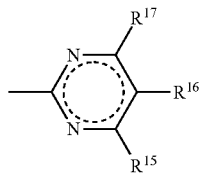

wherein $R^{15}$, $R^{16}$ and $R^{17}$ are independently hydrogen, hydroxyl, alkyl, alkenyl, alkynyl, alkylene, alkenylene, alkoxy, alkenyloxy, cycloalkyl, cycloalkenyl, cycloalkynyl, cycloalkoxy, aryl, aryloxy, arylalkoxy, aroyl, heteroaryl, heterocyclic, acyl, acyloxy, amino, imino, azido; thiol, thioalkyl, thioalkoxy, thioaryl, nitro, cyano, halo, sulfoxide, sulfate, sulfonyl, sulfenyl, sulfonyl, sulfonate, silyl, silyloxy, silylalkyl, silylthio, =O, phosphonate, ureido, carboxyl, carbonyl, carbamoyl, or carboxamide.

Therefore, certain aspects of the invention contemplate a composition, in particular a formulation or dosage form, effective to provide lower risk of side effects and/or a beneficial pharmacokinetic profile following treatment comprising an amount of a compound of the formula III:

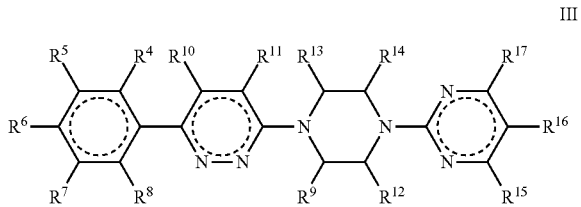

wherein $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, and $R^{17}$ are independently hydrogen, hydroxyl, alkyl, alkenyl, alkynyl, alkylene, alkenylene, alkoxy, alkenyloxy, cycloalkyl, cycloalkenyl, cycloalkynyl, cycloalkoxy, aryloxy, arylalkoxy, aroyl, heteroaryl, heterocyclic, acyl, acyloxy, amino, imino, azido, thiol, thioalkyl, thioalkoxy, thioaryl, nitro, cyano, halo, sulfoxide, sulfate, sulfonyl, sulfenyl, sulfinyl, sulfonate, silyl, silyloxy, silylalkyl, silylthio, =O, =S, ureido, phosphonate, carboxyl, carbonyl, carbamoyl, or carboxamide.

In general, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, and $R^{17}$ in a compound of the formula III cannot all be hydrogen.

The invention relates to compounds of the formula I or III disclosed herein, in particular pure or substantially pure compounds of the formula I, II or III.

The invention also contemplates utilizing in compositions and methods of the invention a compound in FIG. 1, in particular MW01-4-179LKM, MW01-7-084WH, MW01-7-085WH, MW01-7-133WH, MW01-2-151SRM, MW01-5-188WH or MW01-7-057, or isomers, pharmaceutically acceptable salts or derivatives thereof.

A composition of the invention, in particular a formulation or dosage form, may be further characterized by its ability to selectively reduce or block up-regulation of IL-1β and S100B, and/or reduce or prevent loss of PSD-95 and/or synaptophysin.

In aspects, a composition of the invention, in particular a formulation or dosage form, may provide a lower risk of QT-related side effects.

In particular aspects, the invention further provides a composition, in particular a formulation or dosage form, comprising a compound of the formula I, II or III in a therapeutically effective amount to treat a disease disclosed herein while reducing inhibitory activity at hERG potassium channel.

In another particular aspect; the invention provides a composition, in particular a formulation or dosage form, comprising a compound of the formula I, II or III in a therapeutically effective amount to treat a disease disclosed herein while reducing hERG inhibition.

In another particular aspect the invention provides a composition, in particular a formulation or dosage form, comprising a compound of the formula I, II or III in a therapeutically effective amount to treat a disease disclosed herein in a subject receiving a therapeutic or treatment that prolongs QT interval.

The invention contemplates a formulation for the treatment of a disease disclosed herein comprising a therapeutically effective amount of a compound of the formula I, II or III to provide a beneficial pharmacokinetic profile, in particular a sustained pharmacokinetic profile, in a pharmaceutically acceptable carrier, excipient, or vehicle. In an aspect, a formulation comprising a compound of the formula I, II or III is provided which is in a form or which has been adapted for administration to a subject to provide a beneficial pharmacokinetic profile to treat a disease disclosed herein. In an embodiment, a dosage form is provided such that administration of the dosage form to a subject suffering from a disease disclosed herein provides a beneficial pharmacokinetic profile resulting in therapeutic effects including selectively reducing or blocking up-regulation of IL-1β and S100B, and/or reducing or preventing loss of PSD-95 and/or synaptophysin over a dosing period. In particular, the composition is in a form adapted to provide a beneficial pharmacokinetic profile that results in one or more of the following in a subject for a sustained time over a dosing period: selective reduction of up-regulation of IL-1β and S100B, and/or reduction of loss of PSD-95 and/or synaptophysin.

In another aspect, the invention relates to a dosage form comprising amounts of a compound of the formula I, II or III suitable for administration to a subject to provide effective concentrations of the compound in an environment of use or an effective dose that results in therapeutic effects in the prevention, treatment, or control of symptoms of a disease disclosed herein, in particular a neuroinflammatory disease. In aspects of the invention, the environment of is the brain or plasma.

In a further aspect, the invention is directed to a formulation or dosage form suitable for once, twice- or three-times a day administration to treat a disease disclosed herein comprising one or more compound of the formula I, II or III in an amount effective to provide lower risk of side effects and/or a beneficial pharmacokinetic profile in a dosing period.

In a still further aspect, the invention contemplates a dosage form comprising one or more compound of the formula I, II or III in an amount effective to maintain the compound within an effective plasma and/or brain drug concentration that results in therapeutic effects in the subject.

The invention additionally relates to a method of preparing a stable formulation or dosage form of a compound of the formula I, II or III adapted to provide lower risks of side effects anchor beneficial pharmacokinetic profiles following treatment. Formulations may be placed in an appropriate container and labelled for treatment of an indicated disease. For administration of a formulation of the invention, such labelling would include amount, frequency, and method of administration.

The invention also provides methods to make commercially available formulations which contain a compound of the formula I, II or III that provides lower risk of side effects and/or a beneficial pharmacokinetic profile in the treatment of a disease disclosed herein.

The invention relates to the use of at least one compound of the formula I, II or III for the preparation of a medicament for providing lower risks of side effects and/or a beneficial pharmacokinetic profile in treating a disease disclosed herein. The invention additionally relates to uses of a pharmaceutical composition of the invention in the preparation of medicaments for providing lower risks of side effects and/or a beneficial pharmacokinetic profile in the prevention and/or treatment of a disease disclosed herein.

Commercially available formulations or medicaments may be pills, tablets, caplets, soft and hard gelatin capsules, lozenges, sachets, cachets, vegicaps, liquid drops, elixirs, suspensions, emulsions, solutions, syrups, aerosols (as a solid or in a liquid medium) suppositories, sterile injectable solutions, and/or sterile packaged powders, which contain, a compound of the formula I, II or III.

Compounds of the formula I, II or III and compositions of the invention may be administered therapeutically or prophylactically to treat a disease disclosed herein, in particular neuroinflammatory disease. Therefore the invention provides a method for treating a disease disclosed herein, in particular a neuroinflammatory disease, comprising administering a therapeutically effective amount or prophylactically effective amount of a compound of the formula I, II or III. In an aspect, the invention provides a method for treating a disease disclosed herein in particular a neuroinflammatory disease comprising administering a compound of the formula I, II or III in an amount effective to lower risks of side effects and/or provide a beneficial pharmacokinetic profile. In an aspect, a method is provided for treating a disease disclosed herein, in particular a neuroinflammatory disease, comprising administering a compound of the formula I, II or III in an amount effective to selectively inhibit up-regulation of IL-1β and S100B, reduce or prevent loss of PSD-95 and/or synaptophysin, and/or prevent behavioral deficit.

Aspects of the invention provide methods for treating a disease disclosed herein, in particular a neuroinflammatory disease, comprising administering to a subject a compound of the formula I, II or III in an amount effective to lower risk of QT-related side effects in the subject. Certain aspects of the invention provide methods for treating a disease disclosed herein, in particular a neuroinflammatory disease, comprising administering to a subject a therapeutically effective amount of a compound of the formula I, II or III to treat the disease while reducing inhibitory activity at hERG potassium channel. Other aspects of the invention provide methods for treating a disease disclosed herein, in particular a neuroinflammatory disease, comprising administering to a subject a therapeutically effective amount of a compound of the formula I, II or III to treat the disease while reducing hERG inhibition. Further aspects of the invention provide methods for treating a disease disclosed herein in a subject suffering from a disease disclosed herein and receiving a therapeutic or treatment that prolongs QT interval comprising administering to the subject a therapeutically effective amount of a compound of the formula I to reduce the QT-related side effects.

The invention also provides a method for treating and/or preventing a disease disclosed herein in a subject comprising administering to the subject one or more, in particular two, three or four dosages of a formulation comprising one or more compound of the formula I, II or III in an amount effective to maintain the compound within the effective brain and/or plasma drug concentration that results in therapeutic effects in the subject.

In particular aspects of the invention, a method is provided for treating in a subject a disease involving or characterized by inflammation, in particular neuroinflammation, comprising administering to the subject a compound of the formula I, II or III in a therapeutically effective amount that provides beneficial pharmacokinetic profiles, in a pharmaceutically acceptable carrier, excipient, or vehicle.

In a further aspect, the invention provides a method involving administering to a subject a therapeutic compound of the formula I, II or III or a pharmaceutically acceptable salt thereof, or a composition comprising a compound of the formula I, II or III and a pharmaceutically acceptable carrier, excipient, or vehicle which inhibit or reduce neuroflammation, activation of glia, activation of asdocytes, activation of microglia, proinflammatory cytokines, oxidative stress-related enzymes, acute phase proteins and/or components of the complement cascade, and provide lower risk of QT-related side effects and/or a beneficial pharmacokinetic profile.

The invention also provides a kit comprising one or more compound of the formula I, II or III, or a composition of the invention adapted to provide lower risk of side effects and/or a beneficial pharmacokinetic profile. In an aspect, the invention provides a kit for preventing and/or treating a disorder and/or disease disclosed herein, comprising a formulation or dosage form of the invention, a container, and instructions for use.

These and other aspects, features, and advantages of the present invention should be apparent to those skilled in the art from the following drawings and detailed description.

DESCRIPTION OF THE FIGURES

FIG. 1 shows the structures of MW01-2-151SRM, MW01-6-189WH, MW01-7-107WH, MW01-4-179LKM, MW01-7-084WH, MW01-7-085WH, MW01-7-133WH, and MW01-7-057.

FIG. 26 A-E shows graphs illustrating in vivo activity of MW1-2-084SRM in the Aβ infusion mouse model. Graphs are of MW01-2-084SRM suppression of Aβ-induced neuroinflammation and synaptic damage and activity in the Y-maze. Hippocampal sections or extracts from vehicle-infused mice (control), Aβ-infused mice injected with solvent, and Aβ-infused mice injected with MW01-2-084SRM were evaluated for neuroinflammation by measurement of the levels of the pro-inflammatory cytokines HAP (A), and S100B (B), the presynaptic marker, synaptophysin (C), and evaluated for synaptic damage by analysis of the levels of the post-synaptic density protein 95 (PSD-95) (D), and Y-maze (E). Data are from five samples per group analyzed.

DETAILED DESCRIPTION OF EMBODIMENTS

Figure 2:
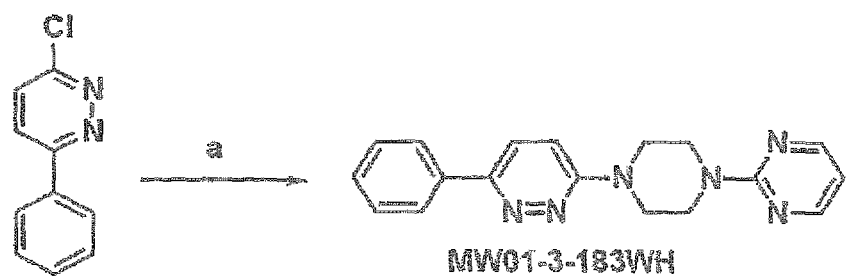
FIG. 2 depicts a synthetic scheme for MW01-3-183WH.

For convenience, certain terms employed in the specification, examples, and appended claims are collected here.

Numerical ranges recited herein by endpoints include all numbers and fractions subsumed within that range (e.g. 1 to 5 includes 1, 1, 5, 2, 2.75, 3, 3.90, 4, and 5). It is also to be understood that all numbers and fractions thereof are presumed to be modified by the term "about." The term "about" means plus or minus 0.1 to 50%, 5-50%, or 10-40%, preferably 10-20%, more preferably 10% or 15%, of the number to which reference is being made. Further, it is to be understood that "a", "an," and "the" include plural referents unless the content clearly dictates otherwise. Thus, for example, reference to a composition comprising "a compound" includes a mixture of two or more compounds.

As used herein the terms "administering" and "administration" refer to a process by which a therapeutically effective amount of a compound of the formula I, II or III or composition contemplated herein is delivered to a subject for prevention and/or treatment purposes. Compositions are administered in accordance with good medical practices taking into account the subject's clinical condition, the site and method of administration, dosage, patient age, sex, body weight, and other factors known to physicians.

As used herein, the term "co-administration" of "co-administered" refers to the administration of at least two compounds or agent(s) or therapies to a subject. In some embodiments, the co-administration of two or more agents/therapies is concurrent. In other embodiments, a first agent/therapy is administered prior to a second agent/therapy in this aspect, each component may be administered separately, but sufficiently close in time to provide the desired effect, in particular a beneficial, additive, or synergistic effect. Those of skill in the art understand that the formulations and/or routes of administration of the various agents/therapies used may vary. The appropriate dosage for co-administration can be readily determined by one skilled in the art. In some embodiments, when agents/therapies are co-administered, the respective agents/therapies are administered at lower dosages than appropriate for their administration alone. Thus, co-administration is especially desirable in embodiments where the co-administration of the agents/therapies lowers the requisite dosage of a known potentially harmful (e.g., toxic) agent(s).

The term "treating" refers to reversing, alleviating, or inhibiting the progress of a disease, or one or more symptoms of such disease, to which such term applies. Depending on the condition of the subject, the term also refers to preventing a disease, and includes preventing the onset of a disease, or preventing the symptoms associated with a disease. A treatment may be either performed in an acute or chronic way. The term also refers to reducing the severity of a disease or symptoms associated with such disease prior to affliction with the disease. Such prevention or reduction of the severity of a disease prior to affliction refers to administration of a compound or composition of the present invention to a subject that is not at the time of administration afflicted with the disease. "Preventing" also refers to preventing the recurrence of a disease or of one or more symptoms associated with such disease. "Treatment" and "therapeutically," refer to the act of treating, as "treating" is defined above. The purpose of prevention and intervention is to combat the disease, condition, or disorder and includes the administration of an active compound to prevent or delay the onset of the symptoms or complications, or alleviating the symptoms or complications, or eliminating the disease, condition, or disorder.

The terms "subject", "individual", or "patient" are used interchangeably herein and refer to an animal preferably a warm-blooded animal such as a mammal. Mammal includes without limitation any members of the Mammalia. A mammal, as a subject or patient in the present disclosure, can be from the family of Primates, Carnivora, Proboscidea, Perissodactyla, Artiodactyla, Rodentia, and Lagomorpha. Among other specific embodiments a mammal of the present invention can be *Canis familiaris* (dog), *Fells catus* (cat), *Elephas maximus* (elephant), *Equus caballus* (horse), *Sus domesticus* (pig), *Camelus drornedarious* (camel), *Cervus axis* (deer), *Giraffe camelopardalis* (giraffe), *Bos taurus* (cattle/cows), *Capra hircus* (goat), *Ovis aries* (sheep), *Mus museums* (mouse), *Lepus brachyurus* (rabbit), *Mesocricetus auratus* (hamster), *Cavia porcellus* (guinea pig), *Meriones unguiculatus* (gerbil), or *Homo sapiens* (human). In a particular embodiment, the mammal is a human. In other embodiments, animals can be treated; the animals can be vertebrates, including both birds and mammals. In aspects of the invention, the terms include domestic animals bred for food or as pets, including equines, bovines, sheep, poultry, fish, porcines, canines, felines, and zoo animals, goats, apes (e.g. gorilla or chimpanzee), and rodents such as rats and mice.

Typical subjects for treatment include persons afflicted with or suspected of having or being pre-disposed to a disease disclosed herein, or persons susceptible to, suffering from or that have suffered a disease disclosed herein. A subject may or may not have a genetic predisposition for a disease disclosed herein. In the context of certain aspects of the invention, the term "subject" generally refers to an individual who will receive or who has received treatment (e.g., administration of a compound of the formula I, II or III, and optionally one or more other agents) for a condition characterized by inflammation, the dysregulation of protein kinase activity, and/or dysregulation of apototic processes. In certain aspects, a subject may be a healthy subject.

In particular aspects, a subject shows signs of cognitive deficits and Alzheimer's disease neuropathology. In embodiments of the invention the subjects are suspectible to; or suffer from Alzheimer's disease.

As utilized herein, the term "healthy subject" means a subject, in particular a mammal, having no diagnosed disease, disorder, infirmity, or ailment, more particularly a disease, disorder, infirmity or ailment known to impair or otherwise diminish memory.

The term "diagnosed," as used herein, refers to the recognition of a disease by its signs and symptoms (e.g., resistance to conventional therapies), or genetic analysis, pathological analysis, histological analysis, and the like.

As used herein, the term "modulate" refers to the activity of a compound (e.g., a compound of the formula I, II or III) to affect (e.g., to promote or retard) an aspect of cellular function, including, but not limited to, cell growth, proliferation, apoptosis, and the like.

"Therapeutically effective amount" relates to the amount or dose of an active compound of the formula I, II or III or composition comprising the same, that will lead to one or more desired effects, in particular, one or more therapeutic effects or beneficial pharmacokinetic profiles. A therapeutically effective amount of a substance can vary according to factors such as the disease state, age, sex, and weight of the subject, and the ability of the substance to elicit a desired response in the subject. A dosage regimen may be adjusted to provide the optimum therapeutic response or pharmacokinetic profile. For example, several divided doses may be administered daily or the dose may be proportionally reduced as indicated by the exigencies of the therapeutic situation.

The term "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

The term "beneficial pharmacokinetic profile" refers to amounts or doses of a compound of the formula I, II or III that provide levels of the compound in plasma and/or brain or a required dose resulting in therapeutic effects in the prevention, treatment, or control of symptoms of a disease disclosed herein, in particular a neuroinflammatory disease, more particularly Alzheimer's disease. The term "sustained pharmacokinetic profile" as used herein refers to a length of time efficacious levels of a biologically active compound of the formula I, II or III is in its environment of use. A sustained pharmacokinetic profile can be such that a single or twice daily administration adequately prevents, treats, or controls symptoms of a disease disclosed herein. A beneficial pharmacokinetic profile may provide therapeutically effective amounts of the compound of the formula I, II or III in the plasma and/or brain for about 12 to about 48 hours, 12 hours to about 36 hours, or 12 hours to about 24 hours.

A "therapeutic effect" refers to an effect of a composition, in particular a formulation or dosage form, or method disclosed herein, including improved biological activity, efficacy, and/or lower risk of side effects (e.g., lower risk of QT-related side effects). A therapeutic effect may be a sustained therapeutic effect that correlates with a continuous plasma and/or brain concentration of a compound of the formula I, II or III over a dosing period, in particular a sustained dosing period. A therapeutic effect may be a statistically significant effect in terms of statistical analysis of an effect of a compound of the formula I, II or III versus the effects without the compound.

"Statistically significant" or "significantly different" effects or levels may represent levels that are higher or lower than a standard. In aspects of the invention, the difference may be 1.5, 2, 3, 4, 5, 6, 7, 8, 9, 10, 15, 20, 25 or 50 times higher or lower compared with the effect obtained without a compound of the formula I, II or III.

In an embodiment, where the disease is neuroinflammatory disease such as Alzheimer's disease, therapeutic effects of a compound or composition or treatment of the invention can manifest as one, two, three, four, five, six, seven, eight, or all of the following, in particular five or more, more particularly seven or more of the following:

a) A reduction in protein kinase activity (e.g. DAPK), in particular at least about a 0.05%, 0.1%, 0.5%, 1%, 2%, 5%, 10%, 15%, 20%, 30%, 33%, 35%, 40%, 45%, 50%, 60%, 70%, 80%, 90%, 95%, or 99% decrease in protein kinase activity.

b) A reduction in glial activation response, in particular, at least about a 0.05%, 0.1%, 0.5%, 1%, 2%, 5%, 10%, 15%, 20%, 30%, 33%, 35%, 40%, 45%, 50%, 60%, 70%, 80%, 90%, 95%, or 99% reduction in glial activation response.

c) A reduction in glial activity in the brain, relative to the levels determined in the absence of a compound of the formula I, II or III in subjects with symptoms of a neuroinflammatory disease. In particular, the compounds induce at least about a 2%, 5%, 10%, 15%, 20%, 30%, 40%, 50%, 60%, 70%, 80%, or 90% decrease in glial activity.

d) A reduction in astrocyte activation response, in particular, at least about a 0.05%, 0.1%, 0.5%, 1%, 2%, 5%, 10%, 15%, 20%, 30%, 33%, 35%, 40%, 45%; 50%, 60%, 70%, 80%, 90%, 95%, or 99% reduction in astrocyte activation response.

e) A reduction in astrocyte activity in the brain, relative to the levels determined in the absence of a compound or treatment according to the invention. In particular, the compounds induce at least about a 2%, 5%, 10%, 15%, 20%, 30%, 40%, 50%, 60%, 70%, 80%, or 90% decrease iii astrocyte activity.

f) A reduction in microglial activation, in particular, at least about a 0.05%, 0.1%, 0.5%, 1%, 2%, 5%, 10%, 15%, 20%, 30%, 33%, 35%, 40%, 45%, 50%, 60%, 70%, 80%, 90%, 95%, or 99% reduction in microglial activation.

g) A reduction in microglial activation response, in particular, at least about a 0.05%, 0.1%, 0.5%, 1%, 2%, 5%, 10%, 15%, 20%, 30%, 33%, 35%, 40%, 45%, 50%, 60%, 70%, 80%, 90%, 95%, or 99% reduction in microglial activation response.

h) A reduction in loss of synaptophysin and/or PSD-95, in particular at least about a 0.05%, 0.1%, 0.5%, 1%, 2%, 5%, 10%, 15%, 20%, 30%, 33%, 35%, 40%, 45%, 50%, 60%, 70%, 80%, 90%, 95%, or 99% reduction in loss of synaptophysin and/or PSD-95.

i) A reduction in oxidative stress-related responses (e.g., nitric oxide synthase production and/or nitric oxide accumulation), in particular at least about a 0.05%, 0.1%, 0.5%, 1%, 2%, 5%, 10%, 15%, 20%, 30%, 33%, 35%, 40%, 45%, 50%, 60%, 70%, 80%, 90%, 95%, or 99% reduction in oxidative stress-related responses such as nitric oxide synthase production and nitric oxide accumulation.

j) A reduction in cellular apoptosis and/or death associated protein kinase activity, in particular a 0.05%, 0.1%, 0.5%, 1%, 2%, 5%, 10%, 15%, 20%, 30%, 33%, 35%, 40%, 45%, 50%, 60%, 70%, 80%, 90%, 95%, or 99% reduction in cellular apoptosis and/or death associated protein kinase activity.

k) A reduction in proinflammatory cytokine responses in particular a 0.05%, 0.1%, 0.5%, 1%, 2%, 5%, 10%, 15%, 20%, 30%, 33%, 35%, 40%, 45%, 50%, 60%, 70%, 80%, 90%, 95%, or 99% reduction in proinflammatory cytokine responses.

l) A reduction in interleukin-1β and/or tumor necrosis factor α production in particular a 0.05%, 0.1%, 0.5%, 1%, 2%, 5%, 10%, 15%, 20%, 30%, 33%, 35%, 40%, 45%, 50%, 60%, 70%, 80%, 90%, 95%, or 99% reduction in interleukin-1β and/or tumor necrosis fulcra production.

m) A slowing of the rate of disease progression in a subject with a neuroinflammatory disease (e.g., Alzheimer's disease).

n) Increase in survival in a subject with symptoms of a neuroinflammatory disease (e.g., Alzheimer's disease).

In particular aspects of the invention therapeutic effects of compounds, compositions or treatments of the invention can manifest as (a) and (b); (a), (b) and (c); (a) through (d); (a) through (e); (a) through (f); (a) through (g); (a) through (h); (a) through (i), (a) through (j), and (a) through (k), (a) through (l), (a) through (m), or (a) through (n).

The term "pharmaceutically acceptable carrier, excipient, or vehicle" refers to a medium which does not interfere with the effectiveness or activity of an active ingredient and which is not toxic to the hosts to which it is administered. A carrier, excipient, or vehicle includes diluents, binders, adhesives, lubricants, disintegrates, bulking agents, wetting or emulsifying agents, pH buffering agents, and miscellaneous materials such as absorbents that may be needed in order to prepare a particular composition. Examples of carriers etc. include but are not limited to saline, buffered saline, dextrose, water, glycerol, ethanol, and combinations thereof. The use of such media and agents for an active substance is well known in the art.

The compounds of the formula I, II or III disclosed herein also include "pharmaceutically acceptable salt(s)". By pharmaceutically acceptable salts is meant those salts which are suitable for use in contact with the tissues of a subject or patient without undue toxicity, irritation, allergic response and the like, and are commensurate with a reasonable benefit/risk ratio. Pharmaceutically acceptable salts are described for example, in S. M, Berge, at al., J. Pharmaceutical Sciences, 1977, 66:1. Suitable salts include salts that may be formed where acidic protons in the compounds are capable of reacting with inorganic or organic bases. Suitable inorganic salts include those formed with alkali metals, e.g. sodium and potassium, magnesium, calcium, and aluminum. Suitable organic salts include those formed with organic bases such as the amine bases, e.g. ethanolamine, diethanolamine, triethanolamine, tromethamine, N-methylglucamine, and the like. Suitable salts also include acid addition salts formed with inorganic acids (e.g. hydrochloric and hydrobromic acids) and organic acids (e.g. acetic acid, citric acid, maleic acid, and the alkane- and arene-sulfonic acids such as methanesulfonic acid and benzenesulfonic acid). When there are two acidic groups present, a pharmaceutically acceptable salt may be a mono-acid-mono-salt or a di-salt; and similarly where there are more than two acidic groups present, some or all of such groups can be salified.

A compound of the formula I, II or III can contain one or more asymmetric centers and may give rise to enantiomers, diasteriomers, and other stereoisomeric forms which may be defined in terms of absolute stereochemistry as (R)- or (S)-.

Thus, compounds of the formula. I, II or III include all possible diasteriomers and enantiomers as well as their racemic and optically pure forms. Optically active (R)- and (S)-isomers may be prepared using chiral synthons or chiral reagents, or resolved using conventional techniques. When a compound of the formula I, II or III contains centers of geometric asymmetry, and unless specified otherwise, it is intended that the compounds include both E and A geometric isomers. All tautomeric forms are also included within the scope of a compound of the formula I, II or III.

A compound of the formula I, II or III includes crystalline forms which may exist as polymorphs. Solvates of the compounds formed with water or common organic solvents are also intended to be encompassed within the term. In addition, hydrate forms of the compounds and their salts are encompassed within this invention. Further prodrugs of compounds of the formula I, II or III are encompassed within the term.

The term "solvate" means a physical association of a compound with one or more solvent molecules or a complex of variable stoichiometry formed by a solute (for example, a compound of the invention) and a solvent, for example, water, ethanol, or acetic acid. This physical association may involve varying degrees of ionic and covalent bonding, including hydrogen bonding. In certain instances, the solvate will be capable of isolation, for example, when one or more solvent molecules are incorporated in the crystal lattice of the crystalline solid. In general, the solvents selected do not interfere with the biological, activity of the solute. Solvates encompass both solution-phase and isolatable solvates. Representative solvates include hydrates, ethanolates, methanolates, and the like. Dehydrate, co-crystals, anhydrous, or amorphous forms of the compounds of the invention are also included. The term "hydrate" means a solvate wherein the solvent molecule(s) is/are $H_2O$, including, mono-, di-, and various poly-hydrates thereof. Solvates can be formed using various methods known in the art.

Crystalline compounds of the formula I, II or III can be in the form of a free base, a salt, or a co-crystal. Free base compounds can be crystallized in the presence of an appropriate solvent in order to form a solvate. Acid salt compounds of the formula I, II or III (e.g. HCl, HBr, benzoic acid) can also be used in the preparation of solvates. For example, solvates can be formed by the use of acetic acid or ethyl acetate. The solvate molecules can form crystal structures via hydrogen bonding, van der Waals forces, or dispersion forces, or a combination of any two or all three forces.

The amount of solvent used to make solvates can be determined by routine testing. For example, a monohydrate of a compound of the formula I, II or III would have about 1 equivalent of solvent ($H_2O$) for each equivalent of a compound of the invention. However, more or less solvent may be used depending on the choice of solvate desired.

Compounds of the formula I, II or III may be amorphous or may have different crystalline polymorphs, possibly existing in different salvation or hydration states. By varying the form of a drug, it is possible to vary the physical properties thereof. For example, crystalline polymorphs typically have different solubilities from one another, such that a more thermodynamically stable polymorph is less soluble than a less thermodynamically stable polymorph. Pharmaceutical polymorphs can also differ in properties such as shelf-life, bioavailability, morphology, vapor pressure, density, color, and compressibility.

The term "prodrug" means a covalently-bonded derivative or carrier of the parent compound or active drug substance which undergoes at least some biotransformation prior to exhibiting its pharmacological effect(s). In general, such prodrugs have metabolically cleavable groups and are rapidly transformed in vivo to yield the parent compound, for example, by hydrolysis in blood, and generally include esters and amide analogs of the parent compounds. The prodrug is formulated with the objectives of improved chemical stability, improved patient acceptance and compliance, improved bioavailability, prolonged duration of action, improved organ selectivity, improved formulation (e.g., increased hydrosolubility), and/or decreased side effects (e.g., toxicity). In general, prodrugs themselves have weak or no biological activity and are stable under ordinary conditions. Prodrugs can be readily prepared from the parent compounds using methods known in the art, such as those described in A Textbook of Drug Design and Development, Krogsgaard-Larsen and H. Bundgaard (eds.), Gordon & Breach, 1991, particularly Chapter 5: "Design and Applications of Prodrugs"; Design of Prodrugs, Bundgaard (ed.), Elsevier, 1985; Prodrugs: Topical and Ocular Drug Delivery, K. B. Sloan (ed.), Marcel Dekker, 1998; Methods in Enzymology, K. Widder et al. (eds.), Vol. 42, Academic Press, 1985, particularly pp. 309 396; Burger's Medicinal Chemistry and Drug Discovery, 5th Ed., M. Wolff (ed.), John Wiley & Sons, 1995, particularly Vol. 1 and pp. 172 178 and pp. 949 982; Pro-Drugs as Novel Delivery Systems, T. Higuchi and V. Stella (eds.), Am. Chem. Soc., 1975; and Bioreversible Carriers in Drug Design, E. B. Roche (ed.), Elsevier, 1987.

Examples of prodrugs include, but are not limited to esters (e.g., acetate, formate, and benzoate derivatives), carbamates (e.g. N,N-dimethylaminocarbonyl) of hydroxy functional groups on compounds of the formula I, II or III, and the like A compound of the formula I, II or III can include a pharmaceutically acceptable co-crystal or a co-crystal salt. A pharmaceutically acceptable co-crystal includes a co-crystal that is suitable for use in contact with the tissues of a subject or patient without undue toxicity, irritation, allergic response and has the desired pharmacokinetic properties.

The term "co-crystal" as used herein means a crystalline material comprised of two or more unique solids at room temperature, each containing distinctive physical characteristics, such as structure, melting point, and heats of fusion. Co-crystals can be formed by an active pharmaceutical ingredient (API) and a co-crystal former either by hydrogen bonding or other non-covalent interactions, such as pi stacking and van der Waals interactions. An aspect of the invention provides for a co-crystal wherein the co-crystal former is a second API. In another aspect, the co-crystal former is not an API. In another aspect, the co-crystal comprises more than one co-crystal former. For example, two, three, four, five, or more co-crystal formers can be incorporated in a co-crystal with an API. Pharmaceutically acceptable co-crystals, are described, for example, in "Pharmaceutical co-crystals," Journal of Pharmaceutical Sciences, Volume 95 (3) Pages 499-516, 2006. The methods producing co-crystals are discussed in the United States Patent Application 20070026078.

A co-crystal former which is generally a pharmaceutically acceptable compound, may be, for example, benzoquinone, terephthalaldehyde, saccharin, nicotinanaide, acetic acid, formic acid, butyric acid, trimesic acid, 5-nittoisophthalic acid, adamantane-1,3,5,7-tetracarboxylic acid, formamide, succinic acid, fumaric acid, tartaric acid, oxalic acid, tartaric acid, malonic acid, benzamide, mandelic acid, glycolic acid, fumaric acid, maleic acid, urea, nicotinic acid, piperazine, p-phthalaldehyde, 2,6-pyridinecarboxylic acid, 5-nitroisophthalic acid, citric acid, and the alkane- and arene-sulfonic acids such as methanesulfonic acid and benzenesulfonic acid.

In general, all physical forms of compounds of the formula I, II or III are intended to be within the scope of the present invention.

A compound of the formula I, II or III may be pure or substantially pure. As used herein, the term "pure" in general means better than 90%, 92%, 93%, 94%, 95%, 96%, 97%, 98% or 99% pure, and "substantially pure" means a compound synthesized such that the compound, as made or as available for consideration into a composition or therapeutic dosage described herein, has only those impurities that can not readily nor reasonably be removed by conventional purification processes.

"Optional" or "optionally" means that the subsequently described event or circumstance may but need not occur, and that the description includes instances where the event or circumstance occurs and instances in which it does not occur. For example, "alkyl group optionally substituted with a halo group" means that the halo may but need not be present, and the description includes situations where the alkyl group is substituted with a halo group and situations where the alkyl group is not substituted with the halo group.

A compound of the formula I, II or III includes derivatives. As used herein the term "derivative" of a compound of the formula I, II or III refers to a chemically modified compound wherein the chemical modification takes place either at a functional group or ring of the compound. Non-limiting examples of derivatives of compounds of the formula I, II or III may include N-acetyl, N-methyl, N-hydroxy groups at any of the available nitrogens in the compound. Derivative groups that may be used to modify the compounds of the formula I, II or III can be found in U.S. Patent Application No. 20030176437 (herein incorporated by reference in its entirety for all purposes).

In aspects of the invention, a compound of the formula I, II or III is a pharmaceutically functional derivative. A "pharmaceutically functional derivative" includes any pharmaceutically acceptable derivative of a compound of the formula I, II, or III, for example, an ester or an amide, which upon administration to a subject is capable of providing (directly or indirectly) a compound of the formula I, II or III or an active metabolite or residue thereof. Such derivatives are recognizable to those skilled in the art, without undue experimentation (see for example Burger's Medicinal Chemistry and Drug Discovery, 5.sup.th Edition, Vol 1: Principles and Practice, which has illustrative pharmaceutically functional derivatives).

A compound of the formula I, II or III may include a carrier. Suitable carriers include a polymer, carbohydrate, or a peptide.

A "polymer" refers to molecules comprising two or more monomer subunits that may be identical repeating subunits or different repeating subunits. A monomer generally comprises a simple structure, low-molecular weight molecule containing carbon. Polymers may optionally be substituted. Polymers that can be used in the present invention include without limitation vinyl, acryl, styrene, carbohydrate derived polymers, polyethylene glycol (PEG), polyoxyethylene, polymethylene glycol, poly-trimethylene glycols, polyvinylpyrrolidone, polyoxyethylene, polyoxypropylene block polymers, and copolymers, salts, and derivatives thereof. In aspects of the invention, the polymer is poly(2-acrylamido-2-methyl-1-propanesulfonic acid); poly(2-acrylamido-2-methyl,-1-propanesulfonic acid-coacrylonitrile, poly(2-acrylamido-2-methyl,-1-propanesulfonic acid-co-styrene), poly(vinylsulfonic acid); poly(sodium 4-styrenesulfonic acid); and sulfates and sulfonates derived therefrom; poly(acrylic acid), poly(methylacrylate), poly(methyl methacrylate), and polyvinyl alcohol).

A "carbohydrate" as used herein refers to a polyhydroxyaldehyde, polyhydroxyketone and derivatives thereof. The term includes monosaccharides such as erythrose, arabinose, allose, altrose, glucose, mannose, threose, xylose, gulose, idose, galactose, talose, aldohexose, fructose, ketohexose, ribose, and aldopentose. The term also includes carbohydrates composed of monosaccharide units, including disaccharides, oligosaccharides, or polysaccharides. Examples of disaccharides are sucrose, lactose, and maltose. Oligosaccharides generally contain between 3 and 9 monosaccharide its and polysaccharides contain greater than 10 monosaccharide units. A carbohydrate group may be substituted at one two, three or four positions, other than the position of linkage to a compound of the formula I, II or III. For example, a carbohydrate may be substituted with one or more alkyl, amino, nitro, halo, thiol, carboxyl, or hydroxyl groups, which are optionally substituted. Illustrative substituted carbohydrates are glucosamine, or galactosamine. In aspects of the invention, the carbohydrate is a sugar, in particular a hexose or pentose and may be an aldose or a ketose. A sugar may be a member of the D or L series and can include amino sugars, deoxy sugars, and their uronic acid derivatives. In embodiments of the invention where the carbohydrate is a hexose, the hexose is glucose, galactose, or mannose, or substituted hexose sugar residues such as an amino sugar residue such as hexosamine, galactosamine; glucosamine, in particular D-glucosamine (2-amino-2-doexy-D-gluoose) or D-galactosamine (2-amino-2-deoxy-D-galactose). Illustrative pentose sugars include arabinose, fucose, and ribose.

A sugar residue may be linked to a compound of the formula I, II or III from a 1,1 linkage, 1,2 linkage, 1,3 linkage, 1,4 linkage, 1,5 linkage, or 1,6 linkage. A linkage may be via an oxygen atom of a compound of the formula I, II or III. An oxygen atom can be replaced one or more times by —CH2- or —S— groups.

The term "carbohydrate" also includes glycoproteins such as lectins (e.g. concanavalin A, wheat germ agglutinin, peanutagglutinin, seromucoid, and orosomucoid) and glycolipids such as cerebroside and ganglioside.

A "peptide" carrier for use in the practice of the present invention includes one, two, three, four, or five or more amino acids covalently linked through a peptide bond. A peptide can comprise one or more naturally occurring amino acids, and analogs, derivatives, and congeners thereof. A peptide can be modified to increase its stability, bioavailability, solubility, etc. "Peptide analogue" and "peptide derivative" as used herein include molecules which mimic the chemical structure of a peptide and retain the functional properties of the peptide. A carrier for use in the present invention can be an amino acid such as alanine, glycine, praline, methionine, serine, threonine, histidine, asparagine, alanyl-alanyl, prolyl-methionyl, or glycyl-glycyl. A carrier can be a polypeptide such as albumin, antitrypsin, macroglobulin, haptoglobin, cacruloplasm, transferring, $\alpha$- or $\beta$-lipoprotein, $\beta$- or $\gamma$-globulin or fibrinogen.

Approaches to designing peptide analogue's, derivatives and mimetics are known in the art. For example, see Farmer, P. S. in Drug Design (E. Ariens, ed.) Academic Press, New York, 1980, vol. 10, pp. 119-143; Ball J. B. and Alewood, P. F. (1990) J. Mol. Recognition 3:55; Morgan, B. A. and Gainor, J. A. (1989) Ann. Rep, Med. Chem. 24:243; and Freidinger, R. M. (1989) Trends Pharmacol. Sci. 10:270. See also Sawyer, T. K. (1995) "Peptidomimetic Design and Chemical Approaches to Peptide Metabolism" in Taylor, M.

D. and Amidon, G. L. (eds.) Peptide-Based Drug Design: Controlling Transport and Metabolism, Chapter 17; Smith, A. B. 3rd, et al, (1995) J. Am. Chem. Soc. 117:11113-11123; Smith, A. B. 3rd, et al. (1994) J. Am. Chem. Soc. 116:9947-9962; and Hirschman, K, et al. (1993) Am. Chem. Soc. 115: 12550-12568.

A peptide can be attached to a compound of the formula I, II or III through a functional group on the side chain of certain amino acids (e.g. serine) or other suitable functional groups. A carrier may comprise four or more amino acids with groups attached to three or more of the amino acids through functional groups on side chains. In an aspect, the carrier is one amino acid, in particular a sulfonate derivative of an amino acid, far example cysteic acid.

The term "alkyl", either alone or within other terms such as "thioalkyl" and "arylalkyl", means a monovalent, saturated hydrocarbon radical which may be a straight chain (i.e. linear) or a branched chain. An alkyl radical for use in the present invention generally comprises from about 1 to 20 carbon atoms, particularly from about 1 to 10, 1 to 8 or 1 to 7, more particularly about 1 to 6 carbon atoms, or 3 to 6. Illustrative alkyl radicals include methyl, ethyl, n-propyl, n-butyl, n-pentyl, n-hexyl, isopropyl, isobutyl, isopentyl, amyl, sec-butyl, tert-butyl, tert-pentyl, n-heptyl, n-actyl, n-nonyl, n-decyl, undecyl, n-dodecyl, n-tetradecyl, pentadecyl, n-hexadecyl, heptadecyl, n-octadecyl, nonadecyl, eicosyl, dosyl, n-tetracosyl, and the like, along with branched variations thereof. In certain aspects of the invention an alkyl radical is a $C_1$-$C_6$ lower alkyl comprising or selected from the group consisting of methyl, ethyl, n-propyl, n-butyl, n-pentyl, n-hexyl, isopropyl, isobutyl, isopentyl, amyl, tributyl, sec-butyl, tert-butyl, tert-pentyl, and n-hexyl. An alkyl radical may be optionally substituted with substituents as defined herein at positions that do not significantly interfere with the preparation of compounds of the formula I, II or III and do not significantly reduce the efficacy of the compounds. In certain aspects of the invention, an alkyl radical is substituted with one to five substituents including halo, lower alkoxy, lower aliphatic, a substituted lower aliphatic, hydroxy, cyano, nitro, thio, amino, keto, aldehyde, ester, amide, substituted amino, carboxyl, sulfonyl, sulfuryl, sulfenyl, sulfate, sulfoxide, substituted carboxyl, halogenated lower alkyl (e.g. $CF_3$), halogenated lower alkoxy, hydroxycarbonyl, lower alkoxycarbonyl, lower alkylcarbonyloxy, lower alkylcarbonylamino, cycloaliphatic, substituted cycloaliphatic, or aryl (e.g., phenylmethyl benzyl)), heteroaryl (e.g., pyridyl), and heterocyclic (e.g., piperidinyl, morpholinyl). Substituents on an alkyl group may themselves be substituted.

In aspects of the invention, "substituted alkyl" includes an alkyl group substituted by, for example, one to five substituents, and preferably 1 to 3 substituents, such as alkyl, alkoxy, oxo, alkanoyl, aryl, aralkyl, aryloxy, alkanoyloxy, cycloalkyl, acyl, amino, hydroxyamino, alkylamino, arylamino, alkoxyamino, aralkylamino, cyano, halogen, hydroxyl, carboxyl, carbamyl, carboxylalkyl, keto, thioketo, thiol, alkylthiol, arylthio, aralkylthio, sulfonamide, thioalkoxy; and nitro.

In respect to certain aspects of the invention, the term "substituted aliphatic" refers to an alkyl or an alkane possessing less than 10 carbons. The term "substituted aliphatic" refers to an alkyl or an alkane possessing less than 10 carbons where at least one of the aliphatic hydrogen atoms has been replaced by a halogen, an amino, a hydroxy, a nitro, a thio, a ketone, an aldehyde, an ester, an amide, a lower aliphatic, a substituted lower aliphatic, or a ring (aryl, substituted aryl, cycloaliphatic, or substituted cycloaliphatic, etc.). Examples of such groups include, but are not limited to, 1-chloroethyl and the like.

As used herein in respect to certain aspects of the invention, the term "lower-alkyl-substituted-amino" refers to any alkyl unit containing up to and including eight carbon atoms where one of the aliphatic hydrogen atoms is replaced by an amino group. Examples of such include, but are not limited to, ethylamino and the like.

As used herein in respect to certain aspects of the invention, the term "lower-alkyl-substituted-halogen" refers to any alkyl chain containing up to and including eight carbon atoms where one of the aliphatic hydrogen atoms is replaced by a halogen. Examples of such include, but are not limited to, chlorethyl and the like.

As used herein, the term "acetylamino" shall mean any primary or secondary amino that is acetylated. Examples of such include, but are not limited to, acetamide and the like.

As used herein the term "alkenyl" refers to an unsaturated, acyclic branched or straight-chain hydrocarbon radical comprising at least one double bond. An alkenyl radical may contain from about 2 to 24 or 2 to 10 carbon atoms, in particular from about 3 to 8 carbon atoms and more particularly about 3 to 6 or 2 to 6 carbon atoms. Suitable alkenyl radicals include without limitation ethenyl, propenyl (e.g., prop-1-en-1-yl, prop-1-en-2-yl, prop-2-en-1-yl (allyl), and prop-2-en-2-yl), buten-1-yl, but-1-en-2-yl, 2-methyl-prop-1-en-1-yl, but-2-en-1-yl, but-2-en-2-yl, buta-1,3-dien-1-yl, beta-1,3-dien-2-3/1, hexen-1-yl, 3-hydroxyhexen-yl, hepten-1-yl, and octen-1-yl, and the like. An alkenyl radical may be optionally substituted similar to alkyl.

In aspects of the invention, "substituted alkenyl" includes an alkenyl group substituted by, for example, one to three substituents, preferably one to two substituents, such as alkyl, alkoxy, haloalkoxy, alkylalkoxy, haloalkoxyalkyl, alkanoyl, alkanoyloxy, cycloalkyl, cycloalkoxy, acyl, acylamino, acyloxy, amino, alkylamino, alkanoylamino, aminoacyl, aminoacyloxy, cyano, halogen, hydroxyl, carboxyl, carboxylalkyl, carbamyl, keto, thioketo, thiol, alkylthio, sulfonyl, sulfonamido, thioalkoxy, aryl, nitro, and the like.

As used herein, the term "alkynyl" refers to an unsaturated, branched or straight-chain hydrocarbon radical comprising one or more triple bonds. An alkynyl radical may contain about 1 to 20, 1 to 15, or 2 to 10 carbon atoms, particularly about 3 to 8 carbon atoms and more particularly about 3 to 6 carbon atoms. Suitable alkynyl radicals include without limitation ethynyl, such as prop-1-yn-1-yl and prop-2-yn-1-yl, butyryls such as but-1-yn-1-yl, but-1-yn-3-yl, and but-3-yn-1-yl, pentynyls such as perityn-1-yl, pentyn-2-yl, 4-methoxypentyn-2-yl, and 3-methylbutyn-1-yl, hexynyls such as hexyn-1-yl, hexyn-2-yl, hexyn-3-yl, and 3,3-dimethylbutyn-1-yl radicals and the like. In aspects of the invention, alkenyl groups include ethenyl (—CH═$CH_2$), n-propenyl (—$CH_2$CH═$CH_2$), iso-propenyl (—C($CH_3$)═$CH_2$), and the like. An alkynyl may be optionally substituted similar to alkyl. The term "cycloalkynyl" refers to cyclic alkynyl groups.

In aspects of the invention, "substituted alkynyl" includes an alkynyl group substituted by, for example, a substituent, such as, alkyl, alkoxy, alkanoyl, alkanoyloxy, cycloalkyl, cycloalkoxy, acyl, acylamino, acyloxy, amino, alkylamino, alkanoylamino, aminoacyl, aminoacyloxy, cyano, halogen, hydroxyl, carboxyl, carboxylalkyl, carbamyl, keto, thioketo, thiol, alkylthio, sulfonyl, sulfonamido, thioalitoxy, aryl, nitro, and the like.

As used herein the term "alkylene" refers to a linear or branched radical having from about 1 to 10, 1 to 8, 1 to 6, or 2 to 6 carbon atoms and having attachment points for two or more covalent bonds. Examples of such radicals are methylene, ethylene, propylene, butylene, pentylene, hexylene, ethylidene, methylethylene, and isopropylidene. When an alkenylene radical is present as a substituent on another radical it is typically considered to be a single substituent rather than a radical formed by two substituents.

As used herein the term "alkenylene" refers to a linear or branched radical having from about 2 to 10, 2 to 8 or 2 to 6 carbon atoms, at least one double bond, and having attachment points for two or more covalent bonds. Examples of alkenylene radicals include 1,1-vinylidene (—$CH_2$=C—), 1,2-vinylidene (—CH=CH—), and 1,4-butadienyl (—CH=CH—CH=CH—).

As used herein the term "halo" refers to a halogen such as fluorine, chlorine, bromine or iodine atoms.

As used herein the term "hydroxyl" or "hydroxy" refers to an —OH group.

As used herein the term "cyano" refers to a carbon radical having three of four covalent bonds shared by a nitrogen atom, in particular —C≡N. A cyano group may be substituted with substituents described herein.

As used herein the term "alkoxy" refers to a linear or branched oxy-containing radical having an alkyl portion of one to about ten carbon atoms, such as a methoxy radical, which may be substituted. In aspects of the invention an alkoxy radical may comprise about 1-10, 1-8, 1-6 or 1-3 carbon atoms. In embodiments of the invention, an alkoxy radical comprises about 1-6 carbon atoms and includes a $C_1$-$C_6$ alkyl-O-radical wherein $C_1$-$C_6$ alkyl has the meaning set out herein. Examples a alkoxy radicals include without limitation methoxy, ethoxy, propoxy, butoxy, isopropoxy and tert-butoxy alkyls. An "alkoxy" radical may, optionally be substituted with one or more substitutents disclosed herein including alkyl atoms to provide "alkylalkoxy" radicals; halo atoms, such as fluoro, chloro or bromo, to provide "haloalkoxy" radicals (e.g. fluoromethoxy, chloromethoxy, trifluoromethoxy, difluoromethoxy, trifluoroethoxy, fluoroethoxy, tetrafluoroethoxy, pentafluoroethoxy, and fluoropropox) and "haloalkoxyalkyl" radicals (e.g. fluoromethoxymethyl, chloromethoxyethyl, trifluorornethoxymethyl, difluoromethoxyethyl, and trifluorocthoxymethyl).

As used herein the term "alkenyloxy" refers to linear or branched oxy-containing radicals having an alkenyl portion of about 2 to 10 carbon atoms, such as an ethenyloxy or propenyloxy radical. An alkenyloxy radical may be a "lower alkenyloxy" radical having about 2 to 6 carbon atoms. Examples of alkenyloxy radicals include without limitation ethenyloxy, propenyloxy, butenyloxy, and isopropenyloxy alkyls. An "alkenyloxy" radical may be substituted with one or more substitutents disclosed herein including halo atoms, such as fluoro, chloro or bromo, to provide "haloalkenyloxy" radicals (e.g. trifluoroethenyloxy, fluoroethenyloxy, difluoroethenyloxy, and fluoropropenyloxy).

A "carbocylic" includes radicals derived from a saturated or unsaturated, substituted or unsubstituted 5 to 14 member organic nucleus whose ring forming atoms (other than hydrogen) are solely carbon. Examples of carbocyclic radicals are cycloalkyl, cycloalkenyl, aryl, in particular phenyl, naphthyl, norbornanyl, bicycloheptadienyl, toluoyl, xylenyl, indenyl, stilbenzyl, terphenylyl, diphenylethylenyl, phenylcyclohexyl, acenapththylenyi, anthracenyl, biphenyl, bibenzylyl, and related bibenzylyl homologs, octahydronaphthyl, tetrahydronaphthyl, octahydroquinolinyl, dimethoxytetrahydronaphthyl and the like.

As used herein, the term "cycloalkyl" refers to radicals having from about 3 to 15, 3 to 10, 3 to 8, or 3 to 6 carbon atoms and containing one, two, three, or four rings wherein such rings may be attached in a pendant manner or may be fused. In aspects of the invention, "cycloalkyl" refers to an optionally substituted, saturated hydrocarbon ring system containing 1 to 2 rings and 3 to 7 carbons per ring which may be further fused with an unsaturated $C_3$-$C_7$ carbocylic ring. Examples of cycloalkyl groups include single ring structures such as cyclopropyl, cyclobutyl, cyclopentyl, cyclohexyl, cycloheptyl, cyclooctyl, cyclononyl, cyclodecyl, cyclododecyl, and the like, or multiple ring structures such as adamantanyl, and the like. Tin certain aspects of the invention the cycloalkyl radicals are "lower cycloalkyl" radicals having from about 3 to 10, 3 to 8, 3 to 6, or 3 to 4 carbon atoms, in particular cyclopropyl, cyclobutyl, cyclopentyl, cyclohexyl and cycloheptyl. The term "cycloalkyl" also embraces radicals where cycloalkyl radicals are fused with aryl radicals or heterocyclyl radicals. A cycloalkyl radical may be optionally substituted with groups as disclosed herein.

In aspects of the invention, "substituted cycloalkyl" includes cycloalkyl groups having from 1 to 5 (in particular 1 to 3) substituents including without limitation alkyl, alkenyl, alkoxy, cycloalkyl, substituted cycloalkyl, acyl, acylamino, acyloxy, amino, aminoacyl, aminoacyloxy, oxyacylamino, cyano, halogen, hydroxyl, carboxyl, carboxylalkyl, keto, thioketo, thiol, thioalkoxy, aryl, aryloxy, heteroaryl, heteroaryloxy, hydroxyamino, alkoxyamino, and nitro.

As used herein in respect to certain aspects of the invention, the term "cycloaliphatic" refers to a cycloalkane possessing less than 8 carbons or a fused ring system consisting of no more than three fused cycloaliphatic rings. Examples of such groups include, but are not limited to, decalin and the like.

As used herein in respect to certain aspects of the invention, the term "substituted cycloaliphatic" refers to a cycloalkane possessing less than 8 carbons or a fused ring system consisting of no more than three fused rings, and where at least one of the aliphatic hydrogen atoms has been replaced by a halogen, a nitro, a thio, an amino, a hydroxy, a ketone, an aldehyde, an ester, an amide, a lower aliphatic, a substituted lower aliphatic, or a ring (aryl, substituted aryl, cycloaliphatic, or substituted cycloaliphatic). Examples of such groups include, but are not limited to, 1-chlorodecalyl and the like.

A used herein, the term "cycloalkenyl" refers to radicals comprising about 4 to 16, 2 to 15, 2 to 10, 2 to 8, 4 to 10, 3 to 8, 3 to 7, 3 to 6, or 4 to 6 carbon atoms, one or more carbon-carbon double bonds, and one, two, three, or four rings wherein such rings may be attached in a pendant manner or may be fused. In certain aspects of the invention the cycloalkenyl radicals are "lower cycloalkenyl" radicals having three to seven carbon atoms. Examples of cycloalkenyl radicals include without limitation cyclobutenyl, cyclopentenyl, cyclohexenyl and cycloheptenyl. A cycloalkenyl radical may be optionally substituted with groups as disclosed herein, in particular 1, 2, or 3 substituents which may be the same or different.

As used herein the term "cycloalkoxy" refers to cycloalkyl radicals (in particular, cycloalkyl radicals having 3 to 15, 3 to 8 or 3 to 6 carbon atoms) attached to an oxy radical. Examples of cycloalkoxy radicals include cyclohexoxy and cyclopentoxy. A cycloalkoxy radical may be optionally substituted with groups as disclosed herein.

As used herein, the term "aryl", alone or in combination, refers to a carbocyclic aromatic system containing one, two or three rings wherein such rings may be attached together in a pendant manner or may be fused, in aspects of the invention an aryl radical comprises 4 to 24 carbon atoms, in particular 4 to 10, 4 to 8, or 4 to 6 carbon atoms. Illustrative "aryl" radicals includes without limitation aromatic radicals such as phenyl, benzyl, naphthyl, indenyl, benzocyclooctenyl, benzocycloheptenyl, pentalenyl, azulenyl, tetrahydronaphthyl, indanyl, biphenyl, acephthylenyl, fluorenyl, phenalenyl, phenanthrenyl, and anthracenyl, preferably phenyl.

An aryl radical may be optionally substituted with groups as disclosed herein, in particular hydroxyl, alkyl, carbonyl, carboxyl, thiol, amino, and/or halo, in particular a substituted aryl includes without limitation arylamine and arylalkylamine.

As used herein in respect to certain aspects of the invention, the term "substituted aryl" includes an aromatic ring, or fused aromatic ring system consisting of no more than three fused rings at least one of which is aromatic, and where at least one of the hydrogen atoms on a ring carbon has been replaced by a halogen, an amino, a hydroxy, a nitro, a thio, an alkyl, a ketone, an aldehyde, an ester, an amide, a lower aliphatic, a substituted lower aliphatic, or a ring (aryl, substituted aryl, cycloaliphatic, or substituted cycloaliphatic). Examples of such include, but are not limited to, hydroxyphenyl, chlorphenyl and the like.

In aspects of the invention, an aryl radical may be optionally substituted with one to four substituents such as alkyl, substituted alkyl, alkenyl, substituted alkenyl, alkynyl, substituted alkynyl, aryl, substituted aryl, aralkyl, halo, trifluoromethoxy, trifluoromethyl, hydroxy, alkoxy, alkanoyl, alkanoyloxy, aryloxy, aralkyloxy, amino, alkylamino, acylamino, aralkylamino, dialkylamino, alkanoylamino, thiol, alkylthio, ureido, nitro, cyano, carboxy, carboxyalkyl, carbamyl, alkoxycarbonyl, alkylthiono, arylthiono, arylsulfonylamine, sulfenic acid, alkysulfonyl, sulfonamido, aryloxy and the like. A substituent may be further substituted by hydroxy, halo, alkyl, alkoxy, alkenyl, alkynyl, aryl or aralkyl. In aspects of the invention an aryl radical is substituted with hydroxyl, alkyl, carbonyl, carboxyl, thiol, amino, and/or halo. The term "aralkyl" refers to an aryl or a substituted aryl group bonded directly through an alkyl group, such as benzyl. Other particular examples of substituted aryl radicals include chlorobenzyl, and amino benzyl.

As used herein, the term "aryloxy" refers to aryl radicals, as defined above, attached to an oxygen atom. Exemplary aryloxy groups include napthyloxy, quinolyloxy, isoquirioliz-inyloxy, and the like.

As used herein the term "arylalkoxy," refers to an aryl group attached to an alkoxy group. Representative examples of arylalkoxy groups include, but are not limited to, 2-phenylethoxy, 3-naphth-2-ylpropoxy, and 5-phenylpentyloxy.

As used herein, the term "aroyl" refers to aryl radicals, as defined above, attached to a carbonyl radical as defined herein, including without limitation benzoyl and toluoyl. An aroyl radical may be optionally substituted with groups as disclosed herein.

As used herein the term "heteroaryl" refers to fully unsaturated heteroatom-containing ring-shaped aromatic radicals having at least one heteroatom selected from carbon, nitrogen, sulfur and oxygen. A heteroaryl radical may contain one, two or three rings and the rings may be attached in a pendant manner or may be fused. In aspects of the invention the term refers to fully unsaturated hetoreatom-containing ring-shaped aromatic radicals having from 3 to 15, 3 to 10, 3 to 8, 5 to 15, 5 to 10, or 5 to 8 ring members selected from carbon, nitrogen, sulfur and oxygen, wherein at least one ring atom is a heteroatom. Examples of "heteroaryl" radicals, include without limitation, an unsaturated 5 to 6 membered heteromonocyclyl group containing 1 to 4 nitrogen atoms, in particular, pyrrolyl, pyrrolinyl, imidazolyl, pyrazolyl, 2-pyridyl, 3-pyridyl, 4-pyridyl, pyridinyl, pyrimidinyl, pyrazinyl, pyridazinyl, triazolyl, tetrazolyl and the like; an unsaturated condensed heterocyclic group containing 1 to 5 nitrogen atoms, in particular, indolyl, isoindolyl, indolizinyl, benzimidazolyl, quinolyl, isoquinolyl, indazolyl, quinazolinyl, pteridinyl, quinolizidinyl, phthalazinyl, naphthyridinyl, quinoxalinyl, cinnolinyl, phenanthridinyl, acridinyl, phenanthrolinyl, phenazinyl, carbazolyl; purinyl, benzimidazolyl, quinolinyl, isoquinolinyl, beazotriazolyl, tetrazolopyridazinyl and the like; an unsaturated 3 to 6-membered heteromonocyclic group containing an oxygen atom, in particular, 2-furyl, pyranyl, and the like; an unsaturated 5 to 6-membered heteromonocyclic group containing a sulfur atom, in particular, thienyl, 2-thienyl, 3-thienyl, and the like; unsaturated 5 to 6-membered heteromonocyclic group containing 1 to 2 oxygen atoms and 1 to 3 nitrogen atoms, in particular, furazanyl, benzofurazanyl, oxazolyl, isoxazolyl, and oxadiazolyl; an unsaturated condensed heterocyclic group containing 1 to 2 oxygen atoms and 1 to 3 nitrogen atoms, in particular benzoxazolyl, benzoxadiazolyl and the like; an unsaturated 5 to 6-membered heteromonocyclic group containing 1 to 2 sulfur atoms and 1 to 3 nitrogen atoms, for example, thiazolyl, isothiazolyl, thiadiazolyl and the like; an unsaturated condensed heterocyclic group containing 1 to 2 sulfur atoms and 1 to 3 nitrogen atoms such as benzothiazolyl, benzothiadiazolyl and the like. The term also includes radicals where heterocyclic radicals are fused with aryl radicals, in particular bicyclic radicals such as benzofuranyl, benzothiophenyl, phthalazinyl, chromenyl, xanthenyl, and the like. A heteroaryl radical may be optionally substituted with groups as disclosed herein, for example with an alkyl, amino, halogen, etc., in particular a heteroarylamine.

In aspects of the invention, the term refers to an unsaturated 5 to 6 membered heteromonocyclyl group containing 1 to 4 nitrogen atoms, in particular, pyrrolyl, pyrrolinyl, imidazolyl, pyrazolyl, 2-pyridyl, 3-pyridyl, pyridinyl, pyrimidinyl, pyrazinyl, pyridazinyl, triazolyl, tetrazolyl and the like.

A heteroaryl radical may be optionally substituted with groups disclosed herein, for example with an alkyl, amino, halogen, etc., in particular a substituted heteroaryl radical is a heteroarylamine.

The term "heterocyclic" refers to saturated and partially saturated heteroatom containing ring-shaped radicals having at least one heteroatom selected from carbon, nitrogen, sulfur and oxygen. A heterocylic radical may contain one, two or three rings wherein such rings may be attached in a pendant manner or may be fused. In an aspect, the term refers to a saturated and partially saturated heteroatom-containing ring-shaped radicals having from about 3 to 15, 3 to 10, 5 to 15, 5 to 10, or 3 to 8 ring members selected from carbon, nitrogen, sulfur and oxygen, wherein at least one ring atom is a heteroatom. Exemplary saturated heterocyclic radicals include without limitation a saturated 3 to 6-membered heteromonocylic group containing 1 to 4 nitrogen atoms [e.g. pyrrolidinyl, imidazolidinyl, and piperazinyl]; a saturated 3 to 6-membered heteromonocyclic group containing 1 to 2 oxygen atoms and 1 to 3 nitrogen atoms [e.g. morpholinyl; sydnonyl]; and, a saturated 3 to 6-membered heteromonocyclic group containing 1 to 2 sulfur atoms and 1 to 3 nitrogen atoms [e.g., thiazolidinyl] etc. Examples of partially saturated heterocyclyl radicals include without limitation dihydrothiophene, dihydropyranyl, dihydrofuranyl and dihydrothiazolyl. Illustrative heterocyclic radicals include without limitation aziridinyl, azetidinyl, 2-pyrrolinyl, 3-pyrrolinyl, pyrrolidinyl, azepinyl, 1,3-dioxolanyl, 211-pyranyl, 4H-pyranyl, piperidinyl, 1,4-dioxanyl, morpholinyl, pyrazolinyl, thiomorpholinyl, 1,2,3,6-tetrahydropyridinyl, oxiranyl, oxetanyl, tetrahydrofuranyl, tetrahydropyranyl, tetrahydropyridinyl, tetrahydrothiopyranyl, thioxanyl, indolinyl, 2H-pyranyl, 4H-pyranyl, dioxanyl, 1,3-dioxolanyl, pyrazolinyl, dihydropyranyl, dihydrothienyl, dihydrofuranyl, pyrazolidinyl, imidazolinyl, imidazolidinyl, quinuelidinyl, quinolizinyl, and the like. In certain compounds of the formula II, when $R^4$, $R^5$, $R^6$, $R^7$, $R^8$, $R^9$, $R^{10}$, $R^{12}$, $R^{13}$, $R^{14}$, $R^{15}$, $R^{16}$, and $R^{17}$ are hydrogen, $R^{11}$ cannot be piperidinyl.

As used herein in respect to certain aspects of the invention, the term "heterocyclic" refers to a cycloalkane and/or an aryl ring system, possessing less than 8 carbons, or a fused ring system consisting of no more than three fused rings, where at least one of the ring carbon atoms is replaced by oxygen, nitrogen or sulfur. Examples of such groups include, but are not limited to, molpholino and the like.

As used herein in respect to certain aspects of the invention, the term "substituted heterocyclic" refers to a cycloalkane and/or an aryl ring system, possessing less than 8 carbons, or a fused ring system consisting of no more than three fused rings, where at least one of the ring carbon atoms is replaced by oxygen, nitrogen or sulfur, and where at least one of the aliphatic hydrogen atoms has been replaced by a halogen, hydroxy, a thio, nitro, an amino, a ketone, an aldehyde, an ester, an amid; a lower aliphatic, a substituted lower aliphatic, or a ring (aryl, substituted aryl, cycloaliphatic, or substituted cycloaliphatic). Examples of such groups include, but are not limited to 2-chloropyranyl.

The foregoing heteroaryl and heterocyclic groups may be C-attached or N-attached (where such is possible).

As used herein the term "sulfonyl", used alone or linked to other terms such as alkylsulfonyl or arylsulfonyl, refers to the divalent radicals $-SO_2-$. In aspects of the invention, the sulfonyl group may be attached to a substituted or unsubstituted hydroxyl, alkyl group, ether group, alkenyl group, alkynyl group, aryl group, cycloalkyl group, cycloalkenyl group, cycloalkynyl group, heterocyclic group, carbohydrate, peptide, or peptide derivative.

The term "sulfinyl", used alone or linked to other terms such as alkylsulfinyl (i.e. $-S(O)$-alkyl) or arylsulfinyl, refers to the divalent radicals $-S(O)-$.

The term "sulfonate" is art recognized and includes a group represented by the formula:

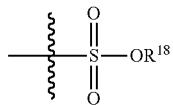

wherein $R^{18}$ is an electron pair, hydrogen, alkyl, cycloalkyl, aryl, alkenyl, alkynyl, cycloalkenyl, cycloalkynyl, heterocyclic, carbohydrate, peptide, or peptide derivative.

The term "sulfate", used alone or linked to other terms, is art recognized and includes a group that can be represented by the formula:

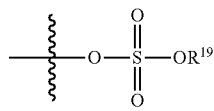

wherein $R^{19}$ is an electron pair, hydrogen, alkyl, alkenyl, alkynyl, cycloalkyl, cycloalkenyl, cycloalkynyl, aryl, heterocyclic, carbohydrate, peptide or peptide derivative.

The term "sulfoxide" refers to the radical $-S=O$.

As used herein the term "amino", alone or in combination, refers to a radical where a nitrogen atom (N) is bonded to three substituents being any combination of hydrogen, hydroxyl, alkyl, cycloalkyl, alkenyl, alkynyl, aryl, silyl, heterocyclic, or heteroaryl which may or may not be substituted. Generally an "amino group" has the general chemical formula $-NR^{20}R^{21}$ where $R^{20}$ and $R^{21}$ can be any combination of hydrogen, hydroxyl, alkyl, cycloalkyl, alkoxy, alkenyl, alkynyl, aryl, carbonyl carboxyl, amino, silyl, heteroaryl, or heterocyclic which may or may not be substituted. Optionally one substituent on the nitrogen atom may be a hydroxyl group ($-OH$) to provide an amine known as a hydroxylamine. Illustrative examples of amino groups are amino alkylamino, acylamino, cycloamino, acycloalkylamino, arylamino, arylalkylamino, and lower alkylsilylamino, in particular methylamino, ethylamino, dimethylamino, 2-propylamino, butylamino, isobutylamino, cyclopropylamino, benzylamino, allylamino, hydroxylamino, cyclohexylamino, piperidinyl, hydrazinyl, benzylamino, diphenylmethylamino, tritylamino, trimethylsilylamino, and dimethyl-tert.-butylsilyiamino, which may or may not be substituted.

As used herein the term "thiol" means $-SH$. A thiol may be substituted with a substituent disclosed herein, in particular alkyl (thioalkyl), aryl (thioaiyl), alkoxy (thioalkoxy) or carboxyl.

The term "sulfenyl" used alone or linked to other terms such as alkylsulfenyl, refers to the radical $-SR^{22}$ wherein $R^{22}$ is not hydrogen. In aspects of the invention $R^{22}$ is substituted or unsubstituted alkyl, cycloalkyl, alkenyl, alkynyl, aryl, silyl, silylalkyl, heterocyclic, heteroaryl, carbonyl, carbamoyl, alkoxy, or carboxyl.

As used herein, the term "thioalkyl", alone or in combination, refers to a chemical functional group where a sulfur atom (5) is bonded to an alkyl, which may be substituted. Examples of thioalkyl groups are thiomethyl, thioethyl, and thiopropyl. A thioalkyl may be substituted with a substituted or unsubstituted carboxyl, aryl, heterocyclic, carbonyl, or heterocyclic.

As used herein the term "thioaryl", alone or in combination, refers to a chemical functional group where a sulfur atom (S) is bonded to an aryl group with the general chemical formula $-SR^{23}$ where $R^{23}$ is aryl which may be substituted. Illustrative examples of thioaryl groups and substituted thioaryl groups are thiophenyl, chlorothiophenol, para-chlorothiophenol, thiobenzyl, 4-methoxy-thiophenyl, 4-nitrothiophenyl, and para-nitrothiobenzyl.

As used herein the term "thioalkoxy", alone or in combination, refers to a chemical functional group where a sulfur atom (S) is bonded to an alkoxy group with the general chemical formula $-SR^{24}$ where $R^{24}$ is an alkoxy group which may be substituted. A "thioalkoxy group" may have 1-6 carbon atoms i.e. a $-S-(O)-C_1-C_6$ alkyl group wherein $C_1-C_6$ alkyl have the meaning as defined above. Illustrative examples of a straight or branched thioalkoxy group or radical having from 1 to 6 carbon atoms, also known as a $C_1-C_6$ thioalkoxy, include thiomethoxy and thioethoxy.

A thiol may be substituted with a substituted or unsubstituted heteroaryl or heterocyclic, in particular a substituted or unsubstituted saturated 3 to 6-membered heteromonocylic group containing 1 to 4 nitrogen atoms [e.g. pyrrolidinyl, imidazolidinyl, piperidinyl, and piperazinyl] or a saturated 3 to 6-membered heteromonocyclic group containing 1 to 2 oxygen atoms and 1 to 3 nitrogen atoms [e.g. morpholinyl; sydrionyl], especially a substituted morpholinyl or piperidinyl.

As used herein, the term "carbonyl" refers to a carbon radical having two of the four covalent bonds shared with an oxygen atom.

As used herein, the term "carboxyl", alone or in combination, refers to —C(O)OR$^{25}$— or —C(=O)OR$^{25}$ wherein R$^{25}$ is hydrogen, alkyl, alkenyl, alkynyl, cycloalkyl, cycloalkenyl, amino, thiol, aryl, heteroaryl, thioalkyl, thioaryl, thioalkoxy, a heteroaryl, or a heterocyclic, which may optionally be substituted. In aspects of the invention, the carboxyl groups are in an esterified form and may contain as an esterifying group lower alkyl groups. In particular aspects of the invention, —C(O)OR$^{25}$ provides an ester or an amino acid derivative. An esterified form is also particularly referred to herein as a "carboxylic ester". In aspects of the invention a "carboxyl" may be substituted, in particular substituted with allyl which is optionally substituted with one or more of amino, amine, halo, alkylamino, aryl, carboxyl, or a heterocyclic. Examples of carboxyl groups are methoxycarbonyl, butoxycarbonyl, tert.alkoxycarbonyl such as tert.butoxycarbonyl, arylmethyoxycarbonyl having one or two aryl radicals including without limitation phenyl optionally substituted by for example lower alkyl, lower alkoxy, hydroxyl, halo, and/or nitro, such as benzyloxycarbonyl, methoxybenzyloxycarbonyl, diphenylmethoxycarbonyl, 2-bromoethoxycarbonyl, 2-iodoethoxycarbonyltert.butylcarborlyl, 4-nitrobenzyloxycarbonyl, diphenylmethoxy-carbonyl, benzhydroxycarbonyl, di-(4-methoxyphenyl-methoxycarbonyl, 2-bromoethoxycarbonyl, 2-iodoethoxycarbonyl, 2-trimethylsilylethoxycarbonyl, or 2-triphenylsilylethoxycarbonyl. Additional carboxyl groups in esterified form are silyloxycarbonyl groups including organic silyloxycarbonyl. The silicon substituent in such compounds may be substituted with lower alkyl (e.g. methyl), alkoxy (e.g. methoxy), and/or halo (e.g. chlorine). Examples of silicon substituents include trimethylsilyi and dimethylter-t.butylsilyl. In aspects of the invention, the carboxyl group may be an alkoxy carbonyl, in particular methoxy carbonyl, ethoxy carbonyl, isopropoxy carbonyl, t-butoxycarbonyl, t-pentyloxycarbonyl, sir heptyloxy carbonyl, especially methoxy carbonyl or ethoxy carbonyl.

As used herein, the term "carbamoyl", alone or in combination, refers to amino, monoalkylamino, dialkylamino, monocycloalkylamino, alkyleycloalkylamino, and dicycloalkylaxaino radicals, attached to one of two unshared bonds in a carbonyl group.

As used herein, the term "carboxamide" refers to the group —CONH—.

As used herein, the term "nitro" means —NO$_2$—.

As used herein, the term "acyl", alone or in combination, means a carbonyl or thiocarbonyl group bonded to a radical selected from, for example, optionally substituted, hydrido, alkyl (e.g. haloalkyl), alkenyl, alkynyl, alkoxy ("acyloxy" including acetyloxy, butyryloxy, iso-valeryloxy, phenylacetyloxy, berizoyloxy, p-methoxybenzoyloxy, and substituted acyloxy such as alkoxyalkyl and haloalkoxy), aryl, halo, heterocyclyl, heteroaryl, sulfonyl (e.g. allylsulfinylalkyl), sulfonyl (e.g. alkylsulfonylalkyl), cycloalkyl, cycloalkenyl, thioalkyl, thioaryl, amino (e.g alkylamino or dialkylamino), and aralkoxy. Illustrative examples of "acyl" radicals are formyl, acetyl, 2-chloroacetyl, 2-bromacetyl, benzoyl, trifluoroacetyl, phthaloyl, malonyl, nicotinyl, and the like.

In aspects of the invention, "acyl" refers to a group —C(O)R$^{26}$, where R$^{26}$ is hydrogen, alkyl, cycloalkyl, cyclohet-eroalkyl, aryl, arylalkyl, heteroalkyl, heteroaryl, and heteroarylalkyl. Examples include, but are not limited to formyl, acetyl, cyclohexylcarbonyl, cyclohexylmethylcarbonyl, benzoyl, beozylcarbonyl and the like.

As used herein the term "phosphonate" refers to a C—PO(OH)$_2$ or C—PO(OR$^{27}$)$_2$ group wherein R$^{27}$ is alkyl or aryl which may be substituted.

As used herein, "ureido" refers to the group "—NH-CONH—". A ureido radical includes an alkylureido comprising a ureido substituted with an alkyl, in particular a lower alkyl attached to the terminal nitrogen of the ureido group. Examples of an alkylureido include without limitation N'-methylareido, N'-ethylureido, N'-n-propylureido, NP-1-propylureido and the like. A ureido radical also includes a N',N'-dialkylureido group containing a radical —NHCON where the terminal nitrogen is attached to two optionally substituted radicals including alkyl, aryl, heterocylic, and heteroaryl.

The terms used herein for radicals including "alkyl", "alkoxy", "alkenyl", "alkynyl", "hydroxyl" etc. refer to both unsubstituted and substituted radicals. The term "substituted," as used herein, means that any one or more moiety on a designated atom (e.g., hydrogen) is replaced with a selection from a group disclosed herein, provided that the designated atom's normal valency is not exceeded, and that the substitution results in a stable compound. Combinations of substituents and/or radicals are permissible only if such combinations result in stable compounds. "Stable compound" refers to a compound that is sufficiently robust to survive isolation to a useful degree of purity from a reaction mixture, and formulation into an efficacious therapeutic agent.

A functional group or ring of a compound of the formula I, II or III may be modified with, or a radical in a compound of the formula I, II or III may be substituted with one or more groups or substituents apparent to a person skilled in the art including without limitation alkyl, alkoxy, alkenyl, alkynyl, alkanoyl, alkylene, alkenylene, hydroxyalkyl, haloalkyl, haloalkylene, haloalkenyl, alkoxy, alkenyloxy, alkenyloxy-alkyl, alkoxyalkyl, aryl, alkylaryl, haloalkoxy, haloalkenyloxy, heterocyclic, heteroaryl, alkylsulfonyl, sulfinyl, sulfonyl, sulfenyl, alkylsulfinyl, aralkyl, heteroaralkyl, cycloalkyl, cyclo alkenyl, cycloalkoxy, cycloalkenyloxy, amino, oxy, halo, azido, thio, =O, =S, cyano, hydroxyl, phosphonato, phosphinato, thioalkyl, alkylamino, arylamino, arylsulfonyl, alkylcarbonyl, arylcarbonyl, heteroarylcarbonyl, heteroarylsulfinyl, heteroarylsulfony, heteroarylamino, heteroaryloxy, heteroaryloxylalkyl, arylacetamidoyl, aryloxy, aroyl, aralkanoyl, aralkoxy, aryloxyalkyl, haloaryloxyalkyl, heteroaroyl, heteroaralkanoyl, heteroaralkoxy, heteroaralkoxyalkyl, thioaryl, arylthioalkyl, alkoxyalkyl, and acyl groups. These groups or substitutents may themselves be substituted. Derivative groups that may be used to modify compounds of the Formula I can also be found in U.S. Patent Application No. 20030176437.

A chemical substituent is "pendant" from a radical if it is bound to an atom of the radical. In this context, the substituent can be pending from a carbon atom of a radical, a carbon atom connected to a carbon atom of the radical by a chain extender, or a heteroatom of the radical. The term "fused" means that a second ring is present (i.e, attached or formed) by having two adjacent atoms in common or shared with the first ring.

A "dosage form" refers to a composition or device comprising a compound of the formula I, II or III and optionally pharmaceutically acceptable carrier(s), excipient(s), or vehicles. A dosage form may be an immediate release dosage form or a sustained release, dosage form.

An "immediate release dosage form" refers to a dosage form which does not include a component for sustained release i.e., a component for slowing disintegration or dissolution of an active compound. These dosage forms generally rely on the composition of the drug matrix to effect the rapid release of the active ingredient agent By "sustained release dosage form" is meant a dosage form that releases active compound for many hours. In an aspect, a sustained dosage form includes a component for slowing disintegration or dissolution of the active compound. A dosage form may be a sustained release formulation, engineered with or without an initial delay period. Sustained release dosage forms may continuously release drug for sustained periods of at least about 4 hours or more, about 6 hours or more, about 8 hours or more, about 12 hours or more, about 15 hours or more, or about 20 hours to 24 hours. A sustained release dosage form can be formulated into a variety of forms, including tablets, lozenges, gelcaps, buccal patches, suspensions, solutions, gels, etc. In aspects of the invention the sustained release form results in administration of a minimum number of daily doses.

A "disease" that can be treated and/or prevented using a compound, composition, or method of the invention includes a condition associated with or requiring modulation of one or more of inflammation (e.g. neuroinflammation); signaling pathways involved in inflammation (e.g., neuroinflammation); cell signaling molecule production; activation of glia or glial activation pathways and responses; proinflammatory cytokines or chemokines (e.g., interleukin (IL), in particular IL-1β) or tumor necrosis factor (TNF, in particular TNFα); activation of astrocytes or astrocyte activation pathways and responses; activation of microglia or microglial activation pathways and responses; oxidative stress-related responses such as nitric oxide synthase production and nitric oxide accumulation; acute phase proteins; loss of synaptophysin and/or 95; components of the complement cascaded loss or reduction of synaptic function; protein kinase activity (e.g., death associated protein kinase activity); cell damage (e.g., neuronal cell damage); cell death (e.g., neuronal cell death); amyloid deposition of amyloid plaques; and behavioral deficits.

In particular a disease is a neurological disease or condition including without limitation, dementing disorder, a neurodegenerative disorder, a CNS demyelinating disorder, a pain disorder, an autoimmune disorder, or a peripheral inflammatory disease.

A disease may be characterized by an inflammatory process due to the presence of macrophages activated by an amyloidogenic protein or peptide. Thus, a method of the invention may involve inhibiting macrophage activation and/or inhibiting an inflammatory process. A method may comprise decreasing, slowing, ameliorating, or reversing the course or degree of macrophage invasion or inflammation in a patient.

Examples of diseases that can be treated and/or prevented using the compounds, compositions and methods of the invention include Alzheimer's disease and related disorders, presenile and senile forms; amyloid angiopathy; mild cognitive impairment; Alzheimer's disease-related dementia (e.g., vascular dementia or Alzheimer dementia); AIDS related dementia, tauopathies (e.g., argyrophilic grain dementia, corticobasal degeneration, dementia pugilistica, diffuse neurcifibrillary tangles with calcification, frontotemporal dementia with parkinsonism, Prion-related disease, Hallervorden-Spatz disease, myotonic dystrophy, Niemann-Pick disease type C, non-Guamanian Motor Neuron disease with neurofibrillary tangles, Pick's disease, postencephalitic parkinsonism, cerebral amyloid angiopathy, progressive subcortical gliosis, progressive supranuclear palsy, subacute sclerosing panencephalitis, and tangle only dementia), alpha-synucleinopathy (e.g., dementia with Lewy bodies, multiple system atrophy with glial cytoplasmic inclusions), multiple system atrophies, Shy-Drager syndrome, spinocerebellar ataxia (e.g., DRPLA or Machado-Joseph Disease); striatonigral degeneration, olivopontocerebellar atrophy, neurodegeneration with brain iron accumulation type I, olfactory dysfunction, and amyotrophic lateral sclerosis); Parkinson's disease (e.g., familial or non-familial); Amyotrophic Lateral Sclerosis; Spastic paraplegia (e.g., associated with defective function of chaperones and/or triple A proteins); Huntington's Disease, spinocerebellar ataxia, Freidrich's Ataxia; cerebrovascular diseases including stroke, hypoxia, ischemia, infarction, intracerebral hemorrhage; traumatic brain injury; Down's syndrome; head trauma with post-traumatic accumulation of amyloid beta peptide; Familial British Dementia; Familial Danish Dementia; Presenile Dementia with Spastic Ataxia; Cerebral Amyloid Angiopathy, British Type; Presenile Dementia With Spastic Ataxia Cerebral Amyloid Angiopathy, Danish Type; Familial encephalopathy with neuroserpin inclusion bodies (FEN); Amyloid Polyneuropathy (e.g., senile amyloid polyneuropathy systemic Amyloidosis); Inclusion Body myositis due to amyloid beta peptide; Familial and Finnish Type Amyloidosis; Systemic amyloidosis associated with multiple myeloma; Mediterranean Fever; multiple sclerosis, optic neuritis; Guillain-Barre Syndrome; chronic inflammatory demyelinating polyneuropathy; chronic infections and inflammations; acute disseminated encephalomyelitis (ADEM); autoimmune inner ear disease (AIED); diabetes; myocardial isehemia and other cardiovascular disorders; pancreatitis; gout; inflammatory bowel disease; ulcerative colitis, Crohn's disease, rheumatoid arthritis, osteoarthritis; artherioselerosis, inflammatory aortic aneurysm; asthma; adult respiratory distress syndrome; restenosis; isehemia/reperfusion injury; glomerulonephritis; sacoidosis cancer; restenosis; rheumatic fever; systemic lupus erythematosus; Reiter's syndrome; psoriatic arthritis; ankylosing spondylitis; coxarthritis; pelvic inflammatory disease; osteomyelitis; adhesive capsulitis; oligoarthritis; periarthritis; polyarthritis; psoriasis; Still's disease; synovitis; inflammatory dermatosis; and, wound healing.

In aspects of the invention, the disease is Alzheimer's disease, vascular dementia, dementia associated with Parkinson's disease, visuospatial deficits, Williams syndrome, encephalitis, meningitis, fetal alcohol syndrome, Korsakoffs syndrome, anoxic brain injury, cardiopulmonary resuscitation injuries, diabetes, Sjogren's syndrome, strokes, ocular diseases such as cataracts and macular degeneration, sleep disorders, and cognitive impairments caused by high cholesterol levels.

In aspects of the invention, a compound, composition, or method disclosed herein may be utilized to prevent and/or treat a disease involving neuroinflammation (i.e., neuroinflammatory disease). Neuroffiflammation is a characteristic feature of disease pathology and progression in a diverse array of neurodegenerative disorders that are increasing, in their societal impact (for a recent review, see, e.g., Prusiner, S. B. (2001) New Engl. J. Med. 344, 1516-1526). These neuroinflammation-related disorders include Alzheimer's disease (AD), amyotrophic lateral sclerosis, autoiminune disorders, priori diseases, stroke and traumatic brain injury. Neuroinflammation is brought about by glial cell (e.g., astrocytes and microglia) activation, which normally serves a beneficial role as part of an organism's homeostatic response to injury or developmental change. However, disregulation of this process through chronic or excessive activation of glia contributes to the disease process through the increased production of proinflammatory cytokines and chemokines, oxidative stress-related enzymes, acute phase proteins, and various components of the complement cascades. (See, e.g., Akiyarna et al., (2000) Neurobiol. Aging 21, 383421). The direct linkage of glial activation to pathology that is a hallmark of disease underscores the importance of understanding the signal transduction pathways that mediate these critical glial cellular responses and the discovery of cell permeable ligands that can modulate these disease relevant pathways.

In certain selected aspects of the invention, the disease is a neurodegenerative disease or neurodegenerative disorder including such diseases and impairments as Alzheimer's disease, dementia, MCI, Huntington's disease, Parkinson's disease, amyotrophic lateral sclerosis, and other similar diseases and disorders disclosed herein.

For Alzheimer's disease (AD) in particular, the deposition of β-amyloid (Aβ) and neurofibrillary tangles are associated with glial activation, neuronal loss and cognitive decline. On a molecular level, Alzheimer's disease is characterized by; increased expression of nitric oxide synthase (NOS) in glial cells surrounding amyloid plaques; neuropathological evidence of peroxynitrite-mediated neuronal damage; and nitric oxide (NO) overproduction involved in Aβ-induced brain dysfunction. NOSH (iNOS) is induced as part of the glial activation response and is an oxidative stress-related enzyme that generates NO. When NO is present in high levels along with superoxide, the highly reactive NO-derived molecule peroxynitrite is generated, leading to neuronal cell death. The pro-inflammatory cytokine IL-1β is also overexpressed in activated glia in AD brain and polymorphisms IL-1β genes are associated with an increased risk of early onset sporadic AD (See, e.g., Du et al., (2000) Neurology 55, 480-483). IL-1β can also influence amyloid plaque development and is involved in additional glial inflammatory and neuronal dysfunction responses (See, e.g., Griffin, et al., (1998) Brain Pathol. 8, 65-72; and Sheng, et al., (1996) Neurobiol. Aging 17, 761-766). Therefore, because glial activation and specific glial products are associated with neurodegenerative disorders (e.g., Alzheimer's disease), the compounds and compositions disclosed herein that are capable of modulating cell signaling pathways (e.g., glial activation pathways) will have particular application in the treatment and prevention of inflammatory disease.

In aspects of the invention, a compound, composition, or method disclosed herein may be utilized to prevent and/or treat a disease involving disregulation of protein kinase signaling Disregulation of protein kinase signaling often accompanies disregulation of cell signaling pathways (e.g., glial cell activation pathways). Protein kinases are a large family of proteins that play a central role in regulating a number of cellular functions including cell growth, differentiation and death. There are thought to be more than 500 protein kinases and 130 protein phosphatases exerting tight control on protein phosphorylation. Each protein kinase transfers the γ-phosphate of ATP to a specific residue(s) of a protein substrate. Protein kinases can be further categorized as tyrosine, serine/threonine or dual specific based on acceptor residue. Examples of serine/threonine kinases include MAP kinase, MAPK kinase (MEK), Akt/PKB, Jun kinase (INK), CDKs, protein kinase A (PRA), protein kinase C (PKC), and calmodulin (CaM)-dependent kinases (CaMKs). Disregulated protein kinase activity (e.g., hyper- or hypo-active) leads to abnormal protein phosphorylation, underlying a great number of diseases including diabetes, rheumatoid arthritis, inflammation, hypertension, and proliferative diseases such as cancer. Therefore, because aberrant kinase activity is associated with inflammatory disease (e.g., neurodegenerative disorders like Alzheimer's disease), the compounds and compositions that are disclosed herein that are capable of modulating kinases involved in cell signaling pathways will have particular application for treatment and prevention of inflammatory disease.

Diseases that may also be treated and/or prevented according to the invention include Demyelinating Diseases, "Demyelinating Diseases" refers to diseases in which myelin is the primary target. These diseases can be divided into two groups Acquired Diseases and Hereditary Metabolic Disorders. Acquired Demyelinating Diseases include Multiple sclerosis (MS) including its alternating relapsing/remitting phases. Hereditary Metabolic Disorders includes the leukodystrophies such as metachromatic leukodystrophy, Refsum's disease, adrenoleukodystrophy, Krabbe's disease, phenylketonuria, Canavan disease, Pelizaeus-Merzbacher disease and Alexander's disease.

Diseases that may also be treated and/or prevented according to the invention include "Demyelinating Conditions". The term refers to conditions that result in deficient myelination. Such conditions include, but are not limited to, Spinal Cord Injury, Traumatic Brain Injury and Stroke.

The term "Spinal Cord Injury (SCI)" refers to a injury to the spinal cord which results in loss of function such as mobility or feeling.

The term "Traumatic Brain Injury (TBI)" refers to an injury which results in damage to the brain. A head injury may be a closed head injury or penetrating head injury. A closed head injury may occur when the head is hit by a blunt object causing the brain to interact with the hard bony surface inside the skull. A closed head injury may also occur without direct external trauma to the head if the brain undergoes a rapid forward or backward movement, (e.g. whiplash). A penetrating head injury may occur when a fast moving object such as a bullet pierces the skull. A closed or penetrating head injury may result in localized and widespread, or diffuse, damage to the brain which may manifest as memory loss, emotional disturbances, motor difficulties, including paralysis, damage to the senses, and death. The term also includes secondary damage that follows an injury including swelling and fluid buildup and the accumulation of substances toxic to surrounding neurons such as the neurotransmitter glutamate.

The term "Stroke" refers to a sudden loss of brain function caused by the interruption of the flow of blood to the brain (an ischemic stroke) or the rupture of blood vessels in the brain (a hemorrhagic stroke). The interruption of the blood flow or the rupture of blood vessels causes neurons in the affected area to die. The term also includes stroke rehabilitation which refers to the intervention resulting in the full or partial recovery of functions that have been lost due to stroke.

A pain disorder may also be treated and/or prevented according to the invention. A "pain disorder" refers to a disorder or condition involving pain and includes without limitation acute pain, persistent pain, chronic pain, inflammatory pain, neuropathic pain, neurogenic pain, and chemokine-induced pain. In aspects of the invention, a pain disorder includes without limitation pain resulting from soft tissue and peripheral damage such as acute trauma; complex regional pain syndrome also referred to as reflex sympathetic dystrophy; postherpetic neuralgia, occipital neuralgia, trigeminal neuralgia, segmental or intercostal neuralgia and other neuralgias; pain associated with osteoarthritis and rheumatoid arthritis; musculo-skeletal pain such as pain associated with strains, sprains and trauma such as broken bones; spinal pain, central nervous system pain such as pain due to spinal cord or brain stem damage; lower back pain, sciatica, dental pain, myofascial pain syndromes, episiotomy pain, gout pain, and pain resulting from burns; deep and visceral pain, such as heart pain; muscle pain, eye pain, inflammatory pain, orofacial pain, for example, odontalgia; abdominal pain, and gynecological pain, for example, dysmenorrhoea, labour pain and pain associated with endometriosis; somatogenic pain; pain associated with nerve and root damage, such as pain associated with peripheral nerve disorders, for example, nerve entrapment, brachial plexus avulsions, and peripheral neuropathies; pain associated with limb amputation, tic douloureux, neuroma, or vasculitis; diabetic neuropathy, chemotherapy-induced-neuropathy, acute herpetic and postherpetic neuralgia; atypical facial pain, nerve root damage, neuropathic lower back pain, HIV related neuropathic pain, cancer related neuropathic pain, diabetes related neuropathic pain and arachnoiditis, trigeminal neuralgia, occipital neuralgia, segmental or intercostal neuralgia, HIV related neuralgias and AIDS related neuralgias and other neuralgias; allodynia, hyperalgesia, idiopathic pain, pain caused by chemotherapy; occipital neuralgia, psychogenic pain, brachial plexus avulsion, pain associated with restless legs syndrome; pain associated with gallstones; pain caused by chronic alcoholism or hypothyroidism or uremia or vitamin deficiencies; neuropathic and non-neuropathic pain associated with carcinoma, often referred to as cancer pain, phantom limb pain, functional abdominal pain, headache, including migraine with aura, migraine without aura and other vascular headaches, acute or chronic tension headache, sinus headache and cluster headache; temperomandibular pain and maxillary sinus pain; pain resulting from ankylosing spondylitis and gout; pain caused by increased bladder contractions; pain associated with gastrointestinal (GI) disorders, disorders caused by *helicobacter pylori* and diseases of the GI tract such as gastritis, proctitis, gastroduodenal ulcers, peptic ulcers, dyspepsia, disorders associated with the neuronal control of viscera, ulcerative colitis, chronic pancreatitis, Crohns's disease and emesis; post operative pain, scar pain, and chronic non-neuropathic pain such as pain associated with HIV, arthralgia and myalgia, vasculitis and fibromyalgia.

The term "Neuropathic pain" refers to pain initiated or caused by a primary lesion or dysfunction in the nervous system. For the purpose of this invention included under this heading or to be treated as synonymous is "Neurogenic Pain" which is defined as pain initiated or caused by a primary lesion, dysfunction or transitory perturbation in the peripheral or central nervous system. In aspects, the uses of the present invention include central or peripheral neuropathic pain or neurogenic pain. In other aspects, neuropathic pain includes the pain caused by either mononeuropathy or polyneuropathy. Neuropathic pain also includes Chemokine-Induced Pain.

"Peripheral neuropathic pain" refers to a pain initiated or caused by a primary lesion or dysfunction in the peripheral nervous system and "peripheral neurogenic pain" refers to a pain initiated or caused by a primary lesion, dysfunction or transitory perturbation in the peripheral nervous system. A peripheral neuropathic pain can be allodynia (i.e., a pain due to a stimulus which does not normally provoke pain); causalgia (i.e., a syndrome of sustained burning pain, allodynia and hyperpathia after a traumatic nerve lesion, often combined with vasomotor and sudomotor dysfunction and later trophic changes); hyperalgesia (i.e., an increased response to a stimulus which is normally painful); hyperesthesia (i.e., increased sensitivity to stimulation, excluding the senses); hyperpathia (i.e., a painful syndrome characterized by an abnormally painful reaction to a stimulus, especially a repetitive stimulus, as well as an increased threshold); neuritis (i.e., inflammation of a nerve or nerves); or neuropathy (i.e, a disturbance of function or pathological change in a nerve). [See IABP, Classification of chronic pain, 2nd Edition, IASP Press (2002), for detailed definitions of these categories of neuropathic pain and neurogenic pain).

Exemplary types of neuropathic pain include infective (e.g., post herpetic neuralgia and HIV neuropathy), metabolic (e.g., diabetic neuropathy and Fabry's disease), toxic (e.g., from lead or chemotherapy), traumatic/stretch injury (e.g., post incisional, trauma, phantom limb pain, and reflex sympathetic dystrophy/complex regional pain syndrome/causalgia), and idiopathic (e.g., trigeminal neuralgia/tic douloureux).

Particular examples of Neuropathic Pain include post-herpetic neuralgia, painful diabetic neuropathy, phantom limb pain, central post-stroke pain, HIV neuropathy, Fabry's disease, peripheral neuropathy, trigeminal neuralgia, post incisional neuropathic pain, phantom limb pain, reflex sympathetic dystrophy, causalgia, anesthesia dolorosa, intercoastal neuralgia, post-traumatic localized pain, atypical facial neuralgia pain after tooth extraction and the like, complex regional pain syndrome, neuropathic pain caused by trauma, lead, or chemotherapy, cancer pain resistant to narcotic analgesics such as morphine.

Treatment of neuropathic pain may be defined as administration of a therapeutic dose of a compound of the formula I, II or III to reduce and preferably eliminate pain that results from nerve injury. Treatment of nerve injury may be defined as administration of a therapeutic dose of a compound of the formula I, II or III to ameliorate injury and to increase the rate of recovery. An increased rate of recovery is defined as a reduction of indications of pain from peripheral nerve injury, such as thermal hyperalgesia and mechanical allodynia, more quickly than would be accomplished without pharmacological or other medical intervention.

"Chemokine-Induced Pain" refers to pain that occurs in response, in whole or in part, to chemokines, in particular pro-inflammatory cytokines (e.g. fractalkine, CCL2, and CCL5). An example of chemokine-induced pain is arthritic pain.

Compounds and Processes

The invention contemplates the use of isolated and pure, in particular, substantially pure, compounds of the formula I wherein $R^1$, $R^4$, $R^5$, $R^6$, $R^7$, $R^8$, $R^9$, $R^{12}$, $R^{13}$, and $R^{14}$ are independently hydrogen, hydroxyl, alkyl, alkenyl, alkynyl, alkylene, alkenylene, alkoxy, alkenyloxy, cycloalkyl, cycloalkenyl, cycloalkynyl, cycloalkoxy, aryl, aryloxy, arylalkoxy, aroyl, heteroaryl, heterocyclic, acyl, acyloxy, amino, imino, azido, thiol, thioalkyl, thioalkoxy, thioaryl, nitro, cyano, halo, sulfate, sulfonyl, sulfonyl, sulfonyl, sulfonate, sulfoxide, silyl, silyloxy, silylalkyl, silylthio, $=$O, $=$S, phosphonate, ureido, carboxyl, carbonyl, carbamoyl, or carboxamide; and X is optionally substituted pyrimidinyl or pyridazinyl, an isomer, a pharmaceutically acceptable salt, or derivative thereof.

The invention also contemplates the use of isolated and pure, in particular, substantially pure, compounds of the formula I wherein $R^1$, $R^4$, $R^5$, $R^6$, $R^7$, $R^8$, $R^9$, $R^{12}$, $R^{13}$, and $R^{14}$ are independently hydrogen, $C_1$-$C_6$ alkyl, $C_2$-$C_6$ alkenyl, $C_2$-$C_6$ alkynyl, $C_1$-$C_6$alkoxy, $C_2$-$C_6$ alkenyloxy, $C_3$-$C_{10}$ cycloalkyl, $C_4$-$C_{10}$cycloalkenyl, $C_3$-$C_{10}$cycloalkoxy, $C_6$-$C_{10}$aryl, $C_6$-$C_{10}$aryloxy, $C_6$-$C_{10}$aryl-$C_1$-$C_3$alkoxy, $C_6$-$C_{10}$aroyl, $C_6$-$C_{10}$heteroaryl, $C_3$-$C_{10}$heterocyclic, $C_1$-$C_6$acyl, $C_1$-$C_6$acyloxy, —NH$_2$, —NHR$^{28}$, —NR$^{28}$R$^{29}$, $=$NR$^{28}$, —S(O)$_2$R$^{28}$, —SH, —SO$_3$H, nitro, cyano, halo, haloalkyl, haloalkoxy, hydroxyalkyl, —CO$_2$H, —CO$_2$R$^{28}$, $=$NHC(O)R$^{28}$, —C(O)NH$_2$, —C(O)NHR$^{28}$, —C(O)NR$^{28}$R$^{29}$, —NHS(O)$_2$R$^{28}$, wherein R$^{28}$ and R$^{29}$ are independently selected from $C_1$-$C_6$alkyl, $C_2$-$C_6$alkenyl, $C_2$-$C_6$alkynyl, $C_3$-$C_{10}$cycloalkyl, $C_4$-$C_{10}$cycloalkenyl, $C_6$-$C_{10}$aryl, $C_6$-$C_{10}$ aryl $C_1$-$C_3$alkyl, $C_6$-$C_{10}$ heteroaryl and $C_3$-$C_{10}$heterocyclic, and X is pyrimidinyl or pyridazinyl, an isomer, a pharmaceutically acceptable salt, or derivative thereof The invention further contemplates the use of isolated and pure, in particular, substantially pure, compounds of the formula II wherein $R^1$, $R^4$, $R^5$, $R^6$, $R^7$, $R^8$, $R^9$, $R^{10}$, $R^{12}$, $R^{13}$, and $R^{14}$ are independently hydrogen, hydroxyl, alkyl, alkenyl, alkynyl, alkylene, alkenylene, alkoxy, alkenyloxy, cycloalkyl, cycloalkenyl, cycloalkynyl, cycloalkoxy, aryl, aryloxy, arylalkoxy, aroyl, heteroaryl, heterocyclic, acyl, acyloxy, sulfoxide, sulfate; sulfonyl, sulfenyl, sulfinyl, sulfonate, amino, imino, azido, thiol, thioalkyl, thioalkoxy, thioaryl, nitro, cyano, halo, silyl, silyloxy, silylalkyl, silylthio, =O, =S, phosphonate, ureido, carboxyl, carbonyl, carbamoyl, or carboxamide; or an isomer, a pharmaceutically acceptable salt, or derivative thereof.

The invention still further contemplates the use of isolated and pure, in particular, substantially pure, compounds of the formula II wherein $R^1$, $R^4$, $R^5$, $R^6$, $R^7$, $R^8$, $R^9$, $R^{10}$, $R^{12}$, $R^{13}$, and $R^{14}$ are independently selected from hydrogen, $C_1$-$C_6$ alkyl, $C_2$-$C_6$ alkenyl, $C_2$-$C_6$ alkynyl, $C_1$-$C_6$alkoxy, $C_2$-$C_6$ alkenyloxy, $C_3$-$C_{10}$ cycloalkyl, $C_4$-$C_{10}$cycloalkenyl, $C_3$-$C_{10}$cycloalkoxy, $C_6$-$C_{10}$aryl, $C_6$-$C_{10}$aryloxy, $C_6$-$C_{10}$aryl-$C_1$-$C_3$ alkoxy, $C_6$-$C_{10}$aroyl, $C_6$-$C_{10}$heteroaryl, $C_3$-$C_{10}$heterocyclic, $C_1$-$C_6$acyl, $C_1$-$C_6$acyloxy, —$NH_2$, —$NHR^{28}$, —$NR^{28}R^{29}$, =$NR^{28}$, —$S(O)_2R^{29}$, —SH, —$SO_3H$, nitro, cyano, halo, haloalkyl, haloalkoxy, hydroxyalkyl, —$CO_2H$, —$CO_2R^{28}$, —$NHC(O)R^{28}$, —$C(O)NH_2$, —$C(O)NHR^{28}$, —$C(O)NR^{28}R^{29}$, —$NHS(O)_2R^{28}$, wherein $R^{28}$ and R are independently selected from $C_1$-$C_6$alkyl, $C_2$-$C_6$alkenyl, $C_2$-$C_6$alkynyl, $C_3$-$C_{10}$cycloalkenyl, $C_6$-$C_{10}$aryl, $C_6$-$C_{10}$ aryl $C_1$-$C_3$alkyl, $C_6$-$C_{10}$ heteroaryl and $C_3$-$C_{10}$heterocyclic, or an isomer, a pharmaceutically acceptable salt, or derivative thereof.

In aspects of the invention, $R^1$ in a compound of the formula I or II is alkyl, alkenyl, alkynyl, alkoxy, or cycloalkyl. In certain aspects of the invention, $R^1$ in a compound of the formula I or II is $C_1$-$C_6$ alkyl, $C_2$-$C_6$ alkenyl, $C_2$-$C_6$ alkynyl, $C_1$-$C_6$alkoxy, or $C_3$-$C_{10}$cycloalkyl. In embodiments, $R^1$ is lower alkyl. In another embodiment, $R^1$ is cyclohexyl.

In aspects of the invention, $R^1$ in a compound of the formula I or II is aryl, in particular phenyl, benzyl, naphthyl, indenyl, benzocyclooctenyl, benzocycloheptenyl, pentalenyl, azulenyl, tetrahydronaphthyl, indanyl, biphenyl, acephthylenyl, fluorenyl, phenalenyl, phenanthrenyl, and anthracenyl. In aspects of the invention $R^1$ is aryl substituted with one or more of hydroxyl, alkyl, carbonyl, carboxyl, thiol, amino, nitro, ketone, aldehyde, ester, amide, lower aliphatic, aryl, cycloalkyl, and halo. In aspects of the invention $R^1$ in a compound of the formula I or II comprises two fused aromatic rings.

In aspects of the invention, $R^1$ in a compound of the formula I or II is aryloxy, particular $C_6$-$C_{10}$aryloxy. In embodiments of the invention, $R^1$ in a compound of the formula or II is napthyloxy, quinolyloxy, isoquinolizinyloxy, and the like.

In aspects of the invention, $R^1$ in a compound of the formula I or II is arylalkoxy, in particular $C_6$-$C_{10}$aryloxy or $C_6$-$C_{10}$aryl-$C_1$-$C_3$alkoxy. In embodiments, $R^1$ in a compound of the formula I or II is 2-phenylethoxy, 3-naphth-2-ylpropoxy, and 5-phenylpentyloxy.

In aspects of the invention, $R^1$ in a compound of the formula I or II is aroyl, in particular $C_6$-$C_{10}$aroyl. In embodiments of the invention $R^1$ in a compound of the formula I or II is benzoyl or toluoyl.

In aspects of the invention, $R^1$ in a compound of the formula I or II is a heteroaryl, in particular $C_6$-$C_{10}$heteroaryl. In aspects, $R^1$ in a compound of the formula I or II comprises one or two rings attached in a pendant manner or fused. In certain aspects of the invention, $R^1$ in a compound of, the formula I or II is: (a) an unsaturated 5 to 6 membered heteromonocyclyl group containing 1 to 4 nitrogen atoms, most particularly, pyrrolyl, pyrrolinyl, imidazolyl, pyrazolyl, 2-pyridyl, 3-pyridyl, 4-pyridyl, pyridinyl, pyrimidinyl, pyrazinyl, pyridazinyl, triazolyl, tetrazolyl and the like; (b) an unsaturated condensed heterocyclic group containing 1 to 5 nitrogen atoms, in particular, indolyl, isoindolyl, indolizinyl, indazolyl, quinazolinyl, pteridinyl, quinolizidinyl, phthalazinyl, naphthyridinyl, quinoxalinyl, cinnolinyl, phenanthridinyl, acridinyl, phenanthrolinyl, phenazinyl, carbazolyl, purinyl, benzimidazolyl, quinolyl, isoquinolyl, quinolinyl, isoquinolinyl, indazolyl, benzotriazolyl, tetrazolopyridazinyl and the like; (c) an unsaturated 3 to 6-membered heteromonocyclic group containing an oxygen atom, in particular, 2-furyl, 3-furyl, pyranyl, and the like; (d) an unsaturated 5 to 6-membered heteromonocyclic group containing a sulfur atom, in particular, thienyl, 2-thienyl, 3-thienyl, and the like; (e) an unsaturated 5 to 6-membered heteromonocyclic group containing 1 to 2 oxygen atoms and 1 to 3 nitrogen atoms, in particular, furazanyl, benzofurazanyl, oxazolyl, isoxazolyl, and oxadiazolyl; (f) an unsaturated condensed heterocyclic group containing 1 to 2 oxygen atoms and it to 3 nitrogen atoms, in particular benzoxazolyl, benzoxadiazolyl and the like; (g) an unsaturated 5 to 6-membered heteromonocyclic group containing 1 to 2 sulfur atoms and 1 to 3 nitrogen atoms, for example, thiazolyl, isothiazolyl, thiadiazolyl and the like; or (h) an unsaturated condensed heterocyclic group containing 1 to 2 sulfur atoms and 1 to 3 nitrogen atoms such as benzothiazolyl, benzothiadiazolyl and the like.

In certain aspects of the invention, $R^1$ in a compound of the formula I or II is a heterocyclic fused with an aryl, in particular benzafuranyl, benzothiophenyl, phthalazinyl, chromenyl, xanthenyl, and the like.

In particular aspects of the invention $R^1$ in a compound of the formula I or II is:

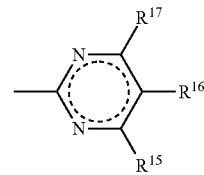

wherein $R^{15}$, $R^{16}$ and $R^{17}$ are independently hydrogen, hydroxyl, alkyl, alkenyl, alkynyl, alkylene, alkenylene, alkoxy, alkenyloxy, cyclo alkyl, cycloalkenyl, cycloalkynyl, cycloalkoxy, aryl, aryloxy, arylalkoxy, aroyl, heteroaryl, heterocyclic, acyl, acyloxy, amino, imino, azido, thiol, thioalkyl, thioalkoxy, thioaryl, nitro, cyano, halo, sulfoxide, sulfate, sulfonyl, sulfenyl, sulfinyl, sulfonate, silyl, silyloxy, silylalkyl, silylthio, =O, =S, phosphonate, ureido, carboxyl, carbonyl, carbamoyl, or carboxamide.

In embodiments of the invention, $R^{15}$, $R^{16}$ and $R^{17}$ are independently hydrogen, hydroxyl, $C_1$-$C_6$ alkyl, $C_2$-$C_6$ alkenyl, $C_2$-$C_6$ alkynyl, $C_1$-$C_6$alkoxy, $C_2$-$C_6$ alkenyloxy, $C_3$-$C_{10}$ cycloalkyl, $C_4$-$C_{10}$cycloalkenyl, $C_3$-$C_{10}$cycloalkoxy, $C_6$-$C_{10}$aryl, $C_6$-$C_{10}$aryloxy, $C_6$-$C_{10}$aryl-$C_1$-$C_3$alkoxy, $C_6$-$C_{10}$aroyl, $C_5$-$C_{10}$heteroaryl, $C_3$-$C_{10}$heterocyclic, $C_1$-$C_6$acyl, $C_1$-$C_6$acyloxy, —$NH_2$, —$NHR^{28}$, —$NR^{28}R^{29}$, nitro, cyano, halo, haloalkyl, haloalkoxy, hydroxyalkyl, —$CO_2R^{28}$, —$NHC(O)R^{28}$, —$C(O)NH_2$, —$C(O)NHR^{28}$, —$C(O)NR^{28}R^{29}$, —$NHS(O)_2R^{28}$, wherein $R^{28}$ and $R^{29}$ are independently selected from $C_1$-$C_6$alkyl, $C_2$-$C_6$alkenyl, $C_2$-$C_6$alkynyl, $C_3$-$C_{10}$cycloalkyl, $C^4$-$C_{10}$cycloalkenyl, $C_6$-$C_{10}$aryl, $C_6$-$C_{10}$ aryl $C_1$-$C_3$alkyl, $C_6$-$C_{10}$ heteroaryl and $C_3$-$C_{10}$heterocyclic.

In other particular aspects of the invention a compound of the formula III is employed,

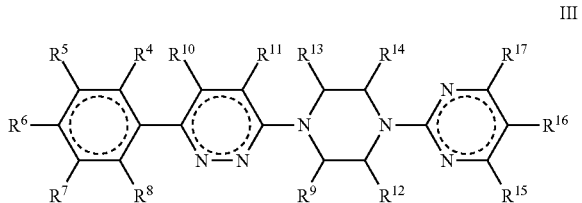

wherein $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, and $R^{17}$ are independently hydrogen, hydroxyl, alkyl, alkenyl, alkynyl, alkylene, alkenylene, alkoxy, alkenyloxy, cycloalkyl, cycloalkenyl, cycloalkynyl, cycloalkoxy, aryl, aryloxy, arylalkoxy, aroyl, heteroaryl, heterocyclic, acyl, acyloxy, amino, imine, azido, thiol, thioalkyl, thioalkoxy, thioaryl, nitro, cyano, halo, sulfoxide, sulfate, sulfonyl, sulfenyl, sulfinyl, sulfonate, silyl, silyloxy, silylalkyl, silylthio, phosphonate, ureido, carboxyl, carbonyl, carbamoyl, or carboxamide.

In aspects of the invention $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, and $R^{17}$ are independently selected from hydrogen, $C_1$-$C_6$ alkyl, $C_2$-$C_6$ alkenyl, $C_2$-$C_6$ alkynyl, $C_1$-$C_6$alkoxy, $C_2$-$C_6$ alkenyloxy, $C_3$-$C_{10}$ cycloalkyl, $C_4$-$C_{10}$cycloalkenyl, $C_3$-$C_{10}$cycloalkoxy, $C_6$-$C_{10}$aryl; $C_6$-$C_{10}$aryloxy, $C_6$-$C_{10}$aryl-$C_1$-$C_3$ alkoxy, $C_6$-$C_{10}$aroyl, $C_6$-$C_{10}$heteroaryl, $C_3$-$C_{10}$heterocyclic, $C_1$-$C_6$acyl, $C_1$-$C_6$ acyloxy, —$NH_2$, —$NHR^{28}$, —$NR^{28}R^{29}$, =$NR^{28}$, —$S(O)_2R^{28}$, —SH, —$SO_3H$, nitro, cyano, halo, haloalkyl, haloalkoxy, hydroxyalkyl, —$CO_2H$, —$CO_2R^{28}$, —NHC(O)$R^{28}$, —C(O)$NH_2$, —C(O)$NHR^{28}$, —C(O)$NR^{28}R^{29}$, —NHS(O)$_2R^{28}$, wherein $R^{28}$ and $R^{29}$ are independently selected from $C_1$-$C_6$alkyl, $C_2$-$C_6$alkenyl, $C_2$-$C_6$alkynyl, $C_3$-$C_{10}$cycloalkyl, $C_4$-$C_{10}$cycloalkenyl, $C_6$-$C_{10}$aryl, aryl $C_1$-$C_3$alkyl, $C_6$-$C_{10}$ heteroaryl and $C_3$-$C_{10}$heterocyclic.

In general, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, and $R^{17}$ in a compound of the formula III cannot all be hydrogen. In aspects of the invention a compound of the formula III is provided wherein both of $R^{10}$ and $R^{11}$ are not hydrogen. In other aspects of the invention a compound of the formula II is provided wherein $R^{11}$ is not hydrogen.

In further aspects of the invention, pure, in particular, substantially pure; compounds of the formula III are employed wherein $R^4$, $R^5$, $R^6$, $R^7$, $R^8$, $R^9$, $R^{10}$, $R^{12}$, $R^{13}$, $R^{14}$, $R^{15}$, $R^{16}$, and $R^{17}$ are independently hydrogen, hydroxyl, alkyl, alkenyl, alkynyl, alkylene, alkenylene, alkoxy, alkenyloxy, cycloalkyl, cycloalkenyl, aryl, aryloxy, arylalkoxy, aroyl, heteroaryl, heterocyclic, acyl, acyloxy, amino, imino, azido, thiol, thioalkyl, thioalkoxy, thioaryl, nitro, cyano, halo, silyl, silyloxy, silylalkyl, silylthio, =O, =S, carboxyl, carbonyl, carbamoyl, or carboxamide, and $R^{11}$ is alkyl, alkenyl, alkynyl, alkylene, alkenylene, alkoxy, alkenyloxy, cycloalkyl, cycloalkenyl, aryl, aryloxy, arylalkoxy, aroyl, heteroaryl, acyl, acyloxy, amino, azido, thiol, thioalkyl, thioalkoxy, thioaryl, nitro, cyano, halo, silyl, silyloxy, silylalkyl, silylthio, =O, =S, carboxyl, carbonyl, carbamoyl, or carboxamide; or an isomer, a pharmaceutically acceptable salt, or derivative thereof. In aspects of the invention $R^{11}$ is $C_1$-$C_6$ alkyl, $C_2$-$C_6$ alkenyl, $C_2$-$C_6$ alkynyl, $C_1$-$C_6$alkoxy, $C_2$-$C_6$ alkenyloxy, $C_3$-$C_{10}$ cycloalkyl, $C_4$-$C_{10}$cycloalkenyl, $C_3$-$C_{10}$cycloalkoxy, $C_6$-$C_{10}$aryl, $C_6$-$C_{10}$aryloxy, $C_6$-$C_{10}$aryl-$C_1$-$C_3$alkoxy, $C_6$-$C_{10}$aroyl, $C_6$-$C_{10}$heteroaryl, $C_3$-$C_{10}$heterocyclic, $C_1$-$C_6$acyl, $C_1$-$C_6$acyloxy, —$NH_2$, —$NHR^{28}$, —$NR^{28}R^{29}$, =$NR^{28}$, —$S(O)_2R^{28}$, —SH, —$SO_3H$, nitro, cyano, halo, haloalkyl, haloalkoxy, hydroxyalkyl, —$CO_2H$, —$CO_2R^{28}$, —NHC(O)$R^{28}$, —C(O)$NH_2$, —C(O)$NHR^{28}$, —C(O)$NR^{28}R^{29}$, —NHS(O)$_2R^{28}$, wherein $R^{28}$ and $R^{29}$ are independently selected from $C_1$-$C_6$alkyl, $C_2$-$C_6$alkenyl, $C_2$-$C_6$alkynyl, $C_3$-$C_{10}$cycloalkyl, $C_4$-$C_{10}$cycloalkenyl, $C_6$-$C_{10}$aryl, $C_6$-$C_{10}$ aryl $C_1$-$C_3$alkyl, $C_6$-$C_{10}$ heteroaryl and $C_3$-$C_{10}$heterocyclic.

In certain aspects a compound of the formula III is employed wherein $R^4$, $R^5$, $R^6$, $R^7$, $R^8$, $R^9$, $R^{12}$, $R^{13}$, $R^{14}$, $R^{15}$, $R^{16}$, and $R^{17}$ are hydrogen, hydroxyl, alkyl, and one or both of $R^{10}$ and $R^{11}$ are independently substituted or unsubstituted hydrogen, hydroxyl, alkyl, alkenyl, alkynyl, alkylene, alkenylene, alkoxy, alkenyloxy, cycloalkyl, cycloalkenyl, aryl, aryloxy, arylalkoxy, aroyl, heteroaryl, heterocyclic, acyl, acyloxy, sulfonyl, sulfinyl, sulfenyl, amino, imino, azido, thiol, thioalkyl, thioalkoxy, thioaryl, nitro, ureido, cyano, halo, silyl, silyalkyl, silyloxy, silylthio, =O, =S, carboxyl, carbonyl, or carbamoyl, or an isomer or a pharmaceutically acceptable salt thereof. In aspects of the invention one or both of $R^{10}$ and $R^{11}$ are independently $C_1$-$C_6$ alkyl, $C_2$-$C_6$ alkenyl, $C_2$-$C_6$ alkynyl, $C_1$-$C_6$alkoxy, $C_2$-$C_6$ alkenyloxy; $C_3$-$C_{10}$ cycloalkyl, $C_4$-$C_{10}$cycloalkenyl, $C_3$-$C_{10}$cycloalkoxy, $C_6$-$C_{10}$aryl, $C_6$-$C_{10}$aryloxy, $C_6$-$C_{10}$aryl-$C_1$-$C_3$alkoxy, $C_6$-$C_{10}$aroyl, $C_6$-$C_{10}$heteroaryl, $C_3$-$C_{10}$heterocyclic, $C_1$-$C_6$acyl, $C_1$-$C_6$acyloxy, —$NH_2$, —$NHR^{28}$, —$NR^{28}R^{29}$, =$NR^{28}$, —$S(O)_2R^{28}$, —SH, —$SO_3H$, nitro, cyano, halo, haloalkyl, haloalkoxy, hydroxyalkyl, —$CO_2R^{28}$, —NHC(O)$R^{28}$, —C(O)$NH_2$, —C(O)$NHR^{28}$, —C(O)$NR^{28}R^{29}$, —NHS(O)$_2R^{28}$, wherein $R^{28}$ and $R^{29}$ are independently selected from $C_1$-$C_6$alkyl, $C_2$-$C_6$alkenyl, $C_2$-$C_6$alkynyl, $C_3$-$C_{10}$cycloalkyl, $C_4$-$C_{10}$cycloalkenyl, $C_6$-$C_{10}$aryl, $C_6$-$C_{10}$ aryl $C_1$-$C_3$alkyl, $C_6$-$C_{10}$ heteroaryl and $C_3$-$C_{10}$heterocyclic.

In certain aspects a compound of the formula III is employed wherein $R^4$; $R^5$, $R^6$, $R^7$, $R^8$, $R^9$, $R^{12}$, $R^{13}$, $R^{14}$, $R^{15}$, $R^{16}$, and $R^{17}$ are hydrogen; and $R^{10}$ is $C_1$-$C_6$ alkyl, $C_2$-$C_6$ alkenyl, $C_2$-$C_6$ alkynyl, $C_1$-$C_6$alkoxy, $C_2$-$C_6$ alkenyloxy, $C_3$-$C_{10}$ cycloalkyl, $C_4$-$C_{10}$cycloalkenyl, $C_3$-$C_{10}$cycloalkoxy, $C_6$-$C_{10}$aryl, $C_6$-$C_{10}$aryloxy, $C_6$-$C_{10}$aryl-$C_1$-$C_3$ alkoxy, $C_6$-$C_{10}$aroyl, $C_6$-$C_{10}$heteroaryl, $C_3$-$C_{10}$heterocyclic, $C_1$-$C_6$acyl, $C_1$-$C_6$acyloxy, —$NHR^{28}$, —$NR^{28}R^{29}$, =$NR^{28}$, —$S(O)_2R^{28}$, —SH, —$SO_3H$, nitro, cyano, halo, haloalkyl, haloalkoxy, hydroxyalkyl, —$CO_2H$, —$CO_2R^{28}$, —NHC(O)$R^{28}$, —C(O)$NH_2$, —C(O)$NHR^{28}$, —C(O)$NR^{28}R^{29}$, —NHS(O)$_2R^{28}$ wherein $R^{28}$ and $R^{29}$ are independently selected from $C_1$-$C_6$alkyl, $C_2$-$C_6$alkenyl, $C_2$-$C_6$alkynyl, $C_3$-$C_{10}$cycloalkyl, $C_4$-$C_{10}$cycloalkenyl, $C_6$-$C_{10}$aryl, $C_6$-$C_{10}$ aryl $C_1$-$C_3$alkyl, heteroaryl and $C_3$-$C_{10}$heterocyclic.

In certain aspects a compound of the formula III is employed wherein $R^4$, $R^5$, $R^6$, $R^7$, $R^8$, $R^9$, $R^{12}$, $R^{13}$, $R^{14}$, $R^{15}$, $R^{16}$, and $R^{17}$ are hydrogen; $R^{10}$ is hydrogen, hydroxyl, alkyl (e.g., $C_1$-$C_6$ alkyl), aryl [e.g., $C_6$-$C_{10}$aryl, in particular, phenyl which is optionally substituted (e.g., with halide)], $C_3$-$C_{10}$heterocyclic (e.g., piperazinyl which may be substituted, for example substituted with a pyrimidinyl; or morpholinyl which may be substituted), —$NR^3OR^{31}$ wherein $R^{30}$ is hydrogen or alkyl, and $R^{31}$ is phenyl which may be substituted or alkyl (e.g., $C_1$-$C_6$ alkyl) which may be substituted [e.g. with amino, in particular —$CH_2CH_2NH_2$; $CH_2CH_2NHCOOC(CH_3)_3$], or —$SR^{32}$ wherein $R^{32}$ is phenyl which may be substituted; and $R^{11}$ is hydrogen, alkyl, or aryl (e.g., $C_6$-$C_{10}$aryl, in particular, e.g. phenyl) which may be substituted.

In aspects of the invention $R^{11}$ is alkyl, halo, aryl, substituted aryl (e.g. alkylaryl), or an unsaturated 5 to 6 membered heteromonocyclyl group containing 1 to 4 nitrogen atoms In an embodiment $R^{11}$ is lower alkyl (e.g., $C_1$-$C_6$ alkyl) or a branched alkyl. In another embodiment, $R^{11}$ is $C_6$-$C_{10}$aryl, in particular phenyl. In another embodiment, $R^{11}$ is halo. In a still further embodiment, $R^{11}$ is an unsaturated 5 to 6 membered heteromonocyclyl group containing 1 to 4 nitrogen atoms, for example, pyrrolyl, pyrrolinyl, imidazolyl, pyrazolyl, 2-pyridyl, 3-pyridyl, 4-pyridyl, pyridinyl, pyrimidinyl, pyrazinyl, pyridazinyl, triazolyl, tetrazolyl and the like. In a particular embodiment, $R^{11}$ is pyridinyl.

In certain aspects of the invention a compound of the formula III is employed wherein $R^{10}$ is hydrogen, halo, optionally substituted hydroxyl, alkyl, pyridinyl, phenyl, benzyl, piperazinyl, amino, morpholinyl, or —$SR^{33}$ wherein $R^{33}$ is alkyl or aryl. In an embodiment, $R^{10}$ is —$NH[CH_2]_m NR^{34}R^{35}$ wherein m is 1 to 6, in particular 2 to 4, $R^{34}$ is hydrogen, $R^{35}$ is a carboxyl, in particular —$COOC(CH_3)_3$.

In particular embodiments of the invention, one of $R^{10}$ and $R^{11}$ in a compound of the formula III is a heteroaryl in particular an unsaturated 5 to 6 membered heteromonocyclyl group containing 1 to 4 nitrogen atoms, more particularly pyridinyl, and the other of $R^{10}$ and $R^{11}$ is hydrogen.

In an aspect of the invention a compound of the formula III is employed wherein $R^{11}$ is hydrogen, halo, optionally substituted alkyl, pyridinyl, piperidinyl, morpholinyl, piperazinyl, or phenyl.

In aspects of the invention, a compound of the formula III is used wherein $R^4$, $R^5$, $R^6$, $R^7$, $R^8$, $R^9$, $R^{10}$, $R^{12}$, $R^{13}$, $R^{14}$, $R^{15}$, $R^{16}$, and $R^{17}$ are hydrogen, alkyl, alkoxy, sulfonyl, sulfinyl, halo, thiol, or carboxyl, and $R^{11}$ is alkyl, alkenyl, alkoxy, alkenyloxy, aryl, heteroaryl, acyl, acyloxy, amino, imino, azide, thiol, thioalkyl, thioalkoxy, thioaryl, nitro, cyano; halo, silyl, =O, =S, carboxyl, carbonyl, carbamoyl, or carboxamide; or an isomer or a pharmaceutically acceptable salt thereof. In particular aspects, $R^{11}$ is $C_1$-$C_6$ alkyl, $C_2$-$C_6$ alkenyl, $C_1$-$C_6$alkoxy, $C_2$-$C_6$ alkenyloxy, $C_6$-$C_{10}$aryl, $C_6$-$C_{10}$heteroaryl, $C_1$-$C_6$acyl, $C_1$-$C_6$acyloxy, —$NH_2$— $NHR^{28}$, —$NR^{28}R^{29}$, —$NR^{28}$, —$S(O)_2R^{28}$, —SH, —$SO_3H$, nitro, cyano, halo, haloalkyl, haloalkoxy, —$CO_2H$, —$CO_2R^{28}$, —$NHC(O)R^{28}$, —$C(O)NH_2$, —$C(O)NHR^{28}$, —$C(O)NR^{28}R^{29}$, —$NHS(O)_2R^{28}$, wherein $R^{28}$ and $R^{29}$ are independently selected from $C_1$-$C_6$alkyl, $C_2$-$C_6$alkenyl, $C_2$-$C_6$alkynyl, $C_3$-$C_{10}$cycloalkyl, $C_4$-$C_{10}$cycloalkenyl, $C_6$-$C_{10}$aryl, $C_6$-$C_{10}$ aryl $C_1$-$C_3$alkyl, heteroaryl and $C_3$-$C_{10}$heterocyclic.

In aspects of the invention, a compound of the formula III is employed wherein $R^4$, $R^5$, $R^6$, $R^7$, $R^8$, $R^9$, $R^{10}$, $R^{12}$, $R^{13}$, $R^{14}$, $R^{15}$, $R^{16}$, and $R^{17}$ are hydrogen, and $R^{11}$ is alkyl, alkenyl, alkynyl, alkylene, alkoxy, aryl, or an unsaturated 5 to 6 membered heteromonocyclyl group containing 1 to 4 nitrogen atoms. In particular aspects, $R^4$, $R^5$, $R^6$, $R^7$, $R^8$, $R^9$, $R^{10}$, $R^{12}$, $R^{13}$, $R^{14}$, $R^{15}$, $R^{16}$, and $R^{17}$ are hydrogen and $R^{11}$ is alkyl or pyridinyl, more particularly $R^{11}$ is alkyl.

In other aspects of the invention, one of $R^{10}$ and $R^{11}$ in a compound of the formula III is alkyl, in particular $C_1$-$C_6$ alkyl and the other of $R^{10}$ and $R^{11}$ is hydrogen.

In particular embodiments of the invention, one of $R^{10}$ and $R^{11}$ in a compound of the formula III is aryl in particular $C_6$-$C_{10}$aryl, more particularly phenyl or benzyl, and the other of $R^{10}$ and $R^{11}$ is hydrogen.

In embodiments of the invention, the compound of the formula II is a compound in Table 1 or 2.

In particular embodiments of the invention, the compound of the formula III is MW01-6-189WH, MW01-5-188WH, MW01-2-151SRM, and/or a salt or derivatives thereof.

In more particular embodiments, the compound of the formula II is 4-methyl-6-phenyl-3-(4-pyrimidin-2-ylpiperazin-1-yl)pyridazine (MW01-2-151SRM), and/or a salt or derivative thereof.

In more particular embodiments, the compound of the formula II is 4,6-diphenyl-3-(4-pyrimidin-2-ylpiperazin-1-yl)pyridazine (MW01-5-188WH), and/or a salt or derivative thereof.

A compound of the formula I, II or III may be in the form of a prodrug that is converted in vivo to an active compound. For example, in a compound of the formula II one or more of $R^{10}$ and $R^{11}$ may comprise a cleavable group that is cleaved after administration to a subject to provide an active (e.g., therapeutically active) compound, or an intermediate compound that subsequently yields the active compound. A cleavable group can be an ester that is removed either enzymatically or non-enzymatically.

A compound of the formula I, II or III may comprise a carrier, such as one or more of a polymer, carbohydrate, peptide or derivative thereof, which may be directly or indirectly covalently attached to the compound. A carrier may be substituted with substituents described herein including without limitation one or more alkyl, amino, nitro, halogen, thiol, thioalkyl, sulfate, sulfonyl, sulfinyl, sulfoxide, hydroxyl groups. In aspects of the invention the carrier is an amino acid including alanine, glycine, praline, methionine, serine, threonine, asparagine, alanyl-alanyl, prolyl-methionyl, or glycyl-glycyl. A carrier can also include a molecule that targets a compound of the formula I, II or III to a particular tissue or organ. Thus, a carrier may facilitate or enhance transport of a compound of the formula I, II or III to the brain.

Compounds of the formula I, II or III can be prepared using reactions and methods generally known to the person of ordinary skill in the art, having regard to that knowledge and the disclosure of this application including the Examples. The reactions are performed in solvent appropriate to the reagents and materials used and suitable for the reactions being effected. It will be understood by those skilled in the art of organic synthesis that the functionality present on the compounds should be consistent with the proposed reaction steps. This will sometimes require modification of the order of the synthetic steps or selection of one particular process scheme over another in order to obtain a desired compound of the invention. It will also be recognized that another major consideration in the development of a synthetic route is the selection of the protecting group used for protection of the reactive functional groups present in the compounds described in this invention. An authoritative account describing the many alternatives to the skilled artisan is Greene and Wuts (Protective Groups In Organic Synthesis, Wiley and Sons, 1991).

The starting materials, and reagents used in preparing compounds or the invention are either available from commercial suppliers or are prepared by methods well known to a person of ordinary skill in the art, following procedures described in such references as Fieser and Fieser's *Reagents for Organic Synthesis*, vols. 1-17, John Wiley and Sons, New York, N.Y., 1991; *Rodd's Chemistry of Carbon Compounds*, vols. 1-5 and supps., Elsevier Science Publishers, 1989; Organic Reactions, vols. 1-40, John Wiley and Sons, New York, N.Y., 1991; March J.; *Advanced Organic Chemistry*, 4th ed., John Wiley and Sons, New York, N.Y.; and Larock: *Comprehensive Organic Transformations*, VCH Publishers, New York, 1989.

The starting materials, intermediates, and compounds of the formula I, II or III may be isolated and purified using conventional techniques, such as precipitation, filtration, distillation, crystallization, chromatography, and the like. The compounds of the formula I, II or III may, be characterized using conventional methods, including physical constants and spectroscopic methods, in particular HPLC.

The compounds of the formula I, II or III which are basic in nature can form a wide variety of different salts with various inorganic and organic acids. In practice is it desirable to first isolate a compound of the formula I, II or III from the reaction mixture as a pharmaceutically unacceptable salt and then convert the latter to the free base compound by treatment with an alkaline reagent and subsequently convert the free base to a pharmaceutically acceptable acid addition salt. The acid addition salts of the base compounds of the formula I, II or III are readily prepared by treating the base compound with a substantially equivalent amount of the chosen mineral or inorganic or organic acid in an aqueous solvent medium or in a suitable organic solvent such as methanol or ethanol. Upon careful evaporation of the solvent, the desired solid salt is obtained.

Compounds of the formula I, II or III which are acidic in nature are capable of forming base salts with various pharmacologically acceptable cations. These salts may be prepared by conventional techniques by treating the corresponding acidic compounds with an aqueous solution containing the desired pharmacologically acceptable cations and then evaporating the resulting solution to dryness, preferably under reduced pressure. Alternatively, they may be prepared by mixing lower alkanolic solutions of the acidic compounds and the desired alkali metal alkoxide together and then evaporating the resulting solution to dryness in the same manner as before. In either case, stoichiometric quantities of reagents are typically employed to ensure completeness of reaction and maximum product yields.

In particular aspects, the present invention provides methods of making the compounds disclosed herein, comprising the steps provided (See, for example, the Figures and Examples).

In an aspect, the invention provides a process for preparing a compound of the formula III wherein $R^{11}$ is hydrogen and $R^{10}$ is an unsaturated 5 to 6 membered heteromonocyclyl group containing 1 to 4 nitrogen atoms, in particular, pyrrolyl, pyrrolinyl, imidazolyl, pyrazolyl, 2-pyridyl, 3-pyridyl, 4-pyridyl, pyridinyl, pyrimidinyl, pyrazinyl, pyridazinyl, triazolyl, tetrazolyl; more particularly pyridinyl, which comprises reacting a compound of the formula III wherein $R^{10}$ is halo, in particular chloro, and $R^{12}$ is hydrogen with boronic acid substituted with an unsaturated 5 to 6 membered heteromonocyclyl group containing 1 to 4 nitrogen atoms, in particular, pyrrolyl, pyrrolinyl, imidazolyl, pyrazolyl, 2-pyridyl, 3-pyridyl, 4-pyridyl, pyridinyl, pyrimidinyl, pyrazinyl, pyridazinyl, triazolyl, or tetrazolyl, more particularly pyridinyl, under suitable conditions to prepare a compound of the formula III wherein $R^{11}$ is hydrogen and $R^{10}$ is an unsaturated 5 to 6 membered heteromonocyclyl group containing 1 to 4 nitrogen atoms, in particular, pyrrolyl, pyrrolinyl, imidazolyl, pyrazolyl, 2-pyridyl, 3-pyridyl, 4-pyridyl, pyridinyl, pyrimidinyl, pyrazinyl, pyridazinyl, triazolyl, or tetrazolyl, more particularly pyridinyl.

In another aspect, the invention provides a process for preparing a compound of the formula III wherein $R^{11}$ is hydrogen and $R^{10}$ is a substituted aryl which comprises reacting a compound of the formula III wherein $R^{11}$ is halo, in particular chloro, and $R^{10}$ is hydrogen, with a substituted aryl boronic acid under suitable conditions to prepare a compound of the formula III wherein $R^{11}$ is hydrogen and $R^{10}$ is a substituted aryl.

In another aspect, the invention provides a process for preparing a compound of the formula III wherein $R^{10}$ is hydrogen and $R^{11}$ is alkyl which comprises reacting a compound of the formula III wherein $R^{11}$ is halo, in particular chloro, and $R^{10}$ is hydrogen, with an alkyl boronic acid under suitable conditions to prepare a compound of the formula III wherein $R^{10}$ is hydrogen and $R^{11}$ is alkyl. In an embodiment, $R^{11}$ is lower alkyl, in particular methyl or ethyl, and a compound of the formula III wherein $R^{11}$ is chloro is reacted with lower alkyl boronic acid, in particular methyl or ethyl boronic acid under suitable conditions.

In another aspect, the invention provides a process for preparing a compound of the formula III wherein $R^{10}$ is hydrogen and $R^{11}$ is aryl which comprises reacting a compound of the formula III wherein $R^{10}$ is hydrogen and $R^{11}$ is halo (e.g., chloro), with pyridazine substituted at the C3 position with halo (e.g., chloro), at the C4 position with aryl, and at the 6 position with phenyl, with 2-(piperidin-4-yloxy)pyrimidine under suitable conditions to prepare a compound of the formula III wherein $R^{10}$ is hydrogen and $R^{11}$ is aryl. In an embodiment, $R^{11}$ is phenyl.

In another aspect, the invention provides a process for preparing a compound of the formula III wherein $R^{10}$ is hydrogen and $R^{11}$ is an unsaturated 5 to 6 membered heteromonocyclyl group containing 1 to 4 nitrogen atoms, in particular, pyrrolyl, pyrrolinyl, imidazolyl, pyrazolyl, 2-pyridyl, 3-pyridyl, 4-pyridyl, pyridinyl, pyrimidinyl, pyrazinyl, pyridazinyl, triazolyl, or tetrazolyl, more particularly pyridinyl which comprises reacting a compound of the formula III wherein $R^{11}$ is halo, in particular chloro, and $R^{10}$ is hydrogen, with a boronic acid substituted with an unsaturated 5 to 6 membered heteromonocyclyl group containing 1 to 4 nitrogen atoms, in particular, pyrrolyl, pyrrolinyl, imidazolyl, pyrazolyl, pyridyl, 4-pyridyl, pyridinyl, pyrimidinyl, pyrazinyl, pyridazinyl, triazolyl, or tetrazolyl, more particularly pyridinyl, wider suitable conditions to prepare a compound of the formula III wherein $R^{10}$ is hydrogen and $R^{11}$ is an unsaturated 5 to 6 membered heteromonocyclyl group containing 1 to 4 nitrogen atoms, in particular, pyrrolyl, pyrrolinyl, imidazolyl, pyrazolyl, 2-pyridyl, 3-pyridyl, 4-pyridyl, pyridinyl, pyrazinyl, pyridazinyl, triazolyl, or tetrazolyl, more particularly pyridinyl.

In an embodiment, the invention provides a process for preparing a compound of the formula III wherein $R^{10}$ is hydrogen and $R^{11}$ is pyridinyl which comprises reacting a compound of the formula III wherein $R^{11}$ is halo, in particular chloro, and $R^{10}$ is hydrogen, with a pyridinyl boronic acid under suitable conditions to prepare a compound of the formula III wherein $R^{10}$ is hydrogen and $R^{11}$ is pyridinyl.

In another aspect, the invention provides a process for preparing a compound of the formula III wherein $R^{10}$ is hydrogen and $R^{11}$ is an unsaturated 5 to 6 membered heteromonocyclyl group containing 1 to 4 nitrogen atoms, in particular, pyrrolyl, pyrrolinyl, imidazolyl, pyrazolyl, 2-pyridyl, 3-pyridyl, 4-pyridyl, pyridinyl, pyrimidinyl, pyrazinyl, pyridazinyl, triazolyl, or tetrazolyl, more particularly pyridinyl which comprises reacting a pyridazine substituted at the C3 position with halo, at the C4 position with an unsaturated 5 to 6 membered heteromonocyclyl group containing 1 to 4 nitrogen atoms, in particular, pyrrolyl, pyrrolinyl, imidazolyl, pyrazolyl, 2-pyridyl; 3-pyridyl, 4-pyridyl, pyridinyl, pyrimidinyl, pyrazinyl, pyridazinyl, triazolyl, or tetrazolyl, more particularly pyridinyl, and at the 6 position with phenyl, with 2-(piperidin-4-yloxy)pyrimidine under suitable conditions to prepare a compound of the formula III wherein $R^{10}$ is hydrogen and $R^{11}$ is an unsaturated 5 to 6 membered heteromonocyclyl group containing 1 to 4 nitrogen atoms, in particular, pyrrolyl, pyrrolinyl, imidazolyl, pyrazolyl, 2-pyridyl, 3-pyridyl, 4-pyridyl, pyridinyl, pyrimidinyl, pyrazinyl, pyridazinyl, triazolyl, or tetrazolyl, more particularly pyridinyl.

In an embodiment, the invention provides a process for preparing a compound of the formula III wherein $R^{10}$ is hydrogen and $R^{11}$ is pyridinyl which comprises reacting a pyridazine substituted at the C3 position with halo, at the C4 position with pyridinyl, and at the 6 position with phenyl, with 2-(piperidin-4-yloxy)pyrimidine under suitable conditions to prepare a compound of the formula III wherein $R^{10}$ is hydrogen and $R^{11}$ is pyridinyl.

In another aspect, the invention provides a process for preparing a compound of the formula III wherein $R^{10}$ is hydrogen and $R^{11}$ is piperidinyl or substituted piperidinyl which comprises reacting a compound of the formula II wherein $R^{11}$ is halo, in particular chloro, and $R^{10}$ is hydrogen with piperazinyl or substituted piperazinyl under suitable conditions to prepare a compound of the formula II wherein $R^{10}$ is hydrogen and $R^{11}$ is piperidinyl or substituted piperidinyl.

In another aspect, the invention provides a process for preparing a compound of the formula III wherein $R^{10}$ is hydrogen and $R^{11}$ is an alkyl which comprises reacting a pyridazine substituted at the C3 position with halo (e.g., chloro), at the C4 position with alkyl, and at the 6 position with phenyl, with 2-(piperidin-4-yloxy)pyrimidine under suitable conditions to prepare a compound of the formula III wherein $R^{10}$ is hydrogen and is an alkyl. In an embodiment, $R^{11}$ is methyl or ethyl.

In a particular aspect, the invention provides a process for preparing a compound of the formula III wherein $R^{10}$ is hydrogen and $R^{11}$ is alkyl comprising reacting a compound of the formula IV

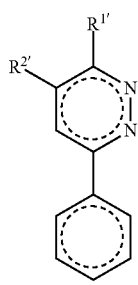

IV wherein $R^{1'}$ is halo, in particular chloro or bromo, more particularly chloro and $R^{2'}$ is alkyl with 2-(piperazin-1-yl)pyrimidine under suitable conditions, in particular under reflux conditions to produce a compound of the formula III wherein $R^{10}$ is hydrogen and $R^{11}$ is alkyl.

Therapeutic efficacy and toxicity of compounds, compositions and methods of the invention may be determined by standard pharmaceutical procedures in cell cultures or with experimental animals such as by calculating a statistical parameter such as the $ED_{50}$ (the dose that is therapeutically effective in 50% of the population) or $LD_{50}$ (the dose lethal to 50% of the population) statistics. The therapeutic index is the dose ratio of therapeutic to toxic effects and it can be expressed as the $ED_{50}/LD_{50}$ ratio. Pharmaceutical compositions which exhibit large therapeutic indices are preferred. By way of example, one or more of the therapeutic effects can be demonstrated in a subject or disease model, for example, a TgCRND8 mouse with symptoms of Alzheimer's disease.

Biological investigations were done with compounds disclosed herein that were >95% homogenous as determined by HPLC/MS analysis. As part of a hierarchal, cell-based screening protocol, the compounds were screened for their ability to block IL-1β and TNFα production by BV-2 mouse microglial cells stimulated with LPS.

Compositions, Methods and Kits

The invention provides dosage forms, formulations, and methods that provide advantages, in particular lower risk of side effects (e.g. lower risk of QT-related side effects) and/or beneficial pharmacokinetic profiles, more particularly sustained pharmacokinetic profiles. A compound of the formula I, II or III can be utilized in dosage forms in pure or substantially pure form, in the form of its pharmaceutically acceptable salts, and also in other forms including anhydrous or hydrated forms.

A beneficial pharmacokinetic profile may be obtained by administering a formulation or dosage form suitable for once, twice a day, or three times a day or more administration comprising one or more compound of the formula I, II or III present in an amount sufficient to provide the required concentration or dose of the compound to an environment of use to treat a disease disclosed herein, in particular a neuroinflammatory disease. In an aspect, the environment of use is the brain and/or plasma.

Embodiments of the invention relate to a dosage form comprising one or more compound of the formula I, II or III that provides peak plasma concentrations of the compound, $C_{max}$, of between about 0.001 to 2 mg/ml, 0001 to 1 mg/ml, 0.0002 to 2 mend, 0.005 to 2 mg/ml, 001 to 2 mg/ml, 0.05 to 2 mg/ml, OA to 2 mg/ml, 0.001 to 0.5 mg/ml, 0.002 to 1 mg/ml, 0.005 to 1 mg/rill, 0.01 to 1 mg/ml, 005 to 1 mg/ml, or 0.1 to 1 mg/ml.

In further aspects, the invention provides a formulation or dosage form comprising one or more compound of the formula I, II or III that provides an elimination $t_{1/2}$ of 0.5 to 20 hours, 0.5 to 15 hours, 0.5 to 10 hours, 0.5 to 6 hours, 1 to 20 hours, 1 to 15 hours, 1 to 10 hours, or 1 to 6 hours.

Further aspects of the invention relate to a formulation or dosage form comprising one or more compound of the formula I, II or III that provides an AUC for plasma of about 3 to 2000 ng·h/ml, 3 to 3000 ng·h/ml, 3 to 4000 ng·h/ml, 2 to 2000 ng·h/ml, 2 to 3000 ng·h/ml, 2 to 4000 ng·h/ml, 1 to 2000 ng·h/ml, 1 to 3000 ng·h/ml, 1 to 4000 ng·h/ml, 1, and in particular 3 to 3000 ng·h/ml A subject may be treated with a compound of the formula I, II or III or composition or unit dosage thereof on substantially any desired schedule. They may be administered one or more times per day, in particular 1 or 2 times per day, once per week, once a month or continuously. However, a subject may be treated less frequently, such as every other day or once a week, or more frequently. A compound or composition may be administered to a subject for about or at least about 24 hours, 2 days, 3 days, 1 week, 2 weeks to 4 weeks, 2 weeks to 6 weeks, 2 weeks to 8 weeks, 2 weeks to 10 weeks, 2 weeks to 12 weeks, 2 weeks to 14 weeks, 2 weeks to 16 weeks, 2 weeks to 6 months, 2 weeks to 12 months, 2 weeks to 18 months, 2 weeks to 24 months, or for more than 24 months, periodically or continuously.

In an aspect, a beneficial pharmacokinetic profile can be obtained by the administration of a formulation or dosage form suitable for once, twice, or three times a day administration, preferably twice a day administration comprising one or more compound of the formula I, II or III present in an amount sufficient to provide the requited dose of the compound. In an aspect, the required dose of a compound of the formula I, II or III administered once twice, three times or more daily is about 0.01 to 3000 mg/kg, 0.01 to 2000 mg/kg, 0.5 to 2000 mg/kg, about 0.5 to 1000 mg/kg, 0.1 to 1000 mg/kg, 0.1 to 500 mg/kg, 0.1 to 400 mg/kg, 0.1 to 300 mg/kg, 0.1 to 200 mg/kg, 0.1 to 100 mg/kg, 0.1 to 50 mg/kg, 0.1 to 20 mg/kg, 0.1 to 10 mg/kg, 0.1 to 6 mg/kg, 0.1 to 5 mg/kg, 0.1 to 3 mg/kg, 0.1 to 2 mg/kg, 0.1 to 1 mg/kg, 1 to 1000 mg/kg, 1 to 500 mg/kg, 1 to 400 mg/kg, 1 to 300 mg/kg, 1 to 200 mg/kg, 1 to 100 mg/kg, 1 to 50 mg/kg, 1 to 20 mg/kg, 1 to 10 mg/kg, 1 to 6 mg/kg, 1 to 5 mg/kg, or 1 to 3 mg/kg, or 1 to 2.5 mg/kg, or less than or about 10 mg/kg, 5 mg/kg, 2.5 mg/kg, 1 mg/kg, or 0.5 mg/kg twice daily or less Certain dosage forms and formulations may minimize the variation between peak and trough plasma and/or brain levels of compounds of the formula I, II or III and in particular provide a sustained therapeutically effective amount of the compounds.

The invention also contemplates a formulation or dosage form comprising amounts of one or more compound of the formula I, II or III that results in therapeutically effective amounts of the compound over a dosing period, in particular a 24 hour dosing period. In aspects of the invention the therapeutically effective amounts of a compound of the formula I, II or III are between about 0.1 to 1000 mg/kg, 0.1 to 500 mg/kg, 0.1 to 400 mg/kg, 0.1 to 300 mg/kg, 0.1 to 200 mg/kg, 0.1 to 100 mg/kg, 0.1 to 75 mg/kg, 0.1 to 50 mg/kg, 0.1 to 25 mg/kg, 0.1 to 20 mg/kg, 0.1 to 15 mg/kg, 0.1 to 10 mg/kg, 0.1 to 9 mg/kg, 0.1 to 8 mg/kg, 0.1 to 7 mg/kg, 0.1 to 6 mg/kg, 0.1 to 5 mg/kg, 0.1 to 4 mg/kg, 0.1 to 3 mg/kg, 0.1 to 2 mg/kg, or 0.1 to 1 mg/kg.

A medicament or treatment of the invention may comprise a unit dosage of at least one compound of the formula I, II or III to provide therapeutic effects. A "unit dosage" or "dosage unit" refers to a unitary, i.e. a single dose, which is capable of being administered to a patient, and which may be readily handled and packed, remaining as a physically and chemically stable unit dose comprising either the active agents as such or a mixture with one or more solid or liquid pharmaceutical excipients, carriers, or vehicles.

A formulation or dosage form of the invention may be an immediate release dosage form or a non-immediate release delivery system, including without limitation a delayed-release or sustained-release dosage form.

In aspects, the invention provides a sustained-release dosage form of a compound of the formula I, II or III which advantageously achieves a more sustained drug plasma and/or brain level response while mitigating or eliminating drug concentration spikes by providing a substantially steady release of the compound over time. A substantially constant plasma concentration preferably correlates with one or more therapeutic effects disclosed herein. In embodiments, the sustained-release dosage form is for oral administration.

A composition, in particular a dosage form or formulation, may be in any form suitable for administration to a subject, including without limitation, a form suitable for oral, parenteral, intravenous (bolus or infusion), intraperitoneal, subcutaneous, or intraffinsculas administration. A dosage form or formulation may be a pill, tablet, caplet, soft and hard gelatin capsule, lozenge, sachet, cachet, vegicap, liquid drop, elixir, suspension, emulsion, solution, syrup, aerosol (as a solid or in a liquid medium) suppository, sterile injectable solution, and/or sterile packaged powder.

In an aspect of the invention a dosage form or formulation is an oral dosage form or formulation such as tablets, caplets, soft and hard gelatin capsules, pills, powders, granules, elixirs, tinctures, suspensions, syrups, and emulsions. In another aspect the dosage form or formulation is a parenteral dosage form such as an active substance in a sterile aqueous or non-aqueous solvent, such as water, isotonic saline, isotonic glucose solution, buffer solution, or other solvents conveniently used for parenteral administration.

A compound of the formula I, II or III of the invention may be formulated into a pharmaceutical composition for administration to a subject by appropriate methods known in the art. Pharmaceutical compositions of the present invention or fractions thereof comprise suitable pharmaceutically acceptable carriers, excipients, and vehicles selected based on the intended form of administration, and consistent with conventional pharmaceutical practices. Suitable pharmaceutical carriers, excipients, and vehicles are described in the standard text, *Remington: The Science and Practice of Pharmacy* (21$^{st}$ Edition. 2005, University of the Sciences in Philadelphia (Editor), Mack Publishing Company), and in The United States Pharmacopeia: The National Formulary (USP 24 NF19) published in 1999. By way of example for oral administration in the form of a capsule or tablet, the active components can be combined with an oral, non-toxic pharmaceutically acceptable inert carrier such as lactose, starch, sucrose, methyl cellulose, magnesium stearate, glucose, calcium sulfate, dicalcium phosphate, mannitol, sorbital, and the like. For oral administration in a liquid form, the chug components may be combined with any oral, non-toxic, pharmaceutically, acceptable inert carrier such as ethanol, glycerol, water, and the like. Suitable binders (e.g., gelatin, starch, corn sweeteners, natural sugars including glucose; natural and synthetic gums, and waxes), lubricants (e.g. sodium oleate, sodium stearate, magnesium stearate, sodium benzoate, sodium acetate, and sodium chloride), disintegrating agents (e.g. starch, methyl cellulose, agar, bentonite, and xanthan gum), flavoring agents, and coloring agents may also be combined in the compositions or components thereof. Compositions as described herein can further comprise wetting or emulsifying agents, or pH buffering agents.

A composition of the invention can be a liquid solution, suspension, emulsion, tablet, pill, capsule, sustained release formulation, or powder. The compositions can be formulated as a suppository, with traditional binders and carriers such as triglycerides. Oral formulations can include standard carriers such as pharmaceutical grades of mannitol, lactose, starch, magnesium stearate, sodium saccharine, cellulose, magnesium carbonate, etc. Various delivery systems are known and can be used to administer a composition of the invention, e.g. encapsulation in liposomes, microparticles, microcapsules, and the like.

Formulations for parenteral administration may include aqueous solutions, syrups, aqueous or oil suspensions and emulsions with edible oil such as cottonseed oil, coconut oil or peanut oil. Dispersing or suspending agents that can be used for aqueous suspensions include synthetic or natural gums, such as tragacanth, alginate, acacia, dextran, sodium carboxymethylcellulose, gelatin, methylcellulose, and polyvinylpyrrolidone.

Compositions for parenteral administration may include sterile aqueous or non-aqueous solvents, such as water, isotonic saline, isotonic glucose solution, buffer solution, or other solvents conveniently used for parenteral administration of therapeutically active agents. A composition intended for parenteral administration may also include conventional additives such as stabilizers, buffers, or preservatives, e.g. antioxidants such as methylhydroxybenzoate or similar additives.

A composition of the invention may be sterilized by, for example, filtration through a bacteria retaining filter, addition of sterilizing agents to the composition, irradiation of the composition, or heating the composition. Alternatively, the compounds or compositions of the present invention may be provided as sterile solid preparations e.g. lyophilized powder, which are readily dissolved in sterile solvent immediately prior to use.

After pharmaceutical compositions have been prepared, they can be placed in an appropriate container and labeled for treatment of an indicated condition. For administration of a composition of the invention, such labeling would include amount, frequency, and method of administration.

According to the invention, a kit is provided. In an aspect, the kit comprises a compound of the formula I, II or III or a formulation of the invention in kit form. The kit can be a package which houses a container which contains compounds of the formula I, II or III or formulations of the invention and also houses instructions for administering the compounds or formulations to a subject. The invention further relates to a commercial package comprising compounds of the formula I, II or III or formulations of the invention together with instructions for simultaneous, separate or sequential use. In particular a label may include amount, frequency, and method of administration.

The invention also provides a pharmaceutical pack or kit comprising one or more containers filled with one or more of the ingredients of a composition of the invention to provide a therapeutic effect. Associated with such container(s) can be various written materials such as instructions for use, or a notice in the form prescribed by a governmental agency regulating the labeling, manufacture, use or sale of pharmaceuticals or biological products, which notice reflects approval by the agency of manufacture, use, or sale for human administration.

The invention also relates to articles of manufacture and kits containing materials useful for treating a disease disclosed herein. An article of manufacture may comprise a container with a label. Examples of suitable containers include bottles, vials, and test tubes which may be formed from a variety of materials including glass and plastic. A container holds compounds of the formula I, II or III or formulations of the invention which are effective for treating a disease disclosed herein. The label on the container indicates that the compounds of the formula I, II or III or formulations of the invention are used for treating a disease disclosed herein and may also indicate directions for use. In aspects of the invention, a medicament or formulation in a container may comprise any of the medicaments or formulations disclosed herein.

The invention also contemplates kits comprising one or more of compounds of the formula I, II or III. In aspects of the invention, a kit of the invention comprises a container described herein. In particular aspects, a kit of the invention comprises a container described herein and a second container comprising a buffer. A kit may additionally include other materials desirable from a commercial and user standpoint, including, without limitation, buffers, diluents, filters, needles, syringes, and package inserts with instructions for performing any methods disclosed herein (e.g., methods for treating a disease disclosed herein). A medicament or formulation in a kit of the invention may comprise any of the formulations or compositions disclosed herein.

In aspects of the invention, the kits may be useful for any of the methods disclosed herein, including, without limitation treating a subject suffering from Alzheimer's disease. Kits of the invention may contain instructions for practicing any of the methods described herein.

The compositions and methods described herein are indicated as therapeutic agents or methods either alone or in conjunction with other therapeutic agents or other forms of treatment. They may be co-administered, combined or formulated with one or more therapies or agents used to treat a condition described herein. Compositions of the invention may be administered concurrently, separately, or sequentially with other therapeutic agents or therapies. Therefore, compounds of the formula I, II or III may be co-administered with one or more additional therapeutic agents for treating diseases disclosed herein including without limitation beta-secretase inhibitors, alpha-secretase inhibitors, and epsilon-secretase inhibitors, acetylcholinesterase inhibitors, agents that are used for the treatment of complications resulting from or associated with a disease disclosed herein, or general medications that treat or prevent side effects.

The invention will be described in greater detail by way of specific examples. The following examples are offered for illustrative purposes, and are not intended, to limit the invention in any manner.

EXAMPLES

Example 1

Synthesis of Pyridazine Compounds

The structures of MW01-2-151SRM, MW01-6-189WH, MW01-7-107WE, MW01-4-179LKM, WM01-7-084WH, MH01-7-085WH, MW01-7-133WH, and MW01-7-057 are shown in FIG. 1 and synthetic schemes for producing the compounds are described below.

A. Preparation of 2-(4-(6-phenylpyridazin-3-yl)piperazin-1-yl)pyrimidine (MW01-3-183WH)

FIG. 2 depicts a synthetic scheme for the preparation of 2-(4-(6-phenylpyridazin-3-yl)piperazin-1-yl)pyrimidine (MW01-3-183WH) Reagents and conditions: (a) 1-BuOH, $NH_4Cl$, and 2-(piperazin-1-yl)pyrimidine. A typical reaction mixture comprising about 0.01 mol of 3-chloro-6-phenylpyridazine by 2-(piperazin-1-yl)pyrimidine, about 0.05 mol of 2-(piperazin-1-yl)pyrimidine and about 0.01 mol of ammonium hydrochloride was prepared in about 15 ml of 1-BuOH. The mixture was stirred at about 130° C. for about 48 h, and then the solvent was removed under reduced pressure. The remaining residue was then extracted with ethyl acetate, washed with water and brine, dried over anhydrous $Na_2SO_4$. Removal of solvent followed by recrystallization from 95% ethanol yielded light yellow crystals, yield 96.4%; HPLC: 97.4% purity; HRMS calculated 318.1587. Found 31801579; $^1H$ NMR ($CDCl_3$): δ 8.356 (d, J=4.5, 2H), 8.011 (d, J=7.5, 11 2H), 7.692 (d, J=9.5, 1H), 7.468 (t, J=6.0, 2H), 7.417 (d, J=7.5, 1H), 7.047 (d, J=9.5, 1H), 6.546 (t, J=4.5, 1H), 4.013 (t, J=5.0, 4H), 3.826 (t, J=5.0, 4H).

B. Preparation of 4-methyl-6-phenyl-3-(4-pyrimidin-2-ylpiperazin-1-yl)pyridazine (MW01-2-151SRM)

Figure 3:
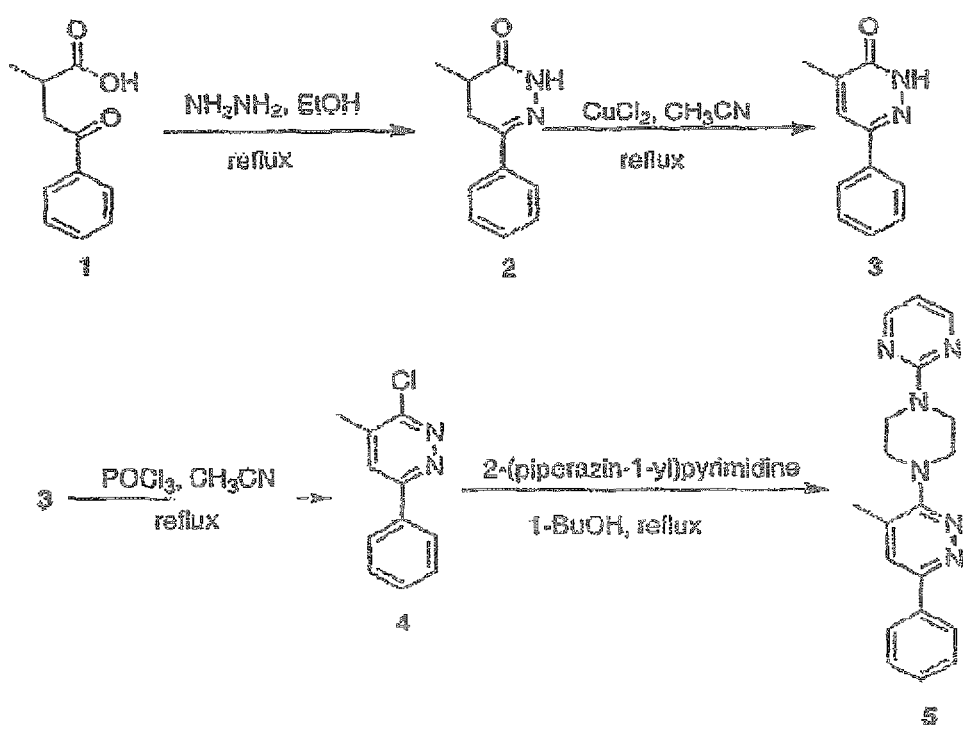
FIG. 3 depicts a synthetic scheme for MW01-2-151SRM.
Figure 4:
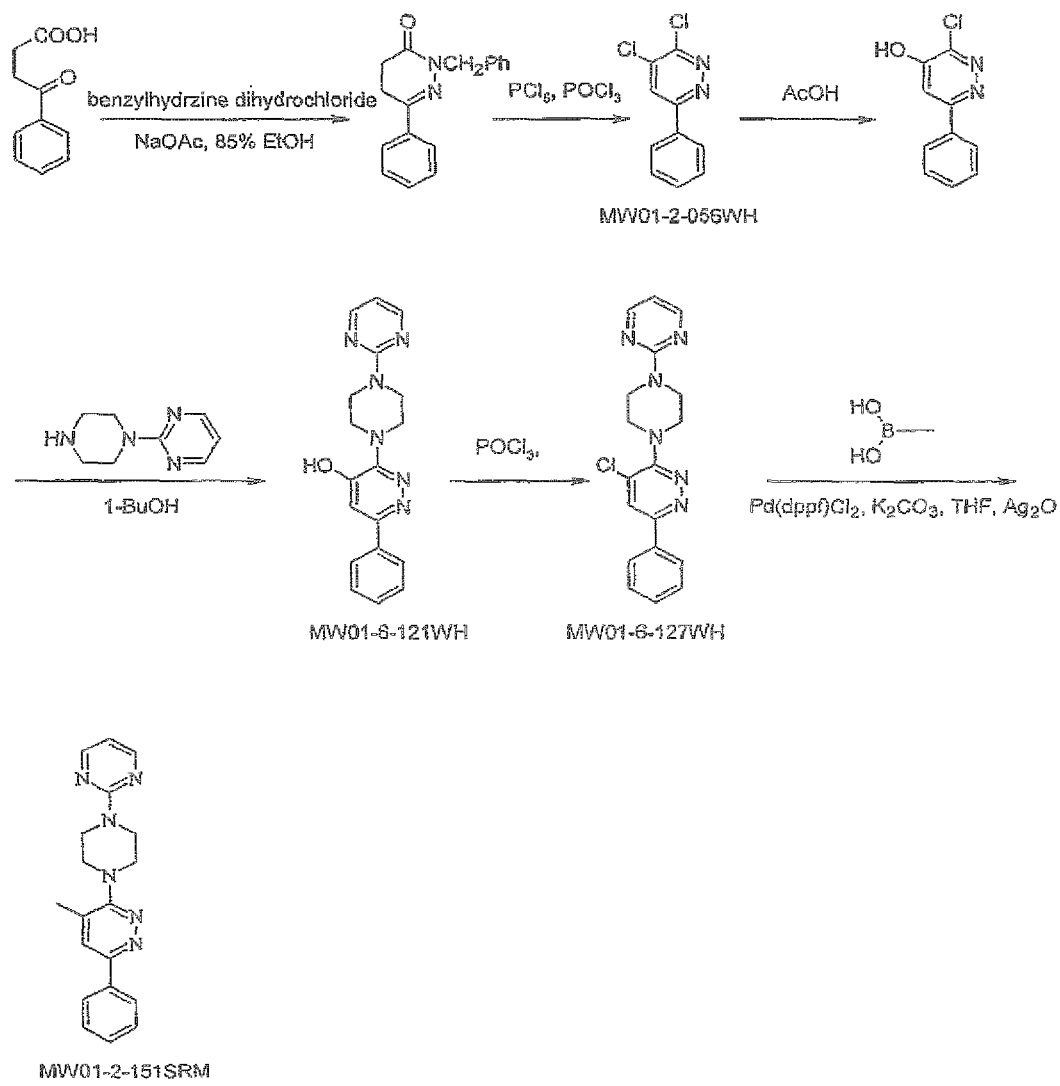
FIG. 4 depicts a synthetic scheme for MW01-2-151SRM.
Figure 5:
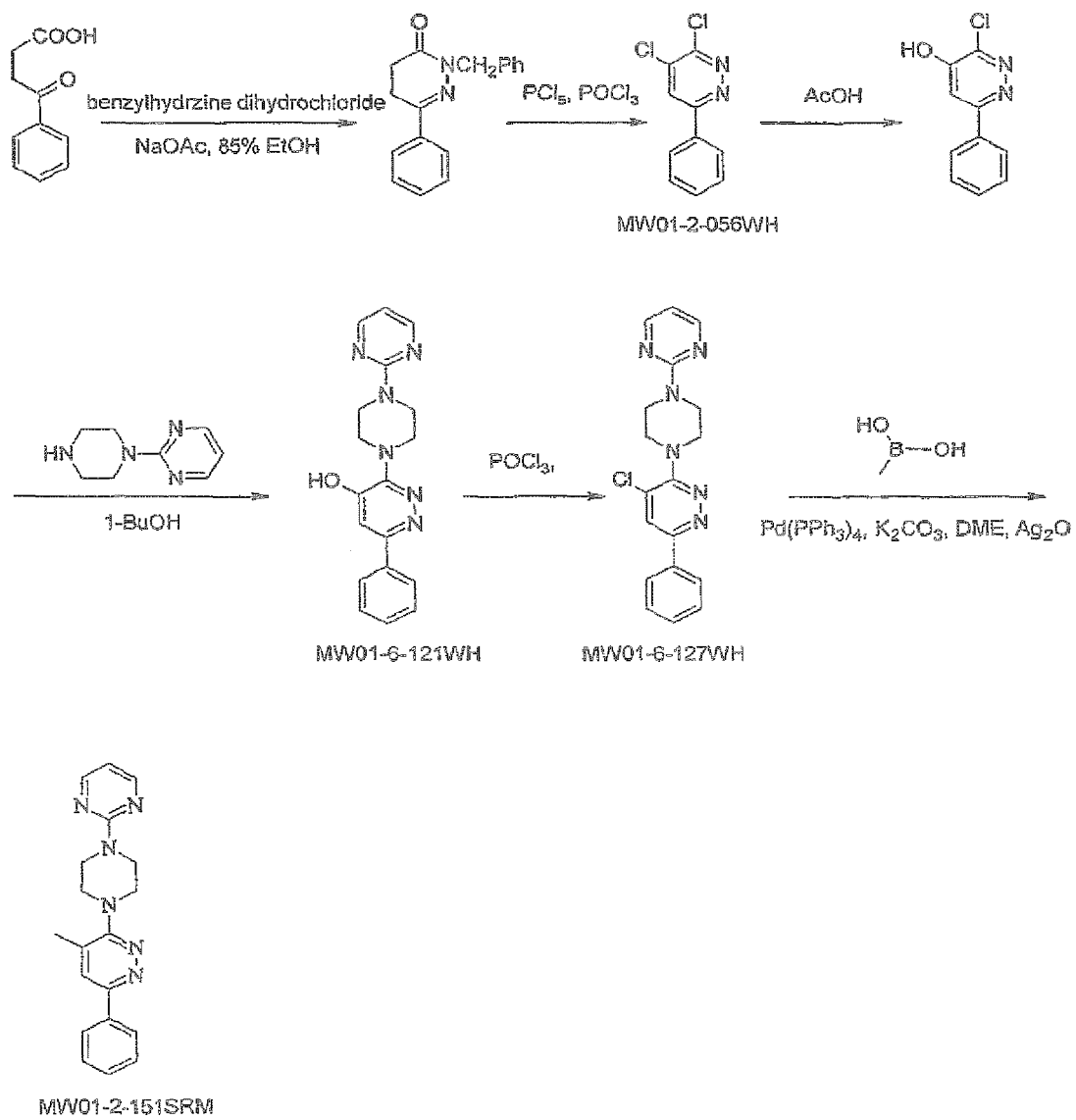
FIG. 5 depicts a synthetic scheme for MW01-2-151SRM.
Figure 6:
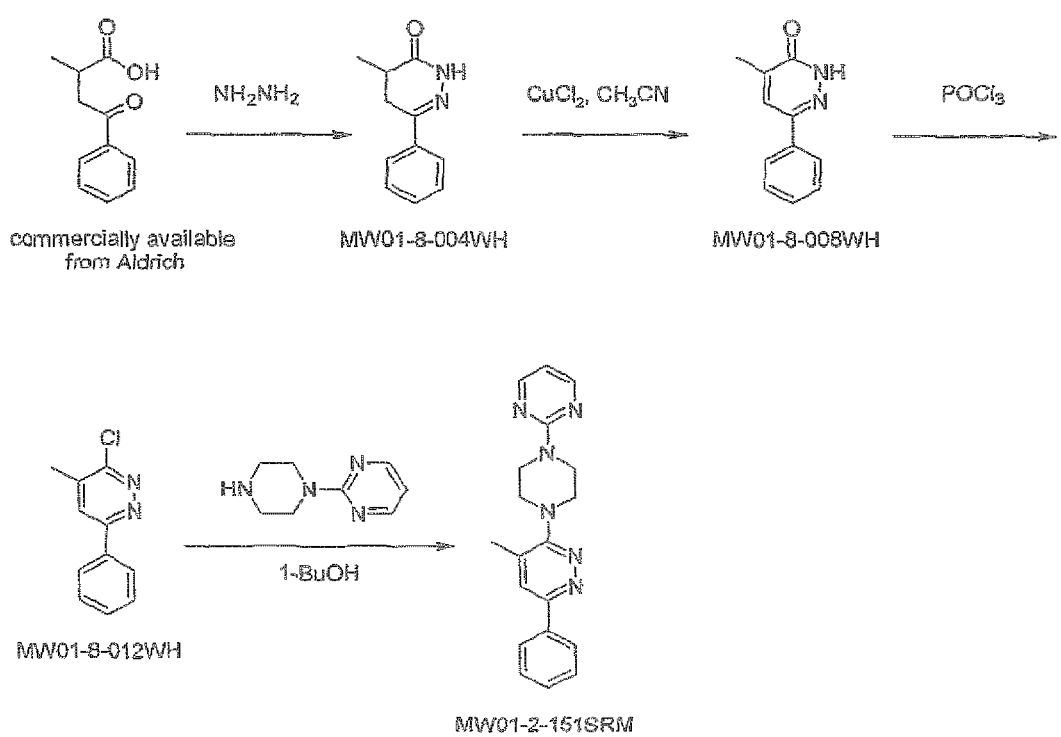
FIG. 6 depicts a synthetic scheme for MW01-2-151SRM.

4-methyl-6-phenyl-3-(4-pyrimidin-2-ylpiperazin-1-yl) pyridazine (MW01-2-151SRM) was prepared by several synthetic schemes as depicted in FIG. 3 (Scheme 1), FIG. 4 (Scheme 2), FIG. 5 (Scheme 3), and FIG. 6 (Scheme 4), which were carried, out as described in detail herein. The various reaction schemes (Schemes 1, 2, and 3) are generally applicable to the compounds of the present invention and are not restricted in utility only to the preparation of MW01-2-151SRM.

Scheme 1 (FIG. 3)

4,5-dihydro-4-methyl-6-phenylpyridazin-3(2H)-one (2)

A 250 mL three-neck round bottom flask fit with a temperature probe and condenser is charged with 7.7 g (40 mmole) of 2-methyl-4-oxo-4-phenylbutanoic acid 1 and 20 ml of ethanol (95%). The suspension is cooled to below 10° C. and 2.2 ml (42 mmole, 1.05 equiv.) of hydrazine monohydrate in 10 mL of ethanol is added dropwise at a rate that maintains the solution temperature at below 20° C. Upon addition, the suspension changes to a pale yellow solution. After addition, the reaction mixture is heated to reflux and stirred for 2 h, and after 20 minutes of heating, a solid is seen in the mixture. Once the reaction is completed, the flask is removed from the oil bath and cooled to ambient temperature. Upon cooling, white crystals form in the flask, which are collected by filtration. The solid is washed first with 30 mL of, 2N $NaHCO_3$, followed by 60 mL Milli-Q water three times, and dried over a medium frit sintered glass funnel in vacuo to give the desired product 2 in 96.1% yield. [See Hansen, K B et al. *Organic process research & development*, 2005, 9, 634-639; Nelson, D A. US 20050137397A1. Coudert, P at al. *Journal of Heterocyclic Chemistry*, 1988, 25(3), 799-802.]

4-methyl-6-phenylpyridazin-3(2H)-one (3)

7.0 g (35 mmole) of 2 is placed in a 250 ml single-necked round bottom flask followed by 30 mL of acetonitrile. The mixture is stirred to allow 2 to dissolve. 11.3 g (84 mole, 2.4 equiv.) of anhydrous copper (II) chloride is added to the solution to give a green-yellow suspension. A reflux condenser is connected to the flask and a dry tube filled with anhydrous $CaCl_2$ is fitted to the top of the condenser. To control the HCl gas that forms during the course of the reaction, a NaOH solution is used to absorb the HCl that escapes from dry tube. The reaction mixture is heated to reflux, and the color of the reaction suspension changes to dark green upon heating. When the reaction is complete (after refluxing for 2 h), the flask is removed from the oil bath and cooled to ambient temperature. The reaction is cooled in an ice-water bath and 150 mL of ice-water is added to quench the reaction. The mixture is stirred vigorously for 10 minutes to give a gray precipitate and blue liquid containing copper (I) chloride. The precipitate is collected by filtration (pH of the filtrate is 0-1) and washed with 100 mL of 1N HCl solution, then 100 mL of water 5 times. To remove remaining copper by products that are trapped in the solid, the filter cake is stirred in 150 mL of 1N HCl solution for 0.5 h and filtered. The filter cake is subsequently washed with Milli-Q water until the filtrate is at pH 7 (approximately 7 washes). The solid is dried over a medium frit sintered glass funnel in vacuo to give 3 as a light gray powder in 93.8% yield. [See Eddy, S et al. *Synthetic Communications*, 2000, 30(1), 1-7.Csende, F et al. *Synthesis*, 1995, 1240-12420]

3-chloro-4-methyl-6-phenylpyridazine (4)

6.0 g (32 mmole) of 3 is placed in a 250 mL single neck round bottom flask and 30 mL of acetonitrile is added to create a pale yellow slurry. 6.0 ml (64 mmole, 2 equiv.) of phosphorus oxychloride is added changing the slurry to a darker color. The flask is fitted with a reflux condenser and a dry tube filled with anhydrous $CaCl_2$ is fitted to the top of the condenser. The reaction mixture is heated at reflux and becomes a dark red liquid. After the reaction is completed (2.5 h), the mixture is cooled to ambient temperature and placed in an ice water bath. Ice water (150 mL) is slowly poured into the reaction mixture with stirring to decompose the phosphorus oxychloride into HCl and $H_3PO_4$, resulting in formation of a pink solid. The solid is collected by filtration and washed three times with 50 of Milli-Q water. The solid is transferred to a 250 rat, beaker, followed by addition of 100 rill, of water to form a suspension. Subsequently, 1N NaOH is added until the aqueous suspension is at pH=8, and the mixture is stirred for 5 minutes to remove all trace of starting material contaminants. The solid is filtered and washed 3 times with 100 mL of water to wash out the excess base. The solid is dried over a medium frit sintered glass funnel in vacuo to provide 4 as a light pink powder in 96% yield. [See Contreras, J M et al. *Journal of Medicinal Chemistry*, 2001, 44(17), 2707-2718; Nelson, D A. US 20050137397A1.]

2-(4-(4-methyl-6-phenylpyridazin-3-yl)piperazin-1-yl)pyrimidine (5)

7.5 g (36.6 mmole) of 4 is placed in a 250 mL, single neck round bottom flask and suspended in 125 mL, of water. 60.17 g (366.0 male, 10 equiv.) of 2-(piperazine-1-yl)pyrimidine is added and the flask fit with a condenser. The reaction mixture is heated at reflux with rapid stirring for 60 h, with continuous amine addition possible to boost reaction rates. When complete, the reaction mixture is cooled to ambient temperature and two layers are observed in the flask consisting of an orange aqueous layer and a brown oil that settles to the bottom of the flask. The water is decanted off, leaving the oil, which is the product 5. The oil is then dissolved in minimal volume of isopropanol and heated to reflux. After 10 minutes of reflux, the solution is cooled to ambient temperature, and cooled to 0° C. to induce crystallization. Pale yellow crystals are filtered from isopropanol and rinsed with minimal cold ether to provide 5. Recovery of the crystals is 50%, but may be increased by recursive crystallization of compound. [Contreras, J M et al. *Journal of Medicinal Chemistry*, 1999, 42(4), 730-741. Chayer, S et al. *Tetrahedron Letters*, 1998, 39, 841-844.]

Scheme 2 (FIG. 4)

3-chloro-6-phenylpyridazin-4-ol was synthesized according to the procedure described by Coudert, P., et al., supra.

6-phenyl-3-(4-(pyrimidin-2-yl)piperazin-1-pyridazin-4-ol (MW01-7-121WH)

This compound was prepared from 3-chloro-4-hydroxy-6-phenylpyridazine (14 g, 68 mmol) in the same manner as described below, yielding white solid (22.1 g, 66 mmol, 97.3%), ESI-MS: m/z 335.2 (M+H+), $^1$H NMR (DMSO), 1H NMR (D 50): d 8.406 (d, 2H), 7.740 (d, J=4.0, 2H), 7.558 (s, 3H), 6.686 (t, J=4.8, J=4.4, 1H), 6.841 (s, 1H), 3.881 (s, 4H), 3.620 (s, 4H), 3.776 (s, 4H).

4-chloro-6-phenyl-3-(4-pyrimidin-2-ylpiperazin-1-yl)pyridazine (MW01-6-127WH)

6-phenyl-3-(4-pyrimidin-2-ylpiperazin-1-yl)pyridazin-4-ol (22.6 g, 66 mmol) was suspended in 75 ml phosphorus oxychloride and heated with stirring at 100° C. for 3 h. After cooling to room temperature the mixture was poured onto crushed ice. The mixture was then neutralized with NaOH solution to give white suspension. The precipitation was filtered off, washed with water, dried over filter funnel to provide white solid (21.3 g, 60.3 mmol, 91.4%). ESI-MS: m/z 353.4 (M+H+). $^1$H NMR ($CDCl_3$): d 8.377 (d, J=4.5, 2H), 8.036 (d, 2H), 7.833 (s, 1H), 7.508 (m, 3H), 6.564 (t, J=4.5, 1H), 4.073 (t, J=4.0, J=4.5, 4H), 3.672 (t, 4H).

4-methyl-6-phenyl-3-(4-pyrimidin-2-ylpiperazin-1-yl)pyridazine (MW01-2-151SRM)

Into a reaction tube were added MW01-6-127WH (1.4 g, 4.0 mmol), $K_2CO_3$ powder (1.7 g, 12.4 mmol), Pd(dppf)$Cl_2$ (326 mg, 0.4 mmol), silver oxide (2.3 g, 10 mmol), methylboronic acid (324 mg, 5.4 mmol) and 20 ml of THF. Argon was then flushed through the tube for 3 min. The tube was then sealed tightly and heated with stirring at 80 degree for 12 h. After cooled down, the mixture was quenched with 10% NaOH solution and extracted with ethyl acetate. The organic phase was concentrated in vacuo and the residue was purified by column chromatography eluting with 1:4, Ethyl Acetate: Petroleum ether. White powder solid was obtained (0.60 g, 1.8 mmol, yield 45.2%). ESI-MS: m/z 333.4 (M+H+). 1H NMR (CDCl$_3$): d 8.380 (d, J=5.0, 2H), 7.065 (d, J=7.0, 2H), 7.626 (s, 1H), 7.473 (m, 3H), 6.567 (t, J=5.0, 1H), 4.056 (t, J=5.0, 4H-1), 3.475 (t, J=5.0, 4H), 2.456 (s, 3H).

Scheme 3 (FIG. 5)

Into a reaction tube were added MW01-6-127WH (1.4 g, 4.0=01), K$_2$CO$_3$ powder (1.7 g, 12.4 mmol), Pd(PPh$_3$)$_4$ (240 mg, 0.2 mmol), silver oxide (2.3 g, 10 mmol), methylboronic acid (324 mg, 5.4 mmol) and 20 ml of DME. Argon was then flushed through the tube for 3 min. The tube was then sealed tightly and heated with stirring at 120° C. for 24 h. After cooled down, the mixture was filter through acelite earth, the filtrate was then concentrated and the residue was purified by column chromatography eluting with 1:4, Ethyl Acetate: Petroleum ether. Waite powder solid was obtained (0.64 g, 1.93 mmol, yield 48.1%), ink 333.4 (M+H+). 1H NMR (CDCl$_3$): d 8380 (d, J=5.0, 2H), 7.065 (d, 2H), 7.626 (s, 1H), 7.473 (m, 3H), 6.567 (t, J=4.5, J=5.0, 1H), 4.056 (t, 4H), 3.475 (t, J=5.0, 4H), 2.456 (s, 3H).

Scheme 4 (FIG. 6)

4,5-dihydro-4-methyl-6-phenylpyridazin-3(2H)-one (MW01-8-004WH)

7.7 g (40 mmole) of 2-methyl-4-oxo-4-phenylbutanoic acid was added to a 100 ml single-necked round bottom flask followed by 3.0 ml (60 mmole) of hydrazine monohydrate and then 20 ml of reagent grade ethanol (100%, 95% of ethanol should be fine also). The flask was fitted with a reflux condenser and the reaction mixture was heated to reflux in an oil bath at 110° C. (temperature of oil bath) and stirred for 2 h. The flask was then removed from the oil bath and the reaction mixture cooled to ambient temperature. The stir bar was removed and the solvent was evaporated in vacuo in a water bath at 45° C. The residue was then treated with 50 ml of Milli-Q water and stirred for 10 minutes to give a suspension. The precipitate was collected by filtering, washed with 100 ml of 2N NaHCO$_3$, then washed with 60 ml Milli-Q water three times, and dried over a medium frit sintered glass funnel in vacuo to give 7.15 g of white crystals (Syn. ID, WH-8-004). Yield, 95%, confirmed by ESI-MS. ESI-MS: m/z 189.2 (M+H+).

4-methyl-6-phenylpyridazin-3(2H)-one (MW01-8-008WH)

790 g (35 mmole) of MW01-8-004WH was placed in a 100 ml single-necked round bottom flask followed by 9.4 g (70 mmole) of anhydrous copper (II) chloride and then 30 ml of acetonitrile to give a brown yellow suspension. A reflux condenser was connected to the flask and a dry tube filled with CaCl$_2$ was fitted to the top of the condenser. The reaction mixture was heated to reflux in an oil bath (110° C.) for 3 h. The color of the reaction suspension changed to dark yellow once the reflux started. After the completion of the reaction (monitored by HPLC), the flask was removed from the oil bath and cooled to ambient temperature. The mixture was poured on to 300 g of crushed ice and stirred vigorously for 10 minutes to give a gray precipitate and blue liquid. The precipitate was then collected by filtering (pH of the filtrate was 1.5-2.0), and washed with 100 ml of a 1N HCl solution to rid the solid of any remaining copper byproducts. This is followed by washing with 100 ml Milli-Q water to get rid of the acid in the solid, and is monitored by checking the pH value of the filtrate. The solid was washed until the filtrate shows a pH of 7, after approximately 5 washes. The solid was dried ewer a medium frit sintered glass funnel in vacuo to give 63 g of a blue gray solid. Yield was 963% and confirmed by ESI-MS. ESI-MS: m/z 1873 (M+H+).

3-chloro-4-methyl-6-phenylpyridazine (MW01-8-012WH)

6.0 g (32 mmole) of MW01-8-008WH and 30 ml (320 mmole) of phosphorus oxychloride were placed in a 100 ml single-necked round bottom flask. The flask was connected with a reflux condenser and a dry tube filled with anhydrous CaCl$_2$ was fitted to the top of the condenser, (HCl gas is formed in the reaction so a basic solution such as NaOH may be needed to absorb HCl in a large-scale synthesis). The reaction mixture was stirred in an oil bath (90° C.) for 2 h, then cooled to ambient temperature and poured onto crushed ice (phosphorus oxychloride can be decomposed by water to give HCl and H$_3$PO$_4$). The mixture was then stirred vigorously for 10 minutes to give a white suspension. The suspension was neutralized with a 2N NaOH solution until the pH of the suspension was pH=7. The precipitate was filtered, washed three times with 100 ml of water and dried over a medium frit sintered glass funnel in vacuo to provide 5.9 g of a light pink powder (Syn. ID, WH-8-012). Yield was 89.4% and confirmed by ESI-MS. ESI-MS: m/z 205.4 (M+H+).

2-(4-(4-methyl-6-phenylpyridazin-3-yl)piperazin-1-yl)pyrimidine (MW01-2-151SRM)

0.82 g (4.0 mmole) of WE-8-012 was placed in a 30 ml pressure vessel followed by addition of 2.6 g (16.0 mmole) of 1-(2-pyrimidyl) piperazine and then 15 ml of 1-BuOH. The vessel was sealed tightly and placed into an oil bath and stirred at 130° C. (temperature of oil bath) for 2.5 days. The reaction mixture was then cooled to ambient temperature and transferred to a single-necked flask for evaporation under reduced pressure. Removal of solvent gave rise to a brown-red residue that was treated with 30 ml of water to give a brown sticky oil. The mixture was kept at ambient temperature overnight while the oil solidified gradually. The formed solid was then broken into small pieces with a steel spatula. The solid was collected by filtering and washed with 50 ml of Milli-Q water three times and dried over a filter funnel in vacuo to provide 1.25 g of light yellow solid (Syn. ID, WH-8-020). Yield was 94%. (Alternative separation is to use a precipitation procedure instead of a solidification process. Solidification is a simple and cheap operation, yet time-consuming. Precipitation is time efficient, yet more costly than the former one. So it is up to the process chemist to decide which procedure to pick for the manufacture. The precipitation process is below. The oil product was dissolved completely in 10 ml of reagent grade ethanol or acetone to form a solution. The solution was then added dropwise to 150 ml of ice water under vigorous stirring. Light yellow suspension was then formed gradually. The solid was collected by filtering, washed with Milli-Q water, dried over filter funnel in vacuo to give the desired product.) The final compound was confirmed by ESI-MS and NMR. ESI-MS: m/z 333.8 (M+H+), 1H NMR (CDCl₃): d 8.380 (d, J=5.0, 2H), 7.065 (d, J=7.0, 2H), 7.626 (s, 1H), 7.473 (m, 3H), 6.567 (t, J=4.5, J=5.0, 1H), 4.056 (t, J=5.0, 4H), 3.475 (t, J=5.0, 4H), 2.456 (s, 3H).

C. Preparation of 4,6-diphenyl-3-(4-pyrimidin-2-yl)piperazin-1-yl)pyridazine (MW01-5-188WH)

Figure 7:
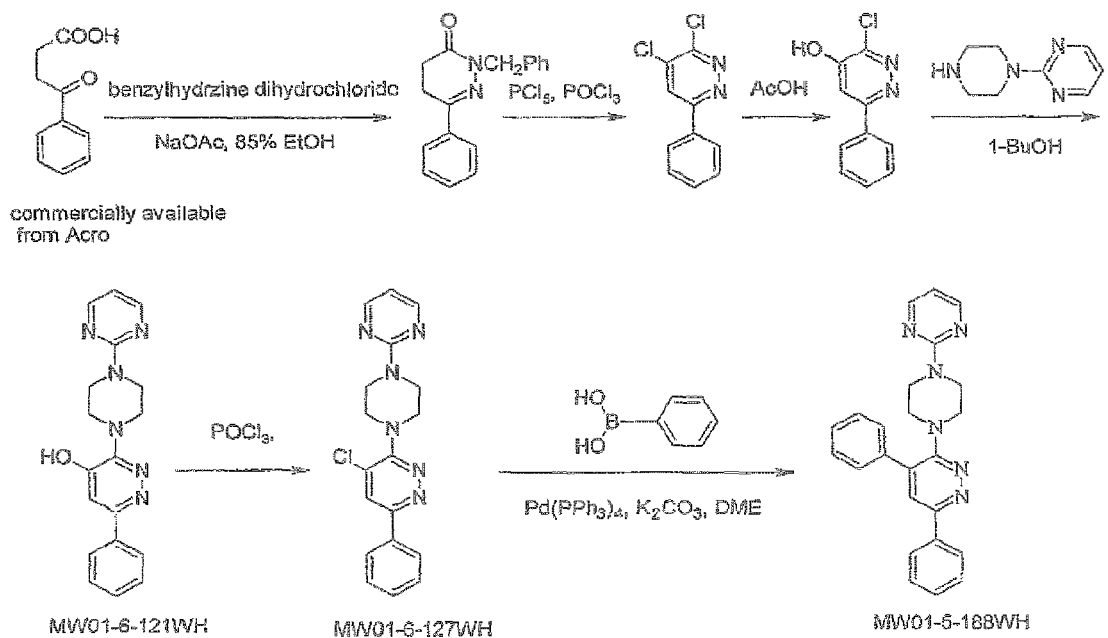
FIG. 7 depicts a synthetic scheme for MW01-5-188WH.
Figure 8:
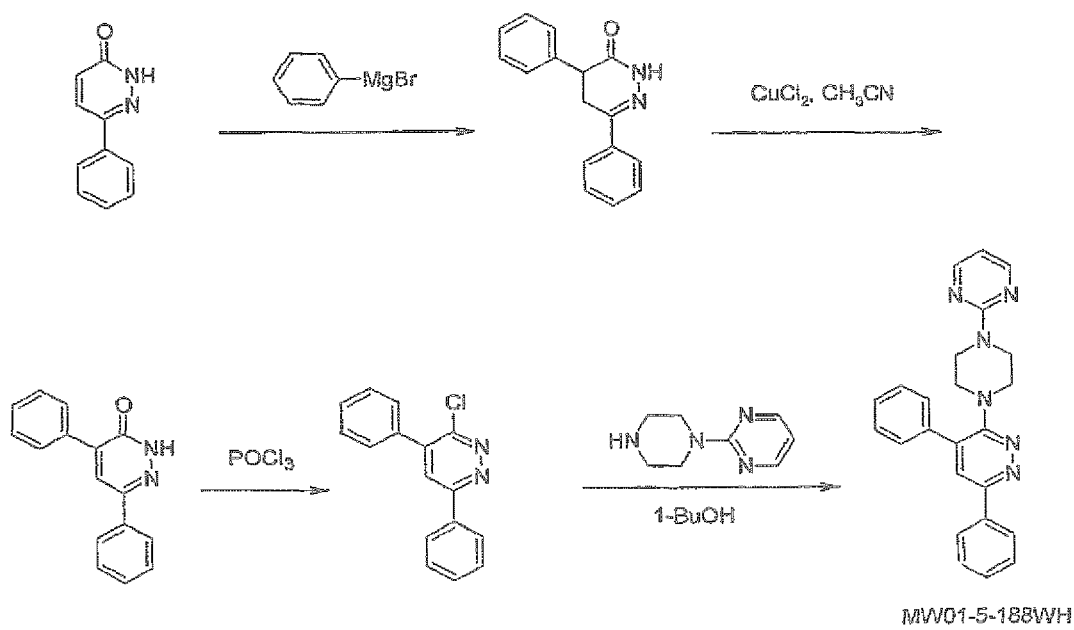
FIG. 8 depicts a synthetic scheme for MW01-5-188WH.
Figure 9:
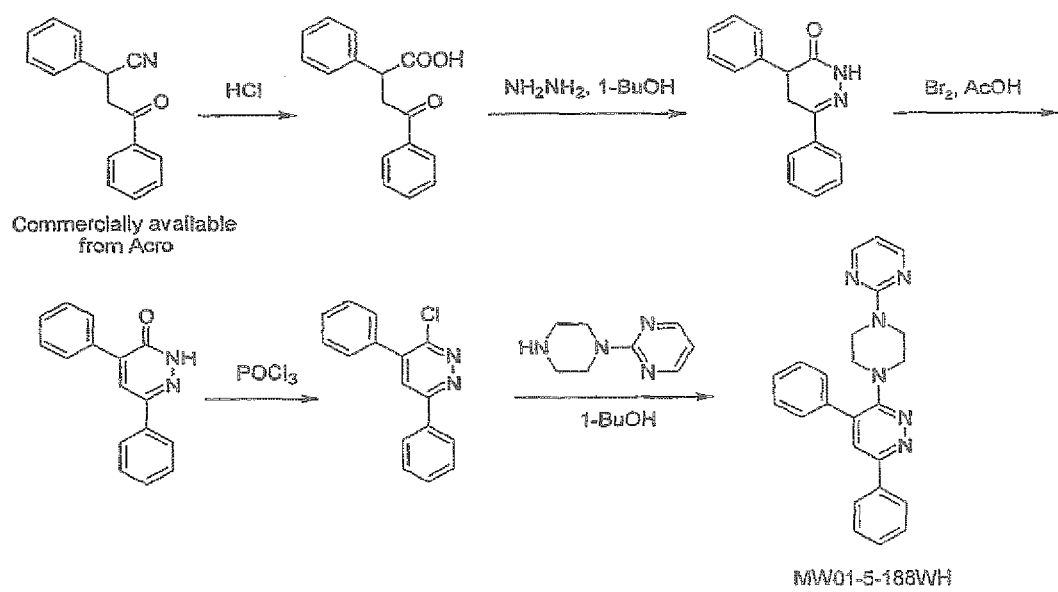
FIG. 9 depicts a synthetic scheme for MW01-5-188WH.

4,6-diphenyl-3-(4-pyrimidin-2-ylpiperazin-1-yl)pyridazine (MW01-5-188WH) was prepared by several synthetic schemes as depicted in FIG. 7 (Scheme 1), FIG. 8 (Scheme 2), and FIG. 9 (Scheme 3), which were carried out as described in detail herein. The various reaction schemes (Schemes 1, 2, and 3) are generally applicable to the compounds of the present invention and are not restricted in utility only to the preparation of MW01-2-188WH.

Scheme 1 (FIG. 7)

3-chloro-6-phenylpyridazin-4-ol was synthesized according to the procedure described by Coudert, P., et al. supra.

6-phenyl-3-(4-(pyrimidin-2-yl)piperazin-1-yl)pyridazin-4-ol (MW01-7-121WH)

The compound was prepared from 3-chloro-4-hydroxy-6-phenylpyridazine (14 g, 68 mmol). A mixture of 3-chloro-4,6-diphenylpyridazine (267 mg; 1.0 mmol), 1-(2-pyrimidyl)piperazine (656 mg, 4.0 mmol) in 3 ml of 1-BuOH was heated with stirring at 130° C. for 3 days. The solvent was removed by evaporation in vacuo the residue was treated with water to give a suspension. The solid was then filtered off, washed with water, dried over filter funnel in vacuo to give light pink solid, yielding white solid (22.1 g, 66 mmol, 97.3%). ESI-MS: m/z 335.2 (M+H+), 1H NMR (DMSO): 1H NMR (DMSO): d 8.406 (d, J=6.5, 2H), 7.740 (d, J=4.0, 2H), 7.558 (s, 3H), 6.686 (t, J=4.8, J=4.4, 1H), 6.841 (s, 1H), 3.881 (s, 4H), 3.620 (s, 4H), 3.776 (s, 4H).

4-chloro-6-phenyl-3-(4-pyrimidin-2-ylpiperazin-1-yl)pyridazine (MW01-6-127WH)

6-phenyl-(4-pyrimidin-2-ylpiperazin-1-yl)pyridazin-4-ol (22.0 g, 66 mmol) was suspended in 75 ml phosphorus oxychloride and heated with stirring at 100° C. for 3 h. After cooling to room temperature the mixture was poured onto crushed ice. The mixture was then neutralized with NaOH solution to give white suspension. The precipitation was filtered off, washed with water, dried over fitter funnel to provide white solid (21.3 g, 60.3 mmol, 91.4%). ESI-MS: m/z 353.4 (M+H+). 1H NMR (CDCl₃): d 8377 (d, J=4.5, 2H), 8.036 (d, J=7.5, 2H), 7.833 (s, 1H), 7.508 (m, 3H), 6.564 (t, J=4.5, 1H), 4.073 (t, J=4.5, 4H), 3.672 (t, J=4.5, 4H).

4,6-diphenyl-3-(4-pyrimidin-2-ylpiperazin-1-yl)pyridazine (MW01-5-188WH)

A mixture of 3-chloro-4,6-diphenylpyridazine (267 mg, 1.0 mmol), 1-(2-pyrimidyl)piperazine (656 mg, 4.0 mmol) in 3 ml of 1-BuOH was heated with stirring at 130° C. for 3 days. The solvent was removed by evaporation in vacuo the residue was treated with water to give a suspension. The solid was then filtered off, washed with water, dried over filter funnel in vacuo to give light pink solid. (320 mg, 0.81 mmol, yield 81.1%). ESI-MS: m/z 395.5 (M+H+). HRMS calcd 395.1979. Found 395.1973; 1H NMR (CDCl₃): d 8.329 (d, J=5.0, 2H), 8.101 (d, J=7.5, 2H), 7.734 (d, J=7.5, 2H), 7.655 (s, 1H), 7.509 (m, 6H), 6.530 (t, 1H), 3.836 (t, J=4.5, J=5.0, 4H), 3.394 (t, J=5.0, J=4.5, 4H).

Scheme 2 (FIG. 8)

4,5-dihydro-6-phenyl-4-phenylpyridazin-3(2H)-one 135 ml (135 mmole) of a solution of phenylmagnesium bromide (1M) in THF was added to a hot suspension of 6-phenylpyridazinone compound 7.8 g (45 mmole) in dry toluene (50 ml). The mixture was refluxed for 8 h, left overnight at ambient temperature, then decomposed with a saturated solution of ammonium chloride. The organic layer was separated, and the aqueous layer was extracted with 100 ml of ethyl acetate. The solvent was removed and the residue was crystallized from ethanol. The crystals were collected by filtering and dried over a medium frit sintered glass funnel in vacuo to give 5.6 g of white crystals. Yield was 50%, confirmed by ESI-MS, ESI-MS: m/z 250.1 (M+H+).

6-phenyl-4-phenylpyridazin-3(2H)-one 4.4 g (17.5 mmole) of 6-pyridazinone obtained above was placed in a 50 ml single-necked round bottom flask followed by 4.7 g (35 mmole) of anhydrous copper (II) chloride and then 20 ml of acetonitrile to give a brown yellow suspension. A reflux condenser was connected to the flask and a dry tube filled with CaCl₂ was fitted to the top of the condenser. The reaction mixture was heated to reflux in an oil bath (110° C.) for 3 h. The color of the reaction suspension changed to dark yellow once the reflux started. After the completion of the reaction (monitored by HPLC), the flask was removed from the oil bath and cooled to ambient temperature. The mixture was poured on to 200 g of crushed ice and stirred vigorously for 10 minutes to give a gray precipitate and blue liquid. The precipitate was then collected by filtering (pH of the filtrate was 1.5-2.0), and washed with 50 ml of a 1N HCl solution to rid the solid of any remaining copper byproducts. This is followed by washing with 100 ml of Milli-Q water to get rid of the acid in the solid, and is monitored by checking the pH value of the filtrate. The solid was washed until the filtrate shows a pH of 7, after approximately 5 washes. The solid was dried over a medium frit sintered glass funnel in vacuo to give 3.9 g of a blue gray solid. Yield was 90%, confirmed by ESI-MS. ESI-MS: m/z 248.1 (M+H+).

3-chloro-6-phenyl-4-phenylpyridazine 2.0 g (8 mmole) of 6-phenylpyridazinone obtained above and 10 ml (54 mmole) of phosphorus oxychloride (reagent grade, Aldrich) were placed in a 50 ml single-necked round bottom flask. The flask was connected with a reflux condenser and a dry tube filled with CaCl₂ was fitted to the top of the condenser. (HCl gas is formed in the reaction so a basic solution such as NaOH may be needed to absorb HCl in a large-scale synthesis). The reaction mixture was stirred in an oil bath (90° C.) for 2 h, then cooled to ambient temperature and poured onto crushed ice. (Phosphorus oxychloride can be decomposed by water to give HCl and H₃PO₄). The mixture was then stirred vigorously for 10 minutes to give a white suspension. The suspension was neutralized with a 2N NaOH solution until the pH of the suspension was pH=7. The precipitate was filtered, washed three times with 100 ml of water and dried over a medium frit sintered glass funnel in vacuo to provide 1.8 g of a light pink powder. Yield was 85%, confirmed by ESI-MS. ESI-MS: m/z 266.4 (M+H+).

2-(4-(6-phenyl-4-phenylpyridazin-3-yl)piperazin-1-yl)pyrimidine 1.1 g (4.0 mmole) of 3-chloropyridazine obtained above was placed in a 30 ml pressure vessel followed by addition of 2.6 g (16.0 mmole) of 1-(2-pyrimidyl) piperazine and then 15 ml of 1M BuOH (reagent grade). The vessel was sealed tightly and placed into an oil bath and stirred at 130° C. (temperature of oil bath) for 3 days. The reaction mixture was then cooled to ambient temperature and transferred to a single-necked flask for evaporation under reduced pressure. Removal of solvent gave rise to a brown-red residue that was treated with 30 ml of water to give a brown suspension. The solid was collected by filtering and washed with 50 mL of water three times and dried over a filter funnel in vacuo to provide 0.96 g of light yellow solid. Yield was 90%, ESI-MS: m/z 395.5 (M+H+). HRMS calcd 395.1979. Found 395.1973; 1H NMR (CDCl$_3$): d 8.329 (d, J=5.0, 2H), 8.101 (d, J=7.5, 2H), 7.734 (d, J=7.5, 2H), 7.655 (s, 1H), 7.509 (m, 6H), 6.530 (t, J=4.5, 1H), 3.836 (t, J=4.5, J=5.0, 4H), 3.394 (t, J=5.0, J=4.5, 4H).

Scheme 3 (FIG. 9)

3-chloro-6-phenylpyridazin-4-ol was synthesized according to the procedure described by Coudert, P., et al, supra.

4,6-diphenyl-3-(4-pyrimidin-2-ylpiperazin-1-yl)pyridazine (MW01-5-188WH)

A mixture of 3-chloro-4,6-diphenylpyridazine (267 mg, 1.0 mmol), 1-(2-pyrimidyl)piperazine (656 mg, 4.0 mmol) 3 ml of 1-BuOH was heated with stirring at 130° C. for 3 days. The solvent was removed by evaporation in vacuo the residue was treated with water to give a suspension. The solid was then filtered off, washed with water, dried over filter funnel in vacuo to give light pink solid. (320 mg, 0.81=01, yield 81.1%). ESI-MS: m/z 395.5 (M+H+), HRMS calcd 395.1979. Found 395.1973; 1H NMR (CDCl$_3$): d 8.329 (d, 2H), 8.101 (d, J=7.5, 2H), 7.734 (d, J=7.5, 2H), 7.655 (s, 1H), 70509 (m, 6H), 6.530 (t, J=4.5, 1H), 3.836 (1, J=4.5, J=5.0, 4H), 3.394 (t, J=5.0, J=4.5, 4H).

Preparation of 4-pyridyl-6-phenyl-3-(4-pyrimidin-2-ylpiperazin-1-yl)pyridazine (MW01-6-189 WH)

Figure 10A:
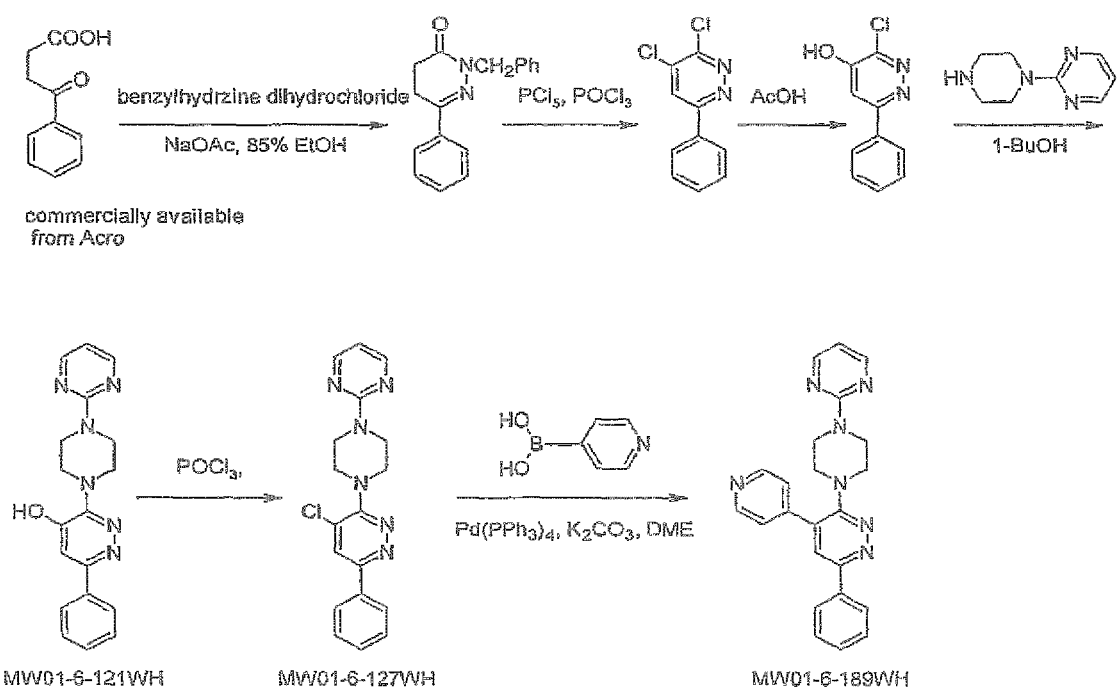
FIGS. 10A and 10B depict synthetic schemes for MW01-6-189WH
Figure 10B:
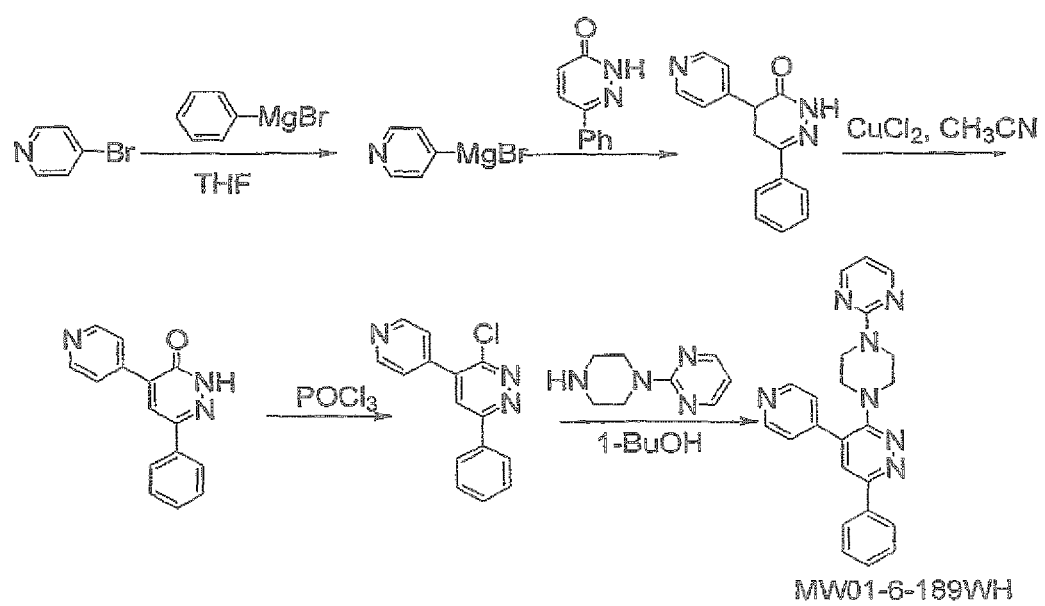

4-pyridyl-6-phenyl-3-(4-pyrimidin-2-ylpiperazin-1-yl)pyridazine (MW01-6-189WH) was prepared by two synthetic schemes as depicted in FIGS. 10A and 10B, which were carried out as described in detail herein. The various reaction schemes (Schemes 1 and 2) are generally applicable to the compounds of the present invention and are not restricted in utility only to the preparation of MW01-2-189WH.

Scheme 1

3-chloro-6-phenylpyridazin-4-ol was synthesized according to the procedure described by Coudert, P., et al., supra.

6-phenyl-3-(4-(pyrimidin-2-yl)piperazin-1-yl)pyridazin-4-ol (MW01-7-121WH)

This compound was prepared from 3-chloro-4-hydroxy-6-phenylpyridazine (14 g, 68 mmol). A mixture of 3-chloro-4,6-diphenylpyridazine (267 mg, 1.0 mmol), 1-(2-pyrimidyl)piperazine (656 mg, 4.0 mmol) in 3 ml of 1-BuOH was heated with stilling at 130° C. for 3 days. The solvent was removed by evaporation in vacuo the residue was treated with water to give a suspension. The solid was then filtered off, washed with water, dried over filter funnel in vacuo to give light pink solid, yielding white solid (22.1 g, 66 mmol, 97.3%). ESI-MS: m/z 335.2 (M+H+). $^1$H NMR (DMSO): 1H NMR (DMSO): d 8.406 (d, J=6.5, 2H), 7.740 (d, J=4.0, 2H), 7.558 (s, 3H), 6.686 (t, J=4.8, J=4.4, 1H), 6.841 (s, 1H), 3.881 (s, 4H), 3.620 (s, 4H), 3.776 (s, 4H).

4-chloro-6-phenyl-3-(4-pyrimidin-2-ylpiperazin-1-yl)pyridazine (MW01-6-127WH)

6-phenyl-3-(4-pyrimidin-2-ylpiperazin-1-yl)pyridazin-4-ol 1 h (22.0 g, 66 mmol) was suspended in 75 ml phosphorus oxychloride and heated with stirring at 100° C. for 3 h. After cooling to room temperature the mixture was poured onto crushed ice. The mixture was then neutralized with NaOH solution to give white suspension. The precipitation was filtered off, washed with water, dried over filter funnel to provide white solid (21.3 g, 60.3 mmol, 91.4%). ESI-MS: m/z 353.4 (M+H+). 1H NMR (CDCl$_3$): d 8.377 (d, J=4.5, 2H), 8.036 (d, J"7.5, 2H), 7.833 (s, 1H), 7.508 (m, 3H), 6.564 (t, J=4.5, 1H), 4.073 (t, J=4.0, J=4.5, 4H), 3.672 (t, J=4.0, J=4.5, 4H).

4-pyridyl-6-phenyl-3-(4-pyrimidin-2-ylpiperazin-1-yl)pyridazine (MW01-6-189WH)

Into a reaction tube were added WH-6-127 (1.4 g, 4.0 mmol), K$_2$CO$_3$ powder (13 g, 12.4 mmol), Pd(PPh$_3$)$_4$ (240 mg, 0.2 ol), 4-pyridineboronic acid (664 mg, 5.4 mmol) and 20 ml of DME. Argon was then flushed through the tube for 3 min. The tube was then sealed tightly and heated with stirring at 120 degree for 24 h. After cooled down, the mixture was filter through a celite earth, the filtrate was then concentrated and the residue was purified by column chromatography eluting with 1:4, Ethyl Acetate: Petroleum ether. Light yellow needle crystals were obtained (0.65 g, 1.65 mmol, yield 41.2%). Confirmed by ESI-MS and NMR. ESI-MS: m/z 3962 (M+H+). $^1$H NMR (CDCl$_3$): d 8.809 (d, J=6.0, 2H), 8.335 (d, J=5.0, 2H), 8.090 (d, J=7.5, 2H), 7.750 (m, 6H), 6.543 (t, J=4.5, 1H), 3.868 (t, 4H), 3:404 (t, 4H).

Scheme 2

4,5-dihydro-6-phenyl-4-(pyridin-4-yl)pyridazin-3(2H)-one

To a 200 ml, three-necked, round-bottomed flask equipped with a magnetic stir bar, 150 ml pressure-equalizing addition funnel, reflux condenser and a glass stopper, was added 21 g (135 mole) of 4-bromopyridine and 70 of anhydrous THF. The system was oven-dried and flushed with argon before use, 135 ml (135 mmole) of THF solution of phenylmagnesium bromide (1M) was placed in the pressure-equalizing addition funnel. Then, the Grignard solution was added dropwise over a period of 10 minutes. After the addition, the reaction was stirred for 15 minutes for completion. The solution of Grignard reagent was then obtained. A solution of 4-pyridylmagnesium bromide obtained above was added to a hot suspension of 6-phenylpyridazinone compound 7.8 g (45 mmole) in dry toluene (50 ml). The mixture was refluxed for 8 h, left overnight at ambient temperature, then decomposed with a saturated solution of ammonium chloride. The organic layer was separated, and the aqueous layer was extracted with 100 ml of ethyl acetate. The solvent was removed and the residue was crystallized from ethanol. The crystals were collected by filtering and dried over a medium frit sintered glass funnel in vacuo to give 5.6 g of white crystals. Yield was 50%, confirmed by ESI-MS. ESI-MS: m/z 252.1 (M+H+).

6-phenyl-4-(pyridin-4-yl)pyridazin-3(2H)-one 4.4 g (17.5 mmole) of 6-pyridazinone obtained above was placed in a 50 ml single-necked round bottom flask followed by 4.7 g (35 mmole) of anhydrous copper (II) chloride and then 20 ml of acetonitrile to give a brown yellow suspension. A reflux condenser was connected to the flask and a dry tube filled with $CaCl_2$ was fitted to the top of the condenser. The reaction mixture was heated to reflux in an oil bath (110° C.) for 3 h. The color of the reaction suspension changed to dark yellow once the reflux started. After the completion of the reaction (monitored by HPLC), the flask was removed from the oil bath and cooled to ambient temperature. The mixture was poured on to 200 g of crushed ice and stirred vigorously for 10 minutes to give a gray precipitate and blue liquid. The precipitate was then collected by filtering (pH of the filtrate was 1.5-2.0), and washed with 50 ml of a 1N HCl solution to rid the solid of any remaining copper byproducts. This is followed by washing with 100 ml Milli-Q water to get rid of the acid in the solid, and is monitored by checking the pH value of the filtrate. The solid was washed until the filtrate shows a pH of 7, after approximately 5 washes. The solid was dried over a medium frit sintered glass funnel in vacuo to give 3.9 g of a blue gray solid. Yield was 90%, confirmed by ESI-MS, ESI-MS: m/z 250.1 (M+H+).

3-chloro-6-phenyl-4-(pyridin-4-yl)pyridazine 2.0 g (8 mmole) of 6-phenylpyridazinone obtained above and 10 ml (54 mmole) of phosphorus oxychloride (reagent grade, Aldrich) were placed in a 50 ml single-necked round bottom flask. The flask was connected with a reflux condenser and a dry tube filled with $CaCl_2$ was fitted to the top of the condenser. (HCl gas is formed in the reaction so a basic solution such as NaOH may be needed to absorb HCl in a large-scale synthesis). The reaction mixture was stirred in an oil bath (90° C.) for 2 h, then cooled to ambient temperature and poured onto crushed ice. (phosphorus oxychloride can be decomposed by water to give HCl and $H_3PO_4$). The mixture was then stirred vigorously for 10 minutes to give a white suspension. The suspension was neutralized with a 2N NaOH solution until the pH of the suspension was pH=7. The precipitate was filtered, washed three times with 100 ml of water and dried over a medium fit sintered glass funnel in vacuo to provide 1.8 g of a light pink powder. Yield was 85%, confirmed by ESI-MS, ESI-MS: m/z 268.4 (M+H+).

4-pyridyl-6-phenyl-3-(4-pyrimidin-2-ylpiperazin-1-yl)pyridazine (MW01-6-189WH)

1.1 g (4.0 mmole) of 3-chloropyridazine obtained above was placed in a 30 ml pressure vessel followed by addition of 2.6 g (16.0 mmole) of 1-(2-pyrimidyl) piperazine and then 15 ml of 1-BuOH (reagent grade). The vessel was sealed tightly and placed into an oil bath and stirred at 130° C. (temperature of oil bath) for 3 days. The reaction mixture was then cooled to ambient temperature and transferred to a single-necked flask for evaporation under reduced pressure. Removal of solvent gave rise to a brown red residue that was treated with 30 ml of water to give a brown suspension. The solid was collected by filtering and washed with 50 ml, of water three times and dried over a filter funnel in vacuo to provide 0.96 g of light yellow solid. Yield was 90%, confirmed by ESI-MS and NMR. ESI-MS: m/z 396.2 (M+H+), 1H NMR (CDCl$_3$): d 8.809 (d, 2H), 8.335 (d, J=5.0, 2H), 8.090 (d, J=7.5, 2H), 7.750 (m, 6H), 6.543 (t, 1H), 3.868 (t, J=5.0, 41-1), 3.404 (t, J=5.0, 4H).

E. Preparation of N-(cyclopropylmethyl-6-phenyl-4-(pyridin-4-yl)pyridazin-3-amine (MW01-7-084WH)

Figure 11:
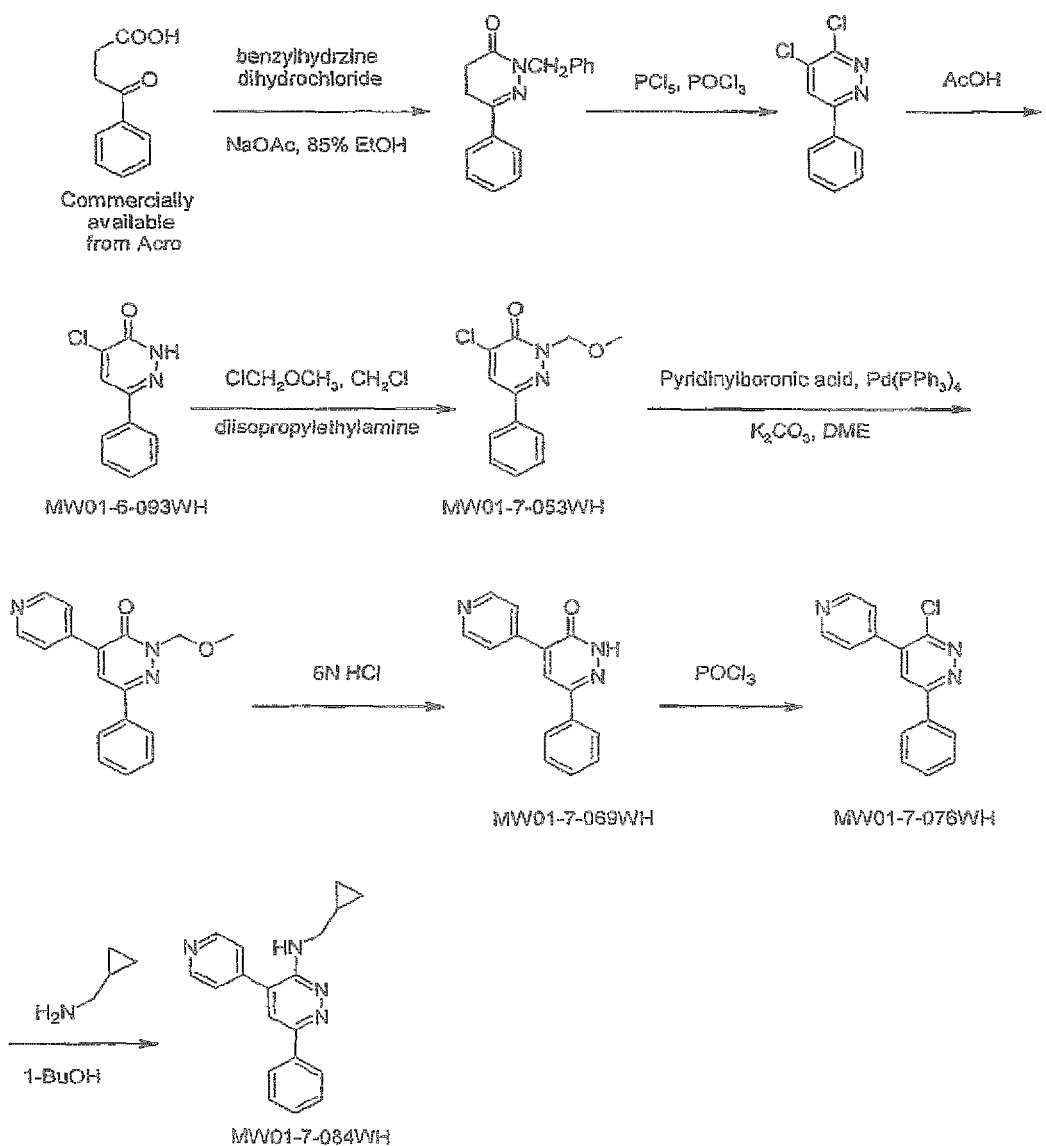
FIG. 11 depicts a synthetic scheme for MW01-7-084WH.

A synthetic scheme for the preparation of N-(cyclopropylmethyl)-6-phenyl-4-(pyridin-4-yl)pyridazin-3-amine (MW01-7-084WH) is depicted in FIG. 11, and synthesis was carried Out as described herein.

4-chloro-6-phenylpyridazin-3(2H)-one (MW01-6-093WH)

4-chloro-6-phenylpyridazin-3(2H)-one was synthesized according to the procedure described by Coudert, P. [18].

4-chloro-2-(methoxymethyl)-6-phenylpyridazin-3(2H)-one (MW01-7-053WH)

A mixture of chloropyridazinone 1 (25.5 g, 0.12 mol), 4-N,N-dimethylaminopyridine (0.20 g) and i-Pr$_2$NEt (263 g, 0.21 mol) in anhydrous $CH_2Cl_2$ (300 mL) was stirred at 0° C. (ice bath) for 30 min. Methoxymethyl chloride (25 g, 0.31 mol) was added and the mixture was stirred at 0° C. for 1 h and then allowed to warm to room temperature. The reaction was stirred at room temperature till complete. The solvent was then removed in vacuo, the residue was treated with water, washed with dilute $Na_2CO_3$ solution and extracted with EtOAc. The organic layer was dried over anhydrous $Na_2SO_4$, filtered and evaporated. The residue was then purified by recrystallization from 95% ethanol to give 20.1 light yellow solid. Yield 66.9%.

6-phenyl-4-(pyridin-4-yl)pyridazin-3(2H)-one (MW01-7-069WH)

The protected pyridazinone MW01-7-053WH (1.0 equiv.) was mixed with arylboronic acid (137 equiv.), Pd(PPh$_3$)$_4$ (0.05 equiv) and $K_2CO_3$ (301 equiv) and 200 mL, of DME in a 350 ml of pressure vessel, flushed with argon for 3 min, and the mixture was then stirred and refluxed (oil bath, 120° C.) until the starting material had disappeared. After cooling, the solution was concentrated to dryness under reduced pressure, the residue was treated with water and filtered off. The filter cake was washed with water over filter funnel and then used for next step directly. The residue obtained above was dissolved in 200 ml of EtOH, 6 N HCl (200 mL) was added and the reaction mixture was refluxed (oil bath, 120° C.) for 6 h, then it was allowed to cool to room temperature, and concentrated to dryness under reduced pressure. The residue was neutralized with dilute NaOH solution. The suspension was then filtered off, washed with water and dried over a filter funnel. Recrystallization from 90% ethanol provided brown yellow solid. Yield 80.4%. ESI-MS: m/z 294.3 (M+H+)

3-chloro-6-phenyl-4-(pyridin-4-yl)pyridazine (MW01-7-076WH)

3-chloro-6-phenyl-4-(pyridin-4-yl)pyridazine (MW01-7-076WH) (66 mmol) was suspended in 75 ml phosphorus oxychloride and heated with stirring at 100° C. for 3 h. After cooling to room temperature the mixture was poured onto crushed ice. The mixture was then neutralized with NaOH solution to give white suspension. The precipitation was filtered off, washed with water, dried over filter funnel to yielding a light yellow solid. ESI-MS: m/z 268.4 (M+WI).

N-(cyclopropylmethyl)-6-phenyl-4-(pyridin-4-yl)pyridazin-3-amine (MW01-7-084WH)

A mixture of N-(cyclopropylmethyl)-6-phenyl-4-(pyridin-4-yl)pyridazin-3-amine (MW01-7-084WH) (0.5 mmol), C-Cyclopropyl-methylamine (2.0 mmol) in 3 ml of 1-BuOH was heated with stirring at 130° C. for 7 days. The solvent was removed by evaporation in vacuo, the residue was treated with water to give a suspension. The solid was then filtered off, washed with water, then 1:3, Ethyl Acetate: Petroleum ether, dried over filter funnel in vacuo yielding gray solid. ESI-MS: m/z 330.4 (M+H+).

F. Preparation 3-(4-methylpiperazin-1-yl)-6-phenyl-4-(pyridin-4-yl)pyridazine (MW01-7-085WH)

Figure 12:
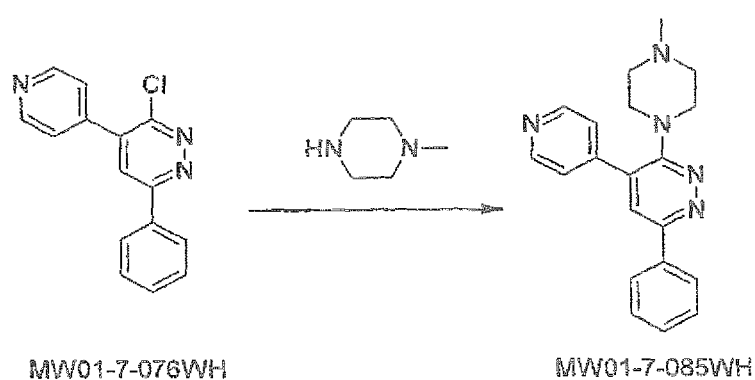
FIG. 12 depicts a synthetic scheme for MW01-7-085WH.

A mixture of 3-chloro-6-phenyl-4-(pyridin-4-yl)pyridazine (MW01-7-076WH) (0.5 mmol), 1-methyl-piperazine (2.0 mmol) in 3 ml of 1-BuOH was heated with stirring at 130° C. for about 7 days. The solvent was removed by evaporation in vacuo the residue was treated with water to give a suspension. The solid was then filtered off, washed with water, then 1:3, Ethyl Acetate: Petroleum ether, dried over filter funnel in vacuo to yield a brown solid. ESI-MS; m/z 332.2 (M+H$^+$). A synthetic reaction scheme for the preparation of 3-(4-methylpiperazin-1-yl)-6-phenyl-4-(pyridin-4-yl)pyridazine (MW01-7-0851WH) is depicted in FIG. 12.

G. Preparation of 4,6-diphenyl-3-piperazinylpyridazine (MW01-7-133WH)

Figure 13:
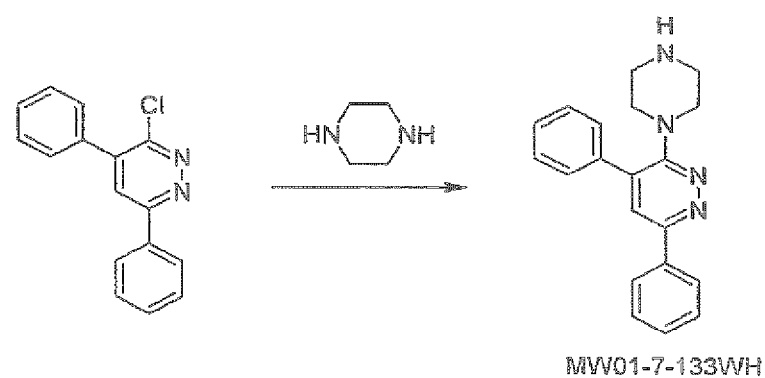
FIG. 13 depicts a synthetic scheme for MW01-7-133WH.

A synthetic reaction scheme for the preparation of 4,6-diphenyl-3-piperazinylpyridazine (MW01-7-133WH) is depicted in FIG. 13, and synthesis was carried out as described herein. The compound was prepared from 3-chloro-4,6-diphenylpyridazine (533 mg, 20 mmole) in the same manner as described for MW01-7-057WH, yielding light yellow solid (550 mg, 17.4 mmole, yield 86.9%). EST-MS: m/z 31703 (M+H+). 1H NMR (CDCl3): d 8.086 (d, J=7.5, 2H), 7.705 (d, J=7.5, 2H), 7.619 (s; 1H), 7.498 (m, 6H), 3.318 (d, 4H), 1932, (d, J=4.0, 4H) 1.896 (s, 1H).

H. Preparation of 2-(4-(6-phenyl-4-(piperidin-1-yl)pyridazin-3-yl)piperazin-1-yl)pyrimidine (MW01-7-107WH)

Figure 14:
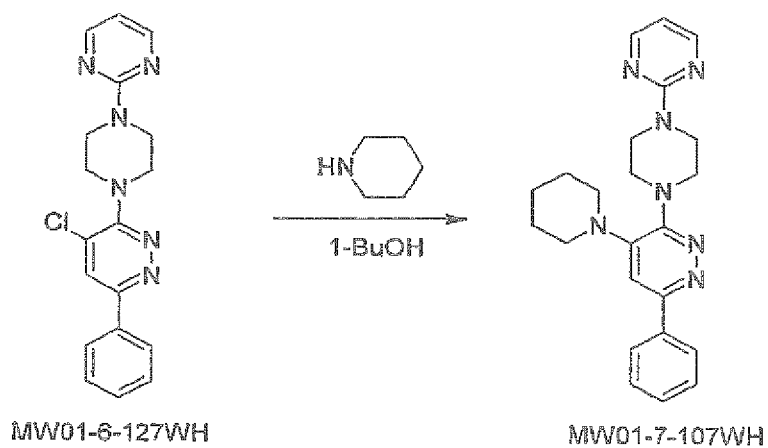
FIG. 14 depicts a synthetic scheme for MW01-7-107WH.

A synthetic reaction scheme for the preparation of 2-(4-(6-phenyl-4-(piperidin-1-yl)pyridazin-3-yl)piperazin-1-yl)pyrimidine (MW01-7107WH) is depicted in FIG. 14, and synthesis was carried out as described herein. The compound was prepared from MW01-6-127WH (200 mg, 0.57 mmole) in the same manner as described for MW01-7-057WH, yielding light yellow solid (220 mg, 0.55 mmole, yield 96.3%). ESI-MS: m/z 402.5 (M+H+).

I. Preparations of 6-methyl-4-phenyl-3-(4-pyrimidin-2-ylpiperazin-1-yl)pyridazine (MW01-7-057)

Figure 15:
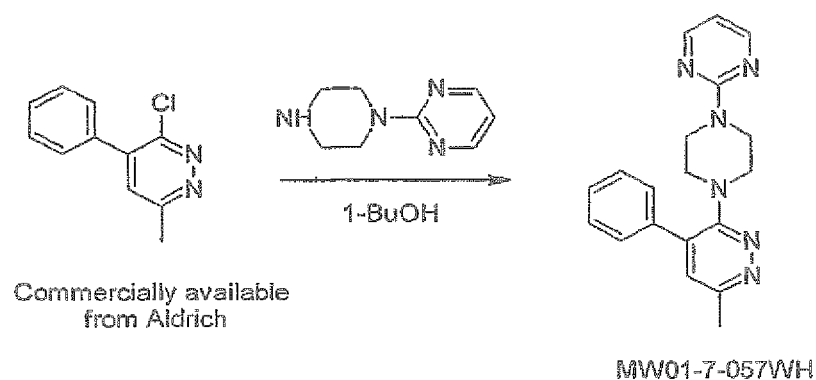
FIG. 15 depicts a synthetic scheme for MW01-7-057.
Figure 16:
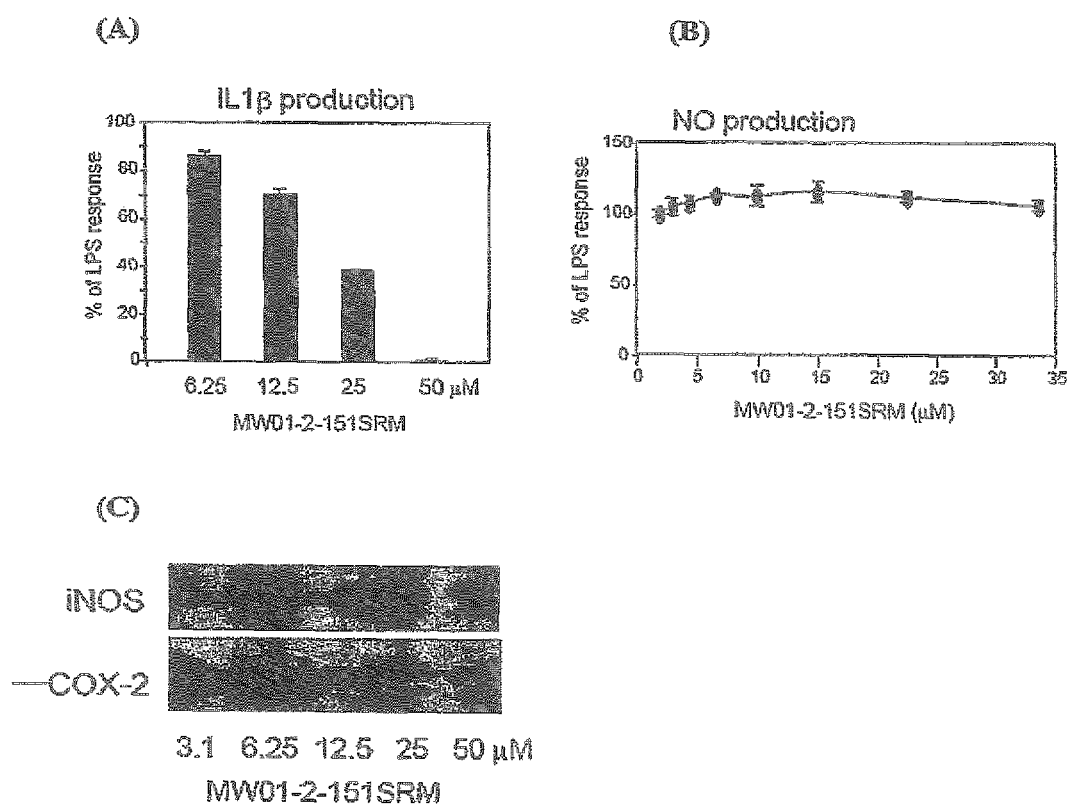
FIG. 16 show graphs and micrographs illustrating proinflammatory cytokine production by MW01-5-151SRM. (A) Concentration dependent inhibition by MW01-5-151SRM of LPS-induced increases of IL-1β in the BV2 microglial cell line, (B) LPS-stimulated accumulation of the NO metabolite, nitrite, was not inhibited by MW01-5-1151SRM at concentrations up to 33 μM. (C) MW01-5-1151SRM does not suppress LPS-induced production of iNOS or COX-2 in activated BV-2 cells.
Figure 17:
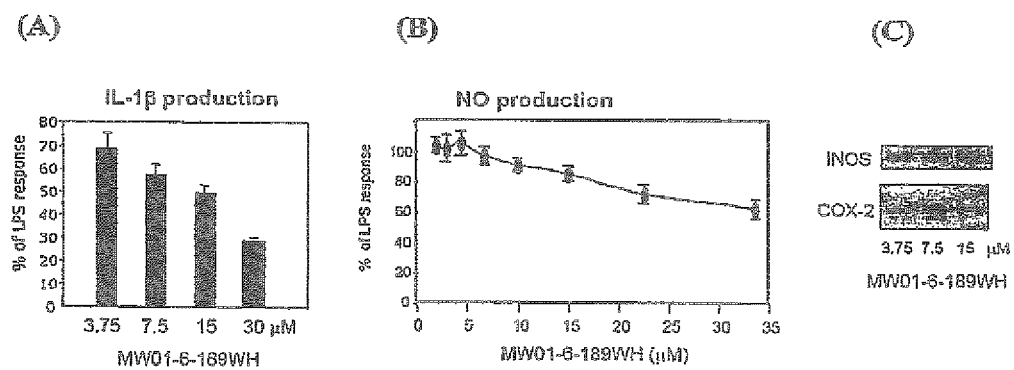
FIG. 17 show graphs and micrographs illustrating proinflammatory cytokine production by MW01-5-189WH. (A) Concentration dependent inhibition by MW01-5-189WH of LPS-induced increases of IL-1β in the BV2 microglial cell line. (B) LPS-stimulated accumulation of the NO metabolite, nitrite, was not inhibited by MW01-5-189WH at concentrations up to 33 μM. (C) MW01-5-189WH does not suppress LPS-induced production of iNOS or COX-2 in activated BV-2 cells.
Figure 18:
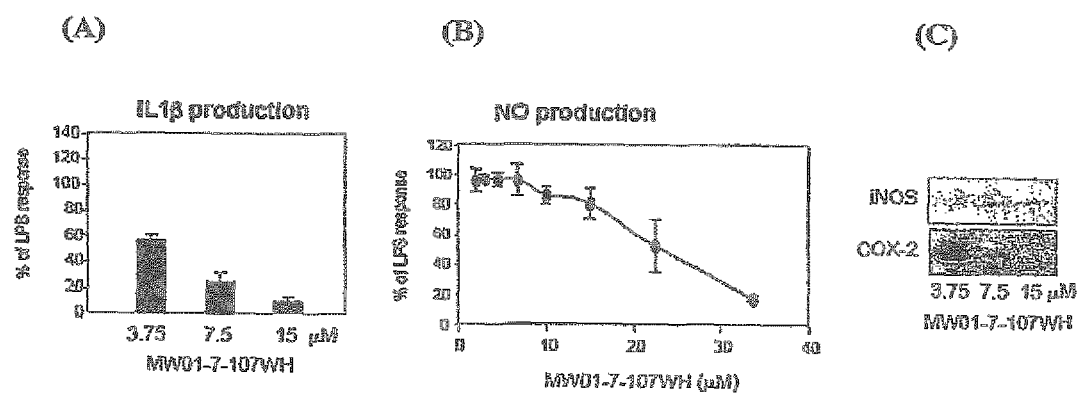
FIG. 18 show graphs and micrographs illustrating proinflammatory cytokine production by MW01-5-107WH. (A) Concentration dependent inhibition by MW01-5-107WH of LPS-Induced increases of IL-1β in the BV2 microglial cell line. (B) LPS-stimulated accumulation of the NO metabolite, nitrite, was inhibited by MW01-5-107WH. (C) MW01-5-107WH also inhibited LPS-induced production of iNOS or COX-2 in activated BV-2 cells.
Figure 19:
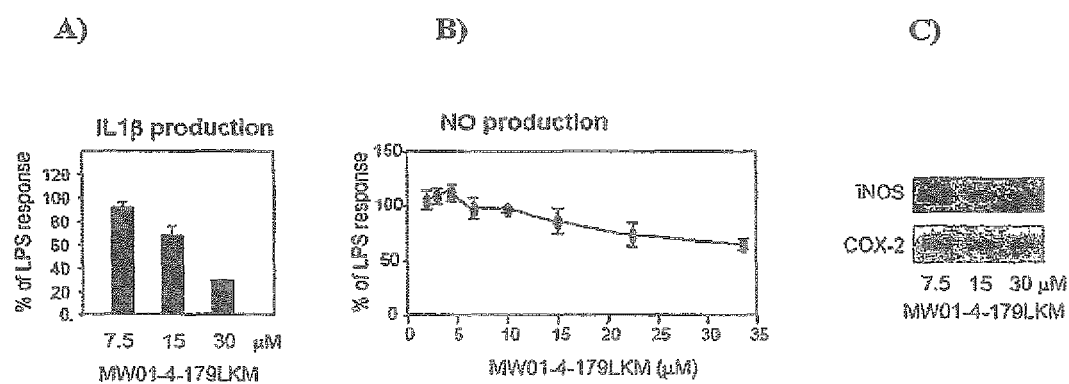
FIG. 19 show graphs and micrographs illustrating proinflammatory cytokine production by MW01-5-179WH. (A) Concentration dependent inhibition by MW01-5-179WH of LPS-included increases of IL-1β in the BV2 microglial cell line. (B) LPS-stimulated accumulation of the NO metabolite, nitrite, was not inhibited by MW01-5-179WH at concentrations up to 33 μM, (C) MW01-5-179WH does not suppress LIDS-induced production of iNOS or COX-2 in activated BV-2 cells.
Figure 20:
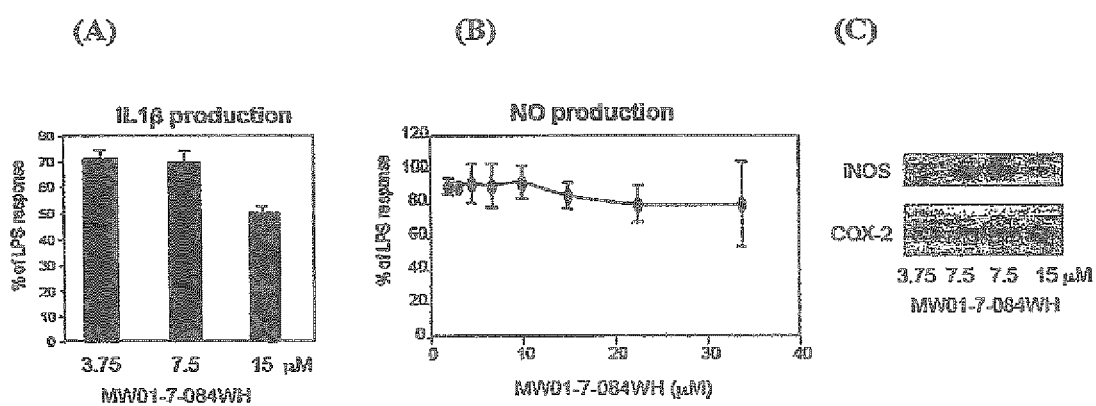
FIG. 20 show graphs and micrographs illustrating proinflammatory cytokine production by MW01-5-084WH. (A) Concentration dependent inhibition by MW01-5-084WH of LPS-induced increases of IL-1β in the BV2 microglial cell line. (B) LPS-stimulated accumulation of the NO metabolite, nitrite, was not inhibited by MW01-5-084WH at concentrations up to 33 μM, (C) MW01-5-084WH does not suppress LPS-induced production of iNOS or COX-2 in activated BV-2 cells.
Figure 21:
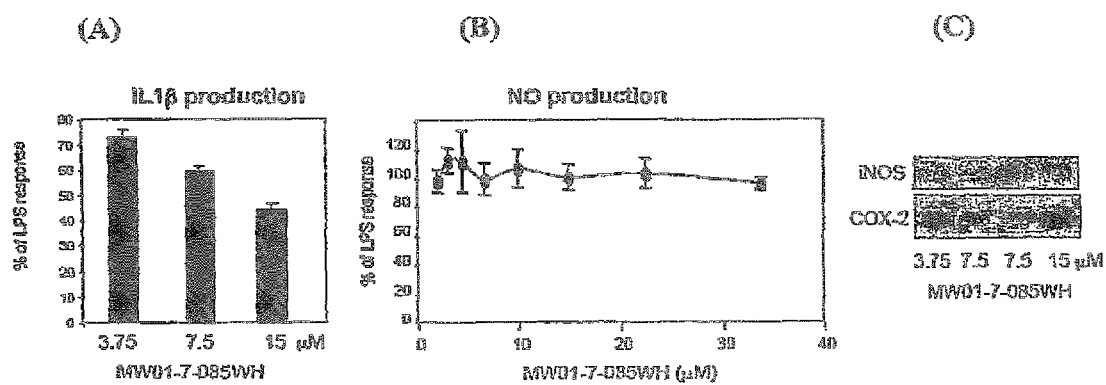
FIG. 21 show graphs and micrographs illustrating proinflammatory cytokine production by MW01-5-085WH. (A) Concentration dependent inhibition by MW01-5-085WH of LPS-induced increases of IL-1β in the BV2 microglial cell line. (B) LPS-stimulated accumulation of the NO metabolite, nitrite, was not inhibited by MW01-5-085WH at concentrations up to 33 μM. (C) MW01-5-085WH does not suppress LPS-induced production of iNOS or COX-2 in activated BV-2 cells.
Figure 22:
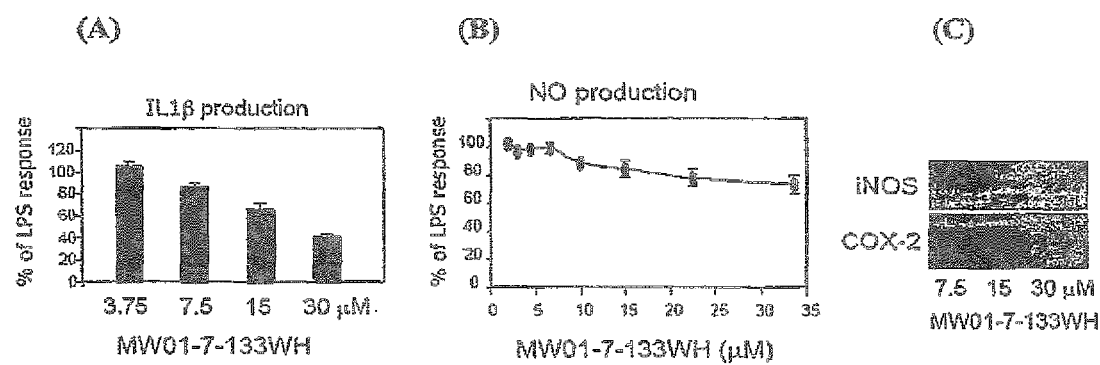
FIG. 22 show graphs and micrographs illustrating proinflammatory cytokine production by MW01-5-0133WH. (A) Concentration dependent inhibition by MW01-5-133WH of LPS-induced increases of IL-1β, in the BV2 microglial cell line, (B) LPS-stimulated accumulation of the NO metabolite, nitrite, was not inhibited by MW01-5-133WH at concentrations up to 33 μM. (C) MW01-5-133WH does not suppress LPS-induced production of iNOS or COX-2 in activated BV-2 cells.
Figure 23:
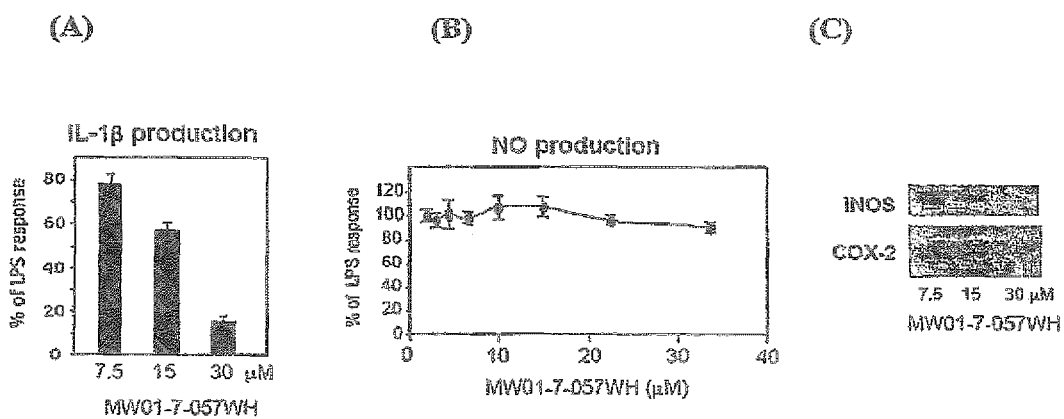
FIG. 23 show graphs and micrographs illustrating proinflammatory cytokine production by MW01-5-057WH. (A) Concentration dependent inhibition by MW01-5-057WE of LPS-induced increases of IL-1β in the BV2 microglial cell line. (B) stimulated accumulation of the NO metabolite, nitrite, was not inhibited by MW01-5-057WH at concentrations up to 33 μM. (C) MW01-5-057WH does not suppress LPS-induced production of iNOS or COX-2 in activated BV-2 cells.
Figure 24:
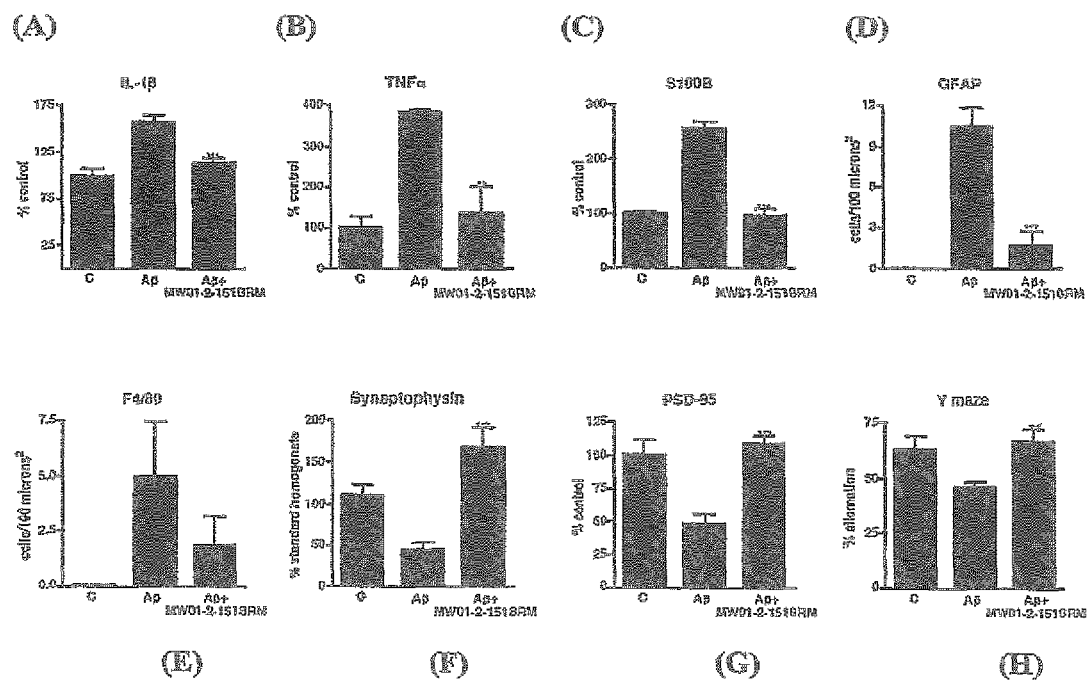
FIG. 24 A-H shows graphs illustrating in vivo activity of MW01-2-151SRM in the Aβ infusion mouse model. Graphs are of MW01-2-151SRM suppression of Aβ-induced neuroinflammation and synaptic damage and activity in the Y-maze. Hippocampal sections or extracts from vehicle-infused mice (control), Aβ-infused mice injected with solvent, and Aβ-infused mice injected with MW01-2-151SRM were evaluated for neuroinflammation by measurement of the levels of the pro-inflammatory cytokines IL-1β (A), TNFα (B), and S100B (C), and the number of GFAP-positive astrocytes (D), F4/80 (F), the presynaptic marker, synaptophysin (F), and evaluated for synaptic damage by analysis of the levels of the post-synaptic density protein 95 (PSD-95) (G), and Y-maze (H). Data are from one of two independent experiments, and are the mean±SEM for 4-5 mice per experimental group.
Figure 25:
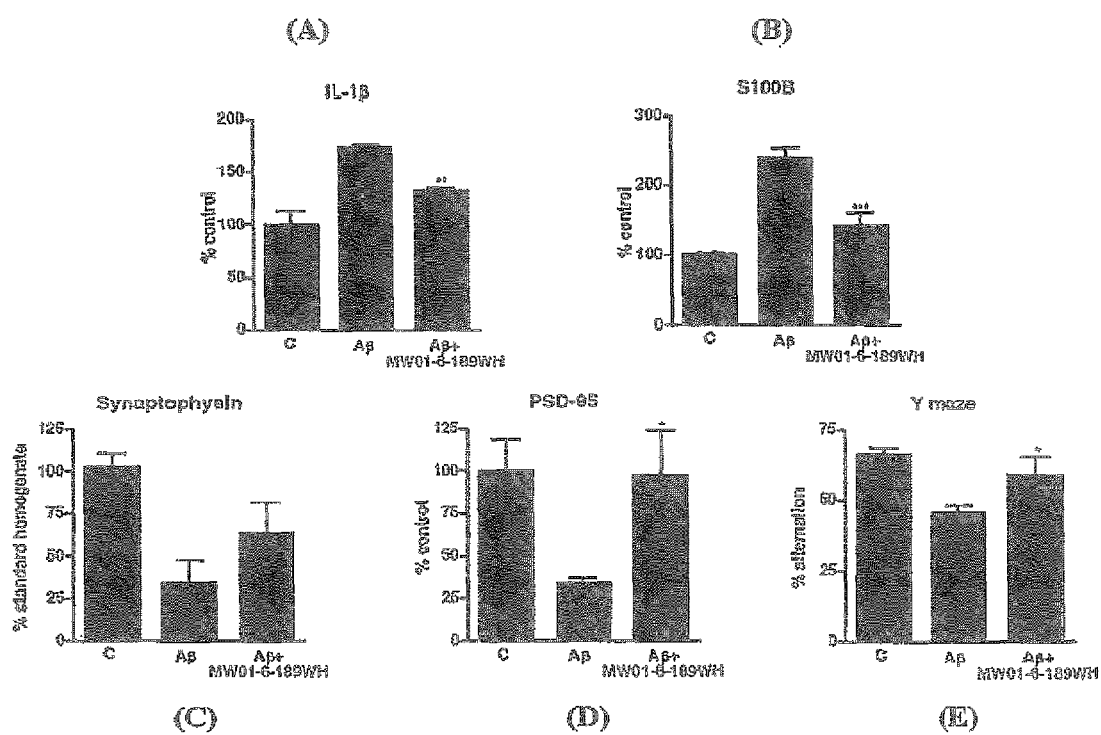
FIG. 25 A-E shows graphs illustrating in vivo activity of MW01-2-189SRM in the Aβ infusion mouse anode. Graphs are of MW01-2-189SRM suppression of Aβ-induced neuroinflammation and synaptic damage and activity in the Y-maze. Hippocampal sections or extracts from vehicle-infused mice (control), Aβ-infused mice injected with solvent, and Aβ-infused mice injected with MW01-2-189SRM were evaluated for neuroinflammation by measurement of the levels of the pro-inflammatory cytokines IL-1β (A), and 8100B (B), the presynaptic marker, synaptophysin (C), and evaluated for synaptic damage by analysis of the levels of the post-synaptic density protein 95 (PSD-95) (D), and Y-maze (E). Data are from three samples in the MW01-2-189SRM were analyzed.
Figure 27:
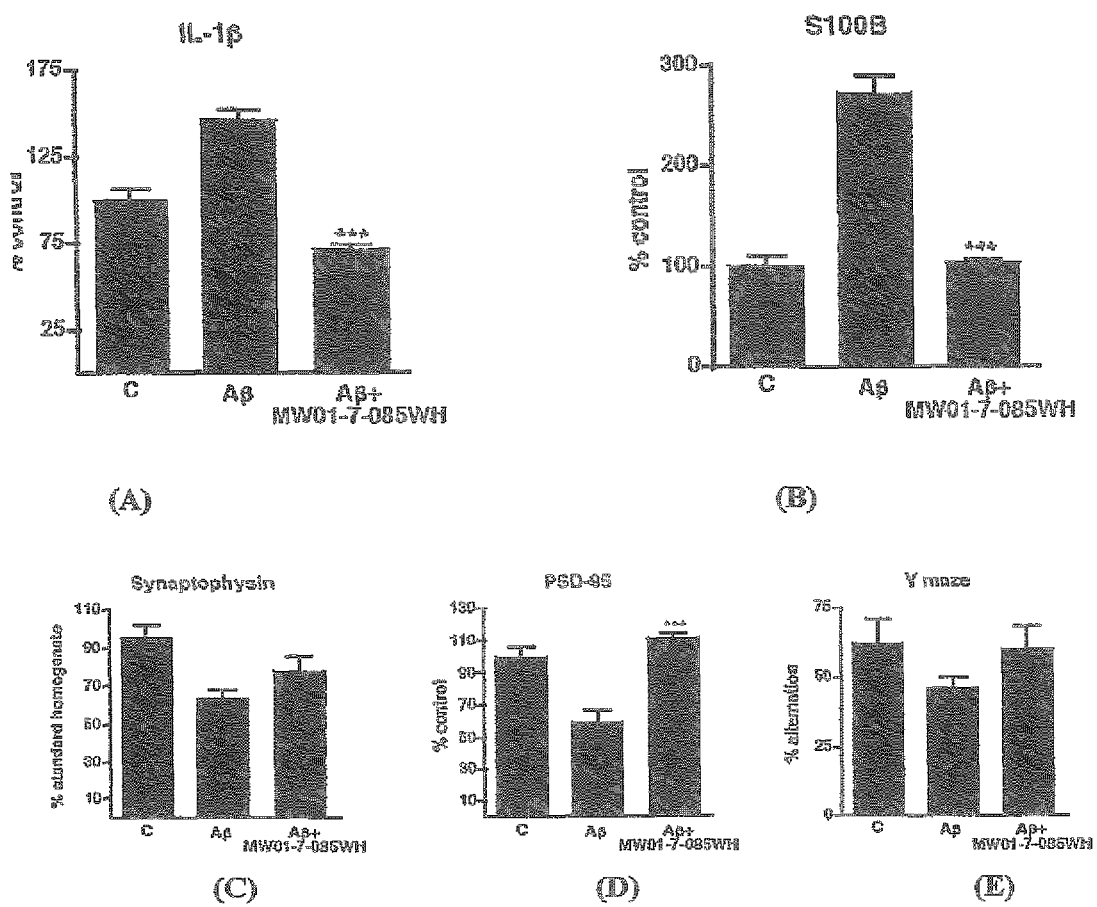
FIG. 27 A-E shows graphs illustrating in vivo activity of MW01-2-085SRM in the Aβ infusion mouse model. Graphs are of MW01-2-085SRM suppression of Aβ-induced neuroinflammation and synaptic damage and activity in the Y-maze. Hippocampal sections or extracts from vehicle-infused mice (control), Aβ-infused mice injected with solvent, and Aβ-infused mice injected with MW01-2-085SRM were evaluated for neuroinflammation by measurement of the levels of the pro-inflammatory cytokines IL-1β (A), and MOB (B), the presynaptic marker, synaptophysin (C), and evaluated for synaptic damage by analysis of the levels of the postsynaptic density protein 95 (PSD-95) (D), and Y-maze (E). Data are from three samples in the MW01-2-085SRM were analyzed.
Figure 28:
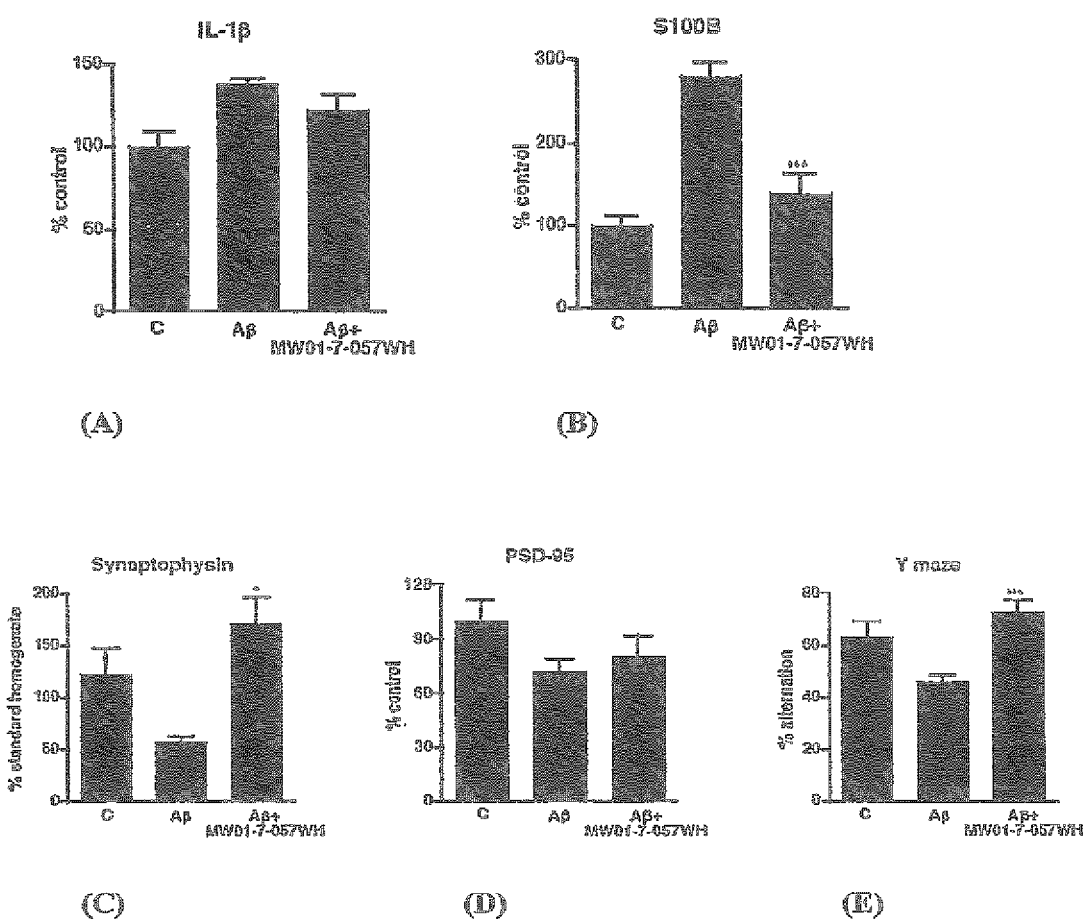
FIG. 28 A-E shows graphs illustrating in vivo activity of MW01-2-057WH in the Aβ-infusion mouse model. Graphs are of MW01 suppression of Aβ-induced neuroinflammation and synaptic damage and activity in the Y-maze. Hippocampal sections or extracts from vehicle-infused mice (control), Aβ-infused mice injected with solvent, and Aβ-infused mice injected with MW01-2-057WH were evaluated for neuroinflammation by measurement of the levels of the pro-inflammatory cytokines IL-1β (A), and S100B (B), the presynaptic marker, synaptophysin (C), and evaluated for synaptic damage by analysis of the levels of the post-synaptic density protein 95 (PSD-95) (D), and Y-maze (E). Data are from three samples in the MW01-2-057SRM were analyzed. There was no significant effect on PSD-95.

A synthetic reaction scheme for the preparation of 6-methyl-4-phenyl-3-(4-pyrimidin-2-ylpiperazin-1-yl)pyridazine (MW01-7-057) is depicted in FIG. 15, and synthesis was carried out as described herein. A mixture of 3-chloro-6-methyl-4-phenylpyridazine (100 mg, 0.5 mmol), 1-(2-pyrimidyl)piperazine (400 mg, 2.0 mmol) in 3 ml of 1-BuOH was heated with stirring at 130° C. for 7 days. The solvent was removed by evaporation in vacuo the residue was treated with water to give a suspension. The solid was then filtered off, washed with water, then 1:3, Ethyl Acetate: Petroleum ether, dried over filter funnel in vacuo to give light yellow solid (68 mg, 0.20 mmol, yield 41.7%). Purity>95%; ESI-MS: m/z 3311 (M+H+). 1H NMR (CDCl$_3$): d 8.310 (d, J=5.0, 2H), 7.678 (d, J=7.5, 2H), 7476 (m, 3H), 7.119 (s, H), 6.509 (t, J=4.5, 1H), 3.785 (t, J=4.5, J=5.0, 4H), 3.277 (t, J=4.5, J=5.0, 4H), 2.669 (s, 3H).

Example 2

Assays for Confirming Activity of Pyridazine Compounds

The following assays can be used to confirm the activity of the pyridazine compounds.

Cell Culture Assays.

Cell-based assays of the concentration-dependent activity of a compound of the invention will be conducted using methods previously described (Mirzoeva et al., J Med Chem 45:563-566, 2002). BV-2 mouse microglial cells ($1.25 \times 10^4$ cells/well in a 48-well plate) will be cultured for one day in αMEM media containing 10% fetal bovine serum (PBS), and then treated in serum-free media for 16 hrs with either control buffer or the standard glial activating stimulus lipopolysaccharide (LPS, from *Salmonella typhimurium*; 100 ng/ml final concentration) in the presence of diluent or compound. Stock solutions (20 of compounds will be prepared in dimethylsulfoxide (DMSO). Solutions for cell treatments will be prepared by dilution of stock solutions into serum-free media immediately before adding to the cells. Control wells will contain the same final concentration of DMSO as the compound-containing wells. It has been previously determined that this concentration of DMSO is not toxic, to the cells (Mirzoeva et al., Brain Res, 844:126434, 1999). The accumulation of nitrite, the stable metabolite of nitric oxide (NO), will be measured in BV-2 conditioned media by the Griess assay as previously described (Mirzoeva et al., Brain Res. 844:126-134, 999; Mirzoeva et al., J Med Chem 45:563-566, 2002). Levels of IL-1β in cell lysates and TNFα in conditioned media will be measured by ELISA (Biosource International) as per the manufacturer's instructions. Cell lysates will be analyzed by Western blots as described (Mirzoeva et al., J Med Chem, 2002) to determine the levels of inducible nitric oxide synthase (iNOS), cyclooxygenase-2 (COX-2) and apolipoprotein E (apoE). For apeE measurements, rat primary mixed glia will be prepared and stimulated with human oligomeric $A\beta_{1-42}$ (10 μM) as previously described (Mirzoeva et al., 2002, supra). Antibodies and dilutions used for Western blots will be as follows: anti-COX-2 (1:1000, Santa Cruz), anti-iNOS (1:1000, Transduction Laboratories), anti-apoE (1:1000). Antibody against β-actin (1:500,000 dilution, Sigma) will be used to confirm equal protein loading among the samples.

In Vivo Efficacy Studies in Mice.

The study design and treatment paradigm for intracerebroventricular (ICV) infusion of human oligomerie $A\beta_{1-42}$ into the mouse will be as described previously (Craft et al., Neurobiol Aging 25:1283-1292, 2004b), except that compound administration will be by mouth. Female C57Bl/6 mice (Harlan) weighing 20-25 g (3-4 months old) will be housed in a pathogen free facility under an approximate 12 h/12 h dark and light cycle and they will have access ad libitum to food and water.

Mice will be administered by oral gavage either test compound (2.5 mg/kg/day) or solvent control (10% DMSO) in a, 0.5% (w/v) carboxymethylcellulose suspension. Once per day treatment will begin at day 21 after start of Aβ ICV infusion and continue for 14 days. Beginning at day 50 after start of Aβ ICV infusion, the Y maze test of spontaneous alternation will be used to evaluate hippocampus dependent spatial learning as described previously (Craf et al., J Mol. Neurosci. 24:115-122, 2004a). Briefly, each mouse will be placed in the "start" arm and then released to choose one of the two other arms. The mouse will be blocked from exiting the chosen arm for 30 s then they will be placed back in the start arm and released again to choose one of the two other arms. If the second choice is different from the first one, the mouse will be scored as alternating. Mice will be tested for 10 days with one trial per day, and a mean percent alternation will be calculated for each mouse. At day 60 after start of AβICV infusion, mice will be anesthetized with pentobarbital (50 mg/kg) and perfused with a HEPES buffer (10 mM, pH 72) containing a protease inhibitor cocktail (1 μg/ml leupeptin, dithithreitol, 2 mM sodium vanadate, 1 μM phenylmethylsulphonylfluoride). The brain will be removed and longitudinally bisected as described previously (Craft et al., Neurobiolo Aging 25:12834292, 2004b). The right half of the brain will be fixed in 4% (v/v) paraformaldehyde and paraffin-embedded for histology. The hippocampus will be dissected from the left half of the brain and snap-frozen for subsequent biochemical evaluation. Hippocampal extract supernatants will be prepared by dounce and sonication in the HEPES buffer containing a protease inhibitor cocktail, followed by centrifugation as described (Craft et al., 2004b, supra).

Levels of IL-1β and TNFα in hippocampal supernatants will be measured by ELISA (Biosource International) per the manufacturer's instructions. S100B levels in hippocampal supernatants will be measured by a empium-based ELISA essentially as previously described (Van Eldik and Griffin, Biochem Biophys Acta 1223:398-403, 1994). Synaptophysin levels in hippocampal supernatants will be quantified by ELISA following the procedure described previously (Craft at al, 20041, supra). PSD-95 levels will be determined by Western blots using anti-PSD-95 antibodies (1:100,000 dilution; Upstate Biotechnology) as described (Craft et al., 2004b).

Immunohistochemical detection of activated astrocytes and microglia will be performed on 10 μm a sections as described previously (Craft et al, 2004b, supra), with anti-GFAP (1:1500; Sigma) and anti-F4/80 (1:100; Serotek) antibodies, respectively, using the mouse on mouse or Vectastain Universal Elite ABC irnimunodetection kits (rlectoriNovocastra) and development with diaminobetizidine (DAB) substrate. Cell bodies will be manually counted in the hippocampus of three GFAP and F4/80 labeled sections positioned at −1.8, −2.1, and −2.3 mm from bregma. Aβ immunohistochemistry will be done with a rabbit anti-human Aβ antibody as previously described (Craft et al., 2004b, supra). Cell counts and amyloid plaque counts will be determined by two blinded observers and amyloid plaque area will be determined as previously described (Craft et al., 2004b, supra). Peroxynitrite-mediated neuronal damage will be measured with an anti-nitrotyrosine antibody (1:125; Chemicon), using the Vectastain Rabbit Elite ABC kit. For nitrotyrosine cell counts, all DAB stained cell bodies in the neuronal layers of the hippocampus and subiculum will be counted on three sections roughly adjacent to those used for F4/80 and GFAP analysis, as described (Craft et al., 2004b, supra).

In Vitro Stability, Oral Bioavailability and Brain Uptake.

The stability of compounds (1 in a standard incubation with rat liver microsomes (ED Biosciences) and an NADPH-regenerating system will be done at 37° C. for 30 and 120 min. Reactions will be stopped by acetonitrile, and the reaction mixture will be centrifuged at 16 000×g for 10 min. 10 μl of the supernatant will be analyzed by calibrated HPLC to quantify the percentage of the initial amount of compound remaining after the incubation. The HPLC system (Dionex Corp., Sunnyvale, Calif.) includes a Dionex P480 pump, a Phenornenex Luna C18 column (250×2.0 mm, 5 μm) with a guard column (Phenomenex, Torrance, Calif.) and a Dionex UVD340U Ultraviolet (UV) detector. The mobile phase will consist of 0.1% formic acid as reagent A and 0.08% formic acid/water in 80% acetonitrile as reagent B, at a flow rate of 0.2 ml per minute. The gradient will consist of the following linear and isocratic gradient elution changes in reagent B: isocratic at 60% from 0 to 5 min, 60% to 90% from 5 to 39 mica, isocratic at 90% until 44 min. Peak quantification will be done based on absorption measured at 260 nm relative to a standard curve obtained by using serial dilutions of the compound.

To estimate oral bioavailability (concentration of compound in the blood as a function of tithe after oral administration) and to gain insight into potential brain uptake, a compound (2.5 mg/kg) will be administered to mice by oral gavage in a 0.5% (w/v) carboxymethylcellulose suspension. At 5, 15, 60 and 120 min after compound administration, the animals will be anesthetized with, pentobarbital (50 μg/kg). Blood will be harvested by intracardiac puncture, collected in heparinized tubes, and plasma will be obtained by centrifugation Mice will lace perfused with a HEPES buffer (10 mM, pH 7.2) containing a protease inhibitor cocktail (1 μg/ml leupeptin, 1 μM dithithreitol, 2 mM sodium vanadate, 1 μM phenylmethylsulphonylfluoride), and brains will be removed and weighed. Brain homogenates will be prepared by dounce and sonication in the HEPES buffer containing a protease inhibitor cocktail. Brain homogenates will be centrifuged at 12000×g for 10 minutes and the supernatant acidified by diluting 1:3 with 0.1% formic acid (Fluka). Solid phase extraction followed by HPLC analysis will be used to quantify the amount of compound in brain supernatants. Briefly, cartridges (Sep-Pak® C18, Waters) will be conditioned with 1 ml of acetonitrile (HPLC grade, EMD Biosciences) and equilibrated with 1 ml of water. A structural analog of the compound will be used as an internal standard. The acidified brain supernatant will be added to the cartridge followed by a 1 ml wash with 30% acetonitrile. The compound will be eluted from the cartridge using 80% acetonitrile. The eluate will be evaporated to dryness, reconstituted in 0.08% formic acid/water in 80% acetonitrile and analyzed by HPLC using the following gradient in reagent B: 0% to 60% from 2 to 5 min, isocratic at 65% until 7 min, 65% to 80% from 7 to 12 min, isocratic at 80% until 15 min, 89% to 100% from 15 to 18 min and isocratic at 100% until 23 rain. Plasma samples will be deproteinized in 0.1M perchloride acid and centrifuged at 12000×g for 10 min. The supernatant will be neutralized with 1M NaOH then extracted with dichloromethane, and the layers separated at 3000×g for 5 min. The organic phases from three successive extractions will be pooled and then evaporated to dryness under reduced pressure. The dried residue will be reconstituted in 50 μl of reagent B, and 10 μl of the reconstituted material will be analyzed by HPLC using the gradient described above for brain supernatants.

Suppression of CNS Versus Peripheral Inflammation.

Mice will be administered by oral gavage of compound (2.5 mg/kg/day) or diluent (10% DMSO) in a 0.5% (w/v) carboxymethylcellulose suspension once daily for two weeks. After the last administration, mice will be injected intraperitoneally (i.p) with 10 mg/kg of LPS. Control mice will be injected with saline. Six hours after the LPS challenge, mice will be anesthetized with pentobarbital (50 mg/kg) and blood will be drawn by intracardiac puncture, allowed to clot, and centrifuged for serum preparation. Brains will be removed and processed as described above. Levels of IL-1β and TNFα in brain supernatants and serum will be measured using a MSD multiplex assay per the manufacturer's instructions (Mesa Scale Discovery, Gaithersburg, Md.).

Liver Toxicity after Chronic In Vivo Administration of Compound

Mice will be administered by oral gavage either test compound (2.5 mg/kg/day) or diluent (10% DMSO) in a 0.5% (wfv) carboxymethylcellulose suspension once daily for two weeks. Mice will be anesthetized and sacrificed as described above. Livers will be removed, fixed in 4% (v/v) paraformaldehyde and paraffin-embedded for histology. To assess histological toxicity, 4 μm liver sections will be stained with haematoxylin and eosin. Two independent observers blinded to the treatment groups will perform microscopic assessment of the tissue for injury.

Morris Water Maze.

This test is based on the swimming maze test for spatial memory (Morris, Learn. Mot 12:239-260, 1981; J Neurosci Methods 11:47-60, 1984) and takes advantage of the natural swimming ability of rodents and the ease of manipulating cues around the maze. In this task, a mouse is placed in a pool of liquid that is made opaque by the addition of non-toxic tempera powdered paint. The mouse then swims until an escape platform (hidden just under the surface of the water) is found. Finding the platform enables the mouse to escape from the water and therefore is positively reinforced. When the platform is kept in the same position, the animal quickly learns to use distal cues to locate the position of the platform, even if the mouse is placed in the pool at different starting positions. The experimental protocol for the Morris maze test is as described in Ohno et al, (Eur. J. Neurosci, 2006, 23(8): 223540; Learn Mem 2005, 12(3): 211-5). Briefly, the pool is 1.2 m in diameter and made of white metal. The water is maintained at 25±1° C. and is made opaque with nontoxic white paint to hide the square, white escape platform (10 cm×10 cm). During training, the platform is submerged (1 cm) below the water surface and remains in the same position to avoid quandrant biases. The mice receive six trials per day for 4 days (3 blocks of two trials; 1 min intertrial intervals, 1-hour interblock intervals). The mouse is placed into the water facing the wall of the pool and is allowed to search for the platform. The starting position varies among four locations in a pseudorandom manner for each trial. The trial ends when an animal climbs onto the platform or when a maximum of 60 sec has elapsed. The mouse is placed on the platform for 60 see before and after each trial. At the end of the training, all mice are given a probe test with the platform removed froth the pool. The behaviour of the mouse is recorded by a video camera and analyzed computationally for several parameters such as latency to finding the platform, total distance traveled, and percent of time spent in the target quadrant.

At post-operative day 60 mice will be anesthetized and perfused with a Hopes buffer containing a protease inhibitor cocktail. The brains are then removed and longitudinally bisected. The right half of the brain is fixed in a paraformaldehyde/phosphate buffer solution and embedded in paraffin for histological examination, while the hippocampus is isolated from the left hemisphere and snap frozen for biochemical evaluation of endpoints.

Example 3

Efficacy in the Tg6799 5× FAD Mouse Model

MW01-2-151SRM will be tested in the Tg6799 mouse at 5, 10 and 25 mg/kg. As above, neuroinflammation and synaptic dysfunction biochemical endpoints and Y-maze behavioral endpoint will be determined. A higher dose is proposed based on the start of administration to animals that are already showing signs of pathology based on characterization of strain. More animals needed for significance are compared to the infusion model and longer time due to required expansion of colony via breeding.

Example 4

Selection of Lead Drug Compound

The following eight compounds were synthesized: MW01-4-179LKM; MW01-2-151SRM; MW01-7-107WH; MW01-6-189WH; MW01-7-084WH; MW01-7-085WH7) MW01-7-133WH; and MW01-7-057WH (See FIGS. 1 to 15 and Example 1).

A. The compounds were tested in glial cell-based assays for concentration-dependent suppression of neuroinflammation endpoints (nitric oxide, IL-1β). All eight compounds inhibited LPS-induced IL-1β production in BV-2 microglia cells in a concentration-dependent manner. Most compounds were also selective, in that they did not inhibit production of nitric oxide (NO). The lack of an effect on NO production was further validated by showing no effect on up-regulated levels of iNOS. No effect over the same concentration range was seen on up-regulation of COX-2. The following were selective compounds: MW01-2-151SRM; MW01-4-179LKM; MW01-6-189 WH; MW01-7-084WH; MW01-7-085WH; MW01-7-133WH; and MW01-7-057WH. One compound, MW01-7-107WH, was nonselective in that it also inhibited production of NO, iNOS and COX-2 over the same concentration ranges. (See FIGS. 16 to 23 showing the results of the cell-based activity of MW01-2-151SRM; MW01-6-189WH; MW01-4-107WH; MW01-4-179LKM; MW01-7-084WH; MW01-7-085WH; MW01-7-133WH; and MW01-7-057WH in BV-2 microglial cells.)

B. Testing of Compounds in the human Aβ infusion mouse model for suppression of neuroinflammation and neuronal dysfunction biochemical endpoints (IL-1β, S100B, synaptophysin). Specifically, the following five active compounds were tested in vivo: MW01-2-151SRM; MW01-6-189WH; MW01-7-084WH MW01-7-085WH; and MW01-7-057WH. The best compounds in vivo were MW01-2-151SRM and MW01-6-189WH. These two compounds blocked the up-regulation of IL-1β and S100B, and prevented the loss of PSD-95, MW01-2-151SRM also prevented the loss of synaptophysin. MW01-6-189WH showed a trend toward preventing the synaptophysin loss; however, statistical significance was not reached due to limitations in sample size. MW01-7-084WH and MW01-7-085WH blocked the upregulation of IL-1β and S100B, and prevented loss of PSD-95. They were not as effective as MW01-2-151SRM in preventing the synaptophysin loss. MW01-7-057WH blocked S100B upregulation and synaptophysin loss, but did not block IL-1β upregulation car PSD-95 loss. (See FIGS. 24 to 28 showing the results of in vivo activity of MW01-2-

151SRM; MW01-6-189WH; MW01-7-084WH, MW01-7-085WH; and MW01-7-057WH in the Aβ infusion mouse model.)

C. The lead compounds were tested in the human Aβ infusion mouse model using the Y maze behavioral assay at 1.25, 2.5, 5, and 10 mg/kg. Neuroinflammation biochemical endpoints (hippocampus levels of IL-1α, TNFα) are based on proposed mechanism of action, and a synaptic dysfunction biochemical endpoint (hippocampus levels of synaptophysin) is used, as well as a Y-maze behavioral endpoint. MW01-2-151SRM, MW01-6-189WH, and MW01-7-057WH were significantly effective in preventing the Y-maze behavioral deficit brought about by human Aβ infusion. MW01-7-084WH and MW01-7-085WH showed a trend toward preventing the Y maze behavioral deficit.

Example 5 hERG Channel Inhibition Assays and Cardiac QT Interval Assays

Compounds have been screened for hERG (human ether-a-go-go) potassium ion channel binding and inhibition in order to eliminate early in the process any compounds with high potential to induce prolongation of cardiac QT interval in later studies due to off target toxicities. The hERG channel conducts rapidly activating delayed rectifier potassium currents that critically contribute to cardiac repolarization. Mutations in the hERG channel gene and drag-induced blockade of the currents have been linked to delayed repolarization of action potentials resulting in prolonged QT interval (Finlayson et al., 2004; Recanatini et at, 2005; Roden, 2004). QT prolongation is considered a significant risk factor against cardiac safety of new drugs. Therefore, consideration of cardiac safety early in the development process by testing for hERG channel inhibition provides an efficient and predictive means to assess potential compound cardiac safety liabilities. In addition, the FDA (USA) is considering this as an approval criteria in the future and has specific recommendations. The assays done to date have been by a commercial service (MDS PharmaService).

The initial assay is a radioligand binding assay that tests the ability of the test compound to compete with $^3$H-astemizole (a reference standard that binds to hERG channels with nM affinity) for binding to recombinant hERG channels stably expressed on human. HEK-293 cells. This cell line was chosen because it is of human origin, has been fully characterized with regard to hERG electrophysiology and pharmacology and displays the expected characteristics of $I_{Kr}$ current as well as expected pharmacological sensitivities, and is easy to maintain in culture (Zhou et al., J. Gen Physiol. 1998, 111(6): 781-94). A single concentration (10 μM) of test compound is assayed, and % inhibition of $^3$H-astemizole binding is calculated. Generally, any compounds that show>50% inhibition are tested further in the hERG channel activity assay. This is usual for medium throughout screens but is not recommended in the FDA document and tends to give false positives, as evidenced by the results reported below.

The hERG channel activity inhibition assay provides whole cell electrophysiological data about compound effects on the hERG K$^+$ channel function. Whole cell patch clamp methodology is generally considered to be the gold-standard determination of ion channel activity, rather than simply measuring channel binding. The standard testing procedure is to use 3 to 5 concentrations of compound at log dilutions with each concentration tested in triplicate (three cells). This allows a balance between achieving a reasonably accurate IC$_{50}$ measurement against a broad concentration range, and reducing cell attrition that would occur during more protracted experiment durations. After completion of compound dose-response procedures, a known hERG channel inhibitor, such as astemizole, is applied as a positive control.

Compounds which exhibit inhibition of hERG channel activity are verified as positives (the hERG channel activity assay can give false positives and false negatives) by testing in vivo for prolongation of cardiac QT interval. The QT interval studies are performed by evaluating compounds for effects on QT interval in Lead II electrocardiograms measured in anesthetized guinea pigs (Hirohashi et al., 1991, Arzneim.-Forsch./Drug Res 41:9-18), one of the species recommended in the FDA white paper. Vehicle or compound is administered orally at 15 mg/kg (dosing volume of 10 ml/kg) to groups of male guinea pigs (weighing 330-350 g), with 5 animals per group. This dose corresponds approximately to 20-fold the therapeutic dose by taking into account the body surface area of the animals. Heart rate, arterial blood pressure, and QT intervals are measured at baseline, and at 15, 30, 45, and 60 min after compound administration. Sotalol administered iv at 0.3 mg/kg serves as the positive control compound. The QT intervals are corrected for changes in heart rate using both Bazetes and Fridericia's formulae. Any increase in QT interval values over baseline values exceeding the upper 95% confidence limit of the mean changes at the corresponding time point in the vehicle-treated control group for two consecutive observation times indicates significant QT interval prolongation in the individually treated animals. This functional testing in early discovery provides a rapid and cost-effective method to better anticipate and eliminate compounds that may have adverse QT prolongation potential in humans.

Calculations of Amount of Compound Needed:
Competition binding assay: 1-2 mg
Patch clamp assay: 1-2 mg
QT interval assay: 5 mg/animal/dose=25 mg per assay at 15 mg/kg dose Because the ex vivo activity assays are subject to false positives and negatives, it is considered better to complete studies of in vivo QT interval assay following the guidelines of the FDA position paper.

Results:
Competition Inhibition Assay:
MW01-5-188WH, MW01-2-151SRM, and MW01-6-127WH were tested at 10 μM concentration.
MW01-5-188WH showed 91% inhibition at 10 μM. MW01-2-151SRM and MW01-6-127WH were negative, showing only 8% and 19% inhibition, respectively.
Patch Clamp Inhibition Assay:
MW0192-151SRM and MW01-6-189WH were tested at three concentrations (0.1, 1, 10 μM). These compounds showed minimal inhibition, with IC$_{50}$ values of 4.81 μM for MW01-6-189WH and 9.21 μM for MW01-2451SRM.
Cardiac QT Interval Prolongation Assay
A summary of the results as well as the materials and methods are set out below.

SUMMARY

Figure 29:
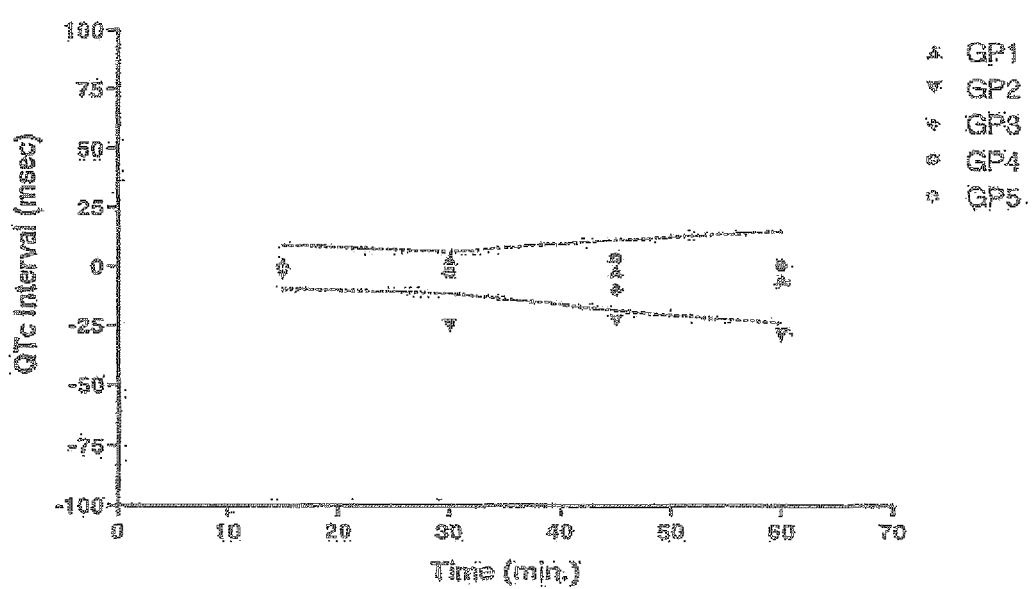
FIG. 29 is a graph showing QTc interval of MW01-2-151SRM (15 mg/10 ml/kg/po) (Bazatt's). Changes in QTc following oral administration of MW01-2151SRM at 15 mg/kg in guinea pigs. QT intervals were corrected for heart rate changes using Bazett's formula. The broken lines represent 95% confidence limits (mean±2SD) for QTc changes in the vehicle (2% Tween 80 in Distilled Water)—treated control. The five treated animals are represented by individual symbols.
Figure 30:
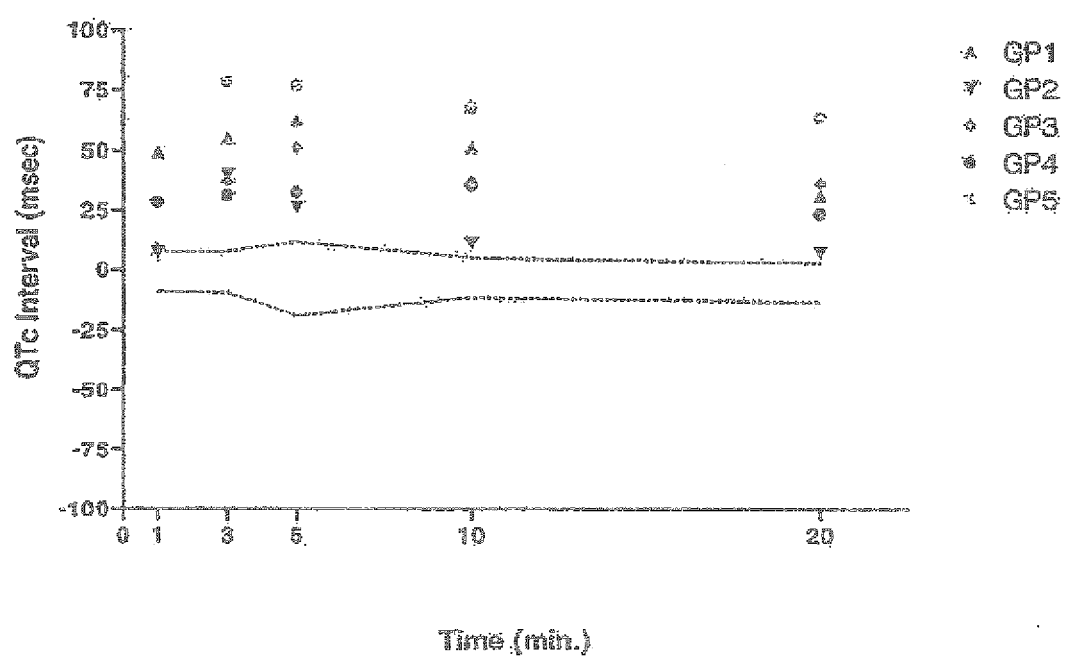
FIG. 30 is a graph showing QTc interval of Sotalol (0.3 mg/kg/iv) (Bazett's). Changes in QTc following intravenous administration of Sotalol at 03 mg/kg in guinea pigs. QT intervals were corrected for heart rate changes using Bazett's formula. The broken lines represent 95% confidence limits (mean±2SD) for QTc changes in the vehicle (0.9% NaCl) treated control. The five treated animals are represented by individual symbols.
Figure 31:
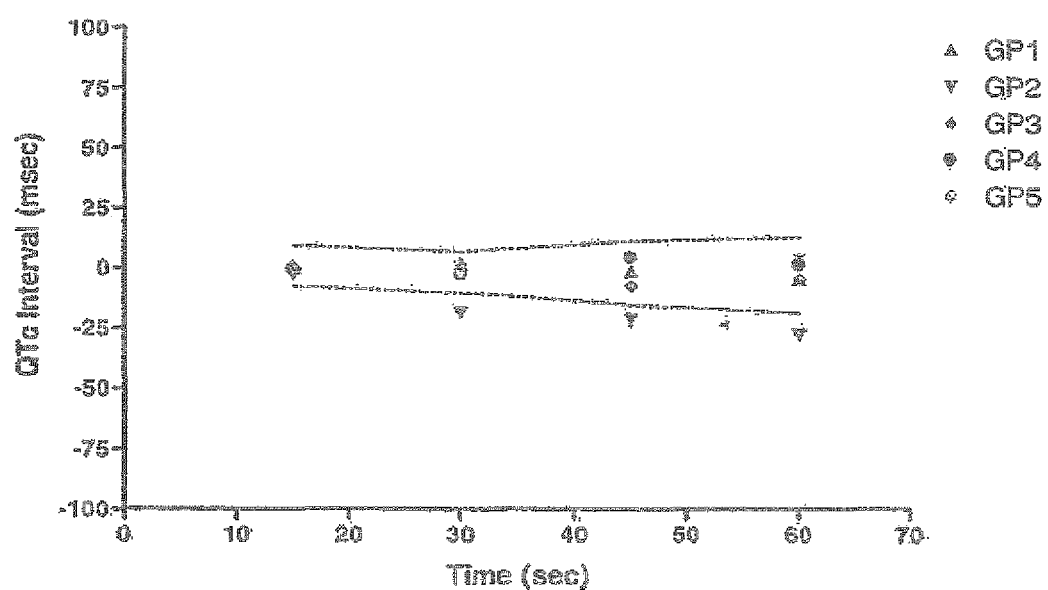
FIG. 31 is a graph showing QTc interval of MW01-2-151SRM (15 mg/10 ml/kg/pa) (Fredericia's). Changes in QTc following oral administration of MW01-2-151SRM at 15 mg/kg in guinea pigs. QT intervals were corrected for heart rate changes using Federicia's formula. The broken lines represent 95% confidence limits (mean±25D) for QTc changes in the vehicle (2% Tween 80 in Distilled Water)—treated control. The five treated animals are represented by individual symbols.
Figure 32:
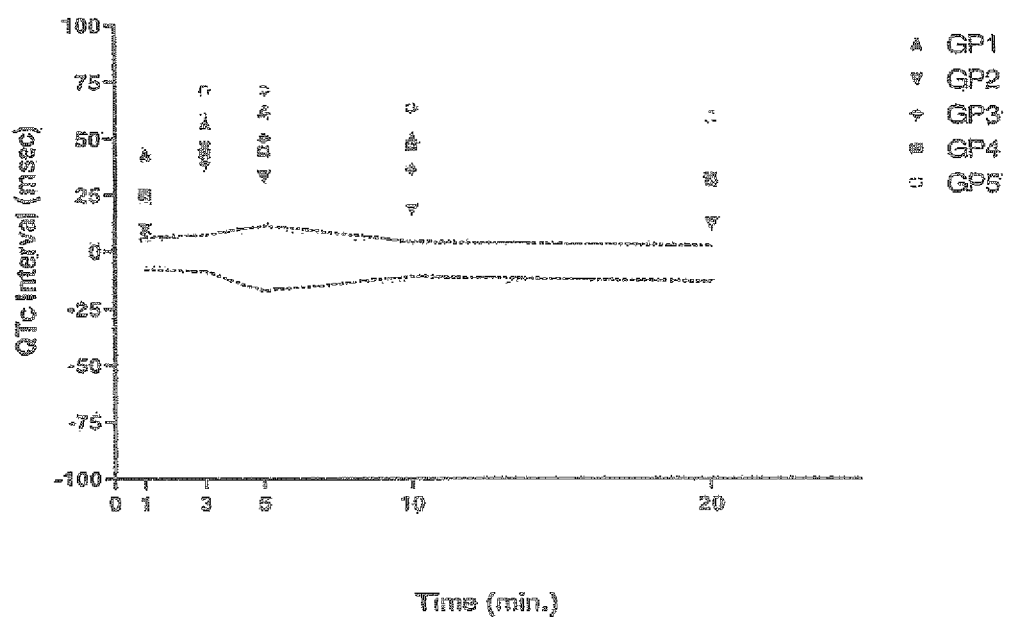
FIG. 32 is a graph showing QTc interval of Sotalol (0.3 mg/kg/iv) (Fredericia's). Changes in QTc following intravenous administration of Sotalol at 03 mg/kg in guinea pigs. QT intervals were corrected for heart rate changes using Fredericia's formula. The broken lines represent 95% confidence limits (mean±0.2SD) for QTc changes in the vehicle (0.9% NaCl)—treated control. The five treated animals are represented by individual symbols.

A test substance (e.g., MW01-2-151SRM) was evaluated for possible effects on QT interval in Lead II electrocardiogram measure in anesthetized guinea pigs. The QT intervals (QTc) were corrected for changes in heart rate using both Bazett's and Fridericia's formulae. Any increase in QTc values over baseline values exceeding the upper 95% confidence limit of the change at corresponding time point in the vehicle-treated control group for 2 consecutive observation times indicates significant QTc prolongation in the individually treated animals. The test substance at 15 mg/kg PO did not cause any significant prolongation in QTc interval in all of the 5 treated animals during the 60-minute period post-dosing (FIGS. 29 and 31). On the other hand, intravenous administration of sotalol at 0.3 mg/kg caused significant prolongation in QTc interval in all (5.5) animals (FIGS. 30 and 32). The results reached similar conclusion by using either Bazett's or Fridericia's formula for QT correction.

MW01-5-188WH and MW01-2-151SRM were administered PO at 15 mg/kg to 5 guinea pigs (330-350 g weight), QT intervals were obtained at baseline and at 15 min, 30 min, 45 min, and 60 min after compound administration. Neither compound increased cardiac QT interval above the mean+ 2SD of corresponding values in the vehicle control group. There were also no significant effects on mean blood pressure or heart rate after compound administration.

Figure 33:
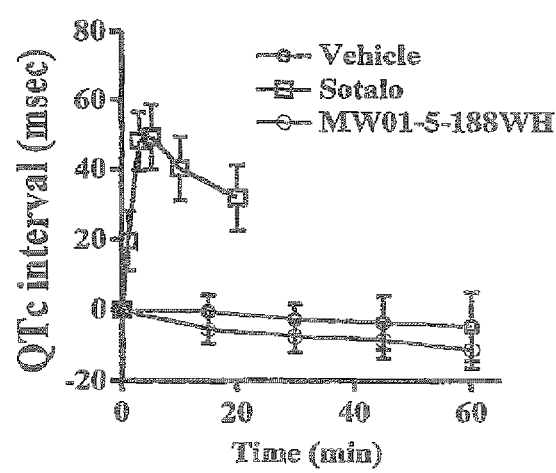
FIG. 33 is a graph showing QTc interval of oral administration of MW01-5-188WH (15 mg/kg p.o.) in guinea pig.

Example data for MW0195-188WH are shown in FIG. 33. The positive control compound, sotalol, induces a significant increase in cardiac QTc interval.

Materials and Methods

The test substance was dissolved in 2% Tween 80 and administered by oral administration. The substance was treated at 15 mg/kg with a dosing volume of 10 ml/kg with a dosing volume of 10 ml/kg. Duncan Hartley derived guinea pigs provided by MDS Pharma Services—Taiwan Ltd were used. Sotalol was obtained from Sigma, USA.

Groups of guinea pigs (weighing 330-350 g) with 5 animals each were employed. The animals were anesthetized with urethane (1500 mg/kg, IV bolus injection in a volume of 5 ml/kg) and breathed spontaneously. Lead II ECG was obtained with subdermal needle electrodes and ECG signal conditioner. Heart rate was measured with a pulse rate tachometer. The carotid artery was cannulated with a catheter that was connected to a pressure transducer and a pressure processor for measurements of arterial blood pressure (BP). Five parameters [HR, Q-T Interval, QTc (Bazett's), QTc (Fridericia's), BP] were recorded and displayed on a Digital Acquisition Analysis and Archive System (PO-NE-MAH, Inc. USA). QTC intervals were obtained by correction for heart rate changes using Bazett's and Fridericia's formulae. Increase in QTc interval in individual treated guinea pigs that lies outside the upper limit of 95% confidence limits (mean±SD) of the changes for the vehicle-treated control at corresponding time points for two consecutive times is considered significant.

Example 6

Acute and Chronic Toxicity Assays

Liver toxicity is an especially important, initial consideration for orally administered compounds, as the liver is the major site of initial drug metabolism and is critical to overall metabolism and homeostasis of an animal. Liver injury is also a component of idiopathic tissue injury seen in certain chronically administered drugs. Therefore, it is important to do initial assessments of liver toxicity after oral administration of compounds to mice.

Methods:

A standard approach is to test compounds in two initial in vivo toxicity assays: an acute, escalating-dose paradigm and a chronic, therapeutic dose regimen. For the escalating-dose, acute toxicity assays, mice (5 per experimental group) are administered either compound or vehicle in 0.5% carboxymethylcellulose (alternatively, castor oil or sesame oil can be used) by oral gavage once daily for 3 days. Standard compound doses are 3.1, 12.5, and 50 mg/kg; the highest dose is 20× a therapeutic dose. On the $4^{th}$ day, mice are sacrificed and the liver harvested and fixed for histology. Paraffin-embedded, hematoxylin & eosin (H&E)-stained sections of liver tissue are analyzed microscopically for injury by two individuals blinded to the treatment groups. A semi-quantitative histological scoring system from 0 (best) to 9 (worst) is applied that considers architecture features (normal to extensive fibrosis), cellular features (normal to extensive edema and widespread necrosis), and degree of inflammatory infiltrate (normal to extensive infiltrate). For each acute toxicity assay, 15 mg of compound is required.

For the therapeutic dose, chronic toxicity assays, mice (5 per experimental group) are administered either compound or vehicle in 0.5% carboxymethylcellulose by oral gavage once daily for 2 weeks at a therapeutic dose of 2.5 mg/kg/day. After two weeks of treatment, mice are sacrificed and liver toxicity analyzed as described above. For each chronic toxicity assay, 5 mg of compound is required.

Figure 34:
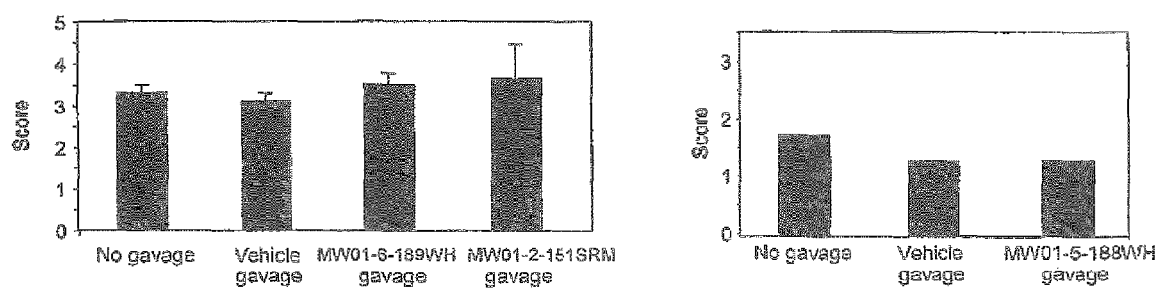
FIG. 34 are graphs of results of liver toxicity studies with MW01-5-188WH, 2-151SRM, and MW01-6-189WH. Compounds were administered to C57Bl/6 mice by oral gavage (2.5 mg/kg/day, once daily for 2 weeks). Histological liver toxicity was assessed by examination of tissue architecture, cell necrosis, and inflammatory infiltrate. The scoring scale ranges from 0 (best) to 9 (worst). MW01-5-188WH, MW01-2-151SRM, and MW01-6-189 show no significant differences in liver toxicity score from the control mice receiving either no gavage or vehicle gavage.

Results:

The results of the toxicity study are shown in FIG. 34.

MW01-5-188WH has been tested in the acute, escalating-dose assay and the chronic, therapeutic dose assay. There was no histological evidence of tissue toxicity at the lower doses but some vacuolisation was observed at the 50 mg/kg dose.

MW01-2-151SRM has been tested in the chronic, therapeutic dose assay. There was no histological evidence of tissue toxicity; no differences were seen by histology in livers from mice treated with vehicle or with compound.

MW01-6-189WH has been tested in the chronic, therapeutic dose assay. There was no histological evidence of tissue toxicity; no differences were seen by histology in livers from mice treated with vehicle or with compound.

MW01-5-188WH was tested in the chronic, therapeutic dose assay. In particular, mice were administered by oral gavage either MW01-5-188WH (2.5 mg/kg) or diluent (10% DMSO) in a 0.5% (w/v) carboxymethylcellulose suspension once daily for 2 weeks. Mice were anesthetized and killed as described above. Livers were removed, fixed in 4% (v/v) paraformaldehyde, and paraffin-embedded for histology. To assess histological toxicity, 4 pan liver sections were stained with hematoxylin and eosin. Two independent observers blinded to the treatment groups performed microscopic assessment of the tissue for injury. Histological assessment of liver tissue showed that oral administration of MW01-5-188WH at 2.5 mg/kg daily for 2 weeks did not induce any indices of hepatotoxic tissue injury compared with mice treated with the diluent.

Example 7

In vitro stability, oral bioavailability, and brain uptake. The stability of MW01-5-188WH (1 μM) in a standard incubation with rat liver microsomes (BD Biosciences, Bedford, Mass.) and an NADPH-regenerating system was done at 37° C. for 30 and 120 min. Reactions were stopped by acetonitrile, and the reaction mixture was centrifuged at 16,000 μg for 10 min. Ten microliters of the supernatant were analyzed by calibrated HPLC to quantify the percentage of the initial amount of MW01-5-188WI-1 remaining after the incubation. The HPLC system (Dionex, Sunnyvale, Calif.) includes a Dionex P680 pump, a Phenornenex (Torrance, Calif.) Luna C18 column (250×2.0 mm; 5 μm) with a guard column, and a Dionex UVD34015 ultraviolet detector. The mobile phase consisted of 0.1% formic acid as reagent A and 0.08% formic acid/water in 80% acetonitrile as reagent B at a flow rate of 0.2 ml per minute. The gradient consisted of the following linear and isocratic gradient elution changes in reagent B: isocratic at 60% from 0 to 5 min, 60-90% from 5 to 39 min, isocratic at 90% until 44 min. Peak quantification was done based on absorption measured at 260 nm relative to a standard Curve obtained by using serial dilutions of MW01-5-188WH. To estimate oral bioavailability (concentration of compound in the blood as a function of time after oral administration) and gain insight into potential brain uptake, MW01-5-188WH (2.5 mg/kg) was administered to mice by oral gavage in a 0.5% (w/v) carboxymethylcellulose suspension. At 5, 15, 60, and 120 min after compound administration, the animals were anesthetized with pentobarbital (50 mg/kg). Blood was harvested by intracardiac puncture, collected in heparinized tubes, and plasma obtained by ceritifugation. Mice were perfused with PBS. Brain homogenates were centrifuged at 12,000 µg for 10 min and the supernatant acidified by diluting 1:3 with 0.1% formic acid (Fluka, Sigma, Aldrich, St. Louis, Mo.). Solid phase extraction followed by HPLC analysis was used to quantify the amount of compound in brain supernatants. Briefly, cartridges (Sep-Pale. C18; Waters Associates, Milford, Mass.) were conditioned with 1 ml of acetonitrile (HPLC grade; EMD Biosciences, San Diego, Calif.) and equilibrated with 1 ml of water. A structural analog of MW01-5-188WIT was used as an internal standard. The acidified brain supernatant was added to the cartridge followed by a lint wash with 30% acetonitrile. MW01-5-188WH was eluted from the cartridge using 80% acetonitrile. The eluate was evaporated to dryness, reconstituted in 0.08% formic acid/water in 80% acetonitrile, and analyzed by HPLC using the following gradient in reagent B: 0-60% from 2 to 5 min, isocratic at 65% until 7 min, 65-80% from 7 to 12 min, isoeratic at 80% until 15 min, 89-100% from 15 to 18 min, and isocratic at 100% until 23 min. Plasma samples were deproteinized in 0.1 M perchioric acid and centrifuged at 12,000 µg for 10 min. The supernatant was neutralized with 1 M NaOH, then extracted with dichloromethane, and the layers separated at 3000 µg for 5 min. The organic phases from three successive extractions were pooled and then evaporated to dryness under reduced pressure. The dried residue was reconstituted in 50 µl of reagent B, and 10 µl of the reconstituted material was analyzed by HPLC using the gradient described above for brain supernatants.

Results:
Oral bioavailability and brain uptake of MW01-5-188WH

Integrative chemical biology tools for neurosciences and CNS targeted drugs must exhibit appropriate bioavailability and brain uptake or penetration of the blood-brain barrier. Daily oral administration is the preferred method of administration for longer-term and tune delimited in vivo studies using animal models and is the preferred mode in drug development for a variety of reasons, including better patient compliance. In this regard, it is critical to demonstrate bioavailability and appropriate rates of initial brain uptake for an inhibitor, to fully interpret the outcomes from in vivo studies. Therefore, the rate of MW01-5488WH concentration change in the blood after oral administration (oral bioavailability) and its rate of change in the brain were determined. Using the protocols described above for the quantitative analysis of MW01-5-188WH extracted from biological samples, the rates of appearance in blood and brain after a low-dose oral administration (25 mg/kg) to mice were examined. The appearance of MW01-5-188WH in the blood (FIG. 35 A) is readily detected within the earliest possible time point, 5 min, with a peak concentration being reached within 15 min and bulk clearance happening within 120 min after oral administration. This demonstrates that MW01-5-188WH has good oral bioavailability properties. A similar pattern of time-dependent change in concentration is seen for the brain (FIG. 35B), indicative of MW01-5-188WH initial brain uptake reflecting that of the blood. However, the MW01-5-188WH peak brain/blood concentration ratio is >33, comparable with those of CNS drugs in clinical use. For example, the brain/blood ratio for minaprinc, a 6-phenylaminopyridazine CNS drug, is about 2 (Caccia et al., 1985 Xenobiotics, 15(12): 1111-9). These results demonstrate that MW01-5-188WH fulfills criteria that typically exclude many compounds that are active in cell culture from being used for in vivo investigations and indicate its potential to work in vivo after oral administration and within the experimental constraints imposed by the human AβICY infusion model.

MW01-5-188 dosing is Selective for CNS Inflammation

Figure 35:
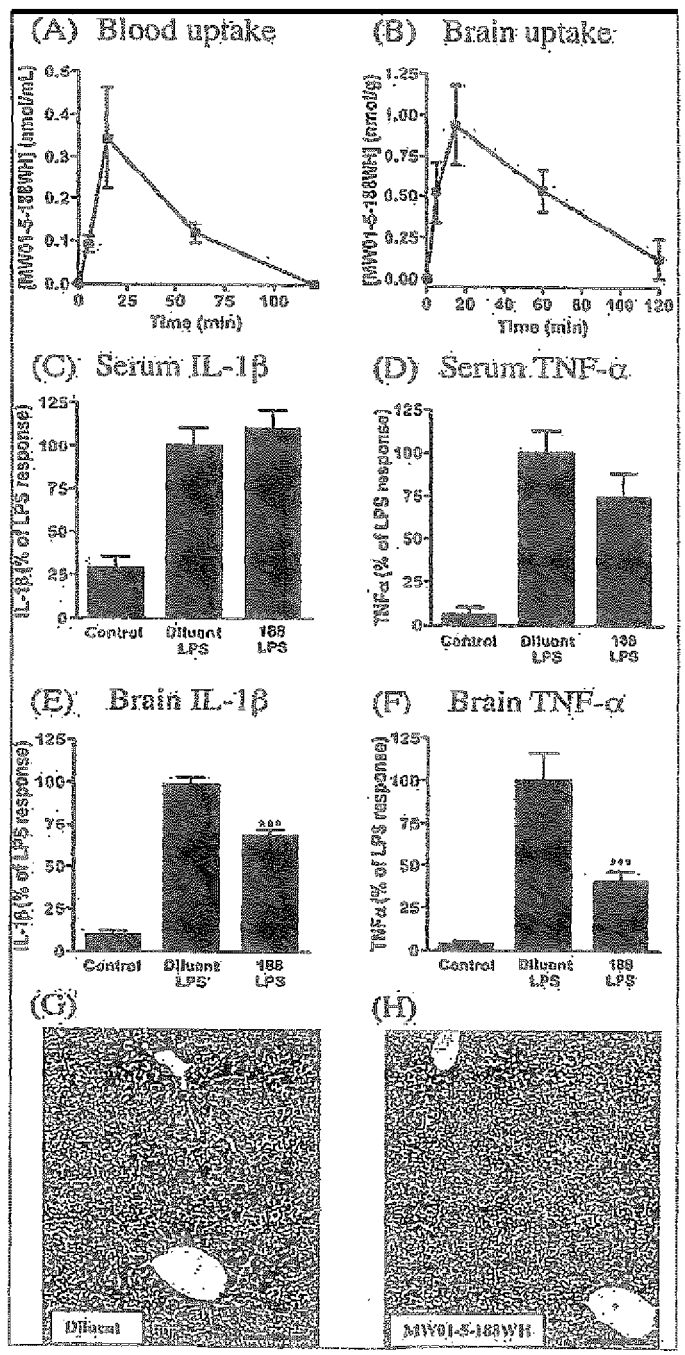
FIG. 35 shows that MW01-5-188WH is readily detected in the plasma and the brain after a single oral dose administration and does not suppress peripheral tissue inflammatory responses or cause liver injury after chronic oral administration. C57BL/6 mice were administered MW01-5-188WH (2.5 mg/kg) by oral gavage, blood and brain processed at different times after administration, and compound levels in plasma and brain determined as described herein. MW01-5-188WH rapidly appears in plasma (A) and brain (B), reaches a peak at 15 min, and then slowly declines to basal levels by 120 min. Data are the mean_SEM from three to six mice at each time point. MW01-5-188WH does not inhibit increased production of (C) and TNF-α (D) in the serum but does suppress the cytokine response in the brains from the same mice (E, F). Mice (n=3-6 per group) were administered by oral gavage either diluent or MW01-5-188WH (2.5 mg/kg) once daily for 2 weeks and then challenged with LPS (10 mg/kg, i.p.) for 6 h. Control mice were injected with saline. IL-1β and TNF-α levels in the serum and in brain supernatants were determined. Data represent mean±SEM. ***p_0.001, significantly different from diluent. Daily oral administration of diluent (G) or MW01-5-188WH (H) (2.5 mg/kg) does not result in any histological liver toxicity. Representative liver sections from mice treated as in C-F were stained with hematoxylin and eosin. Scale bar, 125 μm. 188, were stained with hematoxylin and eosin. Scale bar, 125 μm. 188, MW01-5-188WH.
Figure 36:
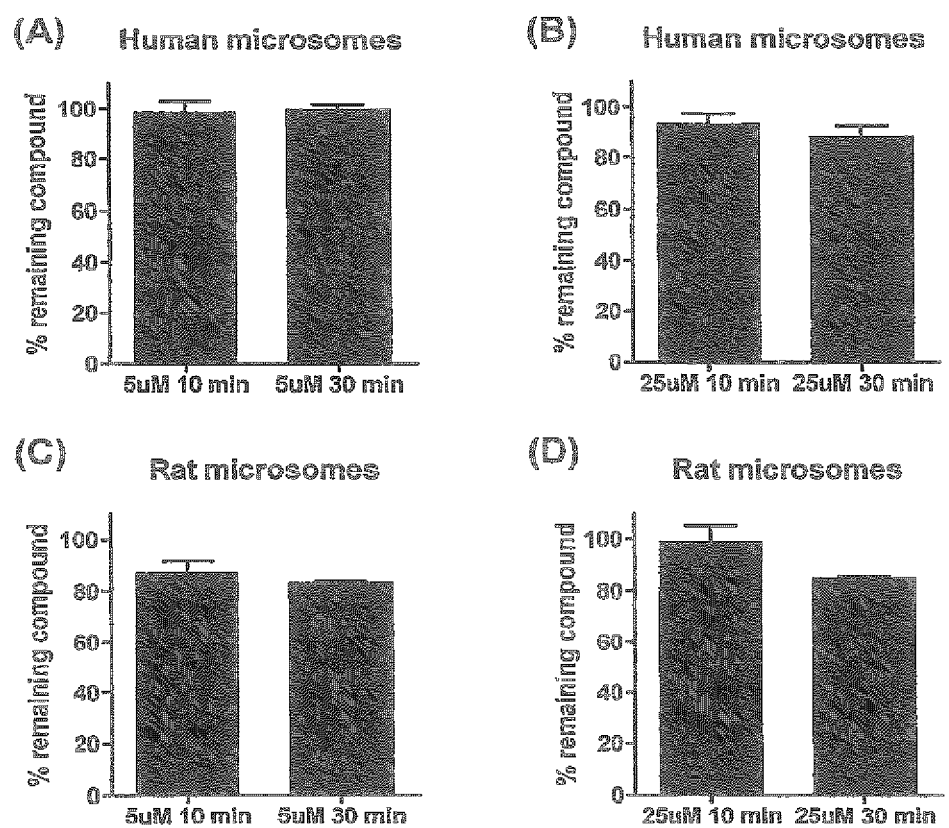
FIG. 36 are graphs of stability data using human (A, B) and rat (C, D) microsomes with MW01-2-151SRM in two different amounts, for two tithe periods. E and F show human (E) and (F) rat microsomes with MW01-2-151SRM stability for different time periods compared to minaprine.
Figure 36:
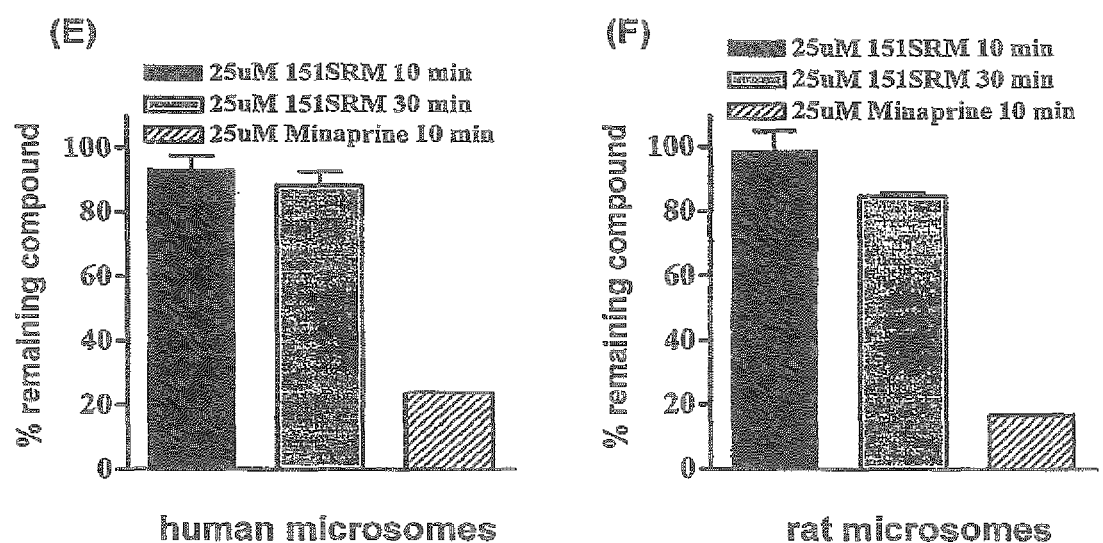

The de nova focus on suppression of selected glia activation pathways and the excellent brain uptake properties of orally administered MW01-5-188WH raised the possibility that the compound might exhibit selectivity for CNS proinflammatory cytokine suppression versus suppression of proinflammatory cytokine production by peripheral tissues. To examine this possibility, MW01-5-188WH was administered daily at a standard therapeutic dose (2.5 mg/kg) by oral gavage for 2 weeks, and then mice were challenged with an intraperitoneal injection of bacterial LBS. Six hours after the LPS challenge, the scrum and brain levels of IL-1β and TNF-α were measured. As anticipated, the LBS challenge induced an increase in the levels of IL-1β and TNF-α the serum (FIG. 35C,D) and brain (FIG. 35E,F), compared with control mice injected with saline. The interesting finding was that treatment with MW01-5-188WH for 2 weeks suppressed the LBS-induced upregulation of IL-1β and TNF-α, production in the brain (FIG. 35E,F) but did not suppress the serum response (FIG. 35 C,D). The suppression of brain cytokine responses by MW01-5-188WH is consistent with its ability to suppress proinflammatory cytokine production by activated glia and its oral bioavailability and brain uptake properties shown above.

Example 8

Pharmacokinetics Studies

Plasma Pharmacokinetics and Absolute Bioavailability in Dog and/or Rat

Two groups (3 animals per group; male animals) will be dosed PO and IV. There will be one dose level (2.5 mg/kg), and a crossover design will be used with 1 week washout between dose periods. Plasma drug concentrations will be measured at not less than eight time points not exceeding 24 hrs post-dose (e.g. 15, 30, 60, 90, 120; 240, and 480 minutes and 24 hr after administration of single dose). PK parameters that will be derived include $C_{max}$, $T_{max}$, $t_{1/2}$, AUC, CI/F, $V_d$ and MRT. Dosing formulation: oral gavage/CMC solution.

Mass Balance Study in Dog and/or Rat

A study may be performed utilizing $^{14}C$-labelled minozac (MW01-2-151SRM) to analyze excretion (urine, feces) and plasma distribution.

Dose Range Finding Study in Rat

Phase A of the study will be a single dose MTD (3M/3F for each dose level, to MTD or MFD found). Dose levels to be designed based on available data if any; doses provided below may be utilized for example purposes only. Dosing will be by oral gavage with CMC solution.

Dose level 1: 10 mg/kg; Dose level 2: 100 mg/kg; Dose level 3: 500 mg/kg; Dose level 4: 1000 mg/kg; Dose level 5: 3000 mg/kg;

Result: An estimated single-dose MTD/MFD (sdMTD)

Phase B of the study may be performed. The phase comprises a 7-day dose range finding study (3M/3F in each group, n=24). There will be a control plus one dose level (a fraction of sdMTD); additional dose level(s) will be incorporated as required by the outcome of the initial 7-day dose range finding study.

Result: An estimated repeat-dose MTD in rats

Dose Range Finding Study in Dog

This study will utilize a single dose MTD (5M crossover study, n=up to MTD or MFD found). Dose levels will be designed based on available data. Examples of doses are provided below. The dosing will be by oral gavage with a CMC solution preferred; alternatively, filled gelatin capsules will be utilized.

Oral dose level 1: 30 mg/kg; Oral close level 2: 100 mg/kg; Oral dose level 300 mg/kg IV dose 1: 100 mg/kg; IV dose 2: 300 mg/kg; Oral dose level 4: 1000 mg/kg; Oral dose level 5: 3000 mg/kg.

Each subsequent dosing will be followed by an appropriate washout period (2 days or 5 days after IV exposure). Pharmacokinetics and absolute bioavailability will be determined for dose levels 1 and 2. Plasma drug concentrations will be measured at eight time points not exceeding 24 hrs post-dose (e.g. 15, 30, 60, 120, 240 and 480 minutes after administration of single oral doses). PK parameters to be derived include $C_{max}$, $T_{max}$, $t_{1/2}$, AUC, Cl/F, $V_d$ and MRT.

28-Day Repeat Dose Toxicology Study in Rats

The Main Study will involve 10M/10F in each treatment group, n=80. The dosing will be by oral gavage with CMC solution. There will be a Control, Low dose, Mid dose, and High dose. Results: PK (plasma and CSF drug levels) will be determined at Day 1 and Day 28. Necropsy will be determined after the completion of treatment. Mortality, clinical observations, body weights, food consumption, clinical pathology, ophthalmoscopy, gross pathology, and organ weights will be determined. Histopathology will be determined on control and high dose groups.

A Recovery Study with 5M/5F in each treatment group, n=20 will be conducted. There will be a Control and High dose. Results: Necropsy will be determined after 28 days additional follow-up period. Mortality, clinical observations, body weights, food consumption, clinical pathology, ophthalmoscopy, gross pathology, and organ weights will also be determined. Histopathology will be determined if required by observation of treatment effects.

28-Day Repeat Dose Toxicology Study in Dogs

A Main Study utilizing 3M/3F in each treatment group, n=24 will be conducted. Dosing will be by oral gavage with CMC solution preferred; alternatively, filled gelatin capsules will be used if required. There will be a Control, Low dose, Mid dose, and High dose. Results PK (plasma and CSF drag levels) will be determined at Day 1 and Day 28 Necropsy will be determine after the completion of treatment. Mortality, clinical observations, body weights, food consumption, clinical pathology, gross pathology, and organ weights Will be determined. Histopathology will be done on all dose groups A Recovery Study using 3M/3F in each treatment group, n=12 will also be conducted. The study will use Control and High dose. Results: Necropsy will be determined after 28 days additional follow-up period. Mortality, clinical observations, body weights, food consumption, clinical pathology, ophthalmoscopy, gross pathology, and organ weights will be determined. Histopathology if required will be determined by observation of treatment effects.

Example 9

General Methods

Chemicals were generally purchased from Aldrich (Milwaukee, Wis.) or through VWR International and used as received. All solvents were used as received unless stated otherwise in the text. All organic solutions were dried with magnesium sulfate before final evaporation. Microwave irradiation was carried out using the CEM-Discover microwave synthesis system (Matthews, N.C.).

All intermediates were characterized by MS (ESI) and HPLC and in some cases by $^1$H-NMR. Final compounds were characterized by HRMS, HPLC and $^1$H-NMR, and in some cases, by elemental analysis. NMR spectra were acquired on a Varian Inova 500 MHz spectrometer at room temperature. Electrospray mass spectra (EI-MS) were collected on a Micromass Quattro II Triple Quadrupole HPLC/MS/MS Mass Spectrometer. High resolution mass spectra (FIR-MS) were obtained on a VG70-250SE mass spectrometer.

All syntheses were monitored by analytical HPLC. HPLC traces were obtained on a Rainin Instruments HPLC on commercially available SUPELCO C18 reverse phase column (25×4.6 mm, 5 μm). The mobile phase consisted of 0.1% formic acid in Milli-0 water as reagent A and 0.08% formic acid/Milli-0, water in 80% acetonitrile as reagent B. The flow rate of 1.5 ml/min was used in a gradient of 0 to 100% of reagent B over 22 minutes. The HPLC traces were tracked by UV absorption at 260 nm.

A separate HPLC system was used to obtain final compound purity. The HPLC system (Dionex, Sunnyvale, Calif.) consisted of the following components: a Dionex P680 pump, a Dionex ASI-100 autosampler, a Phenomenex (Torrance, Calif.) Luna C18 column (250×2.0 mm; 5 μm) with a guard column, and a Dionex UVD1700 ultraviolet detector. The mobile phase consisted of 0.1% formic acid in Milli-Q water as reagent A and 0.08% formic acid/Milli-Q water in 80% acetonitrile as reagent B. The flow rate of 0.2 ml/min was used, unless stated otherwise in the text. For determination of compound purity, the gradient consisted of a linear change from 0 to 100% of reagent B over 30 minutes. UV absorption was monitored at four wavelengths (215, 230, 260 and 300 nm) with the 260 nm trace being reported. Compounds were injected at concentrations 100-times greater than the lower detection limit of the instrument (500 ng injected).

Elemental analysis was carried out by Quantitative Technologies. Inc. (QTI, Whitehouse, N.Y.). Melting point data for the dichloro monohydrate salt 26 (234.1-234.7° C.) and of compound 16 (>215° C., decomposes to black solid) were acquired on a Buchi Melting Point B-540 (Dawn, Switzerland).

Figure 37:
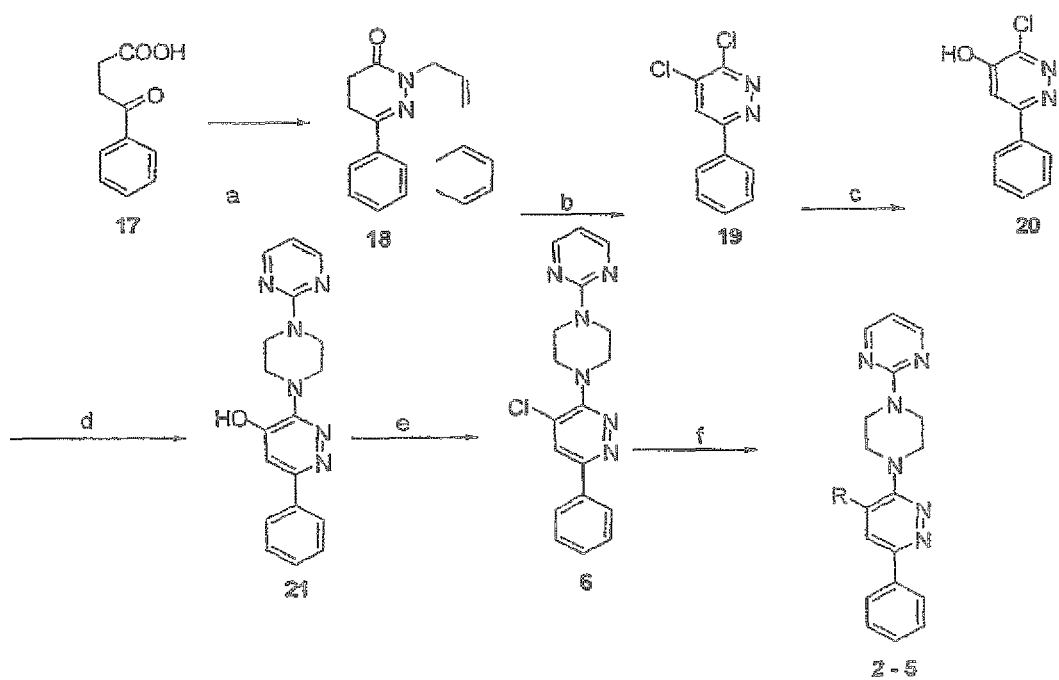
FIG. 37 shows a synthetic scheme for synthesis of compounds of the formula I where $R^{11}$ is benzyl, 4-pyridyl, isobutyl, or methyl. Reagents and conditions: a) $PhCH_2NH_2NH_2$, $CH_3COONa$, ethanol, reflux, 29 h; b) $POCl_3$, $PCL_5$, 120° C., 12 h; c) $CH_3COOH$, reflux, 5 h; d) 1-(2-pyrimidyl)piperazine, 1-butanol, 130° C., 41 h; e) $POCl_3$, 100° C., 3 h; f) boronic acid, Pd(0). 2R benzyl; 3 R=4-pridyl; 4R iso-butyl; 5R methyl.

Synthesis of R4 Analogs (FIG. 37))

2-benzyl-6-phenyl-4,5-dihydropyridazin-3(2H)-one (18)

3-benzoylpropionic acid 17 (17.8 g, 0.1 mol), beozylhydrazine dihydrochloride (19.5 g, 0.1 mol) and sodium acetate (74.9 g, 0.55 mol) were suspended in 500 mL ethanol (95%). The white suspension was heated under reflux for 29 hours. Ethanol was removed under reduced pressure and the residue was treated with water (300 mL). The pH of the aqueous layer was adjusted with concentrated solution of sodium carbonate to pH=8 and extracted with ethylacetate (1×200 mL). The organic layer was washed with brine and concentrated to dryness under reduced pressure. The product 18 was obtained

3,4-dichloro-6-phenylpyridazine (19)

Compound 18 (26 g, 0.079 mol=estimated on 80% purity), phosphorus oxychloride (59 mL, mol, 6.5 equiv) and phosphorus pentachloride (133.2 g, 0.64 mol, 6.5 equiv) were heated at 120° C. for 12 hrs. To control the HO gas forming during the course of reaction, a NaOH solution was used to absorb the acid. Most of the phosphoryl chloride was distilled under reduced pressure, ice water was added to the residue and stirred for 30 min. The yellow crystalline solid which separated upon cooling was filtered, washed with water (3×100 mL) and recrystallized from anhydrous ethanol to give desired product 19 as yellow needles in 44% yield. $^1$H NMR (CDCl$_3$) δ 8.06 (dd, $^3$J=6.5 Hz, $^4$J=2.5 Hz, 2H), 7.98 (s, 1H), 7.56 (t, $^3$J=6.5 Hz, 3H). HPLC (t$_r$/purity) min, >95%.

3-chloro-6-phenylpyridazin-4-ol (20)

A mixture of 19 (158 g, 0.7 mol) and acetic acid (700 mL) was heated under reflux for 5 hrs. The reaction mixture was cooled to room temperature, the precipitate filtered and the bright yellow filter cake washed with water (5×500 mL). The filter cake was recrystallized from ethyl acetate (200 mL), filtered and dried over a medium frit sintered glass funnel in vacuo to give the desired product 20 in 32% yields. HPLC (t$_r$/purity): 15.37 min, >95%. ESI m/z (MeOH): 2073 (MH$^+$).

6-phenyl-3-(pyrimidin-2-yl)piperazin-1-yl)pyridazin-4-ol (21)

Compound 20 (14 g, 0.068 mol) was placed in a reaction tube with 1-butanol (30 mL) and 4 equiv of 1-(2-pyrimidyl) piperazine (45 g, 0.27 mol, 4 equiv). The flask was capped and heated at 130° C. for 41 h. The reaction mixture was cooled to ambient temperature, and the 1-butanol removed under reduced pressure to give a dark oil residue. The oil was treated with water to give a suspension which is then filtered and washed with water. The filter cake was dried over a medium frit sintered glass funnel in vacuo to give the desired product 21 in 97% yields. HPLC (t$_r$/purity): 1.7.30 min, >99%. ESI m/z (MeOH): 334.38 (MH$^+$).

4-chloro-6-phenyl-3-(4-(pyridin-2-yl)piperazin-1-yl) pyridazine (6)

Compound 21 (22 g, 0.066 mol) was suspended in phosphorus oxychloride (80 mL). The reaction mixture was heated at 100° C. for 3 h, cooled to room temperature and pared on crashed ice (2 kg). The aqueous mixture was neutralized with NaOH solution to give white suspension. The precipitate was filtered and dried over a medium fit sintered glass funnel in vacuo to give the desired product 6 in 91% yields (21 g). $^1$H NMR (CDCl$_3$): δ 8.35 (d, J=4.6 Hz; 2H), 8.01 (d; J=7.5 Hz; 2H), 7.81 (s, 1H), 7.50 (t, J=7.0 Hz, 2H), 7.48 (t, J=7.0 Hz, 1H), 6.54 (t, J=4.4 Hz, 1H), 4.05 (t, 4.4 Hz, 4H), 3.65 (t, J=4.4 Hz, 4H). HPLC (t$_r$/purity): 22.4 thin, >99%; HRMS calcd for C$_{18}$H$_{17}$ClN$_6$ 3'52.1198. Found 352.1201.

4-Benzyl-6-phenyl-3-(4-pyrimidin-2-yl)piperazin-1-yl)pyridazine (2)

Following the procedure of Zou et al (*Tet Lett.* 2001 42: 7213-7215), compound 6 (100 mg, 0.28 mmol) was suspended in THF with the 1.37 equiv of benzyl boronic acid (42 mg, 0.31 mmol), 0.2 equiv of Pd(dppf)Cl$_2$CH$_2$Cl$_2$ (23 mg, 0.02 mmol), 2.5 equiv of silver oxide (164 mg, 0.71 mmol) and 3 equiv of potassium carbonate (117 mg, 0.85 mmol). The mixture was purged with argon and was heated at 120° C. for 16 h in a sealed tube. The reaction mixture teas then cooled to ambient temperature and quenched with either 33% hydrogen peroxide or 10% sodium hydroxide. The aqueous layer was extracted with ether (3×30 mL) and the ethereal layers are combined and evaporated under reduced pressure. The crude mixture is run on a silica gel column and eluted with hexanes: ethyl acetate (1:1 v/v). The product 2 is obtained as a pale pink solid in 45% yield. $^1$H NMR (CDCl$_3$): δ 836 (d, J=4.4 Hz, 2H), 7.94 (d, J=7.1 Hz, 2H), 7.46-7.42 (m, 3H), 7.41 (s, 1H), 736 (t, J=7.3 Hz, 2H), 730 (t, J=7.1 Hz, 1H), 7.22 (d, J=73 Hz, 2H), 6.55 (t, J=4.4 Hz, 1H), 4.10 (s, 2H), 4.01 (s, 4H), 3.44 (s, 4H). HPLC (t$_r$/purity): 3032 min, >95%; HRMS calcd for C$_{25}$H$_{24}$N$_6$ 408.2057. Found 408.2066.

6-Phenyl-4-(pyridin-4-yl)-3-(4-pyrimidin-2-yl)piperazin-1-yl)pyridazine (3)

Compound 6 (700 mg, 2.0 mmol) was placed n a reaction vessel with 3.1 equiv potassium carbonate (851 mg, 6.2 mmol), 1.37 equiv (330 mg, 2.7 mmol) 4-pyridinylboronic acid and 0.05 equiv Pd(PPh$_3$)$_4$ (120 mg, 0.1 mmol). DME (10 mL) was added and the mixture was purged with argon. The reaction mixture was sealed and heated at 110° C. for 20 h. The solution was cooled to ambient temperature and filtered through celite. The filtrate was concentrated under reduced pressure, dissolved in ethyl acetate (30 mL) and washed with 2N HCl (50 mL). The organic layer was concentrated under reduced pressure and recrystallized with ethyl acetate/petroleum ether mixture to give the product 3 as light yellow needles in yield. $^1$H NMR (CDCl$_3$): δ 8.79 (d, J=5.5 Hz, 2H), 8.32 (d, J=5.0 Hz, 2H), 8.07 (d, 7.5 Hz, 2H), 7.68 (d, J=5.5 Hz, 2H), 7.63 (s, 1H), 7.51 (t, −7.0 Hz, 2H), 7.48 (t, J=7.0 Hz, 1H), 6.53 (t, J=4.5 Hz, 1H), 3.85 (d, J=4.5 Hz, 4H), 3.39 (t, J=5.0 Hz, 4H). HPLC (t$_r$/purity): 21.61 min, >95%; HEWS calcd for C$_{23}$H$_{21}$N$_7$ 395.1853. Found 395 1852.

4-Isobutyl-6-phenyl-3-(4-pyrimidin-2-yl)piperazin-1-yl)pyridazine (4)

Following the procedure of Zou et al (supra), compound 6 (200 mg, 0.56 mmol) was suspended in THF with the 1:37 equiv of (2-methylpropyl)boronic acid (79 mg, 0.77 mmol), 0.2 equiv of Pd(dppf)Cl$_2$CH$_2$Cl$_2$ (92.5 mg, 0.11 mmol), 2.5 equiv silver oxide (328 mg, 1.41 mmol) and 3 equiv of potassium carbonate (234 mg, 1.7 mmol). The mixture was purged with argon and heated at 120° C. for 42 hours in a sealed tube. The reaction was cooled to ambient temperature and the reaction was quenched with aqueous solution of sodium hydroxide (10%) and extracted with ether (3×50 ml). The ethereal layers were combined, dried with magnesium sulfate and evaporated under reduced pressure leaving a sticky solid. The crude mixture was purified with column chromatography and eluted with 40% ethyl acetate in hexanes to give 4 as a white powder in 52.5% yield. $^1$H NMR (CDCl$_3$): δ 8.36 (d, J=4.2 Hz, 2H), 8.06 (d, J=7.1 Hz, 2H), 7.60 (s, 1H), 7.51 (t, J=7.0 Hz, 2H), 7.47 (t, J=7.0 Hz, 1H), 6.55 (t, J=402 Hz, 1H), 4.03 (s, 4H), 3.42 (s, 4H), 2.62 (d, J=6.7 Hz, 2H), 2.18 (sp, J=6.4 Hz, 1H), 0.97 (d, J=6.2 Hz, 61-1). HPLC (f$_r$/purity): 29.5 min, >95%; HRMS calcd for C$_{22}$H$_{26}$N$_6$ 374.2213. Found 374.2208.

4-Methyl-6-phenyl-3-(4-pyrimidin-2-yl)piperazin-1-yl)pyridazine (5)

Following the procedure of Zou et al (supra), compound 6 (250 mg, 0.71 mmol) was suspended in THF with the 1.37 equiv of methylboronic acid (59 mg, 0.97 mol), 0.25 equiv of Pd(dppf)Cl$_2$CH$_2$Cl$_2$ (144 mg, 0.18 mmol), 2.5 equiv of silver oxide (410 mg, 1.78 mmol) and 3 equiv of potassium arbonate (294 mg, 2.1 mmol). The mixture was purged with argon and was heated at 120° C. for 18.5 h in a sealed tube. After cooling to ambient temperature the reaction was quenched with aqueous sodium hydroxide (10%) and extracted with ether (3×75 ml). The compound was purified by column chromatography and eluted with a mixture of ethyl acetate:hexanes (1:3 v/v). The compound 5 was a white crystallize solid obtained in 45.8% yield. NMR (CDCl$_3$): δ 8.36 (d, 4.5 Hz, 2H), 8.05 (d, J=7.5 Hz, 2H), 7.61 (s, 1H), 7.50 (t, J=7.1 Hz, 2H), 7.44 (t, J=7.1 Hz, 1H), 6.55 (t, J=4.5 Hz, 1H), 4.04 (t, J=4.5 Hz, 4H), 3.46 (t, J=4.5 Hz, 4H), 2.45 (s, 3H). HPLC (t$_r$/purity): 24.91 min, >95%; MMS calcd for C$_{19}$H$_{20}$N$_6$ 332.1744. Found 332.1740. Anal. Calcd for C$_{19}$H$_{20}$N$_6$C, 68.65; H, 6.06; N, 25.28. Found C, 68.73; H, 5.97; N, 25.22.

Figure 38:
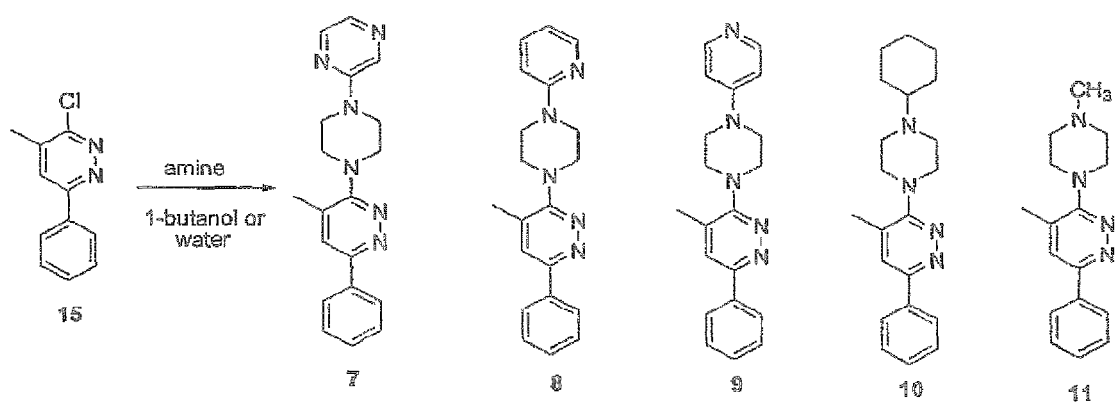
FIG. 38 shows a synthetic scheme for synthesis of compounds of the formula I where $R^1$ is methyl.

Synthesis of R3 Analogs (FIG. 38)

4-Methyl-6-phenyl-3-(4-pyrazin-2-yl)piperazin-1-yl)pyridazine (7)

Compound 15 (500 mg, 2.4 mmol) was placed in a capped flask and suspended in 20 mL water. 2.5 equiv (1 g, 6 mmol) of 1-(2-pyrazinyl)piperazine and 5 equiv (1.69 mL, 12 mmol) of triethylamine were added and the flask was capped and heated to 130° C. for 160 h. The reaction was cooled to ambient temperature to give a dark brown oil at the bottom of the flask. The water was decanted off of the oil, the oil was dissolved in minimal isopropanol and heated to 70° C. Upon cooling, a brown solid formed and was filtered on a sintered glass funnel and rinsed with hexanes to afford product 7 as a brown powder in 28.8% yield. $^1$H NMR (CDCl$_3$): δ 8.25 (bs, 1H), 8.16 (bs, 1H), 8.08 (d, J=7.0 Hz, 2H), 7.93 (bs, 1H), 7.69 (s, 1H), 7.54-4.48 (m, 3H), 183 (t, 15.0 Hz, 4H), 337 (bs, 4H), 2.48 (s, 3H) HPLC (t$_r$/purity): HRMS calcd for C$_{19}$H$_{20}$N$_6$. Found. Given in Apr. 21, 2006.

4-Methyl-6-phenyl-3-(4-pyridin-2-yl)piperazin-1-yl)pyridazine (8)

Compound 15 (190 mg, 093 mmol) was placed in a reaction tube with 1-butanol and 4 equiv of 1-(pyridin-2-yl)piperazine (605 mg, 17 mmol), capped and heated at 140° C. for 48 h. The reaction mixture was cooled to ambient temperature and the 1-butanol removed under reduced pressure to give a dark oil residue. The oil was treated with water to give a suspension which is filtered and washed first with water, then with a mixture of ethyl acetate:hexanes (1:6 v/v) to afford the product 8 as a brown yellow powder in 54.5% yield. $^1$H NMR (CDCl$_3$): δ 823 (d, J=3.7 Hz, 1H), 8.05 (d, J=7.5 Hz, 2H), 7.60 (s, 1H), 7.54 (t, J=6.8 Hz, 1H), 7.49 (t, J=7.1 Hz, 2H), 7.44 (t, J=7.3 Hz, 1H), 635 (d, J=8.2 Hz, 1H), 6.68 (t, 15.5 Hz, 1H), 176 (s, 4H), 3.51 (t, J=4.8 Hz, 4H), 2.43 (s, 3H). HPLC (t$_r$/purity): 15.66 min, >95%; HRMS calcd for C$_{20}$H$_{21}$N$_5$ 331.1791. Found 331.1800.

4-Methyl-6-phenyl-3-(4-pyridin-4-yl)piperazin-1-yl)pyridazine (9)

Compound 15 (190 mg, 093 mmol) was placed in a reaction tube with 1-butanol and 4 equiv of 4-piperazino-pyridazine (605 mg, 3.7 mmol). The flask was capped and heated at 140° C. for 72 h. The reaction mixture was cooled to ambient temperature and the 1-butanol removed under reduced pressure to give a dark red oil residue. The oil was treated with 20 mL of water, aid then extracted with 10 mL of ethyl acetate. A brown suspension was formed in the organic layer. The precipitate was collected by filtration and washed with 10 mL of water and then 10 mL of ethyl acetate to afford the product 9 as a brown yellow powder in 34.1% yield. $^1$H NMR (CDCl$_3$): δ 8.33 (d, J=4.9 Hz, 2H), 8.06 (d, J=7.1 Hz, 2H), 7.64 (s, 1H), 7.52 (t, J=1.6 Hz, 2H), 7.48 (t, 17.1 Hz, 1H), 6.79 (d, J=5.8 Hz, 2H), 3.58 (s, 4H), 3.56 (s, 4H), 2.45 (s, 3H). HPLC (t$_r$/purity): 14.95 min, >95%; HRMS calcd for C$_{20}$H$_{21}$N$_5$ 331.1791. Found 331.1799.

3-(4-cyclohexylpiperazin-1-yl)-4-methyl-6-phenylpyridazine (10)

Compound 15 (200 mg, 0.96 mmol) was suspended in 5 ml, water with 4 equiv cyclohexyl piperazine (651.5 mg, 3.87 mmol) in a 10-mL microwave glass vessel and capped with a septum Microwave irradiation of 75 W was used, the temperature being ramped from room temperature to 175° C. Once 175° C. was reached, the reaction mixture was held at this temperature for 3 h. The reaction mixture was allowed to cool to room temperature, the dark brown solution was poured over water to give a suspension, which was filtered to afford a beige solid. The solid was washed with 20 mL, saturated sodium bicarbonate to give 10 in 95% yield. $^1$H NMR (CDCl$_3$): δ 7.56 (s, 1H), 7.49 (t, J=7.5 Hz, 3H), 7.44 (m, 2H), 3.41 (s, 4H), 2.79 (s, 4H), 2.38 (s, 3H), 2.34 (m, 1H), 1.62 (m, 2H), 1.26 (m, 8H). HPLC (t$_r$/purity): PENDING min, >95%; HRMS calcd for C$_{21}$H$_{28}$N$_4$. Found GIVEN Apr. 21, 2006.

4-Methyl-3-(4-methylpiperazin-1-yl)-6-phenylpyridazine (11)

Compound 15 (500 mg, 2.4 mmol) was suspended in 20 ml water in a capped flask with 4 equiv 1-methyl-piperazine (961 mg, 9.6 mmol). The vessel was capped and heated at 120° C. for 120 h until complete. The mixture was cooled to ambient temperature to afford a pale yellow solution with a white solid precipitate. The reaction was filtered, and the aqueous filtrate washed with ether to remove trace starting materials and then extracted with ethyl acetate (5×10 mL). The organic washes are combined, dried with magnesium sulfate and the ethyl acetate removed under reduced pressure. The remaining oil was treated with ether and cooled, resulting in the product 11 as yellow needles in 38.7% yield, $^1$H NMR (CDCl$_3$): δ 8.02 (d, 7.0 Hz, 2H), 7.55 (s, 1H), 7.47 (t, 7.0 Hz, 2H), 7.43 (m, 1H), 3.41 (t, J=4.5 Hz, 4H), 2.63 (bs, 4H), 2.38 (s, 3H), 2.36 (s, 3H). HPLC (t$_r$/purity): PENDING 95%; HRMS calcd for C$_{16}$H$_{20}$N$_4$ Given Apr. 21, 2006

Figure 39:
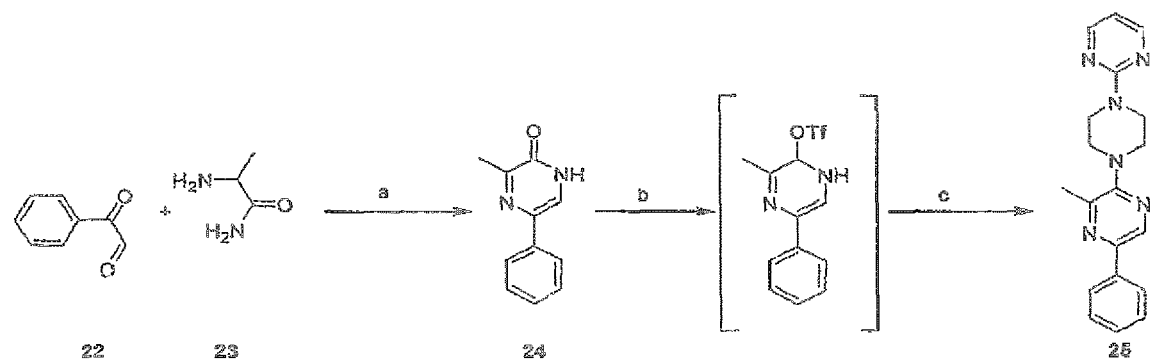
FIG. 39 shows a synthetic scheme for synthesis of pyrazine analogs of the invention. a) NaOH, −41° C., MeOH; b) $Tf_2O$, DMAP, Pyridine, rt; e) 1-(2-pyrimidyl)piperazine, DMSO, 60° C.

Synthesis of a Pyrazine Analog (FIG. 39)

3-methyl-5-phenylpyrazine-2(1H)-one (24)

This compound was prepared following the procedure of Jones (*J. Amer. Chem. Soc.* 1949, 71, 78-81). Briefly, commercially available phenylglyoxal 22 (1.02 g, 7.62 mmol) was dissolved in methanol and cooled to 41° C. Commercially available alanine amide 23 (672 mg, 7.62 mmol) was dissolved in 25 ml methanol and added to the reaction mixture. A 12.5 N NaOH (0.760 mL, 9.53 mmol) solution was added dropwise while stirring, maintaining the temperature of the reaction below 40° C. When the addition was complete, the reaction was placed at =5° C. for 2 h. The reaction was then warmed to room temperature and quenched with 12 N HCl solution (0.76 mL), followed by sodium bicarbonate to neutralize the solution. The methanol was removed under reduced pressure, and the residue was extracted with chloroform and precipitated with ethyl acetate. The compound was isolated as a white powder to give 24 in 18% yield. HPLC ($t_r$/purity): 1531 min, >97%. ESI m/z (MeOH): 187.35 (MH$^+$).

2-(4-(3-methyl-5-phenylpyrazin-2-yl)piperazin-1-yl) pyrimidine (25)

This compound was prepared via the pyrazine triflate with 1-(2-pyrimidyl)piperazine as the amine following the procedure of Adams et al (*Synlett* 2004, 11, 2031-2033). Pyridine was used as an anhydrous reagent kept under argon in a sure-seal bottle (Aldrich). The compound 24 (100 mg, 0.52 nmol) and DMAP (65.7, 0.52 mmol) were dissolved in pyridine and methylene chloride (0.5:4 ml v/v), and cooled to 0° C. The trifluoromethane sulfonic acid (0.8 mmol, 135.5 µL) was added dropwise and stirred for 15 min at 0° C. and then 3 h at RT. The triflate was confirmed by ESI (363.7 (MH+)) and HPLC ($t_R$=25.33 min). The reaction mixture was diluted with dichloromethane and washed one time each with 20 ml of water, sodium bicarbonate and brine. The dichloromethane was removed under reduced pressure, and the remaining residue was dissolved directly in DMSO. 1-(2-pyrimidyl)piperazine (5.3 mmol, 750 µL) was added and the reaction heated to 60° C. and stirred for 2 h. When complete, the reaction was diluted with ethyl acetate and washed with 1N HCl, after washes with brine and water to remove remaining pyridine. The organics were then dried and evaporated in vacuo to give 25 as a yellow solid (63% yield). HPLC ($t_r$/purity): 24.74 min, >98%. ESI m/z (CH$_2$Cl$_2$) 333.29 (MH$^+$). $^1$H NMR (500 MHz, CDCl$_3$): δ 8.56 (s, 1H); 8.36 (d, J=4 Hz, 2H); 8.01 (d, J=7.5 Hz, 2H); 7.48-7.40 (m, 3H); 6.54 (bs, 1H); 4.03 (bs, 4H), 3.42 (bs, 4H); 2.62 (s, 6H). HRMS calculated GIVEN Apr. 21, 2006

Synthesis of 26

4,6-diphenyl-3-(4-pyrimidin-2-yl)piperazine-1-yl) pyridazine dichloro monohydrate salt (26)

700 mg (1.77 mmol) of 1 was suspended in 10 mL of anhydrous isopropanol and heated to 70° C. 2.5 eq (0.375 mL, 4.4 mmol) of concentrated NCl was added at once to the solution. The suspension was stirred at 70° C. for 10 rain, cooled to ambient temperature and cooled on ice for 1 h. The precipitate was collected by filtration and washed once with cold isopropanol (5 mL) to provide the product 26 as bright yellow powder in 55% yield. $^1$H NMR (DMSO-d$_6$): δ 8.55 (s, 2H); 8.16 (s, 2H), 7.86 (s, 1H), 7.7 (s, 2H), 758 (s, 6H), 6.84 (s, 1H), 4.14 (s, 4H), 3.57 (s, 4H). HPLC ($t_r$/purity): PENDING min, >98%. EA calculated for C$_{24}$H$_{26}$Cl$_2$N$_6$O C, 59.38; H, 5.40; N, 17.31. Found C, 59.38; H, 5.40; N, 17.31.

Production Scheme for Pyrazine Analogs 4,5-dihydro-4-methyl-6-phenylpyridazin-3(2H)-one (13)

(Hansen, K B et al. *Org. Process Res. Dev.,* 2005, 9, 634-639, Nelson, D A. US 20050137397A1). A 250 ml three-neck round bottom flask fit with a temperature probe and condenser was charged with 7.7 g (40 mmol) of 2-methyl-4-oxo-4-phenylbutanoic acid 12 and 20 ml of ethanol (95%). The suspension was cooled to below 10° C. and 2.2 ml (42 mmol, 1.05 equiv) of hydrazine monohydrate in 10 ml of ethanol was added dropwise. After addition, the reaction mixture was heated to reflux and stirred for 2 h. The reaction mixture was cooled to ambient temperature and forming white crystals were collected by filtration. The solid was then washed with 2N NaHCO$_3$ (1×30 mL), Milli-Q water (3×60 mL) and dried over a medium frit sintered glass funnel in vacuo to give the desired product 13 in 96.1% yield. $^1$H NMR, (DMSO-d$_6$): δ 10.84 (s, 1H), 7.75 (m, 2H), 7.41 (m, 3H), 3.12 (m, 1H), 2.60 (m, 1H), 2.50 (m, 1H), 1.13 (d, J=7 Hz, 3H). HPLC ($t_r$/purity): PENDING min, >95%; ESI (MeOH) 189.08 (MH$^+$)

4-methyl-6-phenylpyridazin-3(2H)-one (14)

(Csende, F et al. *Synthesis,* 1995, 1240-1242) 7.0 g (35 mmol) of 13 was dissolved in 30 ml of acetonitrile in a 250 ml single-necked round bottom flask. 11.3 g (84 mmol, 2.4 equiv) of anhydrous copper (H) chloride Was added to the solution and the reaction mixture was heated to reflux for 2 hours. To control the HCl gas that formed during the course of the reaction, a NaOH solution was used to absorb the HCl that escapes from dry tube. The reaction mixture was cooled to ambient temperature, and placed into an ice-water bath. 150 mL of ice-water was added to quench the reaction. The mixture was stirred vigorously for 10 minutes to give a gray precipitate and blue liquid containing copper (I) chloride. The precipitate was then collected by filtration (pH of the filtrate is 0-1) and washed first with 1N HCl (100 mL), then with Milli-Q water (5×100 mL). To remove remaining copper by-products, the filter cake was stirred in 1N HCl (150 mL) for 0.5 h and then filtered. The filter cake was washed with water until the filtrate is at pH 7 (approximately 7 washes). The solid was dried over a medium flit sintered glass funnel in vacuo to give 14 as a light gray powder in 93.8% yield, $^1$H NMR (DMSO-d$_6$): δ 7.95 (s, 1H), 7.85 (d, J=7.5 Hz; 2H), 7.47 (m, 2H), 7.43 (m, 1H), 2.13 (s, 3H). HPLC ($t_r$/purity): 21.48 min, >97%; ESI m/z (MeOH) 187.36 (MH$^+$).

3-chloro-4-methyl-6-phenylpyridazine (15)

6.0 g (32 mmol) of 14 was placed in a 250 nit single neck round bottom flask and 30 ml acetonitrile was added to create a pale yellow slurry. 6.0 ml (64 mmol, 2 equiv) of phosphorus oxychloride was added and the reaction mixture was heated at reflux for 2.5 h. After the reaction was completed, the Mixture was cooled to ambient temperature and placed in an ice water bath. Ice water (150 mL) was slowly poured into the reaction mixture with stirring to decompose the phosphorus oxychloride into HCl and H$_3$PO$_4$. The solid was then collected by filtration and washed with Milli-Q water (3×50 mL). The solid was suspended in 100 mL of water and 1N NaOH was added until the aqueous suspension was at pH=8. The mixture was stirred for 5 minutes to remove all trace starting material contaminants. The solid was filtered and washed with Milli-Q water (3×100 mL). The product was dried over a medium frit sintered glass funnel in vacuo to provide 15 as a light pink powder in 96% yield. $^1$H NMR (DMSO-d$_6$): δ 829 (s, 1H), 8.10 (at, 2H), 7.53 (m, 3H), 2.41 (s, 3H), HPLC ($t_r$/purity): 2888.98 min, >94%. ESI m/z (MeOH) 205.49 (MH$^+$).

2-(4-(4-methyl-6-phenylpyridazin-3-yl)piperazin-1H)pyrimidine (5)

7.5 g (36.6 mmol) of 15 was suspended in 125 mL of Milli-Q water. 60.17 g (366.0 mmol, 10 equiv.) of 1-(2-pyrimidyl)piperazine was added and the reaction mixture was heated at reflux with rapid stirring for 60 h. When complete, the reaction mixture was cooled to ambient temperature and two layers were observed in the flask consisting of an orange aqueous layer and a brown oil that settled to the bottom of the flask. The water was decanted off, the oil was dissolved in minimal volume of isopropanol and heated to reflux. After 10 minutes of reflux, the solution was slowly cooled to 0° C. to induce crystallization. Pale yellow crystals were filtered from isopropanol and rinsed with minimal cold ether to provide 5 in 54% yield. $^1$H NMR (CDCl$_3$): δ 8.36 (d, J=4.5 Hz, 2H), 8.05 (d, J=7.5 Hz, 2H), 7.61 (s, 1H), 7.50 (t, J=7.1 Hz, 2H), 7.44 (1, J=7.1 Hz, 1H), 6.55 (t, J=4.5 Hz, 1H), 4.04 (t, J=4.5 Hz, 4H), 3.46 (t, J=4.5 Hz, 4H), 2.45 (s, 3H). HPLC (t$_r$/purity): 24.91 min, >95%; HRMS calcd for $C_{19}H_{20}N_6$ 332.1744. Found 332.1740. Anal. Calcd for $C_{19}H_{20}N_6$: C, 68.65; H, 6.06; N, 25.28. Found. C, 68.73; H, 5.97; N, 25.22.

2-(4-(4-methyl-6-phenylpyridazin-3-yl)piperazin-1-yl)pyrimidine dihydrochloride monohydrate salt (16)

(Wermuth C G, Stahl P H. Selected Procedures for the Preparation of Pharmaceutically Acceptable Salts, in Stahl P H., Wermuth C G. (Ed.) Handbook, of Pharmaceutical Salts, Wiley-VCH, p 249-264). 63 g (19.0 mmol) of 5 was suspended in 50 mL of anhydrous isopropanol and heated to 70° C. 2.5 eq (4.0 mL) of concentrated HCl was added at once to the solution. The suspension was stirred at 70° C. for 10 min, cooled to ambient temperature and cooled on ice 0.5 h. The precipitate is collected by filtration and washed once with cold isopropanol (30 mL) to provide the product 16 as a yellow powder in 93.3% yield. $^1$H NMR (DMSO-d$_6$): δ 8.47 (s, 3H), 8.07 (d, J=4.0 Hz, 2H), 7.61 (s, 3H), 6.76 (d, J=2.7 Hz, 2H), 3.99 (s, 4H), 3.60 (s, 4H), 2.59 (s, 3H). HPLC (t$_r$/purity): 25.06 min, 99%. HRMS calcd for $C_{19}H_{20}N_6$ 332.1744. Found 332.1744. EA calculated for $C_{19}H_{22}Cl_2N_6$: C, 53.91; H, 5.71; N, 19.85; Cl, 16.75; 0, 3.78. Found C, 53.66; H, 5.52; N, 19.67; Cl, 16.86; 0, 4.12. Copper found to be 2 ppm.

Example 10

Physicochemical Properties

Materials/Methods:

The HPLC system (Dionex Corp., Sunnyvale, Calif.) consisted of the following components: a Dionex P680 Pump, a Dionex ASI-100 autosampler, a Phenomenex (Torrance, Calif.) Luna 08 column (250×2.0 mm; 5 µM) with a guard column, and a Dionex UVD170U detector. The mobile phase consisted of 0.1% formic acid (Fluka) in Milli-Q water as solvent A and 80% acetonitrile (Burdick & Jackson), with 0.08% formic acid in Milli-Q water as solvent B. Peak quantification was performed based upon absorption at 254 nm relative to a standard curve obtained by serial dilutions of the compound.

Capillary tubes used in the micro scale aqueous solubility determination were purchased from Büchi, Switzerland. The weighting of the compounds was performed on SartoriusAG (Germany) analytical balance. Milli-Q water was obtained using Millipore System (Bedford, Mass.). The orbital shaker/incubator was purchased from Barnstead International (Melrose Park, Ill.).

Micro Scale Aqueous Solubility Determination

Dry, clean borosilicate capillary tubes were weighed using an analytical balance. Between 17-30 mg of 16 was weighed and added to the tubes. Distilled, purified Milli-Q water was added to the tubes to create solutions with concentrations ranging from 1-2 g/ml. Sample tubes were mixed manually to ensure sufficient wetting and were placed in an incubator set at 37° C. overnight. A sample was collected from each tube, centrifuged at 10,000 rpm for 10 min, and injected onto a reversed-phase HPLC, Macro Scale Aqueous Solubility Determination Dry, clean glass Erlenmeyer flasks were weighed using an analytical balance. Up to 30 mg of 26 was added to the flasks. Distilled, purified water was added to the flask to create a saturated solution. The flasks were placed in an orbital shaker/incubator at 37° C., 175 rpm for 72 hours. Samples were removed at 24 hour intervals, centrifuged at 10,000 rpm for 10 min to remove particulate and injected onto a reversed-phase HPLC system.

Partition Coefficient Determination

The partition coefficients of 16 and 26 were determined using 1-octanol (Sigma) and water. Between 0.5-1 mg/ml of each compound was dissolved in Milli-Q water and allowed to partition into presaturated octanol. The samples were placed horizontally in an orbital shaker/incubator at 37° C. for 1 hour. After 1 h, the samples were centrifuged for 5 min at 1500 rpm and the aqueous phase separated. The concentration of compound in both the aqueous and octanol phases was determined.

Activity Assays

Cell Culture Assays.

Glia cell-based assays of the concentration-dependent activity of the compounds were done as previously described (Hu T, Ralay Ranaivo et al., Current Alzheimer's Research 2005, 2:197-205; Mirzoeva. S, et al., J Med Chem 2002, 45:563-566; Ralay Ranaivo H, et al., 3 Neurosci 2006, 26:662-670). BV-2 mouse microglial cells were cultured for one day in multiwell plates and then treated in serum-free media for 16 his with either control buffer or the standard glial activating stimulus lipopolysaccharide (LPS, front Salmonella typhimurium; 100 ng/ml) in the presence of diluent or different concentrations of compounds. The accumulation of nitrite, the stable metabolite of nitric oxide (NO), was measured in V-2 conditioned media by the Griess assay as previously described (Hu W, Ralay Ranaivo et al., Current Alzheimer's Research 2005, 2:197-205; Mirzoeva S, et al, J Med Chem 2002, 45:563-566; Mirzoeva 5, et al., Brain Res 1999, 844:126434). Levels of IL-1β, TNFα, MCP-1 and IL-1β in cell lysates were measured by the Mesoscale Discovery system as per the manufacturer's instructions. Cell lysates were analyzed by Western blots as described (Mirzoeva 5, et al., J. Med Chem 2002, 45:563-566; Ralay Ranaivo H, et al J Neurosci 2006, 26:662-670) to determine the levels of inducible nitric oxide synthase (iNOS) and cyclooxygenase-2 (COX-2). Results for compounds of the invention are shown in Table 1.

Oral Bioavailability and Brain Uptake

To estimate oral bioavailability (concentration of compound in the blood as a function of time after oral administration) and to gain insight into potential brain uptake, compound 5 (2.5 mg/kg) was administered to mice by oral gavage in a 0.5% (w/v) carboxymethylcellulose suspension (Ralay Ranaivo H, et al., J Neurosci 2006, 26:662-670). At 5, 15, 30, 60 and 120 min after oral administration, mice were sacrificed, perfused and their blood and brain were harvested. Brains were homogenized in acetonitrile and then centrifuged at 12000×g for 10 minutes. Next, the plasma and the brain supernatant were acidified by diluting with 0.1% formic acid (Fluka) 1:1 and 1:3, respectively. Solid phase extraction followed by analysis was used to quantify the amount of compound in the plasma brain supernatants. Briefly, cartridges (Sep-Pak® C18, Waters) were conditioned with 1 ml of acetonitrile (HPLC grade, EMD Biosciences) and equilibrated with 1 ml of water. A structural analog, 6-methyl-4-phenyl-3-(4(pyrimidin-2-yl)piperazin-1-yl)pyridazine (MW01-7-057WH), was used as an internal recovery standard. Acidified samples were loaded to the cartridge followed by a 1 ml wash with 10% acetonitrile. Compound 5 was eluted from the cartridge using 80% acetonitrile. The eluate was evaporated to dryness, reconstituted in 0.08% formic acid/water in 80% acetonitrile and analyzed by HPLC with 0.1% formic acid in water as reagent A and 0.1% formic acid in acetonitrile as reagent B using the following gradient in reagent B: 0% to 50% to 3 min, isocratic at 50% until 6 min, 50% to 70% from 6 to 10 min, isocratic at 70% until 13 min, 70% to 80% from 13 to 18 min, isocratic at 80% until 21 min, 80% to 70% from 21 to 23 min, and finally returning from 7.0% to 0% from 23 to 28 min.

In Vivo Efficacy Studies in Mice.

The study design and treatment paradigm for intracerebroventricular (Icy) infusion of human oligomeric $A\beta_{1-42}$ into the mouse were as described previously (Craft J M, et al., *Neurobiol Aging* 2004, 25: 1283-1292) except that compound administration was by mouth (Ralay Ranaivo H, et al., J Neurosci 2006, 26:662-670). It was previously shown that Aβ-induced neuroinflammation is an early event associated with the onset and progression of pathophysiology, and can be suppressed by an inhibitor of glial activation. Female C57Bl/6 mice (Harlan) weighing 20=25 g (3-4 months old) were housed in a pathogen free facility under an approximate 12 h/12 h dark and light cycle and had access ad libitum to food and water. All animal procedures were approved by the Northwestern Animal Care and Use Committee.

Mice were administered by oral gavage either compound 5 (2.5 mg/kg/day) or solvent control (10% DMSO) in a 0.5% (w/v) carboxymethylcellulose suspension, once per day treatment began at day 21 after start of Aβ ICY infusion and continued for 14 days (Ralay Ranaivo H, et al., J Neurosci 2006, 26:662-670). Beginning at day 50 after start of Aβ ICY infusion, the Y maze test of spontaneous alternation was used to evaluate hippocampus-dependent spatial learning as described previously (Ralay Ranaivo H, et al, J Neurosci 2006, 26:662-670). At day 60 after start of Aβ ICY infusion, mice were sacrificed, perfused with a HEPES buffer (10 mM, pH 7.2) containing a protease inhibitor cocktail and brain was harvested and dissected as described previously (Ralay Ranaivo H, et al., J Neurosci 2006, 26:662=670). Levels of IL-1β and TNFα, S100B, synaptophysin, PSD-95, levels in hippocampal supernatants were measured as previously described (Ralay Ranaivo H, et al., J Neurosci 2006, 26:662=670; Craft J M, et al., Neurobiol Aging 2004, 25: 1283-1292; Eldik, L J, 1994).

Immunohistochemical detection of GFAP-positive activated astrocytes and F4/80 positive microglia was performed on 10 µm sections as described previously (Ralay Ranaivo H, et al., 3 Neurosci. 2006, 26:662-670; Craft S M, et al., Neurobiol Aging 2004, 25: 1283-1292).

Statistical Analyses.

Experimental and control groups were compared using one-way ANOVA with Newinan-Keuls post-hoc analysis using a statistical software package (GraphPad Prism version 4.00, (GraphPad Software, San Diego Calif.). Statistical significance was assumed when p<0.05.

The present invention is not to be limited in scope by the specific embodiments described herein, since such embodiments are intended as but single illustrations of one aspect of the invention and any functionally equivalent embodiments are within the scope of this invention. Indeed, various modifications of the invention in addition to those shown and described herein will become apparent to those skilled in the art from the foregoing description and accompanying drawings. Such modifications are intended to fall within the scope of the appended claims.

All publications, patents and patent applications referred to herein are incorporated by reference in their entirety to the same extent as if each individual publication, patent or patent application was specifically and individually indicated to be incorporated by reference in its entirety. All publications, patents and patent applications mentioned herein are incorporated herein by reference for the purpose of describing and disclosing the methods etc. which are reported therein which might be used in connection with the invention. Nothing herein is to be construed as an admission that the invention is not entitled to antedate such disclosure by virtue of prior invention.

TABLE 1

Medicinal chemistry refinement

| | R4 | R3 | MW* | log S* | log P* | IL-1β⊥ | NO⊥ |
|---|---|---|---|---|---|---|---|
| 1 | phenyl | pyrimidin-2-yl | 894.47 | −5.40 | 8.88 | 2.5 ± 1.6 | >25 |
| 2 | 4-methylphenyl | pyrimidin-2-yl | 408.50 | −5.33 | 8.82 | 5.3 ± 0.6 | >25 |
| 3 | pyridin-2-yl | pyrimidin-2-yl | 395.46 | −4.41 | 2.40 | 25.8 ± 7.0 | >25 |

TABLE 1-continued

Medicinal chemistry refinement

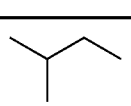

| | R4 | R3 | MW* | log S* | log P* | IL-1β[⊥] | NO[⊥] |
|---|---|---|---|---|---|---|---|
| 4 |  |  pyrimidine | 374.48 | −4.89 | 3.71 | 6.1 ± 2.5 | 22 ± 3 |
| 5 | CH₃ |  pyrimidine | 332.40 | −4.08 | 2.29 | 8.3 ± 5.8 | >25 |
| 6 | Cl |  pyrimidine | 352.82 | −4.64 | 2.76 | 9.5 ± 4.0 | 19 ± 8 |
| 7 | CH₃ |  pyrazine | 332.40 | −1.48 | 2.01 | 46.1 ± 23.3 | |
| 8 | CH₃ |  pyridine | 331.41 | −2.11 | 2.45 | 7.6 ± 2.9 | >25 |
| 9 | CH₃ |  pyridine | 331.41 | −2.09 | 2.38 | 17.7 ± 7.2 | >25 |
| 10 | CH₃ | cyclohexyl | 336.47 | −2.80 | 3.88 | 31.4 ± 4.9 | |
| 11 | CH₃ | CH₃ | 268.36 | −1.22 | 1.83 | 48.9 ± 23.2 | |

*Calculated using ACD/Solubility DB 9.03.
logS is intrinsic solubility of neutral form of compounds.
PSA: 1,2,4-7 = 58.04; 8 = 70.93; 8,9 = 46.15; 10,11 = 32.26.
[⊥]Concentration (μM) required for 50% inhibition[8].
IL-1β = interleukin-1β;
NO = nitric oxide.

TABLE 2

| Compounds of the formula II | |
|---|---|
| Compound | Final Code |
| (structure) | MWo1-2-069A-SRM |
| (structure) | MW01-6-127WH |
| (structure) | MW01-6-189WH |
| (structure) | WH 151SRM |
| (structure) | MW01-2-069A-SRM |
| (structure) | MW01-1-030A-LKM |

TABLE 2-continued

Compounds of the formula II

| Compound | Final Code |
|---|---|
| (structure) | MW01-2-127LKM |
| (structure) | MW01-2-134LKM |
| (structure) | MW01-2-146LKM |
| (structure) | MW01-2-147LKM |
| (structure) | MW01-1-045MAS |
| (structure) | MW01-2-023SRM |

TABLE 2-continued

Compounds of the formula II

| Compound | Final Code |
|---|---|
| (structure) | MW01-2-177A-WH |
| (structure) | MW01-2-191A-WH |
| (structure) | MW01-3-003WH |
| (structure) | MW01-3-019A-WH |
| (structure) | MW01-5-188WH |
| (structure) | MW01-2-023SRM |
| (structure) | MW01-2-141SRM |
| (structure) | MW01-2-163MAS |

TABLE 2-continued

Compounds of the formula II

| Compound | Final Code |
|---|---|
| 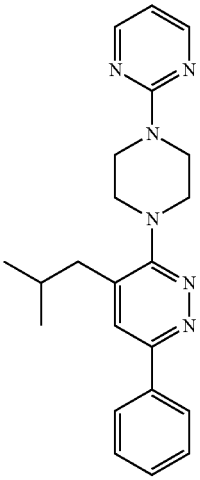 [SMILES: CC(C)Cc1cc(-c2ccccc2)nnc1N1CCN(c2ncccn2)CC1] | MW01-3-024SRM |
| 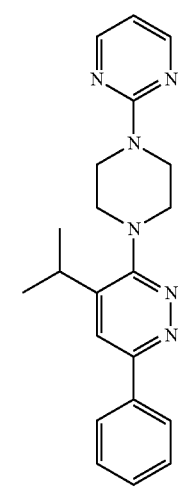 [SMILES: CC(C)c1cc(-c2ccccc2)nnc1N1CCN(c2ncccn2)CC1] | MW01-3-027SRM |
| 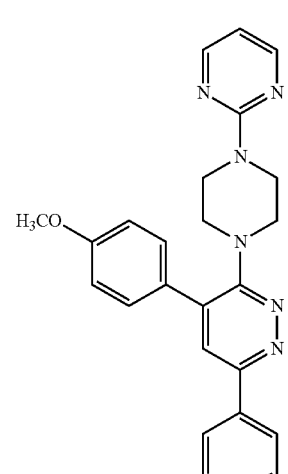 | MW01-7-100WH |
| 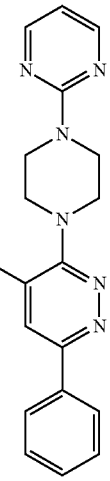 | MW01-2103LPI |

What is claimed is:

1. A method of treating a traumatic brain injury in a subject in need of treatment of a traumatic brain injury comprising administering to the subject a composition comprising a compound having the following structure:

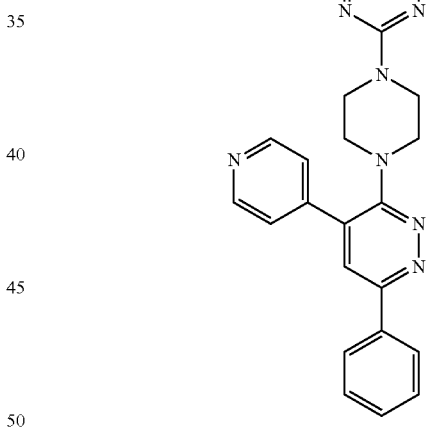

or a pharmaceutically acceptable salt thereof, and a pharmaceutically acceptable carrier, excipient or vehicle.

2. A method of claim 1, wherein the compound is administered in a dose of 1.0 to 100 mg/kg body weight of the subject.

3. A method of claim 1, wherein the compound is administered in a dose of 1.0 to 50 mg/kg body weight of the subject.

4. A method of claim 1, wherein the compound is administered in a dose of 1.0 to 20 mg/kg body weight of the subject.

5. A method of claim 1, wherein the traumatic brain injury is a closed head injury or a penetrating head injury.

6. A method of claim 1, wherein the traumatic brain injury is a closed head injury resulting from a hit to the head by a blunt object.

7. A method of claim 1, wherein the traumatic brain injury is whiplash.

8. A method of claim 1, wherein the traumatic brain injury is a penetrating head injury resulting from a bullet.

9. A method of claim 1, wherein the traumatic brain injury comprises secondary damage following an injury.

10. A method of claim 9, wherein the secondary damage comprises swelling and fluid buildup and the accumulation of the neurotransmitter glutamate.

\* \* \* \* \*